United States Patent
Allen et al.

(10) Patent No.: US 7,528,148 B2
(45) Date of Patent: May 5, 2009

(54) PYRAZOLO[3,4-B]PYRIDINE COMPOUNDS, AND THEIR USE AS PHOSPHODIESTERASE INHIBITORS

(75) Inventors: David George Allen, Stevenage (GB); Diane Mary Coe, Stevenage (GB); Caroline Mary Cook, Stevenage (GB); Anthony William James Cooper, Stevenage (GB); Michael Dennis Dowle, Stevenage (GB); Christopher David Edlin, Stevenage (GB); Julie Nicole Hamblin, Stevenage (GB); Martin Redpath Johnson, Stevenage (GB); Paul Spencer Jones, Stevenage (GB); Mika Kristian Lindvall, Emeryville, CA (US); Charlotte Jane Mitchell, Stevenage (GB); Alison Judith Redgrave, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 334 days.

(21) Appl. No.: 10/540,371

(22) PCT Filed: Dec. 19, 2003

(86) PCT No.: PCT/EP03/14867

§ 371 (c)(1),
(2), (4) Date: Feb. 21, 2006

(87) PCT Pub. No.: WO2004/056823

PCT Pub. Date: Aug. 7, 2004

(65) Prior Publication Data

US 2006/0252790 A1    Nov. 9, 2006

(30) Foreign Application Priority Data

Dec. 23, 2002 (GB) ................... 0230045.7
Dec. 24, 2002 (GB) ................... 0230165.3
Apr. 7, 2003  (GB) ................... 0307998.5

(51) Int. Cl.
C07D 471/02 (2006.01)
C07D 491/02 (2006.01)
C07D 498/02 (2006.01)
C07D 513/02 (2006.01)
C07D 515/02 (2006.01)
A01N 43/42 (2006.01)
A61K 31/44 (2006.01)

(52) U.S. Cl. ..................... 514/303; 546/119
(58) Field of Classification Search ............... 546/119; 514/303
See application file for complete search history.

(56) References Cited

U.S. PATENT DOCUMENTS

| 3,755,340 A | 8/1973 | Hoehn et al. |
| 3,833,594 A | 9/1974 | Hoehn et al. |
| 3,833,598 A | 9/1974 | Denzel et al. |
| 3,840,546 A | 10/1974 | Hoen et al. |
| 3,856,799 A | 12/1974 | Hoehn et al. |
| 3,925,388 A | 12/1975 | Hoehn et al. |
| 3,966,746 A | 6/1976 | Hoehn et al. |
| 3,979,399 A | 9/1976 | Hoehn et al. |
| 4,115,394 A | 9/1978 | Hoehn et al. |
| 5,593,997 A | 1/1997 | Dow et al. |
| 2005/0043319 A1 | 2/2005 | Schweighoffer et al. |
| 2006/0089375 A1 | 4/2006 | Allen et al. |
| 2006/0252790 A1 | 11/2006 | Allen et al. |
| 2007/0111995 A1 | 5/2007 | Allen et al. |

FOREIGN PATENT DOCUMENTS

| CA | 1003419 | 1/1977 |
| CH | 553 799 | 9/1974 |
| EP | 0 076 035 | 4/1983 |

(Continued)

OTHER PUBLICATIONS

Montana et al., Annual Reports in Medicinal Chemistry, 2001, vol. 36, pp. 41-56.*

(Continued)

*Primary Examiner*—D. Margaret Seaman
*Assistant Examiner*—Niloofar Rahmani
(74) *Attorney, Agent, or Firm*—James M. Kanagy; Stephen Venetianer; Charles M. Kinzig

(57) ABSTRACT

The invention relates to a compound of formula (I)

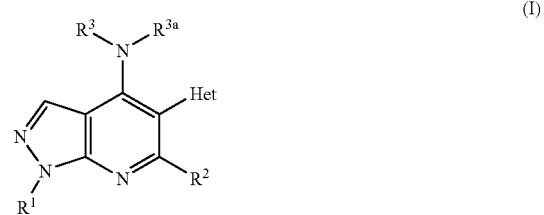

or a salt thereof: wherein: $R^1$ is $C_{1-4}$alkyl, $C_{1-3}$fluoroalkyl or —$(CH_2)_2OH$; $R^2$ is a hydrogen atom (H), methyl or $C_1$fluoroalkyl; $R^{3a}$ is a hydrogen atom (H) or $C_{1-3}$alkyl; $R^3$ is optionally substituted branched $C_{3-6}$alkyl, optionally substituted $C_{3-8}$cycloalkyl, optionally substituted mono-unsaturated-$C_{5-7}$cycloalkenyl, optionally substituted phenyl, or an optionally substituted heterocyclic group of sub-formula (aa), (bb) or (cc): in which $n^1$ and $n^2$ independently are 1 or 2; and Y is O, S, $SO_2$, or $NR^4$; and wherein Het is of sub-formula (i), (ii), (iii), (iv) or (v): The compounds are phosphodiesterase (PDE) inhibitors, in particular PDE4 inhibitors. Also provided is the use of a compound of formula (I), or a pharmaceutically acceptable salt thereof, in the manufacture of a medicament for the treatment and/or prophylaxis of an inflammatory and/or allergic disease in a mammal such as a human, for example chronic obstructive pulmonary disease (COPD), asthma, or allergic rhinitis.

52 Claims, No Drawings

FOREIGN PATENT DOCUMENTS

| | | |
|---|---|---|
| EP | 0 180 318 | 5/1986 |
| GB | 141 7489 | 12/1973 |
| GB | 151 1006 | 4/1975 |
| JP | 2002-020386 | 1/2002 |
| WO | WO-00/15222 | 3/2000 |
| WO | WO 00/15222 | 3/2000 |
| WO | WO-01/23389 A2 | 4/2001 |
| WO | WO-01/44244 A1 | 6/2001 |
| WO | WO-02/060900 | 8/2002 |
| WO | WO-02/081463 | 10/2002 |
| WO | WO-02/098878 | 12/2002 |
| WO | WO-03/016563 | 2/2003 |
| WO | WO-2004/024728 A2 | 3/2004 |
| WO | WO-2004/056823 A1 | 7/2004 |
| WO | WO-2005/058892 | 6/2005 |
| WO | WO-2005/090348 | 9/2005 |
| WO | WO-2005/090353 | 9/2005 |
| WO | WO-2005/090354 | 9/2005 |

OTHER PUBLICATIONS

U.S. Appl. No. 10/598,973, filed Mar. 2005, Cook, et al.
U.S. Appl. No. 10/598,838, filed Mar. 2005, Christensen, IV.
Bare T.M. et al.; Synthesis and structure-activity relationships of a series of anxioselective pyrazolopyridine ester and amide anxiolytic agents; Journal of Medicinal Chemistry; 1989; 32; pp. 2561-2573.
Beer B., et al.; "Enhancement of 3H-diazepam binding by SQ 65,396: a novel anti-anxiety agent"; Pharmacology Biochemistry & Behaviour; 1978; 9; pp. 849-851.
Bondavalli F. et al; Synthesis, molecular modelling studies, and pharmacological activity of selective A1 receptor antagonists; Journal of Medicinal Chemistry; 2002; 45(22); pp. 4875-4887.
Chakravorti; Synthesis of Some Isoquinolylpyrazolo[3,4-b]pyridine Derivatives as Possible Antifilarial Agents; Indian J. Chem.; Feb. 1978; vol. 16B, pp. 161-163.
Chasin M., et al.; "1-Ethyl-4-(isopropylidenehydrazino)-1H-pyrazolo-(3,4-b)-pyridine-5-carboxylic acid, ethyl ester, hydrochloride (SQ 20009)—a potent new inhibitor of cyclic 3',5'-nucleotide phosphodiesterases"; Biochemical Pharmacology; 1972; 21; pp. 2443-2450.
Chemical Abstracts Registry—CAS registry No. 502143-17-1 which has the laboratory code NSC 235755, Apr. 8, 2003.
Daly J. W. et al.; 1-methyl-4-substituted-1H-pyrazolo [3,4-b] pyridine-5-carboxylic acid derivatives: effect of structural alterations on activity at A1 and A2 adenosine receptors; Medicinal Chemistry Research; 1994; 4(5); pp. 293-306; Birkhaeuser; Boston US.
Davis A., et al.,; "Strategic approaches to drug design. II. Modelling studies on phosphodiesterase substrates and inhibitors"; Journal of Computer-Aided Molecular Design; 1987; 1; pp. 97-119.
De Mello, A. Echevarria, et al.; Antileishmanial Pyrazolopyridine Derivatives: Synthesis and Structure-Activity Relationship Analysis; Journal of Medicinal Chemistry; 2004; 47(22); pp. 5427-5432.
Denzel TH.; (translation of title: New Synthesis of 1-Unsubstituted 1H-Pyrazolo [3,4-b] Pyridine-5-Carboxylic Acid Esters); Archiv der Pharmazie; 1974; 307(3); pp. 177-186.
Giembycz M.A.; Phosphodiesterase 4 Inhibitors and the Treatment of Asthma: Where Are We Now and Where Do We Go from Here?; Drugs; 2000; 59(2); pp. 193-212.
Glass II, W. F., et al.; "Inhibition of human lung cyclic GMP and cyclic AMP phosphodiesterases by certain nucleosides, nucleotides, and pharmacological phosphodiesterase inhibitors"; Biochemical Pharmacology; 1979; 28; pp. 1107-1112.
Hoehn H. et al.; 1H-pyrazolo[3,4-b]pyridines; Journal of Heterocyclic Chemistry; 1972; 9(2); pp. 235-253.
Hohn H et al: Potential Antidiabetic Agents. Pyrazolo63,4-b!pyridinesW Journal of Medicinal Chemistry, American Chemical Society. Washington, US, vol. 16, No. 12, 1973, pp. 1340-1346, XP002097814 ISSN: 0022-2623 p. 1343; compound 37.
Horowitz Z. P., et al.; "Cyclic AMP and anxiety"; Psychosomatics; 1972; vol. XIII, No. 2; pp. 85-92.
Kripalani K. J. et al.; "Biotransformation in the monkey of cartazolate (SQ 65,396), a substituted pyrazolopyridine having anxiolytic activity"; Xenobiotica; 1981; 11(7); pp. 481-488.
Ochiai H. et al.; Discovery of new orally active phosphodiesterase (PDE4) inhibitors; Chem. Pharm. Bull.; 2004 (stated to have been published online Jun. 15, 2004); 52(9); pp 1098-1104.
Ochiai H. et al.; Bioorg. Med. Chem. Web Release; 2003.
Ochiai H. et al.; New orally active PDE4 inhibitors with therapeutic potential; Bioorg. Med. Chem.; 2004 (stated to have been available online Jun. 20, 2004); 12(15); pp. 4089-4100.
Ochiai H. et al.; New orally active PDE4 inhibitors with therapeutic poteintial; Bioorg. Med. Chem. Lett.; Jan. 5, 2004 issue (available as "articles in press" version on or before Dec. 4, 2003, possibly Oct. 2003, via internet); 14(1); pp. 29-32.
Patel J.B. and Malick J.B.; Pharmacological properties of tracazolate: a new non-benzodiazepine anxiolytic agent; Eur. J. Pharmacol.; 1982; 78; pp. 323-333.
Patel J.B., et al.; "Pharmacology of pyrazolopyridines"; Pharmacology Biochemistry & Behaviour; 1985; vol. 23; pp. 675-680.
Polson J. B., et al.; "Analysis of the relationship between pharmacological inhibition of cyclic nucleotide phosphodiesterase and relaxation of canine tracheal smooth muscle"; Biochemical Pharmacology; 1979; 28; pp. 1391-1395 RBI 1998, Catalogue No. T-112, Tracazolate; 1998; p. 340.
Sabitha, et al.; A Facile Route to Pyrazolo[3,4-b]Pyridines and [1]Benzopyrano[4',3'-e]Pyrazolo[3,4-b]Pyridines; Indian Institute of Chemical Technology; 1999; 29(4),655-665; Synthetic Communications; India.
Schenone S. et al.; Synthesis and biological data of 4-amino-1-(2-chloro-2-phenylethyl)-1H-pyrazolo[3,4-b]pyridine-5-carboxylic acid ethyl esters, a new series of A1-adenosine receptor (A1AR) ligands; Bioorg. Med. Chem. Lett.; 2001; 11; pp. 2529-2531.
Shi D., et al.; Pyrazolopyridines: effect of structural alterations on activity at adenosine- and GABA-A receptors; Drug Development Research; 1997; 42; pp. 41-56.
Weinryb I., et al.; "Studies in vitro and in vivo with SQ-20,009: an inhibitor of cyclic nucleoside phosphodiesterase with central nervous system activity"; Excerpta Med. Int. Congr. Ser.; 1975; 359; pp. 857-865.
Yu G., Mason H.J., et. al.; Substituted pyrazolopyridines as potent and selective PDE5 inhibitors: potential agents for treatment of erectile disfunction; Journal of Medicinal Chemistry; 2001; 44; pp. 1025-1027.

\* cited by examiner

PYRAZOLO[3,4-B]PYRIDINE COMPOUNDS, AND THEIR USE AS PHOSPHODIESTERASE INHIBITORS

This application claims the benefit of International Application No. PCT/EP2003/014867 filed 19 Dec. 2003.

The present invention relates to pyrazolopyridine compounds, processes for their preparation, intermediates usable in these processes, and pharmaceutical compositions containing the compounds. The invention also relates to the use of the pyrazolopyridine compounds in therapy, for example as inhibitors of phosphodiesterases (PDE) and/or for the treatment and/or prophylaxis of inflammatory and/or allergic diseases such as chronic obstructive pulmonary disease (COPD), asthma, rheumatoid arthritis or allergic rhinitis.

U.S. Pat. Nos. 3,979,399, 3,840,546, and 3,966,746 (E.R.Squibb & Sons) disclose 4-amino derivatives of pyrazolo[3,4-b]pyridine-5-carboxamides wherein the 4-amino group $NR_3R_4$ can be an acyclic amino group wherein $R_3$ and $R_4$ may each be hydrogen, lower alkyl (e.g. butyl), phenyl, etc.; $NR_3R_4$ can alternatively be a 3-6-membered heterocyclic group such as pyrrolidino, piperidino and piperazino. The compounds are disclosed as central nervous system depressants useful as ataractic, analgesic and hypotensive agents.

U.S. Pat. Nos. 3,925,388, 3,856,799, 3,833,594 and 3,755,340 (E.R.Squibb & Sons) disclose 4-amino derivatives of pyrazolo[3,4-b]pyridine-5-carboxylic acids and esters. The 4-amino group $NR_3R_4$ can be an acyclic amino group wherein $R_3$ and $R_4$ may each be hydrogen, lower alkyl (e.g. butyl), phenyl, etc.; $NR_3R_4$ can alternatively be a 5-6-membered heterocyclic group in which an additional nitrogen is present such as pyrrolidino, piperidino, pyrazolyl, pyrimidinyl, pyridazinyl or piperazinyl. The compounds are mentioned as being central nervous system depressants useful as ataractic agents or tranquilisers, as having antiinflammatory and analgesic properties. The compounds are mentioned as increasing the intracellular concentration of adenosine-3',5'-cyclic monophosphate and for alleviating the symptoms of asthma.

H. Hoehn et al., *J. Heterocycl. Chem.*, 1972, 9(2), 235-253 discloses a series of 1H-pyrazolo[3,4-b]pyridine-5-carboxylic acid derivatives with 4-hydroxy, 4-chloro, 4-alkoxy, 4-hydrazino, and 4-amino substituents.

CA 1003419, CH 553 799 and T. Denzel, *Archiv der Pharmazie*, 1974, 307(3), 177-186 disclose 4,5-disubstituted 1H-pyrazolo[3,4-b]pyridines unsubstituted at the 1-position.

U.S. Pat. No. 3,833,598 and GB 1,417,489 (E.R.Squibb & Sons) disclose 4-amino derivatives of pyrazolo[3,4-b]pyridine-6-carboxylic acids and esters. The 4-amino group $NR_3R_4$ can be an acyclic amino group wherein $R_3$ and $R_4$ may each be hydrogen, lower alkyl, $R_6$, $R_7$-phenyl, etc.; or $NR_3R_4$ can be a 5-6-membered heterocyclic group in which an additional nitrogen is present, namely optionally substituted pyrrolidino, piperidino, pyrazolyl, dihydropyridazinyl or piperazinyl. At the 5-position of the pyrazolo[3,4-b]pyridine is group $R_5$ which is hydrogen, lower alkyl, phenyl, phenyl-lower-alkyl or halogen; $R_5$ is preferably hydrogen, methyl or chlorine. The compounds are mentioned as being central nervous system depressants useful as tranquilizers or ataractic agents for the relief of anxiety and tension states. The compounds are also mentioned as increasing the intracellular concentration of adenosine-3',5'-cyclic monophosphate and for alleviating the symptoms of asthma. The compounds are also mentioned as having anti-inflammatory properties and as being useful as anti-inflammatory agents, for example, to reduce local inflammatory conditions such as those of an edematous nature or resulting from proliferation of connective tissue in various mammalian species such as rats and dogs.

U.S. Pat. No. 4,115,394 and GB 1,511,006 (E.R.Squibb & Sons) disclose 4-amino derivatives of 6-phenyl-pyrazolo[3,4-b]pyridines. The 4-amino group $NR_3R_4$ is an acyclic amino group wherein $R_3$ and $R_4$ may each be hydrogen, lower alkyl, phenyl, phenyl-lower-alkyl or substituted phenyl. At the 5-position of the pyrazolo[3,4-b]pyridine is group $R_5$ which is hydrogen, lower alkyl, phenyl or phenyl-lower-alkyl; $R_5$ is preferably hydrogen. The compounds are mentioned as having anti-inflammatory properties and as being useful as anti-inflammatory agents, for example, to reduce local inflammatory conditions such as those of an edematous nature or resulting from proliferation of connective tissue in various mammalian species such as rats and dogs. The compounds are also mentioned (a) as having diuretic activity, and (b) as increasing the intracellular concentration of adenosine-3',5'-cyclic monophosphate and for alleviating the symptoms of asthma.

Japanese laid-open patent application JP-2002-20386-A (Ono Yakuhin Kogyo KK) published on 23 Jan. 2002 discloses pyrazolopyridine compounds of the following formula:

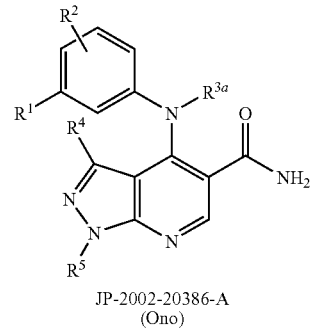

JP-2002-20386-A
(Ono)

wherein $R^1$ denotes 1) a group $-OR^6$, 2) a group $-SR^7$, 3) a C2-8 alkynyl group, 4) a nitro group, 5) a cyano group, 6) a C1-8 alkyl group substituted by a hydroxy group or a C1-8 alkoxy group, 7) a phenyl group, 8) a group $-C(O)R^8$, 9) a group $-SO_2NR^9R^{10}$, 10) a group $-NR^{11}SO_2R^{12}$, 11) a group $-NR^{13}C(O)R^{14}$ or 12) a group $-CH=NR^{15}$. $R^6$ and $R^7$ denote i) a hydrogen atom, ii) a C1-8 alkyl group, iii) a C1-8 alkyl group substituted by a C1-8 alkoxy group, iv) a trihalomethyl group, v) a C3-7 cycloalkyl group, vi) a C1-8 alkyl group substituted by a phenyl group or vii) a 3-15 membered mono-, di- or tricyclic hetero ring containing 1-4 nitrogen atoms, 1-3 oxygen atoms and/or 1-3 sulphur atoms. $R^2$ denotes 1) a hydrogen atom or 2) a C1-8 alkoxy group. $R^3$ denotes 1) a hydrogen atom or 2) a C1-8 alkyl group. $R^4$ denotes 1) a hydrogen atom, 2) a $C_{1-8}$ alkyl group, 3) a C3-7 cycloalkyl group, 4) a C1-8 alkyl group substituted by a C3-7 cycloalkyl group, 5) a phenyl group which may be substituted by 1-3 halogen atoms or 6) a 3-15 membered mono-, di- or tricyclic hetero ring containing 14 nitrogen atoms, 1-3 oxygen atoms and/or 1-3 sulphur atoms. $R^5$ denotes 1) a hydrogen atom, 2) a $C_{1-8}$ alkyl group, 3) a C3-7 cycloalkyl group, 4) a $C_{1-8}$ alkyl group substituted by a C3-7 cycloalkyl group or 5) a phenyl group which may be substituted by 1-3 substituents. In group $R^3$, a hydrogen atom is preferred. In group $R^4$, methyl, ethyl, cyclopropyl, cyclobutyl or cyclopentyl are preferred. The compounds of JP-2002-20386-A are stated as having PDE4 inhibitory activity and as being useful in the prevention and/or treatment of inflammatory diseases and many other diseases.

EP 0 076 035 A1 (ICI Americas) discloses pyrazolo[3,4-b]pyridine derivatives as central nervous system depressants useful as tranquilisers or ataractic agents for the relief of anxiety and tension states.

The compound cartazolate, ethyl 1-ethyl-4-n-butylamino-1H-pyrazolo[3,4-b]-pyridine-5-carboxylate, is known. J. W. Daly et al., *Med. Chem. Res.,* 1994, 4, 293-306 and D. Shi et al., *Drug Development Research,* 1997, 42, 41-56 disclose a series of 4-(amino) substituted 1H-pyrazolo[3,4-b]pyridine-5-carboxylic acid derivatives, including ethyl 4-cyclopentylamino-1-methyl-1H-pyrazolo[3,4-b]pyridine-5-carboxylate, and their affinities and antagonist activities at $A_1$- and $A_{2A}$-adenosine receptors, and the latter paper discloses their affinities at various binding sites of the $GABA_A$-receptor channel. S. Schenone et al., *Bioorg. Med. Chem. Lett.,* 2001, 11, 2529-2531, and F. Bondavalli et al., *J. Med. Chem.,* 2002, vol. 45 (Issue 22, 24 Oct. 2002, allegedly published on the Web on Sep. 24, 2002), pp. 4875-4887, disclose a series of 4-amino-1-(2-chloro-2-phenylethyl)-1H-pyrazolo[3,4-b]pyridine-5-carboxylic acid ethyl esters as A1-adenosine receptor ligands.

WO 02/060900 A2 appears to disclose, as MCP-1 antagonists for treatment of allergic, inflammatory or autoimmune disorders or diseases, a series of bicyclic heterocyclic compounds with a —C(O)—NR$^4$—C(O)—NR$^5$R$^6$ substituent, including isoxazolo[5,4-b]pyridines and 1H-pyrazolo[3,4-b]pyridines (named as pyrazolo[5,4-b]pyridines) with the —C(O)—NR$^4$—C(O)—NR$^5$R$^6$ group as the 5-substituent and optionally substituted at the 1-, 3-, 4-, and/or 6-positions. Bicyclic heterocyclic compounds with a C(O)NH$_2$ substituent instead of the —C(O)—NR$^4$—C(O)—NR$^5$R$^6$ substituent are alleged to be disclosed in WO 02/060900 as intermediates in the synthesis of the —C(O)—NR$^4$—C(O)—NR$^5$R$^6$ substituted compounds.

S. S. Chakravorti et al., *Indian J. Chem.,* 1978, 16B(2), 161-3 discloses the compounds 4-hydroxy-1,3-diphenyl-5-(3',4'-dihydroisoquinol-1'-yl)-pyrazolo[3,4-b]pyridine and 1,3-diphenyl-4-hydroxy-5-(3'-methyl-3',4'-dihydroisoquinol-1'-yl)-pyrazolo[3,4-b]pyridine. These two compounds were tested for antifilarial activity but were found to have no significant microfilaricidal activity.

G. Sabitha et al., *Synthetic Commun.,* 1999, 29(4), 655-665 discloses a synthetic route to 5-substituted-6-amino-1-phenyl-3-(methyl or phenyl)-pyrazolo[3,4-b]pyridines wherein the 5-substituent of the pyrazolo[3,4-b]pyridine is benzimidazol-2-yl, 5-chloro-benzoxazol-2-yl, or benzothiazol-2-yl. Though declared to be "biologically interesting molecules", there is however no disclosure that these compounds had been tested in any pharmacological tests and there is no disclosure of any general or specific biological activity of these compounds.

On 8 Apr. 2003, Chemical Abstracts (CAS) registered on their database a compound with the CAS Registry Number 502143-17-1, with the chemical name "1H-Pyrazolo[3,4-b]pyridin-4-amine, N-butyl-5-(4,5-dihydro-1H-imidazol-2-yl)-1-ethyl-" and bearing the laboratory code NSC 235755. As at 5 Nov. 2003, the CAS entry for this compound had no associated literature references and therefore it appears that no chemical synthesis and no uses of the compound have been disclosed as at 5th Nov. 2003. The structure of the compound from the CAS database is as follows:

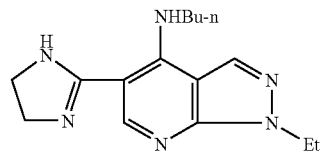

It is desirable to find new compounds which bind to, and preferably inhibit, phosphodiesterase type IV (PDE4).

The present invention provides a compound of formula (I) or a salt thereof (in particular, a pharmaceutically acceptable salt thereof):

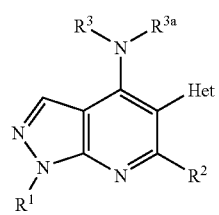

wherein:

R$^1$ is $C_{1-4}$alkyl, $C_{1-3}$fluoroalkyl or —(CH$_2$)$_2$OH;

R$^2$ is a hydrogen atom (H), methyl or $C_1$ fluoroalkyl;

R$^3$ is optionally substituted branched $C_{3-6}$alkyl, optionally substituted $C_{3-8}$cycloalkyl, optionally substituted mono-unsaturated-$C_{5-7}$cycloalkenyl, optionally substituted phenyl, or an optionally substituted heterocyclic group of sub-formula (aa), (bb) or (cc):

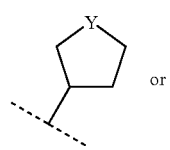

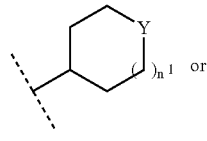

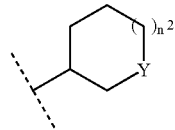

in which $n^1$ and $n^2$ independently are 1 or 2; and Y is O, S, SO$_2$, or NR$^4$; where R$^4$ is a hydrogen atom (H), $C_{1-2}$alkyl, $C_{1-2}$fluoroalkyl, CH$_2$C(O)NH$_2$, C(O)NH$_2$, C(O)—$C_{1-2}$alkyl, or C(O)—$C_1$fluoroalkyl;

wherein in R$^3$ the optionally substituted branched $C_{3-6}$alkyl is optionally substituted with one or two substituents being oxo (=O), OH, $C_{1-2}$alkoxy or $C_{1-2}$fluoroalkoxy; and wherein any such substituent is not substituted at the R$^3$ carbon atom attached (bonded) to the —NH— group of formula (I);

wherein in R³ the phenyl is optionally substituted with one substituent being fluoro, chloro, $C_{1-2}$alkyl, $C_{1-2}$fluoroalkyl, $C_{1-2}$alkoxy, $C_{1-2}$fluoroalkoxy or cyano, or with two or three fluoro substituents;

wherein in R³ the $C_{3-8}$cycloalkyl or the heterocyclic group of sub-formula (aa), (bb) or (cc) is optionally substituted with one or two substituents independently being (e.g. being) oxo (=O); OH; $C_{1-2}$alkoxy; $C_{1-2}$fluoroalkoxy; NHR²¹ wherein R²¹ is a hydrogen atom (H) or $C_{1-4}$ straight-chain alkyl; $C_{1-2}$alkyl; $C_{1-2}$fluoroalkyl (e.g. $C_1$fluoroalkyl such as —CH₂F or —CHF₂); —CH₂OH; —CH₂CH₂OH; —CH₂NHR²² wherein R²² is H or $C_{1-2}$alkyl; —C(O)OR²³ wherein R²³ is H or $C_{1-2}$alkyl; —C(O)NHR²⁴ wherein R²⁴ is H or $C_{1-2}$alkyl; —C(O)R²⁵ wherein R²⁵ is $C_{1-2}$alkyl; fluoro; hydroxyimino (=N—OH); or ($C_{1-4}$alkoxy)imino (=N—OR²⁶ where R²⁶ is $C_{1-4}$alkyl); and wherein any OH, alkoxy, fluoroalkoxy or NHR²¹ substituent is not substituted at the R³ ring carbon attached (bonded) to the —NH— group of formula (I) and is not substituted at either R³ ring carbon bonded to the Y group of the heterocyclic group (aa), (bb) or (cc);

and wherein, when R³ is optionally substituted mono-unsaturated-$C_{5-7}$cycloalkenyl, then the cycloalkenyl is optionally substituted with one or two substituents independently being fluoro or $C_{1-2}$alkyl provided that if there are two substituents then they are not both $C_2$alkyl, and the R³ ring carbon bonded to the —NH— group of formula (I) does not partake in the cycloalkenyl double bond;

and $R^{3a}$ is a hydrogen atom OD or straight-chain $C_{1-3}$alkyl;

provided that when $R^{3a}$ is $C_{1-3}$alkyl then R³ is tetrahydro-2H-pyran-4-yl, cyclohexyl (i.e. unsubstituted), 3-hydroxy-cyclohexyl, 4-oxo-cyclohexyl or 4-(hydroxyimino)cyclohexyl;

and wherein Het is of sub-formula (i), (ii), (iii), (iv) or (v):

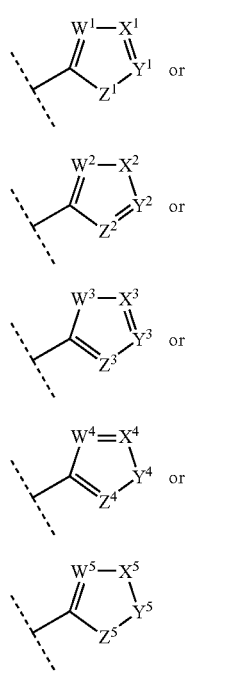

wherein:
W¹, W², W⁴ and W⁵ is N; and W³ is $NR^W$;
X¹, X³ and X⁴ is N or $CR^X$; X² is O, S or $NR^X$; and X⁵ is $CR^{X1}R^{X2}$ or $CR^{X3}R^{X4}$;

Y¹, Y² and Y³ is $CR^Y$ or N; Y⁴ is O, S or $NR^Y$; and Y⁵ is $CR^{Y1}R^{Y2}$;
Z¹ and Z⁵ is O, S or $NR^Z$; and Z², Z³ and Z⁴ is N or $CR^Z$;

wherein:
$R^W$ is a hydrogen atom (H) or $C_{1-2}$alkyl;
$R^X$, $R^{X2}$, $R^Y$ and $R^{Y2}$ independently are:
  a hydrogen atom (H);
  $C_{1-8}$alkyl;
  $C_{3-6}$cycloalkyl optionally substituted by one or two $C_{1-2}$alkyl groups and/or by one oxo (=O) group;
  —(CH₂)$_n^{2a}$—$C_{3-6}$cycloalkyl optionally substituted, in the —(CH₂)$_n^{2a}$-moiety or in the $C_{3-6}$cycloalkyl moiety, by a $C_{1-2}$alkyl group, or optionally substituted in the $C_{3-6}$cycloalkyl moiety by a —CH₂C(O)NHC$_{1-2}$alkyl group, wherein $n^{2a}$ is 1, 2 or 3;
  —(CH₂)$_n^3$—S(O)₂—R⁵, —CH(C$_{1-2}$alkyl)—S(O)₂—R⁵, —CMe₂—S(O)₂—R⁵, or $C_{3-5}$cycloalkyl substituted at the connecting carbon atom by —S(O)₂—R⁵, wherein $n^3$ is 1 or 2;
  and R⁵ is $C_{1-4}$alkyl (e.g. $C_{1-3}$alkyl), —NR¹⁵R¹⁶, phenyl, carbon-linked-pyridinyl or benzyl (wherein the phenyl and benzyl are independently optionally substituted on the aromatic ring by one or two substituents independently being fluoro, chloro, $C_{1-2}$alkyl, $C_1$fluoroalkyl, $C_{1-2}$alkoxy, $C_1$fluoroalkoxy or OH, and wherein the pyridinyl is optionally substituted by one methyl, methoxy or OH (including any tautomer thereof));
  wherein R¹⁵ is H, $C_{1-4}$alkyl (e.g. $C_{1-2}$alkyl), phenyl, benzyl (wherein the phenyl and benzyl are independently optionally substituted on the aromatic ring by one or two substituents independently being fluoro, chloro, $C_{1-2}$alkyl, $C_1$fluoroalkyl, $C_{1-2}$alkoxy or $C_1$fluoroalkoxy), CH(Me)Ph, or carbon-linked-pyridinyl optionally substituted by one methyl, methoxy or OH (including any tautomer thereof);
  and R¹⁶ is H or $C_{1-2}$alkyl;
  or wherein R¹⁵ and R¹⁶ together are —(CH₂)$_n^{3a}$—X$^{3a}$—(CH₂)$_n^{3b}$— in which $n^{3a}$ and $n^{3b}$ independently are 2 or 3 and X$^{3a}$ is a bond, —CH₂—, O, or NR$^{8a}$ wherein R$^{8a}$ is H or $C_{1-2}$alkyl, acetyl, —S(O)₂Me or phenyl, and wherein the ring formed by NR¹⁵R¹⁶ is optionally substituted on a ring carbon by one or two substituents independently being methyl or oxo (=O);
  —(CH₂)$_n^4$—NR⁶R⁷, —CH(C$_{1-2}$alkyl)-NR⁶R⁷, —CMe₂—NR⁶R⁷, or $C_{3-5}$cycloalkyl substituted at the connecting carbon atom by —NR⁶R⁷, wherein $n^4$ is 0, 1, 2 or 3;
  and R⁶ and R⁷ independently are H, $C_{1-6}$alkyl (e.g. $C_{1-4}$alkyl), $C_{3-6}$cycloalkyl, —CH₂—$C_{3-6}$cycloalkyl, —C(O)R¹⁷, —S(O)₂R¹⁸, phenyl, benzyl (wherein the phenyl and benzyl are independently optionally substituted on the aromatic ring by one or two substituents independently being fluoro, chloro, $C_{1-2}$alkyl, $C_1$fluoroalkyl, $C_{1-2}$alkoxy or $C_1$fluoroalkoxy), or carbon-linked-pyridinyl optionally substituted by one methyl, methoxy or OH (including any tautomer thereof);
  and wherein R¹⁷ and R¹⁸ independently are $C_{1-6}$alkyl (e.g. $C_{1-4}$alkyl or $C_{1-2}$alkyl or isopropyl or n-propyl), $C_{3-6}$cycloalkyl, optionally substituted 5-membered heteroaryl being furyl (furanyl, e.g. 2-furyl) or 1,3-oxazolyl or isoxazolyl or oxadiazolyl or thienyl (e.g. 2- or 3-thienyl) or 1,3-thiazolyl or isothiazolyl or pyrrolyl or imidazolyl or pyrazolyl (all independently optionally substituted by one oxo and/or one or two methyl), or phenyl or benzyl (wherein the phenyl and benzyl are independently optionally substituted on the aromatic ring by one or two substituents independently being fluoro, chloro, $C_{1-2}$alkyl, $C_1$fluoroalkyl, $C_{1-2}$alkoxy, $C_1$fluoroalkoxy or OH), or carbon-linked-pyridinyl optionally substituted by one methyl, methoxy or OH (including any tautomer thereof);

or $R^6$ and $R^7$ together are $-(CH_2)_{n^5}-X^5-(CH_2)_{n^6}-$ in which $n^5$ and $n^6$ independently are 2 or 3 and $X^5$ is a bond, $-CH_2-$, O, or $NR^8$ wherein $R^8$ is H, $C_{1-2}$alkyl, acetyl, $-S(O)_2Me$ or phenyl, and wherein the ring formed by $NR^6R^7$ is optionally substituted on a ring carbon by one or two substituents independently being methyl or oxo (=O);

$-(CH_2)_{n^7}-O-R^9$; wherein $n^7$ is 0, 1, 2 or 3 and $R^9$ is H, $C_{1-6}$alkyl, $C_{3-6}$cycloalkyl, $-CH_2-C_{3-6}$cycloalkyl, $-C(O)R^{17}$, phenyl, or benzyl (wherein the phenyl and benzyl are independently optionally substituted on the aromatic ring by one or two of fluoro, chloro, $C_{1-2}$alkyl, $C_1$fluoroalkyl, $C_{1-2}$alkoxy or $C_1$fluoroalkoxy); wherein $n^7$ is 0 only when the $-(CH_2)_{n^7}-O-R^9$ is bonded to a carbon atom in the Het ring; and wherein $n^7$ is not 0 when Het is of sub-formula (v) (i.e. $n^7$ is not 0 for $R^{X2}$ and for $R^{Y2}$);

$-(CH_2)_{n^{11}}-C(O)-NR^{10}R^{11}$, $-CH(C_{1-2}$alkyl$)-C(O)-NR^{10}R^{11}$, $-CMe_2-C(O)-NR^{10}R^{11}$, Or $C_{3-5}$cycloalkyl substituted at the connecting carbon atom by $-C(O)-NR^{10}R^{11}$, wherein $n^{11}$ is 0, 1 or 2;

and wherein $R^{10}$ and $R^{11}$ independently are: H; $C_{1-6}$alkyl; $C_{1-4}$fluoroalkyl; $C_{2-4}$alkyl substituted by one OH or $-OC_{1-2}$alkyl other than at the connection point; $C_{3-6}$cycloalkyl optionally substituted by one or two methyl groups; $-CH_2-C_{3-6}$cycloalkyl optionally substituted by one methyl, $NH_2$ or NHMe group; $-(CH_2)_{n^{17}}-Het^2$; carbon-linked-pyridinyl optionally substituted by one methyl, methoxy or OH (including any tautomer thereof); phenyl; benzyl; or $-CH(C_{1-2}$alkyl)Ph [wherein the phenyl, benzyl, and $-CH(C_{1-2}$alkyl)Ph are independently optionally substituted on the aromatic ring by one or two substituents independently being: fluoro, chloro, $C_{1-2}$alkyl, $C_1$fluoroalkyl, $C_{1-2}$alkoxy, $C_1$fluoroalkoxy, OH, $-NR^{10a}R^{10b}$ (wherein $R^{10a}$ is H or $C_{1-2}$alkyl and $R^{10b}$ is H, $C_{1-2}$alkyl, $-C(O)-C_{1-2}$alkyl or $-S(O)_2-C_{1-2}$alkyl), $-C(O)-NR^{10c}R^{10d}$ (wherein $R^{10c}$ and $R^{10d}$ independently are H or $C_{1-2}$alkyl), or $-S(O)_2-R^{10e}$ (wherein $R^{10e}$ is $C_{1-2}$alkyl, $NH_2$, NHMe or $NMe_2$)], wherein $n^{17}$ is 0, 1 or 2 and wherein $Het^2$ is a 4-, 5- or 6-membered saturated heterocyclic ring containing one O or S ring atom or one $NR^{27}$ ring group wherein $R^{27}$ is H, $C_{1-2}$alkyl, $-C(O)Me$, or $-S(O)_2Me$, wherein the $Het^2$ ring is optionally substituted on a ring carbon by one or two substituents independently being methyl or oxo (=O);

and wherein when $n^{17}$ is 2 then the $Het^2$ ring can optionally contain one additional ring N atom at the $Het^2$ ring position bonded to the $-(CH_2)_{n^{17}}$-moiety, provided that, when $Het^2$ contains one O or S or $NR^{27}$ ring atom/group and one additional ring N atom, then the $O/S/NR^{27}$ ring atom/group and the one additional ring N atom are not directly bonded to each atom, and are separated by more than one carbon atom;

or $R^{10}$ and $R^{11}$ together are $-(CH_2)_{n^8}-X^6-(CH_2)_{n^9}-$ in which $n^8$ and $n^9$ independently are 2 or 3 and $X^6$ is a bond, $-CH_2-$, O, or $NR^{12}$ wherein $R^{12}$ is H, $C_{1-2}$alkyl, acetyl, $-S(O)_2Me$ or phenyl, and wherein the ring formed by $NR^{10}R^{11}$ is optionally substituted on a ring carbon by one or two substituents independently being methyl or oxo (=O);

$-(CH_2)_{n^{12}}-C(O)-OR^{13}$ wherein $n^{12}$ is 0, 1 or 2; and wherein $R^{13}$ is H, $C_{1-6}$alkyl, $C_{3-6}$cycloalkyl, $-CH_2-C_{3-6}$cycloalkyl, phenyl, or benzyl (wherein the phenyl and benzyl are independently optionally substituted on the aromatic ring by one or two of (independently) fluoro, chloro, $C_{1-2}$alkyl, $C_1$fluoroalkyl, $C_{1-2}$alkoxy or $C_1$fluoroalkoxy);

$-(CH_2)_{n^{13}}-C(O)-R^{13a}$ wherein $n^{13}$ is 0, 1 or 2; and wherein $R^{13a}$ is a hydrogen atom (H), $C_{1-6}$alkyl, $C_{1-2}$fluoroalkyl, $C_{3-6}$cycloalkyl, $-CH_2-C_{3-6}$cycloalkyl, benzyl, or phenyl; wherein the phenyl and benzyl are independently optionally substituted on the aromatic ring by one or two of (independently) fluoro, chloro, $C_1$ alkyl, $C_1$fluoroalkyl, $C_{1-2}$alkoxy or $C_1$fluoroalkoxy;

$-(CH_2)_{n^{14}}-Het^1$, $-CH(C_{1-2}$alkyl$)-Het^1$, $-CMe_2-Het^1$, or $C_{3-5}$cycloalkyl substituted at the connecting carbon atom by $Het^1$, wherein $n^{14}$ is 0, 1 or 2 and wherein $Het^1$ is a 4-, 5-, 6- or 7-membered saturated heterocyclic ring; wherein said heterocyclic ring $Het^1$ contains one O or S ring atom and/or one $NR^{14}$ ring group wherein $R^{14}$ is H, $C_{1-4}$alkyl, $C_{3-6}$cycloalkyl, benzyl, phenyl, $-C(O)R^{19}$, or $-S(O)_2R^{19}$;

wherein $R^{19}$, independent of any other $R^{19}$, is $C_{1-6}$alkyl (e.g. $C_{1-4}$alkyl or $C_{1-3}$alkyl), $C_{3-6}$cycloalkyl, thienyl (e.g. 2-thienyl), furyl (furanyl, e.g. furan-2-yl), or phenyl or benzyl; wherein the phenyl and benzyl are independently optionally substituted by one or two of (independently) fluoro, methyl or methoxy;

and wherein said heterocyclic ring $Het^1$ is optionally substituted (at a position or positions other than any $NR^{14}$ position) by one or two oxo (=O) and/or one $C_{1-4}$alkyl substituents;

provided that, when the heterocyclic ring $Het^1$ contains one O or S ring atom and one $NR^{14}$ ring group then: (a) the O/S ring atom and the $NR^{14}$ ring group are not directly bonded to each other, and (b) the O/S ring atom and the $NR^{14}$ ring group are separated by more than one carbon atom unless $Het^1$ contains an $-NR^{14}-C(O)-O-$ or $-NR^{14}-C(O)-S-$ moiety as part of the ring; or $-(CH_2)_{n^{10}}-Ar$, $-CH(C_{1-2}$alkyl$)-Ar$, $-CMe_2-Ar$, or $C_{3-5}$cycloalkyl substituted at the connecting carbon atom by Ar, wherein $n^{10}$ is 0, 1 or 2 and (i) Ar is phenyl optionally substituted by one or two substituents independently being fluoro, chloro, bromo, $C_{1-2}$alkyl, $C_{1-2}$fluoroalkyl, $C_{1-2}$alkoxy, $C_{1-2}$fluoroalkoxy, OH, $-NR^{11a}R^{11b}$ (wherein $R^{11a}$ is H or $C_{1-2}$alkyl and R b is H, $C_{1-2}$alkyl, $-C(O)-C_{1-2}$alkyl or $-S(O)_2-C_{1-2}$alkyl), cyano, $-C(O)-NR^{11c}R^{11d}$ (wherein $R^{11c}$ and $R^{11d}$ independently are H or $C_{1-2}$alkyl), $-C(O)-OR^{11e}$ wherein $R^{11e}$ is H or $C_{1-2}$alkyl, or $-S(O)_2-R^{11f}$ (wherein $R^{11f}$ is $C_{1-2}$alkyl, $NH_2$, NHMe or $NMe_2$); or the phenyl Ar is optionally substituted at two adjacent Ar ring atoms by the two ends of a chain which is: $-(CH_2)_4-$, $-(CH_2)_3-$, or $-CH=CH-CH=CH-$; or (ii) Ar is an optionally substituted 5- or 6-membered heterocyclic aromatic ring containing 1, 2, 3 or 4 heteroatoms (e.g. 1, 2 or 3 heteroatoms) selected from O, N or S; and wherein when the heterocyclic aromatic ring Ar contains 2, 3 or 4 heteroatoms (e.g. 2 or 3 heteroatoms), one is selected from O, N and S and the remaining heteroatom(s) are N; and wherein the heterocyclic aromatic ring Ar is optionally substituted by one or two groups independently being $C_{1-4}$alkyl (e.g. $C_{1-2}$alkyl) or OH (including any keto tautomer of an OH-substituted aromatic ring), or the heterocyclic aromatic ring Ar is optionally substituted at two adjacent Ar ring atoms by the two ends of a chain which is: —$(CH_2)_4$—, —$(CH_2)_3$—, or —CH=CH—CH=CH—;

$R^{X1}$ and $R^{Y1}$ independently are a hydrogen atom (H), $C_{1-2}$alkyl or $C_1$fluoroalkyl;

$R^{X3}$ and $R^{X4}$ together are —$(CH_2)_{n^{15}}$—$X^7$—$(CH_2)_{n^{16}}$— wherein $n^{15}$ and $n^{16}$ independently are 1 or 2 and $X^7$ is a bond, —$CH_2$—, O, or $NR^{X5}$ wherein $R^{X5}$ is H, $C_{1-2}$alkyl, acetyl or —$S(O)_2Me$; and $R^Z$ is a hydrogen atom (H) or $C_{1-2}$alkyl, provided that:

when $R^3$ is the heterocyclic group of sub-formula (bb), $n^1$ is 1, and Y is $NR^4$, then $R^4$ is not $C_{1-2}$alkyl, $C_{1-2}$fluoroalkyl or $CH_2C(O)NH_2$.

Preferably, $R^{3a}$ is a hydrogen atom (H) or methyl.

It is particularly preferred that $R^{3a}$ is a hydrogen atom (H).

In one optional embodiment of the invention, $R^3$ is optionally substituted branched $C_{3-6}$alkyl, optionally substituted $C_{3-8}$cycloalkyl, optionally substituted phenyl, or an optionally substituted heterocyclic group of sub-formula (aa), (bb) or (cc):

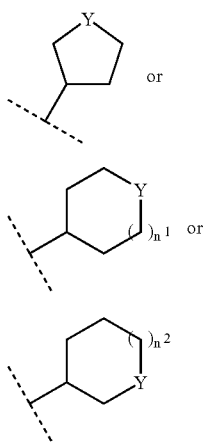

(aa)

(bb)

(cc)

in which $n^1$ and $n^2$ are 1 or 2; and Y is O, S, $SO_2$, or $NR^4$; where $R^4$ is a hydrogen atom, $C_{1-2}$alkyl, $C_{1-2}$fluoroalkyl, $C(O)NH_2$, $C(O)$—$C_{1-2}$alkyl, or $C(O)$—$C_1$fluoroalkyl; provided that Y is not $NR^4$ when the heterocyclic group is of sub-formula (aa).

Alternatively or additionally, in one optional embodiment of the invention, in $R^3$ the branched $C_{3-6}$alkyl is optionally substituted with one or two substituents being oxo (=O), OH, $C_{1-2}$alkoxy or $C_{1-2}$fluoroalkoxy; and wherein any such substituent is not substituted at the $R^3$ carbon atom attached to the —NH— group of formula (I).

Alternatively or additionally, in one optional embodiment of the invention, in $R^3$ the phenyl is optionally substituted with one substituent being fluoro, chloro, $C_{1-2}$alkyl, $C_{1-2}$fluoroalkyl, $C_{1-2}$alkoxy, $C_{1-2}$fluoroalkoxy or cyano.

Alternatively or additionally, in one optional embodiment of the invention, in $R^3$ the $C_{3-8}$cycloalkyl or the heterocyclic group of sub-formula (aa), (bb) or (cc) is optionally substituted with one or two substituents being oxo (=O), OH, $C_{1-2}$alkoxy, $C_{1-2}$fluoroalkoxy, or $C_{1-2}$alkyl; and wherein any OH, alkoxy or fluoroalkoxy substituent is not substituted at the $R^3$ ring carbon attached to the —NH— group of formula (I) and is not substituted at either $R^3$ ring carbon bonded to the Y group of the heterocyclic group (aa), (bb) or (cc).

Alternatively or additionally, in one optional embodiment of the invention, Het is of sub-formula (i), (ii), (iii) or (iv):

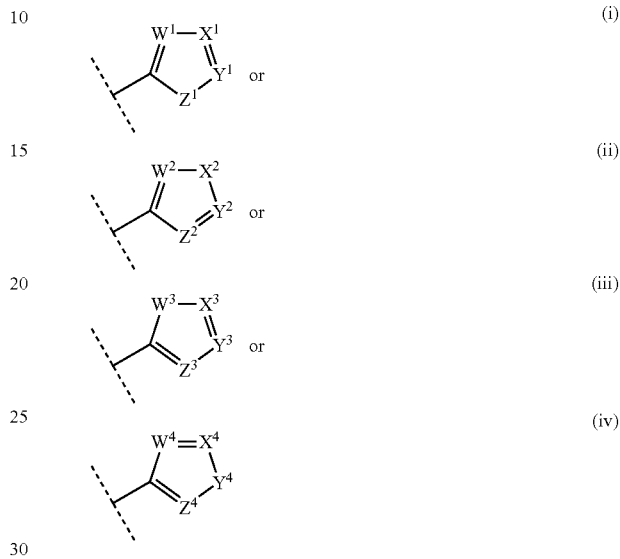

wherein:

$W^1$, $W^2$ and $W^4$ is N; and $W^3$ is $NR^W$;
$X^1$, $X^3$ and $X^4$ is N or $CR^X$; and $X^2$ is O, S or $NR^X$;
$Y^1$, $Y^2$ and $Y^3$ is $CR^Y$ or N; and $Y^4$ is O, S or $NR^Y$;
$Z^1$ is O, S or $NR^Z$; and $Z^2$, $Z^3$ and $Z^4$ is N or $CR^Z$;

and wherein:

$R^W$ is a hydrogen atom (H) or $C_{1-2}$alkyl; and
$R^Z$ is a hydrogen atom (H) or $C_{1-2}$alkyl.

Alternatively or additionally, in one optional embodiment of the invention, $R^X$ and $R^Y$ independently are:

a hydrogen atom (H);
$C_{1-8}$alkyl;
$C_{3-6}$cycloalkyl;
—$(CH_2)_{n^3}$—$SO_2$—$R^5$ wherein $n^3$ is 1 or 2 and $R^5$ is $C_{1-3}$alkyl or —NH—$C_{1-2}$alkyl;
—$(CH_2)_{n^4}$—$NR^6R^7$ wherein $n^4$ is 0, 1 or 2, and $R^6$ and $R^7$ independently are H, $C_{1-6}$alkyl e.g. $C_{1-4}$alkyl, —$C(O)$—$C_{1-2}$alkyl or —$SO_2$—$C_{1-2}$alkyl; or $R^6$ and $R^7$ together are —$(CH_2)_{n^5}$—$X^5$—$(CH_2)_{n^6}$— in which $n^5$ and $n^6$ independently are 2 or 3 and $X^5$ is a bond, —$CH_2$—, O, or $NR^8$ wherein $R^8$ is H or $C_{1-2}$alkyl;
—$(CH_2)_{n^7}$—O—$R^9$ wherein $n^7$ is 1 or 2 and $R^9$ is H or $C_{1-6}$alkyl;
—$C(O)$—$NR^{10}R^{11}$ wherein $R^{10}$ and $R^{11}$ independently are H or $C_{1-6}$alkyl; or $R^{10}$ and $R^{11}$ together are —$(CH_2)_{n^8}$—$X^6$—$(CH_2)_{n^9}$— in which $n^8$ and $n^9$ independently are 2 or 3 and $X^6$ is a bond, —$CH_2$—, O, or $NR^{12}$ wherein $R^{12}$ is H or $C_{1-2}$alkyl;
—$C(O)$—$OR^{13}$ wherein $R^{13}$ is H or $C_{1-6}$alkyl;
a 4-, 5-, 6- or 7-membered saturated heterocyclic ring containing one O ring atom or one $NR^{14}$ ring group wherein $R^{14}$ is H or $C_{1-4}$alkyl, said heterocyclic ring being optionally substituted (at a position or positions other than any $NR^{14}$ position) by one oxo (=O) and/or one $C_{1-4}$alkyl substituent; or —$(CH_2)_{n^{10}}$—Ar wherein $n^{10}$ is 0, 1 or 2 and
  (i) Ar is phenyl optionally substituted by one or two substituents being fluoro, chloro, $C_{1-2}$alkyl, $C_{1-2}$fluoroalkyl, $C_{1-2}$alkoxy, $C_{1-2}$fluoroalkoxy or cyano; or
  (ii) Ar is an optionally substituted 5- or 6-membered heterocyclic aromatic ring containing 1, 2 or 3 heteroatoms selected from O, N or S; and wherein when the heterocyclic aromatic ring Ar contains 2 or 3 heteroatoms, one is selected from O, N and S and the remaining heteroatom(s) are N; and wherein the heterocyclic aromatic ring Ar is optionally substituted by one or two $C_{1-4}$alkyl groups.

Alternatively or additionally, in one optional embodiment of the invention, Het is of sub-formula (i), (ii), (iii), (iv) or (v):

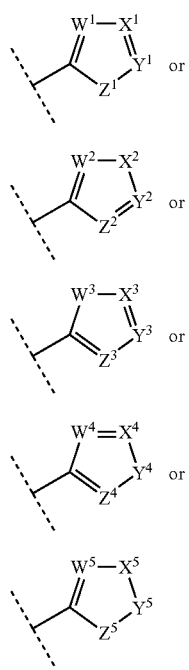

wherein:
$W^1$, $W^2$, $W^4$ and $W^5$ is N; and $W^3$ is $NR^W$;
$X^1$, $X^3$ and $X^4$ is N or $CR^X$; $X^2$ is O, S or $NR^X$; and $X^5$ is $CR^{X1}R^{X2}$;
$Y^1$, $Y^2$ and $Y^3$ is $CR^Y$ or N; $Y^4$ is O, S or $NR^Y$; and $Y^5$ is $CR^{Y1}R^{Y2}$;
$Z^1$ and $Z^5$ is O, S or $NR^Z$; and $Z^2$, $Z^3$ and $Z^4$ is N or $CR^Z$;

and wherein:
$R^W$ is a hydrogen atom (H) or $C_{1-2}$alkyl; and
$R^Z$ is a hydrogen atom (H) or $C_{1-2}$alkyl.

In one optional embodiment of the invention, $R^X$, $R^{X2}$, $R^Y$ and $R^{Y2}$ independently are, or $R^X$ and $R^Y$ independently are:
  a hydrogen atom (H);
  $C_{1-8}$alkyl;
  $C_{3-6}$cycloalkyl optionally substituted by a $C_{1-2}$alkyl group;
  —$(CH_2)_{n^{2a}}$—$C_{3-6}$cycloalkyl optionally substituted, in the —$(CH_2)_{n^{2a}}$-moiety or in the $C_{3-6}$cycloalkyl moiety, by a $C_{1-2}$alkyl group, wherein $n^{2a}$ is 1, 2 or 3;
  —$(CH_2)_{n^3}$—$SO_2$—$R^5$ wherein $n^3$ is 1 or 2 and $R^5$ is $C_{1-3}$alkyl or —NH—$C_{1-2}$alkyl or phenyl;
  —$(CH_2)_{n^4}$—$NR^6R^7$ wherein $n^4$ is 0, 1, 2 or 3, and $R^6$ and $R^7$ independently are H, $C_{1-6}$alkyl e.g. $C_{1-4}$alkyl, $C_{3-6}$cycloalkyl, —$CH_2$—$C_{3-6}$cycloalkyl, —C(O)—$C_{1-2}$alkyl, —$SO_2$—$C_{1-2}$alkyl, phenyl, or benzyl (wherein the phenyl or benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy); or $R^6$ and $R^7$ together are —$(CH_2)_{n^5}$—$X^5$—$(CH_2)_{n^6}$— in which $n^5$ and $n^6$ independently are 2 or 3 and $X^5$ is a bond, —$CH_2$—, O, or $NR^8$ wherein $R^8$ is H or $C_{1-2}$alkyl;
  —$(CH_2)_{n^7}$—O—$R^9$; wherein $n^7$ is 0, 1, 2 or 3 and $R^9$ is H or $C_{1-6}$alkyl; wherein $n^7$ is 0 only when the —$(CH_2)_{n^7}$—O—$R^9$ is bonded to a carbon atom in the Het ring; and wherein $n^7$ is not 0 when Het is of sub-formula (v) (i.e. $n^7$ is not 0 for $R^{X2}$ and for $R^{Y2}$);
  —C(O)—$NR^{10}R^{11}$ wherein $R^1$ and $R^{11}$ independently are H, $C_{1-6}$alkyl, $C_{3-6}$cycloalkyl, —$CH_2$—$C_{3-6}$cycloalkyl, phenyl, or benzyl (wherein the phenyl or benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy); or $R^{10}$ and $R^{11}$ together are —$(CH_2)_{n^8}$—$X^6$—$(CH_2)_{n^9}$— in which $n^8$ and $n^9$ independently are 2 or 3 and $X^6$ is a bond, —$CH_2$—, O, or $NR^{12}$ wherein $R^{12}$ is H or $C_{1-2}$alkyl;
  —C(O)—$OR^{13}$ wherein $R^{13}$ is H, $C_{1-6}$alkyl, $C_{3-6}$cycloalkyl, —$CH_2$—$C_{3-6}$cycloalkyl, phenyl, or benzyl (wherein the phenyl or benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy);
  —C(O)—$R^{13a}$ wherein $R^{13a}$ is a hydrogen atom (H), $C_{1-6}$alkyl, $C_{1-2}$fluoroalkyl, $C_{3-6}$cycloalkyl, —$CH_2$—$C_{3-6}$cycloalkyl, benzyl, or phenyl; wherein the phenyl or benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy;
  a 4-, 5-, 6- or 7-membered saturated heterocyclic ring containing one O ring atom or one $NR^{14}$ ring group wherein $R^{14}$ is H or $C_{1-4}$alkyl, said heterocyclic ring being optionally substituted (at a position or positions other than any $NR^{14}$ position) by one oxo (=O) and/or one $C_{1-4}$alkyl substituent; or
  —$(CH_2)_{n^{10}}$—Ar wherein $n^{10}$ is 0, 1 or 2 and
    (i) Ar is phenyl optionally substituted by one or two substituents being fluoro, chloro, $C_{1-2}$alkyl, $C_{1-2}$fluoroalkyl, $C_{1-2}$alkoxy, $C_{1-2}$fluoroalkoxy or cyano; or
    (ii) Ar is an optionally substituted 5- or 6-membered heterocyclic aromatic ring containing 1, 2 or 3 heteroatoms selected from O, N or S; and wherein when the heterocyclic aromatic ring Ar contains 2 or 3 heteroatoms, one is selected from O, N and S and the remaining heteroatom(s) are N; and wherein the heterocyclic aromatic ring Ar is optionally substituted by one or two $C_{1-4}$alkyl groups; and
$R^{X1}$ and $R^{Y1}$ independently are a hydrogen atom (, $C_{1-2}$alkyl or $C_1$fluoroalkyl.

In compounds, for example in the compounds of formula (I), an "alkyl" group or moiety may be straight-chain or branched. Alkyl groups, for example $C_{1-8}$alkyl or $C_{1-6}$alkyl or $C_{1-4}$alkyl or $C_{1-3}$alkyl or $C_{1-2}$alkyl, which may be employed include $C_{1-6}$alkyl or $C_{1-4}$alkyl or $C_{1-3}$alkyl or $C_{1-2}$alkyl such as methyl, ethyl n-propyl, n-butyl, n-pentyl, or n-hexyl, or any branched isomers thereof such as isopropyl, t-butyl, sec-butyl, isobutyl, 3-methylbutan-2-yl, 2-ethylbutan-1-yl, or the like.

A corresponding meaning is intended for "alkoxy", "alkylene", and like terms derived from alkyl. For example, "alkoxy" such as $C_{1-6}$alkoxy or $C_{1-4}$alkoxy or $C_{1-2}$alkoxy includes methoxy, ethoxy, propyloxy, and oxy derivatives of the alkyls listed above. "Alkylsulfonyl" such as $C_{1-4}$alkylsulfonyl includes methylsulfonyl (methanesulfonyl), ethylsulfonyl, and others derived from the alkyls listed above. "Alkylsulfonyloxy" such as $C_{1-4}$alkylsulfonyloxy includes methanesulfonyloxy (methylsulfonyloxy), ethanesulfonyloxy, et al.

"Cycloalkyl", for example $C_{3-8}$cycloalkyl, includes cyclopropyl, cyclobutyl, cyclopentyl, cyclohexyl, cycloheptyl, cyclooctyl, and the like. Preferably, a $C_{3-8}$ cycloalkyl group is $C_{3-6}$cycloalkyl or $C_{5-6}$cycloalkyl, that is the cycloalkyl group contains a 3-6 membered or 5-6 membered carbocyclic ring respectively.

"Fluoroalkyl" includes alkyl groups with one, two, three, four, five or more fluorine substituents, for example $C_{1-4}$fluoroalkyl or $C_{1-3}$fluoroalkyl or $C_{1-2}$fluoroalkyl such as monofluoromethyl, difluoromethyl, trifluoromethyl, pentafluoroethyl, 2,2,2-trifluoroethyl ($CF_3CH_2-$), 2,2-difluoroethyl ($CHF_2-CH_2-$), or 2-fluoroethyl ($CH_2F-CH_2-$), etc. "Fluoroalkoxy" includes $C_{1-4}$fluoroalkoxy or $C_{1-2}$fluoroalkoxy such as trifluoromethoxy, pentafluoroethoxy, monofluoromethoxy, difluoromethoxy, etc. "Fluoroalkylsulfonyl" such as $C_{1-4}$fluoroalkylsulfonyl includes trifluoromethanesulfonyl, pentafluoroethylsulfonyl, etc.

A halogen atom ("halo") present in compounds, for example in the compounds of formula (I), can be a fluorine, chlorine, bromine or iodine atom ("fluoro", "chloro", "bromo" or "iodo").

When the specification states that atom or moiety A is "bonded" or "attached" to atom or moiety B, it means that atom/moiety A is directly bonded to atom/moiety B usually by means of one or more covalent bonds, and excludes A being indirectly attached to B via one or more intermediate atoms/moieties (e.g. excludes A-C-B); unless it is clear from the context that another meaning is intended.

By "carbon-linked-pyridinyl" is meant pyridin-2-yl, pyridin-3-yl, or pyridin-4-yl.

Preferably, $R^1$ is $C_{1-3}$alkyl, $C_{1-3}$fluoroalkyl or $-(CH_2)_2OH$; more preferably $C_{1-3}$alkyl, $C_{1-2}$fluoroalkyl or $-(CH_2)_2OH$; still more preferably $C_{2-3}$alkyl, $C_2$fluoroalkyl or $-(CH_2)_2OH$; and yet more preferably $C_2$alkyl or $C_2$fluoroalkyl. When $R^1$ is $C_{1-4}$alkyl or $C_{1-3}$fluoroalkyl, it can be straight-chained or branched. $R^1$ can for example be methyl, trifluoromethyl, ethyl, n-propyl, isopropyl, n-butyl, isobutyl, $C_2$fluoroalkyl or $-(CH_2)_2OH$; and more preferably $R^1$ is ethyl, n-propyl, $C_2$fluoroalkyl (e.g. $C_1$fluoroalkyl-$CH_2-$ such as $CF_3-CH_2-$) or $-(CH_2)_2OH$. $R^1$ is most preferably ethyl.

Preferably, $R^2$ is a hydrogen atom (H) or methyl, more preferably a hydrogen atom (H).

Where $R^3$ optionally substituted phenyl, preferably the phenyl is optionally substituted with one substituent being fluoro, chloro, $C_{1-2}$alkyl, $C_{1-2}$fluoroalkyl, $C_{1-2}$alkoxy, $C_{1-2}$fluoroalkoxy or cyano. Where $R^3$ is optionally substituted phenyl, the optional substituent can be at the 2-, 3- or 4-position of the phenyl ring, e.g. at the 4-position. For example, $R^3$ can be phenyl or fluorophenyl; in particular 4-fluorophenyl.

$R^3$ is preferably optionally substituted branched $C_{3-6}$alkyl, optionally substituted $C_{3-8}$cycloalkyl, or an optionally substituted heterocyclic group of sub-formula (aa), (bb) or (cc). $R^3$ is more preferably optionally substituted $C_{3-8}$cycloalkyl, or an optionally substituted heterocyclic group of sub-formula (aa), (bb) or (cc).

Preferably, in $R^3$ there is one substituent or no substituent.

Where $R^3$ is optionally substituted branched $C_{3-6}$alkyl, then preferably $R^3$ is optionally substituted branched $C_{4-5}$alkyl and/or unsubstituted $C_{3-6}$alkyl such as isopropyl, isobutyl, sec-butyl, t-butyl, 3-methylbutan-2-yl, or 2-ethylbutan-1-yl. Where $R^3$ is optionally substituted branched $C_{3-6}$alkyl, it is most preferably isobutyl, sec-butyl, t-butyl or 3-methylbutan-2-yl (for example (R)-3-methylbutan-2-yl or (S)-3-methylbutan-2-yl).

In one optional embodiment, where $R^3$ is optionally substituted $C_{3-8}$cycloalkyl, it is not optionally substituted $C_5$cycloalkyl, i.e. not optionally substituted cyclopentyl. In this case, more preferably, $R^3$ is optionally substituted $C_{6-8}$cycloalkyl or optionally substituted $C_{6-7}$cycloalkyl.

Where $R^3$ is optionally substituted $C_{3-8}$cycloalkyl, it is more preferably optionally substituted $C_6$cycloalkyl (i.e. optionally substituted cyclohexyl); for example $C_6$cycloalkyl optionally substituted with one or two substituents independently being (e.g. being) oxo ($=O$), OH, $C_{1-2}$alkoxy, $C_{1-2}$fluoroalkoxy (e.g. trifluoromethoxy), or $C_{1-2}$alkyl, and wherein any OH, alkoxy or fluoroalkoxy substituent is not substituted at the $R^3$ ring carbon attached (bonded) to the $-NH-$ group of formula (I).

Where $R^3$ is optionally substituted $C_{3-8}$cycloalkyl, the one or two optional substituents preferably comprise (e.g. is or independently are (e.g. is or are)) oxo ($=O$); OH; $C_1$alkoxy, $C_1$fluoroalkoxy (e.g. trifluoromethoxy); $NHR^{21}$ wherein $R^{21}$ is a hydrogen atom (H) or $C_{1-2}$ straight-chain alkyl; $C_{1-2}$alkyl such as methyl; $C_1$fluoroalkyl such as $-CH_2F$ or $-CHF_2$; $-CH_2OH$; $-CH_2NHR^{22}$ wherein $R^{22}$ is H; $-C(O)OR^{23}$ wherein $R^{23}$ is H or methyl; $-C(O)NHR^{24}$ wherein $R^{24}$ is H or methyl; $-C(O)R^{25}$ wherein $R^{25}$ is methyl; fluoro; hydroxyimino ($-N-OH$); or ($C_{1-2}$alkoxy)imino ($=N-OR^{26}$ where $R^{26}$ is $C_{1-2}$alkyl); and wherein any OH, alkoxy, fluoroalkoxy or $NHR^{21}$ substituent is not substituted at the $R^3$ ring carbon attached (bonded) to the $-NH-$ group of formula (I) and is not substituted at either $R^3$ ring carbon bonded to the Y group of the heterocyclic group (aa), (bb) or (cc).

More preferably, where $R^3$ is optionally substituted $C_{3-8}$cycloalkyl, the one or two optional substituents comprise (e.g. is or independently are (e.g. is or are)) oxo ($=O$); OH; $NHR^{21}$ wherein $R^{21}$ is a hydrogen atom (H); $C_{1-2}$alkyl such as methyl; $C_1$fluoroalkyl such as $-CH_2F$ or $-CHF_2$; $-C(O)OR^{23}$ wherein $R^{23}$ is H or methyl; $-C(O)NHR^{24}$ wherein $R^{24}$ is H or methyl; fluoro; hydroxyimino ($=N-OH$); or ($C_{1-2}$alkoxy)imino ($=N-OR^{26}$ where $R^{26}$ is $C_{1-2}$alkyl).

Still more preferably, where $R^3$ is optionally substituted $C_{3-8}$cycloalkyl, the one or two optional substituents comprise (e.g. is or independently are (e.g. is or are)) oxo ($=O$); OH; $NHR^{21}$ wherein $R^{21}$ is a hydrogen atom (H); methyl; $-CH_2F$; $-CHF_2$; $-C(O)OR^{23}$ wherein $R^{23}$ is H; fluoro; hydroxyimino ($=N-OH$); or ($C_{1-2}$alkoxy)imino ($=N-OR^{26}$ where $R^{26}$ is $C_{1-2}$alkyl). Yet more preferably, where $R^3$ is optionally substituted $C_{3-8}$cycloalkyl, the one or two optional substituents comprise (e.g. is or independently are (e.g. is or are)) oxo ($=O$); OH; methyl; fluoro; hydroxyimino ($=N-OH$); or ($C_{1-2}$alkoxy)imino ($=N-OR^{26}$ where $R^{26}$ is $C_{1-2}$alkyl).

Most preferably, where $R^3$ is optionally substituted $C_{3-8}$cycloalkyl, the one or two optional substituents comprise (e.g. is or independently are (e.g. is or are)) OH, oxo ($=O$) or hydroxyimino ($=N-OH$). For example, where $R^3$ is optionally substituted $C_{3-8}$cycloalkyl, the one or two optional substituents preferably comprise (e.g. is or are) OH and/or oxo ($=O$).

Optionally, in $R^3$, the $C_{3-8}$cycloalkyl is unsubstituted.

Where $R^3$ is optionally substituted $C_{3-8}$cycloalkyl, e.g. optionally substituted $C_{5-8}$cycloalkyl such as optionally substituted $C_6$cycloalkyl (optionally substituted cyclohexyl), the one or two optional substituents if present preferably comprise a substituent (for example is or are substituent(s)) at the 3-, 4- or 5-position(s) of the $R^3$ cycloalkyl ring. (In this connection, the 1-position of the $R^3$ cycloalkyl ring is deemed to be the connection point to the —NH— in formula (I)).

Where $R^3$ is optionally substituted $C_{3-8}$cycloalkyl, any OH, alkoxy, fluoroalkoxy, —$CH_2OH$, —$CH_2CH_2OH$, —$CH_2NHR^{22}$, —$C(O)OR^{23}$, —$C(O)NHR^{24}$, —$C(O)R^{25}$ or fluoro substituent (particularly any OH substituent) is more preferably at the 3-, 4- or 5-position, e.g. the 3- or 5-position, of the $R^3$ cycloalkyl (e.g. $C_{6-8}$cycloalkyl) ring. For example, any OH, alkoxy, fluoroalkoxy, —$CH_2OH$, —$CH_2CH_2OH$, —$CH_2NHR^{22}$, —$C(O)OR^{23}$, —$C(O)NHR^{24}$, —$C(O)R^{25}$ or fluoro substituent (particularly any OH substituent) can be at the 3-position of a $R^3$ $C_5$cycloalkyl(cyclopentyl) ring or at the 3-, 4- or 5-position, e.g. 3- or 5-position, of a $R^3$ $C_6$cycloalkyl (cyclohexyl) ring. (In this connection, and also below, the 1-position of the $R^3$ cycloalkyl ring is deemed to be the connection point to the —NH— in formula (I)).

Where $R^3$ is optionally substituted $C_{3-8}$cycloalkyl, any $NHR^{21}$ substituent is preferably at the 2-, 3-, 4- or 5-position, preferably the 2- or 3-position or more preferably the 3-position, of the $R^3$ cycloalkyl (e.g. $C_{6-8}$cycloalkyl e.g. cyclohexyl) ring.

Where $R^3$ is optionally substituted $C_{3-8}$cycloalkyl, any alkyl or fluoroalkyl substituent is preferably at the 1-, 2-, 3-, 4 or 5-position, more preferably the 1-, 2-, 3- or 5-position, still more preferably the 1- or 3-position, of the $R^3$ cycloalkyl (e.g. $C_{6-8}$cycloalkyl e.g. cyclohexyl) ring.

Where $R^3$ is optionally substituted $C_{3-8}$cycloalkyl, any oxo (=O), hydroxyimino (=N—OH); or ($C_{1-4}$alkoxy)imino (=N—$OR^{26}$) substituent is preferably at the 3- or 4-position, preferably at the 4-position, of the $R^3$ cycloalkyl (e.g. $C_{6-8}$cycloalkyl e.g. cyclohexyl) ring.

Where $R^3$ is optionally substituted $C_{3-8}$cycloalkyl, $R^3$ is preferably cyclohexyl (i.e. unsubstituted) or cyclohexyl substituted by one oxo (=O), OH, $NHR^{21}$, $C_{1-2}$alkyl, $C_{1-2}$fluoroalkyl, —$CH_2OH$, —$C(O)OR^{23}$, —$C(O)NHR^{24}$, —$C(O)R^{25}$, fluoro, hydroxyimino (=N—OH) or ($C_{1-4}$alkoxy)imino (=N—$OR^{26}$) substituent, or cyclohexyl substituted by two fluoro substituents. More preferably, $R^3$ is cyclohexyl (i.e. unsubstituted), or cyclohexyl substituted by one oxo (=O), OH, $NHR^{21}$, $C_{1-2}$alkyl, $C_{1-2}$fluoroalkyl, —$C(O)OR^{23}$, fluoro, hydroxyimino (=N—OH) or ($C_{1-4}$alkoxy)imino (=N—$OR^{26}$) substituent, or cyclohexyl substituted by two fluoro substituents. Still more preferably $R^3$ is cyclohexyl (i.e. unsubstituted) or cyclohexyl substituted by one oxo (=O), hydroxyimino (=N—OH), $C_{1-2}$alkyl or OH substituent, for example $R^3$ can be cyclohexyl (i.e. unsubstituted) or cyclohexyl substituted by one oxo (=O) or OH substituent. The optional substituent can be at the 3- or 4-position, e.g. 3-position, of the $R^3$ cyclohexyl ring; more preferably any OH substituent is preferably at the 3-position of the $R^3$ cyclohexyl ring, and/or any oxo (=O), hydroxyimino (=N—OH) or ($C_{1-4}$alkoxy)imino (=N—$OR^{26}$) substituent is preferably at the 4-position of the $R^3$ cyclohexyl ring.

Where $R^3$ is optionally substituted $C_6$cycloalkyl, $R^3$ can for example be 4-hydroxy-cyclohexyl (i.e. 4-hydroxycyclohexan-1-yl) or 3-oxo-cyclohexyl, but $R^3$ is more preferably cyclohexyl (i.e. unsubstituted), 3-hydroxy-cyclohexyl (i.e. 3-hydroxycyclohexan-1-yl), 4-oxo-cyclohexyl (i.e. 4-oxocyclohexan-1-yl), 4-(hydroxyimino)cyclohexyl (i.e. 4-(hydroxyimino)cyclohexan-1-yl), 4-($C_{1-2}$alkoxyimino)cyclohexyl, 1-methylcyclohexyl or 3-methylcyclohexyl. In one embodiment, $R^3$ can optionally be cyclohexyl (i.e. unsubstituted) or 3-hydroxy-cyclohexyl or 4-oxo-cyclohexyl. Where $R^3$ is optionally substituted $C_6$cycloalkyl, $R^3$ is most preferably cyclohexyl (i.e. unsubstituted), 4-oxo-cyclohexyl (i.e. 4-oxocyclohexan-1-yl) or 4-(hydroxyimino)cyclohexyl (i.e. 4-(hydroxyimino)cyclohexan-1-yl).

Where $R^3$ is optionally substituted $C_5$cycloalkyl (optionally substituted cyclopentyl), $R^3$ can for example be cyclopentyl (i.e. unsubstituted) or 3-hydroxy-cyclopentyl.

Where $R^3$ is optionally substituted mono-unsaturated-$C_{5-7}$ cycloalkenyl, preferably it is optionally substituted mono-unsaturated-$C_{5-6}$cycloalkenyl, more preferably optionally substituted mono-unsaturated-$C_6$cycloalkenyl (i.e. optionally substituted mono-unsaturated-cyclohexenyl=optionally substituted cyclohexenyl). Still more preferably, the $R^3$ cyclohexenyl is optionally substituted cyclohex-3-en-1-yl.

Where $R^3$ is optionally substituted mono-unsaturated-$C_{5-7}$ cycloalkenyl, preferably the $R^3$ cycloalkenyl is optionally substituted with one or two substituents independently being fluoro or methyl; preferably if there are two substituents then they are not both methyl. Preferably, the $R^3$ cycloalkenyl is optionally substituted with one substituent being fluoro or $C_{1-2}$alkyl (e.g. methyl); more preferably the $R^3$ cycloalkenyl is substituted with one fluoro substituent or is unsubstituted. For $R^3$ cycloalkenyl, the optional substituent(s) can be at the 1-, 2-, 3-, 4- or 5-position(s) of the cycloalkenyl ring.

Where $R^3$ is the heterocyclic group of sub-formula (aa), (bb) or (cc), then Y is preferably O, S, $SO_2$, NH or N—C(O)-Me (for example O, S, $SO_2$ or N—C(O)-Me), more preferably O, NH or N—C(O)-Me, still more preferably O or N—C(O)-Me, most preferably O. (When Y is NH or N—C(O)-Me, then $R^4$ is H or —C(O)-Me).

Preferably, $R^4$ is a hydrogen atom (H), $C_{1-2}$alkyl, C(O)$NH_2$, C(O)-Me or C(O)—$CF_3$. Optionally, $R^4$ can be a hydrogen atom (H), $C_{1-2}$alkyl, C(O)-Me or C(O)—$CF_3$, more preferably H, C(O)-Me or C(O)—$CF_3$, still more preferably H or C(O)-Me.

Preferably, Y is not N—C(O)-Me when the heterocyclic group is of sub-formula (aa).

Where $R^3$ is the heterocyclic group of sub-formula (aa), (bb) or (cc), then it is preferable that $R^3$ is the heterocyclic group of sub-formula (aa) or (bb). More preferably, in $R^3$, the heterocyclic group is of sub-formula (bb).

In sub-formula (bb), nil is preferably 1. In sub-formula (cc), $n^2$ is preferably 1. That is, six-membered rings are preferred in the $R^3$ heterocyclic group.

Preferably, in $R^3$, the heterocyclic group of sub-formula (aa), (bb) or (cc) is unsubstituted. (In this connection, where Y is $NR^4$, $R^4$ is not classified as a substituent).

In the $R^3$ heterocyclic group of sub-formula (aa), (bb) or (cc), the one or two optional substituents preferably comprise (e.g. is or independently are (e.g. is or are)): OH; oxo (=O); $C_{1-2}$alkyl (e.g. methyl) or $C_{1-2}$fluoroalkyl (e.g. $C_1$fluoroalkyl such as —$CH_2F$ or —$CHF_2$). More preferably, in the $R^3$ heterocyclic group of sub-formula (aa), (bb) or (cc), the one or two optional substituents comprise (e.g. is or independently are ((e.g. is or are)) OH and/or oxo; most preferably the one or two optional substituents comprise (e.g. is or are) oxo (=O). In the $R^3$ heterocyclic group of sub-formula (aa), (bb) or (cc), any oxo (=O) substituents are preferably on a carbon atom bonded (adjacent) to X, and/or can be at the 2-, 3-, 4- or 5-position(s) of the $R^3$ heterocyclic ring. (In this connection, the 1-position of the $R^3$ heterocyclic ring is deemed to be the connection point to the —NH— in formula (I)). Preferably, only $C_{1-2}$alkyl, $C_{1-2}$fluoroalkyl, fluoro or oxo (=O) substitution or no substitution is allowed at each of the 2- and 6-positions of the $R^3$ heterocyclic ring.

When $R^3$ is the heterocyclic group of sub-formula (aa) and Y is $NR^4$, then preferably $R^4$ is not C(O)-Me. More preferably, when $R^3$ is the heterocyclic group of sub-formula (aa) and Y is $NR^4$, then $R^4$ is preferably not C(O)R, i.e. or e.g. $R^4$ is preferably not $C(O)NH_2$, C(O)—$C_{1-2}$alkyl or C(O)—

$C_1$fluoroalkyl. In one embodiment, Y is O, S, $SO_2$ or NH when $R^3$ is the heterocyclic group of sub-formula (aa).

When $R^3$ is the heterocyclic group of sub-formula (aa), preferably Y is not $NR^4$.

Optionally, according to one embodiment of the invention, $NHR^3$ or $NR^3R^{3a}$ is not

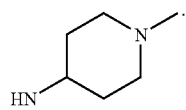

More preferably, when $R^3$ is the heterocyclic group of sub-formula (bb) and Y is $NR^4$, and optionally when $n^1$ is 1, then preferably $R^4$ is not methyl. More preferably, when $R^3$ is the heterocyclic group of sub-formula (bb) and Y is $NR^4$, and optionally when $n^1$ is 1, then $R^4$ is preferably not alkyl or substituted alkyl, i.e. or e.g. $R^4$ is preferably not $C_{1-2}$alkyl, $C_{1-2}$fluoroalkyl or $CH_2C(O)NH_2$. In one embodiment, when $R^3$ is the heterocyclic group of sub-formula (bb), Y is preferably O, S, $SO_2$ or $NR^4$, wherein $R^4$ is H, $C(O)NH_2$, $C(O)$—$C_{1-2}$alkyl or $C(O)$—$C_1$fluoroalkyl or more preferably Y is H or C(O)-Me. More preferably, for sub-formula (bb), Y is O or $NR^4$.

Preferably, $NHR^3$ or $NR^3R^{3a}$ is of sub-formula (a), (a1), (b), (c), (c1), (c2), (c3), (c4), (c5), (d), (e), (f), (g), (g1), (g2), (g3), (g4), (h), (h), (i), (j), (k), (k1), (L), (m), (m1), (m2), (m3), (m5), (n), (o), (o1), (o2), (o3), (o4), (o5), (p), (p2), p3), (p5), (p6), (p7), (p8), (q), (r), (s), (t), (t1) or (t2):

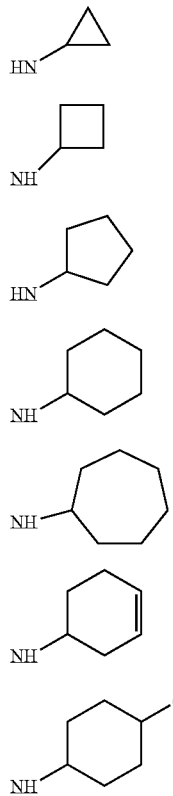

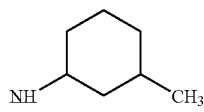

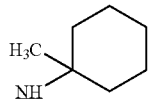

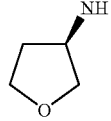

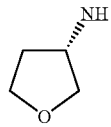

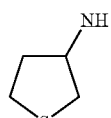

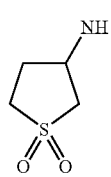

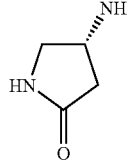

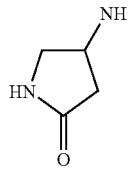

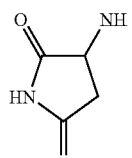

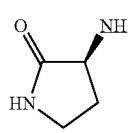

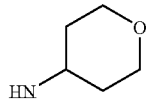

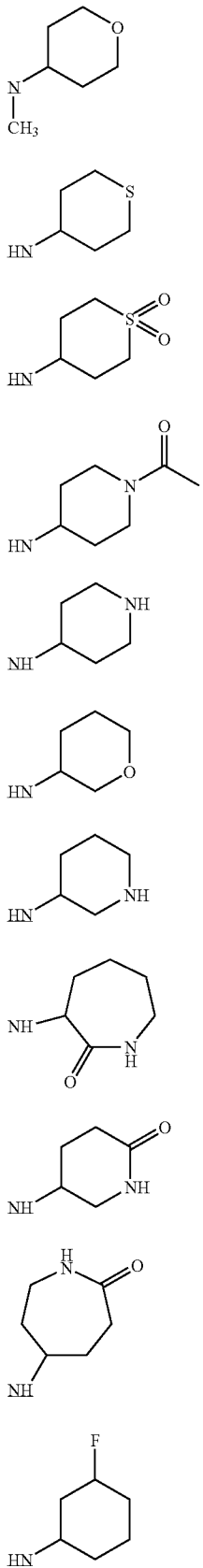
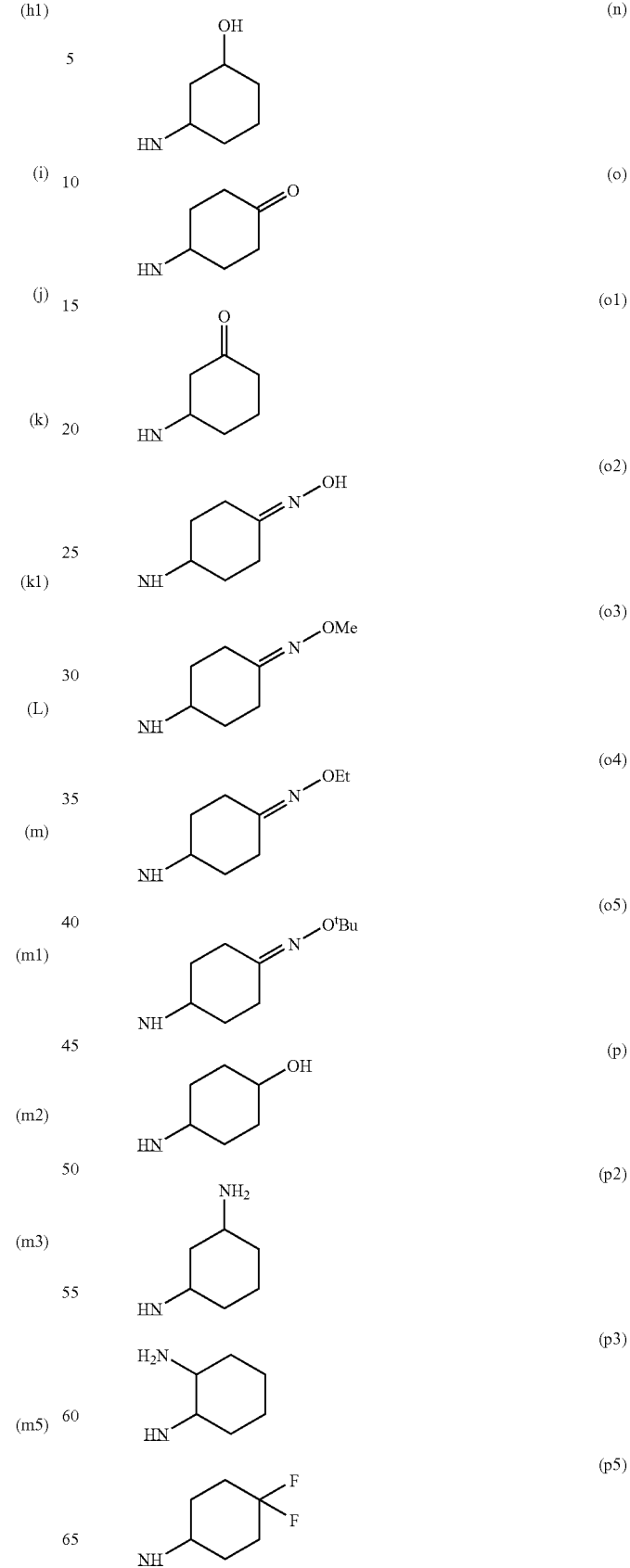

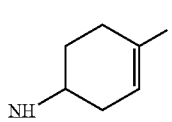
(p6)

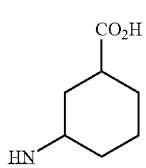
(p7)

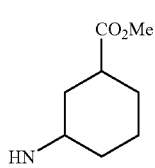
(p8)

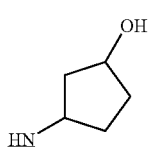
(q)

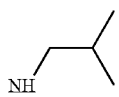
(r)

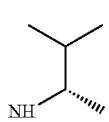
(s)

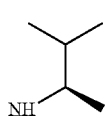
(t)

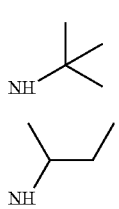
(t1)

(t2)

In the sub-formulae (a) to (t2) etc above, the —NH— connection point of the NHR³ or NR³R³ᵃ group to the 4-position of the pyrazolopyridine of formula (I) is underlined. Generally, in this specification, for a group or radical, where NH or N are underlined, then this indicates the connection point.

Preferably, NHR³ or NR³R³ᵃ is of sub-formula (c), (c1), (c2), (c3), (c4), (c5), (d), (e), (f), (g1), (g4), (h), (h1), (i), (j), (k), (k), (L), (m), (m1), (m2), (m3), (m5), (n), (o), (o1), (o2), (o3), (o4), (o5), (p), (p2), (p3), (p5), p6), (p7), (q), (r), (s), (t), (t1) or (t2). More preferably, NHR³ or NR³R³ᵃ is of sub-formula (c), (c1), (c4), (c5), (h), (i), (j), k), (m1), (m2), (n), (o), (o2), (o3), (p2), (p5), p6), (r), (s) or (t1). Still more preferably, NHR³ or NR³R³ᵃ is of sub-formula (c), (h), (k), (n), (o), (o2) or (s); for example (c), (h), (o), (o2) or (s). Most preferably, R³ is tetrahydro-2H-pyran-4-yl; that is NHR³ or NR³R³ᵃ is most preferably of sub-formula (h), as shown above.

In one embodiment of the invention, NHR³ or NR³R³ᵃ is of sub-formula (a), (b), (c), (d), (e), (f), (g), (h), (i), (j), (k), (L), (m), (n), (o), (p), (q), (r), (s) or (t). In this embodiment, NHR³ or NR³R³ᵃ is preferably of sub-formula (c), (h), k), (n), (o), (r), (s) or (t), still more preferably (c), (h), k), (n), (o) or (s).

In another embodiment of the invention, NHR³ or NR³R³ᵃ is of sub-formula (a), (b), (c), (d), (e), (f), (g), (g1), (g2), (g3), (h), (i), (j), (k), (L), (m), (m1), (n), (o), (o1), (p), (q), (r), (s), (t), (t1) or (t2). In this embodiment, preferably, NHR³ or NR³R³ᵃ is of sub-formula (c), (d), (e), (f), (h), (g1), (i), (l), (k) (m), (m1), (n), (o), (o1), (p), (q), (r), (s), (t), (t1) or (t2). More preferably NHR³ or NR³R³ᵃ is of sub-formula (c), (h), (k), (n), (o), (r), (s), (t) or (t1), still more preferably (c), (h), (k), (n), (o), (s) or (t1). Most preferably, R³ is tetrahydro-2H-pyran-4-yl; that is NHR³ or NR³R³ᵃ is most preferably of sub-formula (h), shown above.

When NHR³ or NR³R³ᵃ is of sub-formula (n), then preferably it is a cis-(3-hydroxycyclohex-1-yl)amino group, eg in any enantiomeric form or mixture of forms but it can be racemic.

Preferably, Het is of sub-formula (i), (ii), (iii) or (v); more preferably Het is of sub-formula (i), (ii), or (v); still more preferably Het is of sub-formula (i).

X¹, X³ and/or X⁴ independently is/are often N (a nitrogen atom).

Y¹, Y² and/or Y³ independently is/are often CRᵞ.

Suitably, Z¹ and/or Z⁵ independently is/are O or S. Preferably, Z¹ and/or Z⁵ is O.

Preferably, Het is of sub-formula (ia), (ib), (ic), (id), (ie), (if) or (ig); more preferably of sub-formula (ia), (ib), (ic), (id), (if) or (ig) or of sub-formula (ia), (ib), (ic), (id), or (ie); still more preferably of sub-formula (ia), (ib), (ic), or (id); yet more preferably preferably of sub-formula (ia), (ic), or (id):

(ia)

(ib)

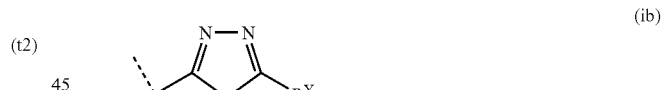
(ic)

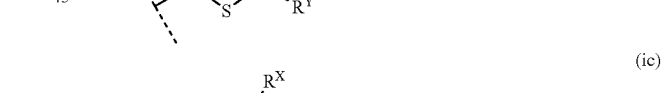
(id)

(ie)

-continued

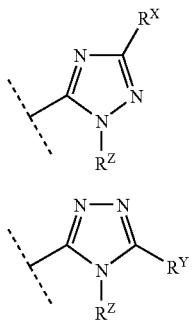

(if)

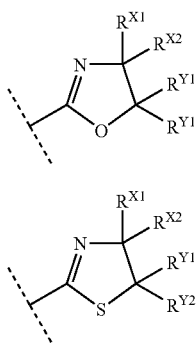

(ig)

Alternatively, when Het is of sub-formula (v), Het can for example be of sub-formula (va) or (vb), more preferably of sub-formula (va):

(va)

(vb)

Alternatively, when Het is of sub-formula (ii), Het can for example be of sub-formula (iia):

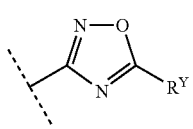

(iia)

Preferably, Het is of sub-formula (ia), (ib), (ic), (id), (if), (ig), (va) or (iia). More preferably, Het is of sub-formula (ia), (ic), (id) or (va).

For the Het group in general, $R^W$ and/or $R^Z$ independently is/are suitably a hydrogen atom (H).

For the Het group in general, preferably, one of $R^X$ and $R^Y$ (or $R^{X2}$ and $R^{Y2}$) is as defined herein and the other of $R^X$ and $R^Y$ (or $R^{X2}$ and $R^{Y2}$) is a hydrogen atom (H) or $C_{1-2}$alkyl. More preferably, one of $R^X$ and $R^Y$ (or $R^{X2}$ and $R^{Y2}$) is as defined herein and the other of $R^X$ and $R^Y$ (or $R^{X2}$ and $R^{Y2}$) is a hydrogen atom (H).

Overall, for the Het group in general, it is preferred that one of $R^X$ and $R^Y$, and for Het of sub-formula (v) one of $R^{X2}$ and $R^{Y2}$, is:

$C_{1-8}$alkyl;
optionally substituted $C_{3-6}$cycloalkyl;
—$(CH_2)_n^3$—$S(O)_2$—$R^5$, —$CH(C_{1-2}alkyl)$-$S(O)_2$—$R^5$, —$CMe_2$—$S(O)_2$—$R^5$, or $C_{3-5}$cycloalkyl substituted at the connecting carbon atom by —$S(O)_2$—$R^5$; preferably —$(CH_2)_n^3$—$S(O)_2$—$R^5$;
—$(CH_2)_n^4$—$NR^6R^7$, —$CH(C_{1-2}alkyl)$-$NR^6R^7$, —$CMe_2$-$NR^6R^7$, or $C_{3-5}$cycloalkyl substituted at the connecting carbon atom by —$NR^6R^7$; preferably —$(CH_2)_n^4$—$NR^6R^7$ or —$CH(Me)$-$NR^6R^7$;
—$(CH_2)_n^{11}$—$C(O)$—$NR^{10}R^{11}$, —$CH(C_{1-2}alkyl)$-$C(O)$—$NR^{10}R^{11}$, —$CMe_2$-$C(O)$—$NR^{10}R^{11}$, or $C_{3-5}$cycloalkyl substituted at the connecting carbon atom by —$C(O)$—$NR^{10}R^{11}$; preferably —$(CH_2)_n^{11}$—$C(O)$—$NR^{10}R^{11}$;
—$(CH_2)_n^{14}$-$Het^1$, —$CH(C_{1-2}alkyl)$-$Het^1$, —$CMe_2$-$Het^1$, or $C_{3-5}$cycloalkyl substituted at the connecting carbon atom by $Het^1$; preferably —$(CH_2)_n^{14}$-$Het^1$;
—$(CH_2)_n^{10}$—$Ar$, —$CH(C_{1-2}alkyl)$-$Ar$, —$CMe_2$—$Ar$, or $C_{3-5}$cycloalkyl substituted at the connecting carbon atom by $Ar$; preferably —$(CH_2)_n^{10}$—$Ar$;

(i) wherein Ar is optionally substituted phenyl, or more preferably (ii) wherein Ar is an optionally substituted 5- or 6-membered heterocyclic aromatic ring.

Overall, for the Het group in general, it is more preferred that one of $R^X$ and $R^Y$, and for Het of sub-formula (v) one of $R^{X2}$ and $R^{Y2}$, is:

—$(CH_2)_n^4$—$NR^6R^7$, —$CH(C_{1-2}alkyl)$-$NR^6R^7$, —$CMe_2$-$NR^6R^7$, or $C_{3-5}$cycloalkyl substituted at the connecting carbon atom by —$NR^6R^7$; preferably —$(CH_2)_n^4$—$NR^6R^7$ or —$CH(Me)$-$NR^6R^7$;
—$(CH_2)_n^{11}$—$C(O)$—$NR^{10}R^{11}$, —$CH(C_{1-2}alkyl)$-$C(O)$—$NR^{10}R^{11}$, —$CMe_2$-$C(O)$—$NR^{10}R^{11}$, or $C_{3-5}$cycloalkyl substituted at the connecting carbon atom by —$C(O)$—$NR^{10}R^{11}$; preferably —$(CH_2)_n^{11}$—$C(O)$—$NR^{10}R^{11}$;
—$(CH_2)_n^{14}$-$Het^1$, —$CH(C_{1-2}alkyl)$-$Het^1$, —$CMe_2$-$Het^1$, or $C_{3-5}$cycloalkyl substituted at the connecting carbon atom by $Het^1$; preferably —$(CH_2)_n^{14}$-$Het^1$; or
—$(CH_2)_n^{10}$—$Ar$ —$CH(C_{1-2}alkyl)$-$Ar$, —$CMe_2$—$Ar$, or $C_{3-5}$cycloalkyl substituted at the connecting carbon atom by $Ar$; preferably —$(CH_2)_n^{10}$—$Ar$;

(i) wherein Ar is optionally substituted phenyl, or or more preferably (ii) wherein Ar is an optionally substituted 5- or 6-membered heterocyclic aromatic ring.

Optionally, one of $R^X$ and $R^Y$ can be: $C_{1-8}$alkyl; $C_{3-6}$cycloalkyl; —$(CH_2)_n^3$—$SO_2$—$R^5$; —$(CH_2)_n^4$—$NR^6R^7$; —$(CH_2)_n^7$—$O$—$R^9$; —$C(O)$—$NR^{10}R^{11}$; —$C(O)$—$OR^{13}$; or the 4-, 5-, 6- or 7-membered optionally substituted saturated heterocyclic ring $Het^1$. More preferably, one of $R^X$ and $R^Y$ is: $C_{1-8}$alkyl; —$(CH_2)_n^3$—$SO_2$—$R^5$; or the 4-, 5-, 6- or 7-membered optionally substituted saturated heterocyclic ring $Het^1$. In these cases, as mentioned above, it is preferred that the other of $R^X$ and $R^Y$ is a hydrogen atom (H) or $C_{1-2}$alkyl.

When $R^X$, $R^{X2}$, $R^Y$ and/or $R^{Y2}$ is $C_{1-8}$alkyl, then preferably it/they independently is/are $C_{1-6}$alkyl, e.g. $C_{3-6}$alkyl and/or $C_{1-4}$alkyl such as methyl, isopropyl, isobutyl or t-butyl.

When $R^X$, $R^{X2}$, $R^Y$ and/or $R^{Y2}$ is optionally substituted $C_{3-6}$cycloalkyl, then optionally it/they independently can be $C_{3-6}$cycloalkyl optionally substituted by a $C_{1-2}$alkyl group.

When $R^X$, $R^{X2}$, $R^Y$ and/or $R^{Y2}$ is optionally substituted $C_{3-6}$cycloalkyl, then preferably it/they independently is/are $C_{3-6}$cycloalkyl (i.e. unsubstituted), for example cyclopropyl or cyclobutyl.

When $R^X$, $R^{X2}$, $R^Y$ and/or $R^{Y2}$ is optionally substituted —$(CH_2)_n^{2a}$—$C_{3-6}$cycloalkyl, then preferably it/they independently is/are —$(CH_2)_n^{2a}$—$C_{3-6}$cycloalkyl optionally substituted, in the —$(CH_2)_n^{2a}$— moiety or in the $C_{3-6}$cycloalkyl moiety, by a $C_{1-2}$alkyl group, wherein $n^{2a}$ is 1, 2 or 3.

When $R^X$, $R^{X2}$, $R^Y$ and/or $R^{Y2}$ is optionally substituted —$(CH_2)_n^{2a}$—$C_{3-6}$cycloalkyl; then $n^{2a}$ is preferably 1 or 2 or more preferably 1; and/or preferably $R^X$, $R^X$, $R^Y$ and/or $R^{Y2}$ independently is/are optionally substituted —$(CH_2)_n^{2a}$—$C_{5-6}$cycloalkyl or optionally substituted —$(CH_2)_n^{2a}$—

$C_6$cycloalkyl. When $R^X$, $R^{X2}$, $R^Y$ and/or $R^{Y2}$ is optionally substituted —$(CH_2)_n{}^{2a}$—$C_{3-6}$cycloalkyl, then preferably it/they independently is/are —$(CH_2)_n{}^{2a}$—$C_{3-6}$cycloalkyl (i.e. not substituted). More preferably $R^X$, $R^{X2}$, $R^Y$ and/or $R^{Y2}$ independently is/are (cyclohexyl)methyl-, that is —$CH_2$-cyclohexyl. When $R^X$, $R^{X2}$, $R^Y$ and/or $R^{Y2}$ is —$(CH_2)_n{}^3$—$S(O)_2$—$R^5$, —$CH(C_{1-2}alkyl)$-$S(O)_2$—$R^5$ (e.g. —$CH(Me)$-$S(O)_2$—$R^5$), —$CMe_2$-$S(O)_2$—$R^5$, or $C_{3-5}$cycloalkyl substituted at the connecting carbon atom by —$S(O)_2$—$R^5$, then preferably it/they independently is/are —$(CH_2)_n{}^3$—$S(O)_2$—$R^5$.

When $R^X$, $R^{X2}$, $R^Y$ and/or $R^{Y2}$ is $C_{3-5}$cycloalkyl substituted at the connecting carbon atom by —$S(O)_2$—$R^5$, then preferably it/they independently is/are $C_3$cycloalkyl (cyclopropyl) substituted at the connecting carbon atom by —$S(O)_2$—$R^5$, for example

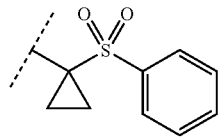

(see for example Example 178).

When $R^X$, $R^{X2}$, $R^Y$ and/or $R^{Y2}$ is —$(CH_2)_n{}^3$—$S(O)_2$—$R^5$, then preferably $n^3$ is 1.

Preferably, $R^5$ is $C_{1-4}$alkyl (e.g. $C_{1-3}$alkyl), —$NR^{15}R^{16}$, or optionally substituted phenyl. $R^5$ is more preferably $C_{1-3}$alkyl or —NH—$C_{1-2}$alkyl or phenyl; still more preferably $R^5$ is $C_{1-3}$alkyl or $C_{1-2}$alkyl such as methyl. Most preferably, —$(CH_2)_n{}^3$—$S(O)_2$—$R^5$ is —$CH_2SO_2Me$.

Preferably, $R^{15}$ is H, $C_{1-4}$alkyl (e.g. $C_{1-2}$alkyl), optionally substituted phenyl or optionally substituted benzyl; and/or preferably $R^{16}$ is H or methyl, e.g. H.

When $R^{15}$ and $R^{16}$ together are —$(CH_2)_n{}^{3a}$—$X^{3a}$—$(CH_2)_n{}^{3b}$—, then: preferably $n^{3a}$ and/or $n^{3b}$ independently are 2; and/or preferably $X^{3a}$ is a bond, —$CH_2$—, O, or $NR^{8a}$ wherein $R^{8a}$ is $C_{1-2}$alkyl or acetyl; and/or preferably the ring formed by $NR^{15}R^6$ is not substituted on a ring carbon or is substituted on a ring carbon by one methyl or oxo (=O) substituent.

When $R^X$, $R^{X2}$, $R^Y$ and/or $R^{Y2}$ is —$(CH_2)_n{}^4$—$NR^6R^7$, —$CH(C_{1-2}alkyl)$-$NR^6R^7$ (e.g. —$CH(Me)$-$NR^6R^7$), —$CMe_2$-$NR^6R^7$, or $C_{3-5}$cycloalkyl (e.g. $C_3$cycloalkyl) substituted at the connecting carbon atom by —$NR^6R^7$, then preferably it/they independently is/are —$(CH_2)_n{}^4$—$NR^6R^7$, —$CH(C_{1-2}alkyl)$-$NR^6R^7$ (e.g. —$CH(Me)$-$NR^6R^7$), or —$CMe_2$-$NR^6R^7$; more preferably it/they independently is/are —$CH(Me)$-$NR^6R^7$ or still more preferably —$(CH_2)_n{}^4$—$NR^6R^7$.

When $R^X$, $R^{X2}$, $R^Y$ and/or $R^{Y2}$ is —$(CH_2)_n{}^4$—$NR^6R^7$, then preferably $n^4$ is 0 only when the —$(CH_2)_n{}^4$—$NR^6R^7$ is bonded to a carbon atom in the Het ring.

When $R^X$, $R^{X2}$, $R^Y$ and/or $R^{Y2}$ is —$(CH_2)_n{}^4$—$NR^6R^7$, then preferably $n^4$ is 0, 1 or 2; more preferably $n^4$ is 0 or 1, still more preferably $n^4$ is 1.

In one optional embodiment of the invention, $R^6$ and $R^7$ independently are H, $C_{1-6}$alkyl e.g. $C_{1-4}$alkyl, $C_{3-6}$cycloalkyl, —$CH_2$—$C_{3-6}$cycloalkyl, —C(O)—$C_{1-2}$alkyl, —$SO_2$—$C_{1-2}$alkyl, phenyl, or benzyl (wherein the phenyl and benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy); or $R^6$ and $R^7$ together are —$(CH_2)_n{}^5$—$X^5$—$(CH_2)_n{}^6$— in which $n^5$ and $n^6$ independently are 2 or 3 and $X^5$ is a bond, —$CH_2$—, O, or $NR^8$ wherein $R^8$ is H or $C_{1-2}$alkyl, and wherein the ring formed by $NR^6R^7$ is not substituted on a ring carbon.

In one optional embodiment of the invention, $R^6$ and $R^7$ independently are H, $C_{1-6}$alkyl e.g. $C_{1-4}$alkyl, —C(O)—$C_{1-2}$alkyl or —$SO_2$—$C_{1-2}$alkyl; or $R^6$ and $R^7$ together are —$(CH_2)_n{}^5$—$X^5$—$(CH_2)_n{}^6$— in which $n^5$ and $n^6$ independently are 2 or 3 and $X^5$ is a bond, —$CH_2$—, O, or $NR^8$ wherein $R^8$ is H or $C_{1-2}$alkyl, and wherein the ring formed by $NR^6R^7$ is not substituted on a ring carbon.

$R^6$ is preferably H or $C_{1-6}$alkyl. $R^7$ is preferably $C_{1-6}$alkyl, —$C(O)R^{17}$ or —$S(O)_2R^{18}$, for example $C_{1-6}$alkyl. Where $R^6$ and/or $R^7$ is $C_{1-6}$alkyl, then it/they independently is/are preferably $C_{1-4}$alkyl e.g. methyl.

Preferably, $R^{17}$ and $R^{18}$ independently are $C_{1-6}$alkyl (e.g. $C_{1-4}$alkyl or $C_{1-2}$alkyl or isopropyl or n-propyl), $C_{3-6}$cycloalkyl, optionally substituted 5-membered heteroaryl being furyl(furanyl, e.g. 2-furyl) or thienyl (e.g. 2- or 3-thienyl) (the furyl or thienyl being independently optionally substituted by one oxo and/or one or two methyl), or phenyl or benzyl (wherein the phenyl and benzyl are independently optionally substituted on the aromatic ring by one or two substituents independently being fluoro, chloro, $C_2$alkyl, $C_1$ fluoroalkyl, $C_{1-2}$alkoxy or $C_1$ fluoroalkoxy).

In an alternative preferable embodiment, $R^6$ and $R^7$ together are —$(CH_2)_n{}^5$—$X^5$—$(CH_2)_n{}^6$—, in which case it is preferable that $n^5$ is 2 and/or $n^6$ is 2. Preferably, when $R^6$ and $R^7$ together are —$(CH_2)_n{}^5$—$X^5$—$(CH_2)_n{}^6$—, and when the ring formed by $NR^6R^7$ is substituted on a ring carbon by one or two substituents being oxo (=O), then the one or two oxo substituents are substituted on a ring carbon atom adjacent to (bonded to) the connecting nitrogen N of $NR^6R^7$. When $R^6$ and $R^7$ together are —$(CH_2)_n{}^5$—$X^5$—$(CH_2)_n{}^6$—, then preferably the ring formed by $NR^6R^7$ is optionally substituted on a ring carbon by one or two substituents independently being methyl or oxo (=O) only when $X^5$ is a bond or —$CH_2$—.

When $R^6$ and $R^7$ together are —$(CH_2)_n{}^5$—$X^5$—$(CH_2)_n{}^6$—, it is preferable that the ring formed by $NR^6R^7$ is not substituted on a ring carbon or is substituted on a ring carbon by one methyl or oxo (=O) substituent.

Preferably, $R^8$ is $C_{1-2}$alkyl or phenyl.

For example, —$(CH_2)_n{}^4$—$NR^6R^7$, —$CH(C_{1-2}alkyl)$-$NR^6R^7$ or —$CMe_2$-$NR^6R^7$ can be: —$CH_2$—$NHC(O)R^{17}$, —$CH_2$—$NMeC(O)R^{17}$, —$CH(Me)$-$NHC(O)R^{17}$, —$CH_2$—$NHS(O)_2R^{18}$, —$CH_2$—$NMeS(O)_2R^{18}$, —$CH(Me)$-$NHS(O)_2R^{18}$, $NMe_2$ ($n^4$=0; $R^6$=$R^7$=Me), or —$CH_2NMe_2$ ($n^4$=1; $R^6$=$R^7$=Me), or

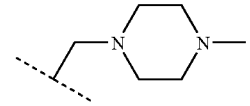

($n^4$=1; $R^6$ and $R^7$ together are —$(CH_2)_2$—$N(Me)$-$(CH_2)_2$—), or

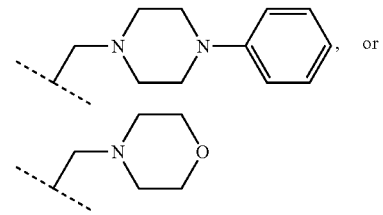

($n^4$=1; $R^6$ and $R^7$ together are —$(CH_2)_2$—O—$(CH_2)_2$—), or

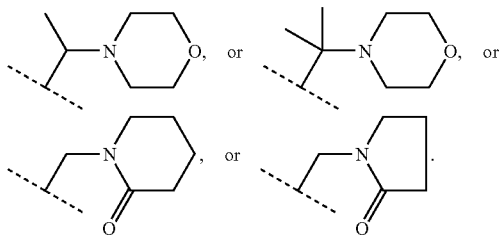

When $R^X$, $R^{X2}$, $R^Y$ and/or $R^{Y2}$ is —$(CH_2)_n{}^7$—O—$R^9$, then in one embodiment $n^7$ is 1, 2 or 3 and/or $R^9$ is H, $C_{1-6}$alkyl or phenyl, or more preferably $R^9$ is H or $C_{1-6}$alkyl. $n^7$ is preferably 1 or 2, more preferably 1. $R^9$ is preferably $C_{1-4}$alkyl such as methyl or t-butyl. For example, —$(CH_2)_n{}^7$—O—$R^9$ can be —$CH_2$—O—$^tBu$ or —$CH_2$—O-Me.

When $R^X$, $R^{X2}$, $R^Y$ and/or $R^{Y2}$ is —$(CH_2)_n{}^{11}$—C(O)—$NR^{10}R^{11}$, —CH($C_{1-2}$alkyl)-C(O)—$NR^{10}R^{11}$ (e.g. —CH(Me)-C(O)—$NR^{10}R^{11}$), —$CMe_2$-C(O)—$NR^{10}R^{11}$, or $C_{3-5}$cycloalkyl (e.g. $C_3$cycloalkyl) substituted at the connecting carbon atom by —C(O)—$NR^{10}R^{11}$, then: preferably it/they independently is/are —$(CH_2)_n{}^{11}$—C(O)—$NR^{10}R^{11}$, —CH($C_{1-2}$alkyl)-C(O)—$NR^{10}R^{11}$ (e.g. —CH(Me)-C(O)—$NR^{10}R^{11}$), or —$CMe_2$-C(O)—$NR^{10}R^{11}$; more preferably —$(CH_2)_n{}^{11}$—C(O)—$NR^{10}R^{11}$; still more preferably —$CH_2$—C(O)—$NR^{10}R^{11}$ or —C(O)—$NR^{10}R^{11}$.

When $R^X$, $R^{X2}$, $R^Y$ and/or $R^{Y2}$ is —$(CH_2)_n{}^{11}$—C(O)—$NR^{10}R^{11}$, then $n^{11}$ is preferably 0 or 1, more preferably 1.

Preferably $R^{10}$ is H or $C_{1-6}$alkyl (e.g. $C_{1-4}$alkyl or $C_{1-2}$alkyl or methyl), or $R^{10}$ and $R^{11}$ together are —$(CH_2)_n{}^8$—$X^6$—$(CH_2)_n{}^9$—.

Preferably, $R^{10}$ and $R^{11}$ independently are, and more preferably $R^{11}$ is: H; $C_{1-6}$alkyl; $C_{1-2}$fluoroalkyl; $C_{2-3}$alkyl substituted by one OH or —$OC_{1-2}$alkyl other than at the connection point; $C_{3-6}$cycloalkyl optionally substituted by one or two methyl groups; —$CH_2$—$C_{3-6}$cycloalkyl optionally substituted by one NHMe group (preferably unsubstituted); —$(CH_2)_n{}^{17}$-$Het^2$; optionally substituted carbon-linked-pyridinyl, optionally substituted phenyl; optionally substituted benzyl; or optionally substituted —CH($C_{1-2}$alkyl)Ph.

More, preferably, $R^{10}$ and $R^{11}$ independently are, and still more preferably $R^{11}$ is: H; $C_{1-6}$alkyl; $C_{3-6}$cycloalkyl optionally substituted by one or two methyl groups; —$CH_2$—$C_{3-6}$cycloalkyl (unsubstituted); —$(CH_2)_n{}^{17}$-$Het^2$; optionally substituted carbon-linked-pyridinyl; optionally substituted phenyl, optionally substituted benzyl; or optionally substituted —CH($C_{1-2}$alkyl)Ph (e.g. optionally substituted —CH(Me)Ph).

Preferably, in $R^{10}$ and/or $R^{11}$, the phenyl, the benzyl and the —CH($C_{1-2}$alkyl)Ph (e.g. —CH(Me)Ph) are independently optionally substituted on the aromatic ring by one or two substituents independently being: fluoro, chloro, $C_{1-2}$alkyl (e.g. methyl), $C_1$fluoroalkyl (e.g. $CF_3$), $C_{1-2}$alkoxy (e.g. methoxy), $C_1$fluoroalkoxy (e.g. $CF_3O$— or $CHF_2O$—), —$NR^{10a}R^{10b}$ (wherein $R^{10a}$ is H or methyl and $R^{10b}$ is H, $C_{1-2}$alkyl (e.g. methyl), —C(O)Me or —S(O)$_2$Me), —C(O)—$NR^{10c}R^{10d}$ (wherein $R^{10c}$ and $R^{10d}$ independently are H or $C_{1-2}$alkyl, e.g. H or Me), or —S(O)$_2R^{10e}$ (wherein $R^{10e}$ is $C_{1-2}$alkyl (e.g. methyl), $NH_2$, NHMe or $NMe_2$). One substituent is preferred.

In $R^{10}$ and/or $R^{11}$, and/or (independently) in $R^5$, and/or (independently) in $R^{15}$, and/or (independently) in $R^6$ and/or $R^7$, and/or (independently) in $R^{17}$, and/or (independently) in $R^{18}$: the carbon-linked-pyridinyl is preferably optionally substituted by one OH (including any keto tautomer thereof), and more preferably is not substituted.

In $R^{10}$ and/or $R^1$, for —$(CH_2)_n{}^{17}$-$Het^2$, preferably $n^{17}$ is 0 or 1; and/or preferably $Het^2$ is a 5- or 6-membered saturated optionally substituted heterocyclic ring containing one O or S (preferably O) ring atom or one $NR^{27}$ ring group. Preferably, $R^{27}$ is $C_{1-2}$alkyl or —C(O)Me. Preferably, the $Het^2$ ring is substituted on a ring carbon by one or two substituents being methyl or is not substituted on a ring carbon.

In one embodiment when $R^X$, $R^{X2}$, $R^Y$ and/or $R^{Y2}$ is —$(CH_2)_n{}^{11}$—C(O)—$NR^{10}R^{11}$, —CH($C_{1-2}$alkyl)-C(O)—$NR^{10}R^{11}$ or —$CMe_2$-C(O)—$NR^{10}R^{11}$, then optionally: $R^{10}$ and $R^{11}$ independently are H or $C_{1-6}$alkyl; or $R^{10}$ and $R^{11}$ together are —$(CH_2)_n{}^8$—$X^6$—$(CH_2)_n{}^9$— in which $n^8$ and $n^9$ independently are 2 or 3 and $X^6$ is a bond, —$CH_2$—, O, or $NR^{12}$ wherein $R^{12}$ is H or $C_{1-2}$alkyl, and wherein the ring formed by $NR^{10}R^{11}$ is not substituted on a ring carbon.

Preferably $R^{10}$ is H and/or optionally $R^{11}$ is $C_{1-6}$alkyl e.g. $C_{1-4}$alkyl such as isopropyl.

For example, —$(CH_2)_n{}^{11}$—C(O)—$NR^{10}R^{11}$ such as —C(O)—$NR^{10}R^{11}$ can be

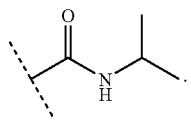

In an alternative preferable embodiment, when $R^{10}$ and $R^{11}$ together are —$(CH_2)_n{}^8$—$X^6$—$(CH_2)_n{}^9$—, then preferably $n^8$ is 2 and/or $n^9$ is 2. When $R^{10}$ and $R^{11}$ together are —$(CH_2)_n{}^8$—$X^6$—$(CH_2)_n{}^9$—, which is a preferable feature of the invention, then preferably $X^6$ is a bond, —$CH_2$—, O, or $NR^{12}$ wherein $R^{12}$ is H or $C_{1-2}$alkyl, and wherein the ring formed by $NR^{10}R^{11}$ is not substituted on a ring carbon.

When $R^{10}$ and $R^{11}$ together are —$(CH_2)_n{}^8$—$X^6$—$(CH_2)_n{}^9$—, it is preferable that the ring formed by $NR^{10}R^{11}$ is not substituted on a ring carbon or is substituted on a ring carbon by one methyl or oxo (=O) substituent.

Most preferably, $NR^{10}R^{11}$ is: $NH_2$, NHMe, $NMe_2$, NHEt, $NH^iPr$,

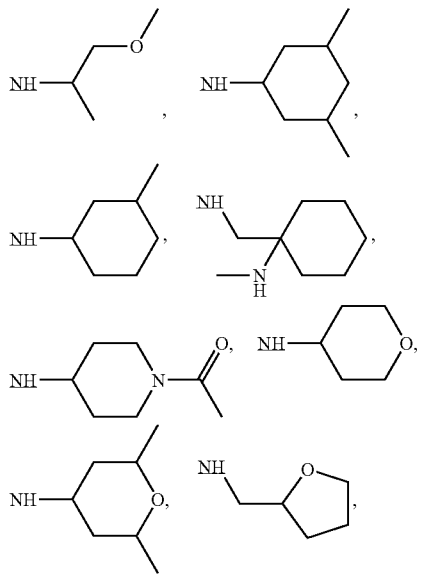

-continued

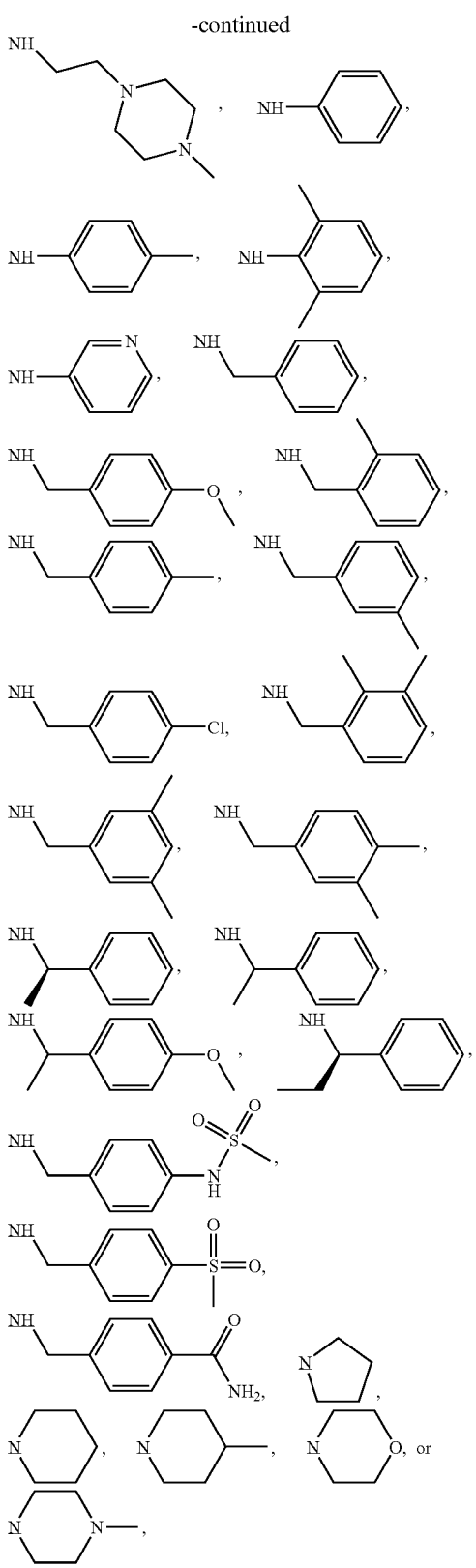

(In the above-illustrated most preferred groups, and generally in this specification for a group or radical, where <u>NH</u> or <u>N</u> are underlined, then this indicates the connection point.)

Still more preferably, When $R^X$, $R^{X2}$, $R^Y$ and/or $R^{Y2}$ is —$(CH_2)_n{}^{11}$—C(O)—$NR^{10}R^{11}$, —CH($C_{1-2}$alkyl)-C(O)—$NR^{10}R^{11}$, —$CMe_2$-C(O)—$NR^{10}R^1$, or $C_{3-5}$cycloalkyl substituted at the connecting carbon atom by —C(O)—$NR^{10}R^{11}$, then preferably it/they independently is/are —$(CH_2)_n{}^{11}$—C(O)—$NR^{10}R^{11}$ (more preferably —$CH_2$—C(O)—$NR^{10}R^{11}$ or —C(O)—$NR^{10}R^{11}$) wherein $NR^{10}R^{11}$ is one of the above-illustrated most preferred $NR^{10}R^{11}$ groups.

The —$(CH_2)_n{}^{11}$—C(O)—$NR^{10}R^{11}$ group is preferably as defined in any of Examples 36, 58, 84, 85-90, 95-96, 126-147 or 148-155. These Examples illustrate some of the above-illustrated preferred $NR^{10}R^{11}$ groups, and some of these Examples give literature references and/or commercial sources for amines $R^{10}R^{11}NH$, which may be used to prepare the compounds of Formula (I) containing the —$(CH_2)_n{}^{11}$—C(O)—$NR^{10}R^{11}$ group as $R^X$, $R^{X2}$, $R^Y$ and/or $R^{Y2}$.

When $R^X$, $R^{X2}$, $R^Y$ and/or $R^{Y2}$ is —$(CH_2)_n{}^{12}$—C(O)—$OR^{13}$, $n^{12}$ is preferably 0 or 1, more preferably 1. In one preferred embodiment when $R^X$, $R^{X2}$, $R^Y$ and/or $R^{Y2}$ is —$(CH_2)_n{}^{12}$—C(O)—$OR^{13}$, $R^{13}$ is H or $C_{1-6}$alkyl. When $R^{13}$ is $C_{1-6}$alkyl, then $R^{13}$ is preferably $C_{1-4}$alkyl or $C_{1-3}$alkyl such as methyl (e.g. $R^X$, $R^Y$ and/or $R^{X2}$ can be —$CO_2Me$) or ethyl.

When $R^X$, $R^{X2}$, $R^Y$ and/or $R^{Y2}$ is —$(CH_2)_n{}^{13}$—C(O)—$R^{13a}$, $n^{13}$ is preferably 0 or 1, more preferably 1. When $R^X$, $R^{X2}$, $R^Y$ and/or $R^{Y2}$ is —$(CH_2)_n{}^{13}$—C(O)—$R^{13a}$, then suitably $R^{13a}$ is $C_{1-6}$alkyl, $C_{1-2}$fluoroalkyl, $C_{3-6}$cycloalkyl, —$CH_2$—$C_{3-6}$cycloalkyl, benzyl, or phenyl (wherein the phenyl and benzyl are independently optionally substituted on the aromatic ring by one or two of (independently) (e.g. one of) fluoro, chloro, $C_{1-2}$alkyl, $C_1$fluoroalkyl, $C_{1-2}$alkoxy or $C_1$fluoroalkoxy). More preferably $R^{13a}$ is $C_{1-6}$alkyl or $C_{1-4}$alkyl or $C_{1-2}$alkyl.

When $R^X$, $R^{X2}$, $R^Y$ and/or $R^{Y2}$ is —$(CH_2)_n{}^{14}$-$Het^1$, —CH($C_{1-2}$alkyl)-$Het^1$ (e.g. —CH(Me)-$Het^1$), —$CMe_2$-$Het^1$, or $C_{3-5}$cycloalkyl (e.g. $C_3$cycloalkyl) substituted at the connecting carbon atom by $Het^1$, wherein $n^{14}$ is 0, 1 or 2, then: (a) $n^{14}$ is preferably 0 or 1, and/or (b)-$(CH_2)_n{}^{14}$-$Het^1$ is more preferred than —CH(Me)-$Het^1$ or —$CMe_2$-$Het^1$, or $C_{3-5}$cycloalkyl substituted at the connecting carbon atom by Ar.

When $R^X$, $R^{X2}$, $R^Y$ and/or $R^{Y2}$ is —$(CH_2)_n{}^{14}$-$Het^1$, —CH($C_{1-2}$alkyl)-$Het^1$ (e.g. —CH(Me)-$Het^1$), —$CMe_2$-$Het^1$, or $C_{3-5}$cycloalkyl (e.g. $C_3$cycloalkyl) substituted at the connecting carbon atom by $Het^1$, wherein $n^{14}$ is 0, 1 or 2 and wherein $Het^1$ is the 4-, 5-, 6- or 7-membered optionally substituted saturated heterocyclic ring containing one O or S ring atom and/or one $NR^{14}$ ring group, then the optionally substituted saturated heterocyclic ring $Het^1$ is preferably 4-, 5- or 6-membered, more preferably preferably 5- or 6-membered. When $Het^1$ is 6-membered, then any O or S ring atom and/or any $NR^{14}$ ring group independently can be present at the 2-, 3- or 4-ring position, preferably at the 4-ring position, with respect to the connecting ring-atom in $Het^1$. When the optionally substituted saturated heterocyclic ring $Het^1$ is 4-membered, then preferably the heterocyclic ring $Het^1$ is not optionally substituted by oxo (═O).

When $R^{14}$ and/or a or the optional ring substituent is $C_{1-4}$alkyl, it is suitably $C_{1-2}$alkyl such as methyl. Preferably, $R^{14}$ is $C_{1-4}$alkyl (e.g. $C_{1-2}$alkyl), $C(O)R^{19}$ or $S(O)_2R^{19}$. Preferably, $R^{19}$ is $C_{1-4}$alkyl (e.g. methyl or isobutyl), $C_{3-6}$cycloalkyl such as cyclopropyl or cyclohexyl, 2-thienyl, furan-2-yl, phenyl (unsubstituted), or benzyl (unsubstituted); more preferably $R^{19}$ is $C_{1-4}$alkyl (e.g. methyl or isobutyl).

When $R^X$, $R^{X2}$, $R^Y$ and/or $R^{Y2}$ is —$(CH_2)_n{}^{14}$-$Het^1$ and $n^{14}$ is 0, and when the saturated heterocyclic ring $Het^1$ is optionally substituted (at a position other than any $NR^{14}$ position) by $C_{1-4}$alkyl, then preferably the optional $C_{1-4}$alkyl is substituted at the carbon atom directly attached to the 5-membered ring in sub-formula (i), (ii), (iii), (iv) or (v) of Het.

The heterocyclic ring Het$^1$ is preferably optionally substituted (at a position or positions other than any NR$^{14}$ position) by one oxo (=O) and/or one C$_{1-4}$alkyl substituent; preferably by one oxo (=O) substituent. Any oxo (=O) substituent is preferably substituted on a ring carbon adjacent to (bonded to) any NR$^{14}$ ring group present. Preferably, in Het$^1$, the one or two oxo (=O) substituents are only present when there is a NR$^{14}$ ring group present.

For example, when R$^X$, R$^{X2}$, R$^Y$ and/or R$^{Y2}$ is —(CH$_2$)$_n$$^{14}$-Het$^1$, —CH(C$_{1-2}$alkyl)-Het$^1$, or —CMe$_2$-Het$^1$, the 4-, 5-, 6- or 7-membered optionally substituted saturated heterocyclic ring Het$^1$ can preferably be: tetrahydro-2H-pyranyl such as tetrahydro-2H-pyran-4-yl, tetrahydrofuran-2-yl, tetrahydrofuran-3-yl,

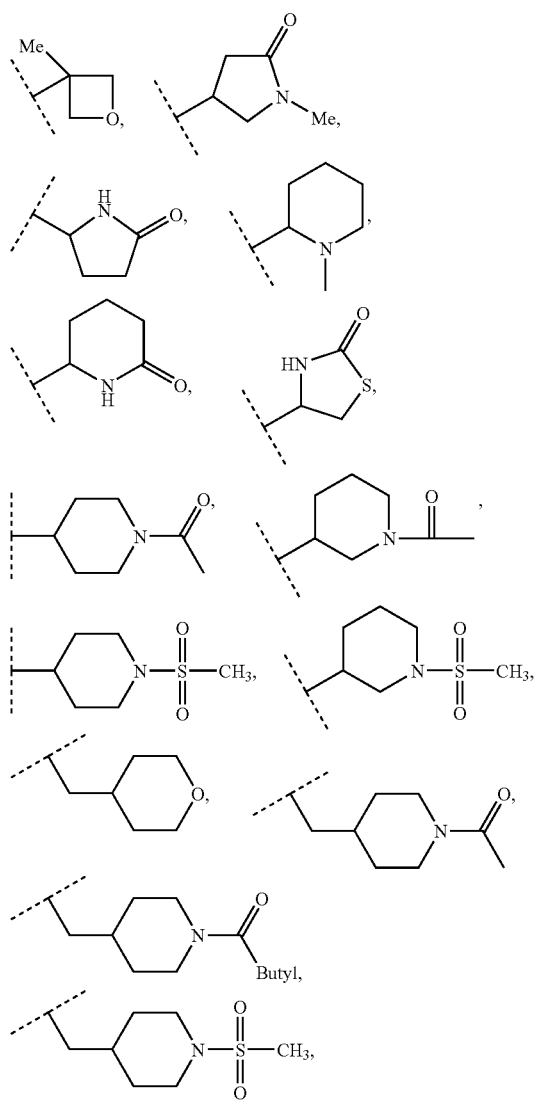

or a positional isomer of any of the foregoing wherein the connection point [which connects to the —(CH$_2$)$_n$$^{14}$—, —CH(C$_{1-2}$alkyl)- or —CHMe$_2$- or connecting-C$_{3-5}$cycloalkyl moiety or connects to the 5-membered ring of sub-formula (i), (ii), (iii), (iv) or (v) in Het] is at a different ring carbon atom of Het$^1$.

When R$^X$, R$^{X2}$, R$^Y$ and/or R$^{Y2}$ is —(CH$_2$)$_n$$^{10}$—Ar, —CH(C$_{1-2}$alkyl)-Ar (e.g. —CH(Me)-Ar), —CMe$_2$—Ar, or C$_{3-5}$cycloalkyl (e.g. C$_3$cycloalkyl) substituted at the connecting carbon atom by Ar, then preferably it/they independently is/are —(CH$_2$)$_n$$^{10}$—Ar or —CH(Me)-Ar, preferably —(CH$_2$)$_n$$^{10}$—Ar such as —CH$_2$—Ar.

When R$^X$, R$^{X2}$, R$^Y$ and/or R$^{Y2}$ is —(CH$_2$)$_n$$^{10}$—Ar then preferably n$^{10}$ is 0 or 1; more preferably n$^{10}$ is 1.

When Ar is optionally substituted phenyl, preferably the phenyl is optionally substituted by one or two substituents (preferably one) independently being fluoro, chloro, bromo, C$_{1-2}$alkyl, C$_1$fluoroalkyl, C$_{1-2}$alkoxy, C$_1$fluoroalkoxy, —NR$^{11a}$R$^{11b}$ (wherein R$^{11a}$ is H or methyl and R$^{11b}$ is H, C$_{1-2}$alkyl, —C(O)Me or —S(O)$_2$Me), —C(O)—NR$^{11c}$R$^{11d}$ (wherein R$^{11c}$ and R$^{11d}$ independently are H or methyl), —C(O)—OR$^{11e}$ wherein R$^{11e}$ is H, or —S(O)$_2$—R$^{11f}$ (wherein R$^{11f}$ is methyl, NH$_2$, NHMe or NMe$_2$). When Ar is optionally substituted phenyl, more preferably —(CH$_2$)$_n$$^{10}$—Ar can be as defined for R$^X$, R$^{X2}$, R$^Y$ and/or R$^{Y2}$ in any of Examples 49-55, 83, 103, 107, 120-125, 179, 181-184, 189 or 190.

When Ar is phenyl optionally substituted at two adjacent Ar ring atoms by the two ends of a chain which is: —(CH$_2$)$_4$—, —(CH$_2$)$_3$—, or —CH=CH—CH=CH—, then it can be for example naphthyl e.g. 1-naphthyl or 2-naphthyl.

When Ar is the optionally substituted 5- or 6-membered heterocyclic aromatic ring containing 1, 2, 3 or 4 heteroatoms (e.g. 1, 2 or 3 heteroatoms) selected from O, N or S, then Ar can be optionally substituted: furyl, thienyl, pyrrolyl, 1,3-oxazolyl, 1,3-thiazolyl, imidazolyl, oxadiazolyl (e.g. 1,3,4- or 1,2,4- or 1,2,5-oxadiazolyl), thiadiazolyl (e.g. 1,3,4- or 1,2,4-), pyridyl, triazolyl (e.g. 1,2,3- or 1,2,4-triazolyl), tetrazolyl, triazinyl, pyridazyl, pyrimidinyl, pyrazolyl, isothiazolyl(1,2-thiazolyl), or isoxazolyl(1,2-oxazolyl). When Ar is the optionally substituted 5- or 6-membered heterocyclic aromatic ring, the ring is preferably optionally substituted by one or two independent C$_{1-2}$alkyl groups or by one OH group (including any keto tautomer thereof); more preferably the ring is optionally substituted by one or two independent C$_{1-2}$alkyl (e.g. methyl) groups; and still more preferably there is/are one or no substituents. When Ar is the optionally substituted 5- or 6-membered heterocyclic aromatic ring, preferably it is 5-membered.

When Ar is the 5- or 6-membered heterocyclic aromatic ring, more preferably —(CH$_2$)$_n$$^{10}$—Ar can be as defined for R$^X$, R$^{X2}$, R$^Y$ and/or R$^{Y2}$ in any of Examples 71, 79, 80, 97-100, 104-106, 108, 112-114, 117, 158 or 186.

When the heterocyclic aromatic ring Ar is substituted at two adjacent Ar ring atoms by the two ends of a chain which is: —(CH$_2$)$_4$—, —(CH$_2$)$_3$—, or —CH=CH—CH=CH—, then e.g. Ar can be

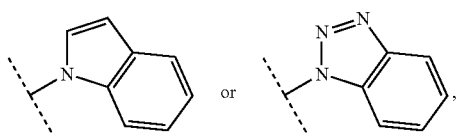

or —(CH$_2$)$_n^{10}$—Ar can be

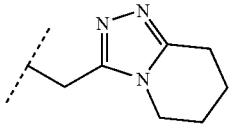

(see for example Example 186). Preferably, in these cases —(CH$_2$)$_n^{10}$—Ar is —CH$_2$—Ar.

In R$^5$, R$^{15}$, R$^6$, R$^7$, R$^{17}$, R$^{18}$, R$^9$, R$^{13}$, R$^{13a}$, and/or R$^{19}$, independent of each other, the phenyl and/or benzyl is/are preferably independently optionally substituted by one substituent; or more preferably the phenyl and/or benzyl is/are not substituted. In R$^{10}$ and/or R$^{11}$, independent of each other, the phenyl, benzyl and/or —CH(C$_{1-2}$alkyl)Ph is/are preferably independently optionally substituted by one substituent; or more preferably the the phenyl, benzyl and/or —CH(C$_{1-2}$alkyl)Ph is/are not substituted. In Ar, the phenyl and/or the heterocyclic aromatic ring is/are preferably independently optionally substituted by one substituent; or more preferably the phenyl and/or the heterocyclic aromatic ring is/are not substituted. In Het$^1$ and/or Het$^2$, independent of each other, the saturated heterocyclic ring is/are preferably independently optionally substituted on a ring carbon by one substituent; or more preferably the saturated heterocyclic ring is/are not substituted on a ring carbon.

When Het is of sub-formula (v), then suitably R$^{X2}$ and/or R$^{Y2}$ independently is/are: a hydrogen atom (H), C$_{1-6}$alkyl (e.g. C$_{1-4}$alkyl such as methyl), C$_{3-6}$cycloalkyl, —C(O)—NR$^{10}$R$^{11}$, —C(O)—OR$^{13}$, or —(CH$_2$)$_n^{10}$—Ar; more preferably H, C$_{1-6}$alkyl, —C(O)—NR$^{10}$R$^{11}$, —C(O)—OR$^{13}$, or —(CH$_2$)$_n^{10}$—Ar; still more preferably H, C$_{1-6}$alkyl (e.g. C$_{1-4}$alkyl such as methyl), —C(O)—NR$^{10}$R$^{11}$, or —(CH$_2$)$_n^{10}$—Ar. In this instance, i.e. when Het is of sub-formula (v), then Ar is preferably optionally substituted phenyl and/or n$^{10}$ is preferably 0 or 1.

Preferably, R$^{X1}$ and/or R$^{Y1}$ independently is/are a hydrogen atom (H) or C$_{1-2}$alkyl, more preferably H or methyl, still more preferably H.

Suitably, Y$^5$ can be CH$_2$ or CMe$_2$. More preferably, Y$^5$ is CH$_2$, i.e. CR$^{Y1}$R$^{Y2}$ wherein R$^{Y1}$=R$^{Y2}$=a hydrogen atom (H). X$^5$ can suitably be CHR$^{X2}$ or CMe$_2$, for example CHMe, CH—CO$_2$Me or CMe$_2$.

It is particularly preferred that the compound of formula (I) or the salt thereof is:

N-Cyclopentyl-1-ethyl-5-(5-methyl-1,3,4-oxadiazol-2-yl)-1H-pyrazolo[3,4-b]pyridin-4-amine,
N-Cyclopentyl-1-ethyl-5-{5-[(methylsulfonyl)methyl]-1,3,4-oxadiazol-2-yl}-1H-pyrazolo[3,4-b]pyridin-4-amine,
N-Cyclopentyl-1-ethyl-5-(5-isopropyl-1,3,4-oxadiazol-2-yl)-1H-pyrazolo[3,4-b]pyridin-4-amine,
N-Cyclopentyl-1-ethyl-5-(5-methyl-1,3,4-thiadiazol-2-yl)-1H-pyrazolo[3,4-b]pyridin-4-amine,
N-Cyclopentyl-1-ethyl-5-{5-[(methylsulfonyl)methyl]-1,3,4-thiadiazol-2-yl}-1H-pyrazolo[3,4-b]pyridin-4-amine,
N-Cyclopentyl-1-ethyl-5-(5-isopropyl-1,3,4-thiadiazol-2-yl)-1H-pyrazolo[3,4-b]pyridin-4-amine,
1-Ethyl-N-4-fluorophenyl)-5-(3-methyl-1,2,4-oxadiazol-5-yl)-1H-pyrazolo[3,4-b]pyridin-4-amine,
N-Cyclopentyl-5-(1,3-dimethyl-1H-1,2,4-triazol-5-yl)-1-ethyl-1H-pyrazolo[3,4-b]pyridin-4-amine,
1-Ethyl-5-(5-isopropyl-1,3,4-oxadiazol-2-yl)-N-tetrahydro-2H-pyran-4-yl-1H-pyrazolo[3,4-b]pyridin-4-amine,
N-Cyclohexyl-1-ethyl-5-(5-isopropyl-1,3,4-oxadiazol-2-yl)-1H-pyrazolo[3,4-b]pyridin 4-amine,
1-Ethyl-N-isobutyl-5-(5-isopropyl-1,3,4-oxadiazol-2-yl)-1H-pyrazolo[3,4-b]pyridin amine,
1-Ethyl-N-isobutyl-5-(5-methyl-1,3,4-oxadiazol-2-yl)-1H-pyrazolo[3,4-b]pyridin-4-amine,
N-Cyclohexyl-1-ethyl-5-(5-methyl-1,3,4-oxadiazol-2-yl)-1H-pyrazolo[3,4-b]pyridin-4-amine,
1-Ethyl-5-(5-methyl-1,3,4-oxadiazol-2-yl)-N-tetrahydro-2H-pyran-4-yl-1H-pyrazolo[3,4-b]pyridin-4-amine,
N-[(1R)-1,2-dimethylpropyl]-1-ethyl-5-(5-methyl-1,3,4-oxadiazol-2-yl)-1H-pyrazolo[3,4-b]pyridin-4-amine,
N-[(1S)-1,2-dimethylpropyl]-1-ethyl-5-(5-methyl-1,3,4-oxadiazol-2-yl)-1H-pyrazolo[3,4-b]pyridin-4-amine,
5-(5-Tert-butyl-1,3,4-oxadiazol-2-yl)-1-ethyl-N-tetrahydro-2H-pyran-4-yl-1H-pyrazolo[3,4-b]pyridin-4-amine,
5-(5-Tert-butyl-1,3,4-oxadiazol-2-yl)-N-cyclohexyl-1-ethyl-1H-pyrazolo[3,4-b]pyridin-4-amine,
5-(5-Tert-butyl-1,3,4-oxadiazol-2-yl)-N-cyclopentyl-1-ethyl-1H-pyrazolo[3,4-b]pyridin-4-amine,
5-(5-Tert-butyl-1,3,4-oxadiazol-2-yl)-1-ethyl-N-isobutyl-1H-pyrazolo[3,4-b]pyridin-4-amine,
5-(5-Tert-butyl-1,3,4-oxadiazol-2-yl)-N-[(1S)-1,2-dimethylpropyl]-1-ethyl-1H-pyrazolo[3,4-b]pyridin-4-amine,
5-(5-Tert-butyl-1,3,4-oxadiazol-2-yl)-N-[(1R)-1,2-dimethylpropyl]-1-ethyl-1H-pyrazolo[3,4-b]pyridin-4-amine,
1-Ethyl-5-{5-[(methylsulfonyl)methyl]-1,3,4-oxadiazol-2-yl}-N-tetrahydro-2H-pyran-4-yl-1H-pyrazolo[3,4-b]pyridin-4-amine,
N-Cyclohexyl-1-ethyl-5-{5-[(methylsulfonyl)methyl]-1,3,4-oxadiazol-2-yl}-1H-pyrazolo[3,4-b]pyridin-4-amine,
1-Ethyl-N-isobutyl-5-{5-[(methylsulfonyl)methyl]-1,3,4-oxadiazol-2-yl}-1H-pyrazolo[3,4-b]pyridin-4-amine,
N-[(1S)-1,2-dimethylpropyl]-1-ethyl-5-{5-[(methylsulfonyl)methyl]-1,3,4-oxadiazol-2-yl}-1H-pyrazolo[3,4-b]pyridin-4-amine,
N-[(1R)-1,2-dimethylpropyl]-1-ethyl-5-{5-[(methylsulfonyl)methyl]-1,3,4-oxadiazol-2-yl}-1H-pyrazolo[3,4-b]pyridin-4-amine,
1-Ethyl-5-(3-methyl-1,2,4-oxadiazol-5-yl)-N-tetrahydro-2H-pyran-4-yl-1H-pyrazolo[3,4-b]pyridin-4-amine,
1-Ethyl-5-[3-(methoxymethyl)-1,2,4-oxadiazol-5-yl]-N-tetrahydro-2H-pyran-4-yl-1H-pyrazolo[3,4-b]pyridin-4-amine,
5-{3-[(Dimethylamino)methyl]-1,2,4-oxadiazol-5-yl}-1-ethyl-N-tetrahydro-2H-pyran-4-yl-1H-pyrazolo[3,4-b]pyridin-4-amine,
1-Ethyl-5-[3-(morpholin-4-ylmethyl)-1,2,4-oxadiazol-5-yl]-N-tetrahydro-2H-pyran-4-yl-1H-pyrazolo[3,4-b]pyridin-4-amine,
5-(5-Cyclopropyl-1,3,4-oxadiazol-2-yl)-1-ethyl-N-tetrahydro-2H-pyran-4-yl-1H-pyrazolo[3,4-b]pyridin-4-amine,
N-(1-Acetylpiperidin-4-yl)-1-ethyl-5-(5-methyl-1,3,4-oxadiazol-2-yl)-1H-pyrazolo[3,4-b]pyridin-4-amine,
1-Ethyl-5-[5-(3-methyloxetan-3-yl)-1,3,4-oxadiazol-2-yl]-N-tetrahydro-2H-pyran-4-yl-1H-pyrazolo[3,4-b]pyridin-4-amine,
1-Ethyl-5-{5-[(4-methylpiperazin-1-yl)methyl]-1,3,4-oxadiazol-2-yl}-N-tetrahydro-2H-pyran-4-yl-1H-pyrazolo[3,4-b]pyridin-4-amine,
5-[1-Ethyl-4-tetrahydro-2H-pyran-4-ylamino)-1H-pyrazolo[3,4-b]pyridin-5-yl]-N-isopropyl-1,3,4-oxadiazole-2-carboxamide,
4-{5-[1-Ethyl-4-(tetrahydro-2H-pyran-4-ylamino)-1H-pyrazolo[3,4-b]pyridin-5-yl]-1,3,4-oxadiazol-2-yl}-1-methylpyrrolidin-2-one, 1-Ethyl-N-tetrahydro-2H-pyran-4-yl-5-(5-tetrahydro-2H-pyran-4-yl-1,3,4-oxadiazol-2-yl)-1H-pyrazolo[3,4-b]pyridin-4-amine,
1-Ethyl-5-[5-(morpholin-4-ylmethyl)-1,3,4-oxadiazol-2-yl]-N-tetrahydro-2H-pyran-4-yl-1H-pyrazolo[3,4-b]pyridin-4-amine,
5-[5-(Tert-butoxymethyl)-1,3,4-oxadiazol-2-yl]-1-ethyl-N-tetrahydro-2H-pyran-4-yl-1H-pyrazolo[3,4-b]pyridin-4-amine, or
methyl 2-[1-ethyl-4-tetrahydro-2H-pyran-4-ylamino)-1H-pyrazolo[3,4-b]pyridin-5-yl]-1,3-oxazole-4-carboxylate;

or a salt thereof, e.g. a pharmaceutically acceptable salt thereof.

Alternatively, the compound of formula (I) or the salt thereof can preferably be:
Methyl 2-[1-ethyl-4-(tetrahydro-2H-pyran-4-ylamino)-1H-pyrazolo[3,4-b]pyridin-5-yl]-4,5-dihydro-1,3-oxazole-4-carboxylate,
1-Ethyl-5-(4-methyl-4,5-dihydro-1,3-oxazol-2-yl)-N-(tetrahydro-2H-pyran-4-yl)-1H-pyrazolo[3,4-b]pyridin-4-amine,
1-(n-Propyl)-5-(5-methyl-1,3,4-oxadiazol-2-yl)-N-(tetrahydro-2H-pyran-4-yl)-1H-pyrazolo[3,4-b]pyridin-4-amine,
1-Ethyl-5-[5-(tetrahydrofuran-2-yl)-1,3,4-oxadiazol-2-yl]-N-(tetrahydro-2H-pyran-4-yl)-1H-pyrazolo[3,4-b]pyridin-4-amine,
1-Ethyl-5-[5-(dimethylamino)-1,3,4-oxadiazol-2-yl]-N-(tetrahydro-2H-pyran-4-yl)-1H-pyrazolo[3,4-b]pyridin-4-amine,
1-Ethyl-5-(5-methyl-1,2,4-triazol-3-yl)-N-(tetrahydro-2H-pyran-4-yl)-1H-pyrazolo[3,4-b]pyridin-4-amine,
N-(1-Acetylpiperidin-4-yl)-1-ethyl-5-(3-methyl-1,2,4-oxadiazol-5-yl)-1H-pyrazolo[3,4-b]pyridin-4-amine, or
N-(1-Acetylpiperidin-4-yl)-1-ethyl-5-[3-(morpholin-4-ylmethyl)-1,2,4-oxadiazol-5-yl]-1H-pyrazolo[3,4-b]pyridin-4-amine;

or a salt thereof, e.g. a pharmaceutically acceptable salt thereof.

Alternatively, the compound of formula (I) or the salt thereof can preferably be:
1-Ethyl-5-[(4R)-4-phenyl-4,5-dihydro-1,3-oxazol-2-yl]-N-(tetrahydro-2H-pyran-4-yl)-1H-pyrazolo[3,4-b]pyridin-4-amine,
1-Ethyl-5-[(4S)-4-phenyl-4,5-dihydro-1,3-oxazol-2-yl]-N-(tetrahydro-2H-pyran-4-yl)-1H-pyrazolo[3,4-b]pyridin-4-amine,
1-Ethyl-5-[(4S)-4-(phenylmethyl)-4,5-dihydro-1,3-oxazol-2-yl]-N-(tetrahydro-2H-pyran-4-yl)-1H-pyrazolo[3,4-b]pyridin-4-amine,
1-Ethyl-5-[(4R)-4-(phenylmethyl)-4,5-dihydro-1,3-oxazol-2-yl]-N-(tetrahydro-2H-pyran-4-yl)-1H-pyrazolo[3,4-b]pyridin-4-amine,
1-Ethyl-5-[(4S,5R)-5-methyl-4-phenyl-4,5-dihydro-1,3-oxazol-2-yl]-N-(tetrahydro-2H-pyran-4-yl)-1H-pyrazolo[3,4-b]pyridin-4-amine,
1-Ethyl-5-[(5R)-5-phenyl-4,5-dihydro-1,3-oxazol-2-yl]-N-(tetrahydro-2H-pyran-4-yl)-1H-pyrazolo[3,4-b]pyridin-4-amine,
1-Ethyl-5-[(5S)-5-phenyl-4,5-dihydro-1,3-oxazol-2-yl]-N-(tetrahydro-2H-pyran-4-yl)-1H-pyrazolo[3,4-b]pyridin-4-amine,
5-(4,4-Dimethyl-4,5-dihydro-1,3-oxazol-2-yl)-1-ethyl-N-(tetrahydro-2H-pyran-4-yl)-1H-pyrazolo[3,4-b]pyridin-4-amine,
2-[1-Ethyl-4-(tetrahydro-2H-pyran-4-ylamino)-1H-pyrazolo[3,4-b]pyridin-5-yl]-1,3-oxazole-4-carboxylic acid,
2-[1-Ethyl-4-(tetrahydro-2H-pyran-4-ylamino)-1H-pyrazolo[3,4-b]pyridin-5-yl]-N-(1-methylethyl)-1,3-oxazole-4-carboxamide,
1-Ethyl-5-[4-(4-morpholinylcarbonyl)-1,3-oxazol-2-yl]-N-(tetrahydro-2H-pyran-4-yl)-1H-pyrazolo[3,4-b]pyridin-4-amine,
1-Ethyl-N-methyl-5-(5-methyl-1,3,4-oxadiazol-2-yl)-N-(tetrahydro-2H-pyran-4-yl)-1H-pyrazolo[3,4-b]pyridin-4-amine,
trans-4-{[1-Ethyl-5-(5-methyl-1,3,4-oxadiazol-2-yl)-1H-pyrazolo[3,4-b]pyridin-4-yl]amino}cyclohexanol,
1-Ethyl-5-(5-methyl-1,3,4-oxadiazol-2-yl)-N-(tetrahydro-2H-pyran-3-yl)-1H-pyrazolo[3,4-b]pyridin-4-amine,
4-{[1-Ethyl-5-(5-methyl-1,3,4-oxadiazol-2-yl)-1H-pyrazolo[3,4-b]pyridin-4-yl]amino}cyclohexanone,
1-Ethyl-5-(5-methyl-1,3,4-oxadiazol-2-yl)-N-n-propyl-N-(tetrahydro-2H-pyran-4-yl)-1H-pyrazolo[3,4-b]pyridin-4-amine,
5-[5-(1,1-Dimethylethyl)-1,3,4-oxadiazol-2-yl]-1-ethyl-6-methyl-N-(tetrahydro-2H-pyran-4-yl)-1H-pyrazolo[3,4-b]pyridin-4-amine,
1-Ethyl-6-methyl-N-(tetrahydro-2H-pyran-4-yl)-5-[5-(tetrahydro-2H-pyran-4-yl)-1,3,4-oxadiazol-2-yl]-1H-pyrazolo[3,4-b]pyridin-4-amine,
5-(5-Cyclobutyl-1,3,4-oxadiazol-2-yl)-1-ethyl-N-(tetrahydro-2H-pyran-4-yl)-1H-pyrazolo[3,4-b]pyridin-4-amine,
5-{5-[1-Ethyl-4-(tetrahydro-2H-pyran-4-ylamino)-1H-pyrazolo[3,4-b]pyridin-5-yl]-1,3,4-oxadiazol-2-yl}-2-pyrrolidinone,
N-({5-[1-Ethyl-4-(tetrahydro-2H-pyran-4-ylamino)-1H-pyrazolo[3,4-b]pyridin-5-yl]-1,3,4-oxadiazol-2-yl}methyl)acetamide,
1-Ethyl-5-[5-(1-methyl-2-piperidinyl)-1,3,4-oxadiazol-2-yl]-N-(tetrahydro-2H-pyran-4-yl)-1H-pyrazolo[3,4-b]pyridin-4-amine,
1-Ethyl-5-{5-[(4-methyl-1,2,5-oxadiazol-3-yl)methyl]-1,3,4-oxadiazol-2-yl}-N-(tetrahydro-2H-pyran-4-yl)-1H-pyrazolo[3,4-b]pyridin-4-amine,
3-{5-[1-Ethyl-4-(tetrahydro-2H-pyran-4-ylamino)-1H-pyrazolo[3,4-b]pyridin-5-yl]-1,3,4-oxadiazol-2-yl}cyclopentanone,
1-Ethyl-5-[5-(tetrahydro-3-furanyl)-1,3,4-oxadiazol-2-yl]-N-(tetrahydro-2H-pyran-4-yl)-1H-pyrazolo[3,4-b]pyridin-4-amine,
(4S)-{5-[1-Ethyl-4-(tetrahydro-2H-pyran-4-ylamino)-1H-pyrazolo[3,4-b]pyridin-5-yl]-1,3,4-oxadiazol-2-yl}-1,3-thiazolidin-2-one,
5-[5-(2,2-Dimethylcyclopropyl)-1,3,4-oxadiazol-2-yl]-1-ethyl-N-(tetrahydro-2H-pyran-4-yl)-1H-pyrazolo[3,4-b]pyridin-4-amine,
N-({5-[1-Ethyl-4-(tetrahydro-2H-pyran-4-ylamino)-1H-pyrazolo[3,4-b]pyridin-5-yl]-1,3,4-oxadiazol-2-yl}methyl)-N-methylacetamide,
1-Ethyl-N-(tetrahydro-2H-pyran-4-yl)-5-[5-(tetrahydro-2H-pyran-4-ylmethyl)-1,3,4-oxadiazol-2-yl]-1H-pyrazolo[3,4-b]pyridin-4-amine,
1-Ethyl-5-[5-(1-methylcyclobutyl)-1,3,4-oxadiazol-2-yl]-N-(tetrahydro-2H-pyran-4-yl)-1H-pyrazolo[3,4-b]pyridin-4-amine,
1-Ethyl-5-[5-(3-methyl-5-isoxazolyl)-1,3,4-oxadiazol-2-yl]-N-(tetrahydro-2H-pyran-4-yl)-1H-pyrazolo[3,4-b]pyridin-4-amine,
1-Ethyl-5-[5-(1-methyl-1H-pyrazol-5-yl)-1,3,4-oxadiazol-2-yl]-N-(tetrahydro-2H-pyran-4-yl)-1H-pyrazolo[3,4-b]pyridin-4-amine, 5-[5-(1-Acetyl-4-piperidinyl)-1,3,4-oxadiazol-2-yl]-1-ethyl-N-(tetrahydro-2H-pyran-4-yl)-1H-pyrazolo[3,4-b]pyridin-4-amine, 1-Ethyl-5-{3-[(4-methyl-1-piperazinyl)methyl]-1,2,4-oxadiazol-5-yl}-N-(tetrahydro-2H-pyran-4-yl)-1H-pyrazolo[3,4-b]pyridin-4-amine, 1-Ethyl-5-[3-(4-fluorophenyl)-1,2,4-oxadiazol-5-yl]-N-(tetrahydro-2H-pyran-4-yl)-1H-pyrazolo[3,4-b]pyridin-4-amine, or 1-Ethyl-5-{3-[2-oxo-2-(1-pyrrolidinyl)ethyl]-1,2,4-oxadiazol-5-yl}-N-(tetrahydro-2H-pyran-4-yl)-1H-pyrazolo[3,4-b]pyridin-4-amine;

or a salt thereof, e.g. a pharmaceutically acceptable salt thereof. For these compounds/salts, the structures of each, as a compound, are disclosed in Examples 49 to 84 hereinafter.

Alternatively, the compound of formula (I) or the salt thereof can preferably be:

2-{5-[1-Ethyl-4-(tetrahydro-2H-pyran-4-ylamino)-1H-pyrazolo[3,4-b]pyridin-5-yl]-1,2,4-oxadiazol-3-yl}-N-phenylacetamide, 2-{5-[1-Ethyl-4-(tetrahydro-2H-pyran-4-ylamino)-1H-pyrazolo[3,4-b]pyridin-5-yl]-1,2,4-oxadiazol-3-yl}-N-(1-phenylethyl)acetamide, 1-Ethyl-5-{3-[2-oxo-2-(1-piperidinyl)ethyl]-1,2,4-oxadiazol-5-yl}-N-(tetrahydro-2H-pyran-4-yl)-1H-pyrazolo[3,4-b]pyridin-4-amine, 2-{5-[1-Ethyl-4-(tetrahydro-2H-pyran-4-ylamino)-1H-pyrazolo[3,4-b]pyridin-5-yl]-1,2,4-oxadiazol-3-yl}-N-phenylmethyl)acetamide, 2-{5-[1-Ethyl-4-(tetrahydro-2H-pyran-4-ylamino)-1H-pyrazolo[3,4-b]pyridin-5-yl]-1,2,4-oxadiazol-3-yl}-N,N-dimethylacetamide, N-Ethyl-2-{5-[1-ethyl-4-(tetrahydro-2H-pyran-4-ylamino)-1H-pyrazolo[3,4-b]pyridin-5-yl]-1,2,4-oxadiazol-3-yl}acetamide, 1-Ethyl-5-{3-[1-(4-morpholinyl)ethyl]-1,2,4-oxadiazol-5-yl}-N-(tetrahydro-2H-pyran-4-yl)-1H-pyrazolo[3,4-b]pyridin-4-amine, 5-[3-(Cyclohexylmethyl)-1,2,4-oxadiazol-5-yl]-1-ethyl-N-(tetrahydro-2H-pyran-4-yl)-1H-pyrazolo[3,4-b]pyridin-4-amine, 1-Ethyl-5-{3-[2-oxo-2-(1-piperidinyl)ethyl]-1,2,4-oxadiazol-5-yl}-N-(tetrahydro-2H-pyran-4-yl)-1H-pyrazolo[3,4-b]pyridin-4-amine, 1-ethyl-5-{3-[2-(4-methyl-1-piperazinyl)-2-oxoethyl]-1,2,4-oxadiazol-5-yl}-N-(tetrahydro-2H-pyranyl)-1H-pyrazolo[3,4-b]pyridin-4-amine, 1-Ethyl-N-(tetrahydro-2H-pyran-4-yl)-5-[5-(1H-1,2,3-triazol-1-ylmethyl)-1,3,4-oxadiazol-2-yl]-1H-pyrazolo[3,4-b]pyridin-4-amine, 5-{5-[(2,4-Dimethyl-1,3-thiazol-5-yl)methyl]-1,3,4-oxadiazol-2-yl}-1-ethyl-N-(tetrahydro-2H-pyran-4-yl)-1H-pyrazolo[3,4-b]pyridin-4-amine, 1-Ethyl-5-[5-(2-furanylmethyl)-1,3,4-oxadiazol-2-yl]-N-(tetrahydro-2H-pyran-4-yl)-1H-pyrazolo[3,4-b]pyridin-4-amine, 1-Ethyl-5-[5-(3-isoxazolylmethyl)-1,3,4-oxadiazol-2-yl]-N-(tetrahydro-2H-pyran-4-yl)-1H-pyrazolo[3,4-b]pyridin-4-amine, 1-ethyl-5-(5-{[4-(methyloxy)phenyl]methyl}-1,3,4-oxadiazol-2-yl)-N-(tetrahydro-2H-pyran-4-yl)-1H-pyrazolo[3,4-b]pyridin-4-amine, 1-Ethyl-N-(tetrahydro-2H-pyran-4-yl)-5-[5-(1H-tetrazol-1-ylmethyl)-1,3,4-oxadiazol-2-yl]-1H-pyrazolo[3,4-b]pyridin-4-amine, 1-Ethyl-5-[5-(5-isothiazolylmethyl)-1,3,4-oxadiazol-2-yl]-N-(tetrahydro-2H-pyran-4-yl)-1H-pyrazolo[3,4-b]pyridin-4-amine, 1-Ethyl-5-{5-[(3-methyl-5-isoxazolyl)methyl]-1,3,4-oxadiazol-2-yl}-N-(tetrahydro-2H-pyran-4-yl)-1H-pyrazolo[3,4-b]pyridin-4-amine, 5-(5-{[4-(Dimethylamino)phenyl]methyl}-1,3,4-oxadiazol-2-yl)-1-ethyl-N-(tetrahydro-2H-pyran-4-yl)-1H-pyrazolo[3,4-b]pyridin-4-amine (1:1), 1-Ethyl-5-{5-[(2-methyl-1,3-thiazol-4-yl)methyl]-1,3,4-oxadiazol-2-yl}-N-(tetrahydro-2H-pyran-4-yl)-1H-pyrazolo[3,4-b]pyridin-4-amine, 2-[1-({5-[1-ethyl-4-(tetrahydro-2H-pyran-4-ylamino)-1H-pyrazolo[3,4-b]pyridin-5-yl]-1,3,4-oxadiazol-2-yl}methyl)cyclopentyl]-N-methylacetamide, N-({5-[1-Ethyl-4-(tetrahydro-2H-pyranylamino)-1H-pyrazolo[3,4-b]pyrin-5-yl]-1,3,4-oxadiazol-2-yl}methyl)cyclopropanecarboxamide, 1-Ethyl-5-{5-[(5-methyl-3-isoxazolyl)methyl]-1,3,4-oxadiazol-2-yl}-N-(tetrahydro-2H-pyran-4-yl)-1H-pyrazolo[3,4-b]pyridin-4-amine, 1-Ethyl-5-{5-[(5-methyl-3-isoxazolyl)methyl]-1,3,4-oxadiazol-2-yl}-N-(tetrahydro-2H-pyran-4-yl)-1H-pyrazolo[3,4-b]pyridin-4-amine, 1-Ethyl-5-{5-[2-(4-methyl-1,3-thiazol-5-yl)ethyl]-1,3,4-oxadiazol-2-yl}-N-(tetrahydro-2H-pyran-4-yl)-1H-pyrazolo[3,4-b]pyridin-4-amine, 5-{5-[(3,5-Dimethyl-4-isoxazolyl)methyl]-1,3,4-oxadiazol-2-yl}-1-ethyl-N-(tetrahydro-2H-pyran-4-yl)-1H-pyrazolo[3,4-b]pyridin-4-amine, N-(1-{5-[1-Ethyl-4-(tetrahydro-2H-pyran-4-ylamino)-1H-pyrazolo[3,4-b]pyridin-5-yl]-1,3,4-oxadiazol-2-yl}ethyl)acetamide, 5-{5-[(1-acetyl-4-piperidinyl)methyl]-1,3,4-oxadiazol-2-yl}-1-ethyl-N-(tetrahydro-2H-pyranyl)-1H-pyrazolo[3,4-b]pyridin-4-amine, 1-Ethyl-5-{5-[(4-methylphenyl)methyl]-1,3,4-oxadiazol-2-yl}-N-(tetrahydro-2H-pyran-4-yl)-1H-pyrazolo[3,4-b]pyridin-4-amine, 1-Ethyl-5-[5-(4-methylphenyl)-1,3,4-oxadiazol-2-yl]-N-(tetrahydro-2H-pyran-4-yl)-1H-pyrazolo[3,4-b]pyridin-4-amine, 5-[5-(3,4-Dimethylphenyl)-1,3,4-oxadiazol-2-yl]-1-ethyl-N-(tetrahydro-2H-pyran-4-yl)-1H-pyrazolo[3,4-b]pyridin-4-amine, 5-[5-(2,4-Dimethylphenyl)-1,3,4-oxadiazol-2-yl]-1-ethyl-N-(tetrahydro-2H-pyran-4-yl)-1H-pyrazolo[3,4-b]pyridin-4-amine, 5-{5-[(4-Bromophenyl)methyl]-1,3,4-oxadiazol-2-yl}-1-ethyl-N-(tetrahydro-2H-pyran-4-yl)-1H-pyrazolo[3,4-b]pyridin-4-amine, 2-[1-Ethyl-4-(tetrahydro-2H-pyran-4-ylamino)-1H-pyrazolo[3,4-b]pyridin-5-yl]-N-(phenylmethyl)-1,3-oxazole-4-carboxamide, 2-[1-Ethyl-4-(tetrahydro-2H-pyran-4-ylamino)-1H-pyrazolo[3,4-b]pyridin-5-yl]-N-{[4-(methyloxy)phenyl]methyl}-1,3-oxazole-4-carboxamide, 2-[1-Ethyl-4-(tetrahydro-2H-pyran-4-ylamino)-1H-pyrazolo[3,4-b]pyridin-5-yl]-N-[(2-methylphenyl)methyl]-1,3-oxazole-4-carboxamide, 2-[1-Ethyl-4-(tetrahydro-2H-pyran-4-ylamino)-1H-pyrazolo[3,4-b]pyridin-5-yl]-N-[(4-methylphenyl)methyl]-1,3-oxazole-4-carboxamide, 2-[1-Ethyl-4-(tetrahydro-2H-pyran-4-ylamino)-1H-pyrazolo[3,4-b]pyridin-5-yl]-N-[(3-methylphenyl)methyl]-1,3-oxazole-4-carboxamide, N-[(4-Chlorophenyl)methyl]-2-[1-ethyl-4-(tetrahydro-2H-pyran-4-ylamino)-1H-pyrazolo[3,4-b]pyridin-5-yl]-1,3-oxazole-4-carboxamide,
N-[(2,3-Dimethylphenyl)methyl]-2-[1-ethyl-4-(tetrahydro-2H-pyran-4-ylamino)-1H-pyrazolo[3,4-b]pyridin-5-yl]-1,3-oxazole-4-carboxamide,
N-[(3,5-Dimethylphenyl)methyl]-2-[1-ethyl-4-(tetrahydro-2H-pyran-4-ylamino)-1H-pyrazolo[3,4-b]pyridin-5-yl]-1,3-oxazole-4-carboxamide,
N-[(3,4-Dimethylphenyl)methyl]-2-[1-ethyl-4-(tetrahydro-2H-pyran-4-ylamino)-1H-pyrazolo[3,4-b]pyridin-5-yl]-1,3-oxazole-4-carboxamide,
2-[1-Ethyl-4-(tetrahydro-2H-pyran-4-ylamino)-1H-pyrazolo[3,4-b]pyridin-5-yl]-N-(1-phenylethyl)-1,3-oxazole-4-carboxamide,
2-[1-Ethyl-4-(tetrahydro-2H-pyran-4-ylamino)-1H-pyrazolo[3,4-b]pyridin-5-yl]-N-{(1R)-1-[4-(methyloxy)phenyl]ethyl}-1,3-oxazole-4-carboxamide,
2-[1-Ethyl-4-(tetrahydro-2H-pyran-4-ylamino)-1H-pyrazolo[3,4-b]pyridin-5-yl]-N-[(1R)-1-phenylpropyl]-1,3-oxazole-4-carboxamide,
2-[1-Ethyl-4-(tetrahydro-2H-pyran-4-ylamino)-1H-pyrazolo[3,4-b]pyridin-5-yl]-N-(4-methylphenyl)-1,3-oxazole-4-carboxamide,
2-[1-Ethyl-4-(tetrahydro-2H-pyran-4-ylamino)-1H-pyrazolo[3,4-b]pyridin-5-yl]-N-({4-[(methylsulfonyl)amino]phenyl}methyl)-1,3-oxazole-4-carboxamide,
2-[1-Ethyl-4-(tetrahydro-2H-pyran-4-ylamino)-1H-pyrazolo[3,4-b]pyridin-5-yl]-N-{[4-(methylsulfonyl)phenyl]methyl}-1,3-oxazole-4-carboxamide,
N-(1-Acetyl-4-piperidinyl)-2-[1-ethyl(tetrahydro-2H-pyran-4-ylamino)-1H-pyrazolo[3,4-b]pyridin-5-yl]-1,3-oxazole-4-carboxamide,
2-[1-Ethyl-4-(tetrahydro-2H-pyran-4-ylamino)-1H-pyrazolo[3,4-b]pyridin-5-yl]-N-(tetrahydro-2H-pyranyl)-1,3-oxazole 4-carboxamide,
2-[1-Ethyl-4-(tetrahydro-2H-pyran-4-ylamino)-1H-pyrazolo[3,4-b]pyridin-5-yl]-N-(tetrahydro-2-furanylmethyl)-1,3-oxazole-4-carboxamide,
2-[1-Ethyl-4-(tetrahydro-2H-pyran-4-ylamino)-1H-pyrazolo[3,4-b]pyridin-5-yl]-N-[2-(4-methyl-1-piperazinyl)ethyl]-1,3-oxazole-4-carboxamide,
N-[1-(Aminomethyl)cyclohexyl]-2-[1-ethyl-4-(tetrahydro-2H-pyran-4-ylamino)-1H-pyrazolo[3,4-b]pyridin-5-yl]-N-methyl-1,3-oxazole-4-carboxamide,
N-(2,6-Dimethylphenyl)-2-[1-ethyl-4-(tetrahydro-2H-pyran-4-ylamino)-1H-pyrazolo[3,4-b]pyridin-5-yl]-1,3-oxazole-4-carboxamide,
N-{[4-(Aminocarbonyl)phenyl]methyl}-2-[1-ethyl-4-(tetrahydro-2H-pyran-4-ylamino)-1H-pyrazolo[3,4-b]pyridin-5-yl]-1,3-oxazole-4-carboxamide,
2-{5-[1-Ethyl-4-(tetrahydro-2H-pyran-4-ylamino)-1H-pyrazolo[3,4-b]pyridin-5-yl]-1,2,4-oxadiazol-3-yl}-N-(tetrahydro-2H-pyran-4-yl)acetamide,
5-{3-[2-(2,6-Dimethyl-4-morpholinyl)-2-oxoethyl]-1,2,4-oxadiazol-5-yl}-1-ethyl-N-(tetrahydro-2H-pyran-4-yl)-1H-pyrazolo[3,4-b]pyridin-4-amine,
1-Ethyl-5-{3-[2-(4-methyl-1-piperidinyl)-2-oxoethyl]-1,2,4-oxadiazol-5-yl}-N-(tetrahydro-2H-pyran-4-yl)-1H-pyrazolo[3,4-b]pyridin-4-amine,
2-{5-[1-Ethyl-4-(tetrahydro-2H-pyran-4-ylamino)-1H-pyrazolo[3,4-b]pyridin-5-yl]-1,2,4-oxadiazol-3-yl}-N-[1-methyl-2-(methyloxy)ethyl]acetamide,
5-{3-[2-(3,5-Dimethyl-1-piperidinyl)-2-oxoethyl]-1,2,4-oxadiazol-5-yl}-1-ethyl-N-(tetrahydro-2H-pyran-4-yl)-1H-pyrazolo[3,4-b]pyridin-4-amine,
1-Ethyl-5-{3-[2-(3-methyl-1-piperidinyl)-2-oxoethyl]-1,2,4-oxadiazol-5-yl}-N-(tetrahydro-2H-pyran-4-yl)-1H-pyrazolo[3,4-b]pyridin-4-amine,
2-{5-[1-Ethyl-4-(tetrahydro-2H-pyran-4-ylamino)-1H-pyrazolo[3,4-b]pyridin-5-yl]-1,2,4-oxadiazol-3-yl}-N-3-pyridinylacetamide,
6-{5-[1-Ethyl-4-(tetrahydro-2H-pyran-4-ylamino)-1H-pyrazolo[3,4-b]pyridin-5-yl]-1,3,4-oxadiazol-2-yl}-2-piperidinone,
1-Ethyl-5-{5-[(3-methyl-1H-1,2,4-triazol-5-yl)methyl]-1,3,4-oxadiazol-2-yl}-N-(tetrahydro-2H-pyran-4-yl)-1H-pyrazolo[3,4-b]pyridin-4-amine,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)acetamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)benzamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-phenylacetamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-methylpropanamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)-3-methylbutanamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)cyclohexanecarboxamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-furancarboxamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)methanesulfonamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)benzenesulfonamide,
N-({5-[1-Ethyl-4-(tetrahydro-2H-pyran-4-amino)-1H-pyrazolo[3,4-b]pyridin-5-yl]-1,2,4-oxadiazol-3-yl}methyl)-1-phenylmethanesulfonamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-propanesulfonamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)-1-propanesulfonamide,
N-({5-[1-Ethyl-4-(tetrahydro-2H-pyran-4-amino)-1H-pyrazolo[3,4-b]pyridin-5-yl]-1,2,4-oxadiazol-3-yl}methyl)cyclopropanesulfonamide,
N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-thiophenesulfonamide,
1-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-pyrrolidinone,
1-({5-[1-Ethyl(tetrahydro-2H-pyran-4-ylamino)-1H-pyrazolo[3,4-b]pyridin-5-yl]-1,2,4-oxadiazol-3-yl}methyl)-2-piperidinone,
5-{3-[(1-Acetyl-4-piperidinyl)methyl]-1,2,4-oxadiazol-5-yl}-1-ethyl-N-(tetrahydro-2H-pyran-4-yl)-1H-pyrazolo[3,4-b]pyridin-4-amine,
1-Ethyl-5-(3-{[1-(3-methylbutanoyl)-4-piperidinyl]methyl}-1,2,4-oxadiazol-5-yl)-N-(tetrahydro-2H-pyran-4-yl)-1H-pyrazolo[3,4-b]pyridin-4-amine, 1-Ethyl-5-(3-{[1-(methylsulfonyl)-4-piperidinyl]methyl}-1,2,4-oxadiazol-5-yl)-N-(tetrahydro-2H-pyranyl)-1H-pyrazolo[3,4-b]pyridin-4-amine, 1-Ethyl-5-{3-[1-(phenylsulfonyl)cyclopropyl]-1,2,4-oxadiazol-5-yl}-N-(tetrahydro-2H-pyran-4-yl)-1H-pyrazolo[3,4-b]pyridin-4-amine, 1-Ethyl-5-[3-(phenylmethyl)-1,2,4-oxadiazol-5-yl]-N-(tetrahydro-2H-pyran-4-yl)-1H-pyrazolo[3,4-b]pyridin-amine, 1-Ethyl-5-[3-(1-phenylethyl)-1,2,4-oxadiazol-5-yl]-N-(tetrahydro-2H-pyran-4-yl)-1H-pyrazolo[3,4-b]pyridin-4-amine, 1-Ethyl-5-(3-{[4-(methyloxy)phenyl]methyl}-1,2,4-oxadiazol-5-yl)-N-(tetrahydro-2H-pyran-4-yl)-1H-pyrazolo[3,4-b]pyridin-4-amine, 5-(3-{[4-(Dimethylamino)phenyl]methyl}-1,2,4-oxadiazol-5-yl)-1-ethyl-N-(tetrahydro-2H-pyran-4-yl)-1H-pyrazolo[3,4-b]pyridin-4-amine, 5-(3-{[3-(Dimethylamino)phenyl]methyl}-1,2,4-oxadiazol-5-yl)-1-ethyl-N-(tetrahydro-2H-pyran-4-yl)-1H-pyrazolo[3,4-b]pyridin-4-amine, 5-(3-{[4-Dimethylamino)phenyl]methyl}-1,2,4-oxadiazol-5-yl)-1-ethyl-N-(tetrahydro-2H-pyran-4-yl)-1H-pyrazolo[3,4-b]pyridin-4-amine, 1-Ethyl-5-{3-[(phenyloxy)methyl]-1,2,4-oxadiazol-5-yl}-N-(tetrahydro-2H-pyran-4-yl)-1H-pyrazolo[3,4-b]pyridin-4-amine, 1-ethyl-N-(tetrahydro-2H-pyran-4-yl)-5-[3-(5,6,7,8-tetrahydro[1,2,4]triazolo[4,3-a]pyridin-3-ylmethyl)-1,2,4-oxadiazol-5-yl]-1H-pyrazolo[3,4-b]pyridin-4-amine, 1-Ethyl-5-{3-[(4-phenyl-1-piperazinyl)methyl]-1,2,4-oxadiazol-5-yl}-N-(tetrahydro-2H-pyran-4-yl)-1H-pyrazolo[3,4-b]pyridin-4-amine, 1-Ethyl-5-(5-ethyl-1,2,4-oxadiazol-3-yl)-N-(tetrahydro-2H-pyran-4-yl)-1H-pyrazolo[3,4-b]pyridin-4-amine, 5-(5-{[4-(Dimethylamino)phenyl]methyl}-1,2,4-oxadiazol-3-yl)-1-ethyl-N-(tetrahydro-2H-pyran-4-yl)-1H-pyrazolo[3,4-b]pyridin-4-amine, 1-Ethyl-5-(5-{[4-(methyloxy)phenyl]methyl}-1,2,4-oxadiazol-3-yl)-N-(tetrahydro-2H-pyran-4-yl)-1H-pyrazolo[3,4-b]pyridin-4-amine, or 5-(3,8-Dioxa-1-azaspiro[4.5]dec-1-en-2-yl)-1-ethyl-N-(tetrahydro-2H-pyran-4-yl)-1H-pyrazolo[3,4-b]pyridin-4-amine;

or a salt thereof, e.g. a pharmaceutically acceptable salt thereof. The structures of each of the above-listed compounds are disclosed in Examples 85 to 191 hereinafter.

Preferably, the compound of formula (I) or the salt thereof is:

1-Ethyl-5-(5-methyl-1,3,4-oxadiazol-2-yl)-N-(tetrahydro-2H-pyran-4-yl)-1H-pyrazolo[3,4-b]pyridin-4-amine (the compound of Example 14), 5-(S-Tert-butyl-1,3,4-oxadiazol-2-yl)-1-ethyl-N-(tetrahydro-2H-pyran-4-yl)-1H-pyrazolo[3,4-b]pyridin-4-amine (the compound of Example 17), 1-Ethyl-5-{5-[(methylsulfonyl)methyl]-1,3,4-oxadiazol-2-yl}-N-(tetrahydro-2H-pyran-4-yl)-1H-pyrazolo[3,4-b]pyridin-4-amine (the compound of Example 23), 1-Ethyl-5-[5-(3-methyloxetan-3-yl)-1,3,4-oxadiazol-2-yl]-N-(tetrahydro-2H-pyran-4-yl)-1H-pyrazolo[3,4-b]pyridin-4-amine (the compound of Example 34), 1-Ethyl-5-{5-[(4-methylpiperazin-1-yl)methyl]-1,3,4-oxadiazol-2-yl}-N-(tetrahydro-2H-pyran-4-yl)-1H-pyrazolo[3,4-b]pyridin-4-amine (the compound of Example 35), 1-Ethyl-N-(tetrahydro-2H-pyran-4-yl)-5-[5-(tetrahydro-2H-pyran-4-yl)-1,3,4-oxadiazol-2-yl]-1H-pyrazolo[3,4-b]pyridin-4-amine (the compound of Example 38), also named: 1-Ethyl-5-[5-(morpholin-4-ylmethyl)-1,3,4-oxadiazol-2-yl]-N-(tetrahydro-2H-pyran-4-yl)-1H-pyrazolo[3,4-b]pyridin-4-amine (the compound of Example 39), 1-Ethyl-5-[5-(tetrahydrofuran-2-yl)-1,3,4-oxadiazol-2-yl]-N-(tetrahydro-2H-pyran-4-yl)-1H-pyrazolo[3,4-b]pyridin-4-amine (the compound of Example 44), 1-Ethyl-N-(tetrahydro-2H-pyran-4-yl)-5-[5-(tetrahydro-2H-pyran-4-ylmethyl)-1,3,4-oxadiazol-2-yl]-1H-pyrazolo[3,4-b]pyridin-4-amine (the compound of Example 77), or 1-Ethyl-5-{3-[2-oxo-2-(1-pyrrolidinyl)ethyl]-1,2,4-oxadiazol-5-yl}-N-(tetrahydro-2H-pyran-4-yl)-1H-pyrazolo[3,4-b]pyridin-4-amine (the compound of Example 84);

or a salt thereof.

A second aspect of the present invention provides a compound of formula (IA) or a salt thereof (in particular, a pharmaceutically acceptable salt thereof):

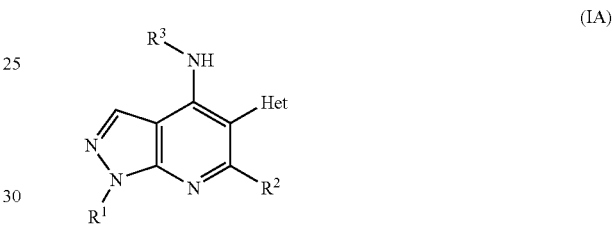

(IA)

wherein:
$R^1$ is $C_{1-4}$alkyl, $C_{1-3}$fluoroalkyl or —$(CH_2)_2OH$;
$R^2$ is a hydrogen atom (H), methyl or $C_1$fluoroalkyl;
$R^3$ is optionally substituted branched $C_{3-6}$alkyl, optionally substituted $C_{3-8}$cycloalkyl, optionally substituted phenyl, or an optionally substituted heterocyclic group of sub-formula (aa), (bb) or (cc):

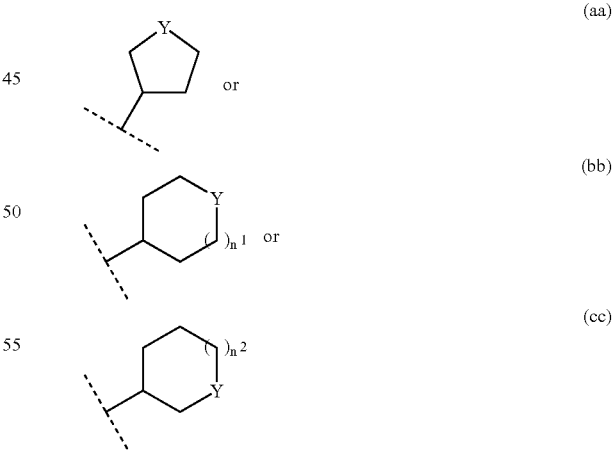

in which $n^1$ and $n^2$ independently are 1 or 2; and Y is O, S, $SO_2$, or $NR^4$; where $R^4$ is a hydrogen atom (H), $C_{1-2}$alkyl, $C_{1-2}$fluoroalkyl, $CH_2C(O)NH_2$, $C(O)NH_2$, $C(O)$—$C_{1-2}$alkyl, or $C(O)$—$C_1$fluoroalkyl;

wherein in $R^3$ the optionally substituted branched $C_{3-6}$alkyl is optionally substituted with one or two substituents being oxo (=O), OH, C$_{1-2}$alkoxy or C$_{1-2}$fluoroalkoxy; and wherein any such substituent is not substituted at the R$^3$ carbon atom attached (bonded) to the —NH— group of formula (IA);

wherein in R$^3$ the phenyl is optionally substituted with one substituent being fluoro, chloro, C$_{1-2}$alkyl, C$_{1-2}$fluoroalkyl, C$_{1-2}$alkoxy, C$_{1-2}$fluoroalkoxy or cyano;

wherein in R$^3$ the C$_{3-8}$cycloalkyl or the heterocyclic group of sub-formula (aa), (bb) or (cc) is optionally substituted with one or two substituents being oxo (=O), OH, C$_{1-2}$alkoxy, C$_{1-2}$fluoroalkoxy, or C$_{1-2}$alkyl; and wherein any OH, alkoxy or fluoroalkoxy substituent is not substituted at the R$^3$ ring carbon attached (bonded) to the —NH— group of formula (IA) and is not substituted at either R$^3$ ring carbon bonded to the Y group of the heterocyclic group (aa), (bb) or (cc);

and wherein Het is of sub-formula (i), (ii), (iii), (iv) or (v):

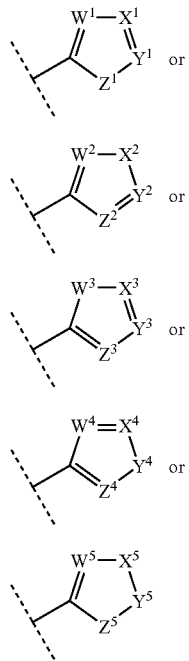

wherein:
W$^1$, W$^2$, W$^4$ and W$^5$ is N; and W$^3$ is NR$^W$;
X$^1$, X$^3$ and X$^4$ is N or CR$^X$; X$^2$ is O, S or NR$^X$; and X$^5$ is CR$^{X1}$R$^{X2}$;
Y$^1$, Y$^2$ and Y$^3$ is CR$^Y$ or N; Y$^4$ is O, S or NR$^Y$; and Y$^5$ is CR$^{Y1}$R$^{Y2}$;
Z$^1$ and Z$^5$ is O, S or NR$^Z$; and Z$^2$, Z$^3$ and Z$^4$ is N or CR$^Z$;

wherein:
R$^W$ is a hydrogen atom (H) or C$_{1-2}$alkyl;
R$^X$, R$^{X2}$, R$^Y$ and R$^{Y2}$ independently are:
  a hydrogen atom (H);
  C$_{1-8}$alkyl;
  C$_{3-6}$cycloalkyl optionally substituted by a C$_{1-2}$alkyl group;
  —(CH$_2$)$_n^{2a}$—C$_{3-6}$cycloalkyl optionally substituted, in the —(CH$_2$)$_n^{2a}$-moiety or in the C$_{3-6}$cycloalkyl moiety, by a C$_{1-2}$alkyl group, wherein n$^{2a}$ is 1, 2 or 3;
  —(CH$_2$)$_n^3$—SO$_2$—R$^5$ wherein n$^3$ is 1 or 2 and R$^5$ is C$_{1-3}$alkyl or —NH—C$_{1-2}$alkyl or phenyl;
  —(CH$_2$)$_n^4$—NR$^6$R$^7$ wherein n$^4$ is 0, 1, 2 or 3, and R$^6$ and R$^7$ independently are H, C$_{1-6}$alkyl e.g. C$_{1-4}$alkyl, C$_{3-6}$cycloalkyl, —CH$_2$—C$_{3-6}$cycloalkyl, —C(O)—C$_{1-2}$alkyl, —SO$_2$—C$_{1-2}$alkyl, phenyl, or benzyl (wherein the phenyl or benzyl are independently optionally substituted on the aromatic ring by one of fluoro, chloro, C$_{1-2}$alkyl, C$_1$fluoroalkyl, C$_{1-2}$alkoxy or C$_1$fluoroalkoxy); or R$^6$ and R$^7$ together are —(CH$_2$)$_n^5$—X$^5$—(CH$_2$)$_n^6$— in which n$^5$ and n$^6$ independently are 2 or 3 and X$^5$ is a bond, —CH$_2$—, O, or NR$^8$ wherein R$^8$ is H or C$_{1-2}$alkyl;
  —(CH$_2$)$_n^7$—O—R$^9$; wherein n$^7$ is 0, 1, 2 or 3 and R$^9$ is H or C$_{1-6}$alkyl; wherein n$^7$ is 0 only when the —(CH$_2$)$_n^7$—O—R$^9$ is bonded to a carbon atom in the Het ring; and wherein n$^7$ is not 0 when Het is of sub-formula (v) (i.e. n$^7$ is not 0 for R$^{X2}$ and for R$^{Y2}$);
  —C(O)—NR$^{10}$R$^{11}$ wherein R$^{10}$ and R$^{11}$ independently are H, C$_{1-6}$alkyl, C$_{3-6}$cycloalkyl, —CH$_2$—C$_{3-6}$cycloalkyl, phenyl, or benzyl (wherein the phenyl or benzyl are independently optionally substituted on the aromatic ring by one of fluoro, chloro, C$_{1-2}$alkyl, C$_1$fluoroalkyl, C$_{1-2}$alkoxy or C$_1$fluoroalkoxy); or R$^{10}$ and R$^{11}$ together are —(CH$_2$)$_n^8$—X$^6$—(CH$_2$)$_n^9$— in which n$^8$ and n$^9$ independently are 2 or 3 and X$^6$ is a bond, —CH$_2$—, O, or NR$^{12}$ wherein R$^{12}$ is H or C$_{1-2}$alkyl;
  —C(O)—OR$^{13}$ wherein R$^{13}$ is H, C$_{1-6}$alkyl, C$_{3-6}$cycloalkyl, —CH$_2$—C$_{3-6}$cycloalkyl, phenyl, or benzyl (wherein the phenyl or benzyl are independently optionally substituted on the aromatic ring by one of fluoro, chloro, C$_{1-2}$alkyl, C$_1$fluoroalkyl, C$_{1-2}$alkoxy or C$_1$fluoroalkoxy);
  —C(O)—R$^{13a}$ wherein R$^{13a}$ is a hydrogen atom (H), C$_{1-6}$alkyl, C$_{1-2}$fluoroalkyl, C$_{3-6}$cycloalkyl, —CH$_2$—C$_{3-6}$ cycloalkyl, benzyl, or phenyl; wherein the phenyl or benzyl are independently optionally substituted on the aromatic ring by one of fluoro, chloro, C$_{1-2}$alkyl, C$_1$fluoroalkyl, C$_{1-2}$alkoxy or C$_1$fluoroalkoxy,
  a 4-, 5-, 6- or 7-membered saturated heterocyclic ring containing one O ring atom or one NR$^{14}$ ring group wherein R$^{14}$ is H or C$_{1-4}$alkyl, said heterocyclic ring being optionally substituted (at a position or positions other than any NR$^{14}$ position) by one oxo (=O) and/or one C$_{1-4}$alkyl substituent; or
  —(CH$_2$)$_n^{10}$—Ar wherein n$^{10}$ is 0, 1 or 2 and
    (i) Ar is phenyl optionally substituted by one or two substituents being fluoro, chloro, C$_{1-2}$alkyl, C$_{1-2}$fluoroalkyl, C$_{1-2}$alkoxy, C$_{1-2}$fluoroalkoxy or cyano; or
    (ii) Ar is an optionally substituted 5- or 6-membered heterocyclic aromatic ring containing 1, 2 or 3 heteroatoms selected from O, N or S; and wherein when the heterocyclic aromatic ring Ar contains 2 or 3 heteroatoms, one is selected from O, N and S and the remaining heteroatom(s) are N; and wherein the heterocyclic aromatic ring Ar is optionally substituted by one or two C$_{1-4}$alkyl groups;

R$^{X1}$ and R$^{Y1}$ independently are a hydrogen atom (H), C$_{1-2}$alkyl or C$_1$fluoroalkyl; and
R$^Z$ is a hydrogen atom (H) or C$_{1-2}$alkyl.

Preferably, in formula (IA), when R$^3$ is the heterocyclic group of sub-formula (bb), n$^1$ is 1, and Y is NR$^4$, then R$^4$ is not C$_{1-2}$alkyl, C$_{1-2}$fluoroalkyl or CH$_2$C(O)NH$_2$.

Examples 1-48 are examples of compounds or salts of the second aspect of the invention (Formula (IA)).

The preferred or optional features for the compound of formula (IA) or salt thereof are the same as or similar to the preferred or optional features for the compound or salt of formula (I), with all necessary changes (for example to the formula, to the R groups and/or to substituents) having been made. Generally, whenever formula (I) is mentioned herein, then in alternative embodiments the statement mentioning formula (I) applies to formula (IA), with all necessary changes having been made.

Salts, Solvates, Isomers, Tautomeric Forms, Molecular Weights, etc.

Because of their potential use in medicine, the salts of the compounds of formula (I) are preferably pharmaceutically acceptable. Suitable pharmaceutically acceptable salts can include acid or base addition salts.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt. In one embodiment, the pharmaceutically acceptable acid addition salt can be a hydrobromide, hydrochloride, sulfate, nitrate, phosphate, succinate, maleate, acetate, fumarate, citrate, tartrate, benzoate, p-toluenesulfonate, methanesulfonate or naphthalenesulfonate salt.

A pharmaceutically acceptable base addition salt can be formed by reaction of a compound of formula (I) with a suitable inorganic or organic base (e.g. triethylamine, ethanolamine, triethanolamine, choline, arginine, lysine or histidine), optionally in a suitable solvent such as an organic solvent, to give the base addition salt which is usually isolated for example by crystallisation and filtration.

Other suitable pharmaceutically acceptable salts include pharmaceutically acceptable metal salts, for example pharmaceutically acceptable alkali-metal or alkaline-earth-metal salts such as sodium, potassium, calcium or magnesium salts; in particular pharmaceutically acceptable metal salts of one or more carboxylic acid moieties that may be present in the the compound of formula (I).

Other non-pharmaceutically acceptable salts, eg. oxalates, may be used, for example in the isolation of compounds of the invention, and are included within the scope of this invention.

The invention includes within its scope all possible stoichiometric and non-stoichiometric forms of the salts of the compounds of formula (I).

Also included within the scope of the invention are all solvates, hydrates and complexes of compounds and salts of the invention.

Certain groups, substituents, compounds or salts included in the present invention may be present as isomers. The present invention includes within its scope all such isomers, including racemates, enantiomers and mixtures thereof.

Certain of the groups, e.g. heteroaromatic ring systems, included in compounds of formula (I) or their salts may exist in one or more tautomeric forms. The present invention includes within its scope all such tautomeric forms, including mixtures. For example, when Het is of sub-formula (i), $Y^1$ is $CR^Y$, and $X^1$ is $CR^X$ wherein $R^X$ is OH, then the compounds of formula (I) or their salts include the keto form (K1), the enol form (E1), and mixtures thereof, as shown below, unless otherwise indicated; and when Het is of sub-formula (i) and $Y^1$ is $CR^Y$ wherein $R^Y$ is OH, then the compounds of formula (I) or their salts include the keto form (K2), the enol or hydroxy-imine form (E2), and mixtures thereof, as shown below, unless otherwise indicated:

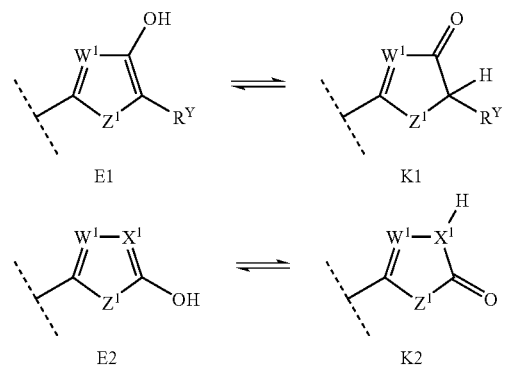

Especially when intended for oral medicinal use, the compound of formula (I) can optionally have a molecular weight of 1000 or less, for example 800 or less, in particular 650 or less or 600 or less. Molecular weight here refers to that of the unsolvated "free base" compound, that is excluding any molecular weight contributed by any addition salts, solvent (e.g. water) molecules, etc.

Synthetic Process Routes

The following processes can be used to make the compounds of formula (I). The methods are sometimes illustrated for the circumstance where $R^2$ is H or Me. However, some or all of these processes are thought to be usable with appropriate modification, e.g. of starting materials and reagents, for making compounds of Formula (I) wherein $R^2$ is $C_1$fluoroalkyl.

Process A

Compounds of formula (I) which are compounds of Formula I(ia) (that is, compounds of formula (I) wherein Het is of sub-formula (ia)) can be prepared by the cyclisation reaction of a compound of Formula II, for example in the presence of a dehydrating agent such as phosphorous oxychloride ($POCl_3$) or Burgess reagent [(Methoxycarbonylsulphamoyl) triethylammonium hydroxide], and/or preferably in a suitable solvent (e.g. organic solvent, preferably anhydrous) such as acetonitrile (e.g. for $POCl_3$) or THF and/or DMF (e.g. for Burgess reagent). The reaction may require heating, for example heating to from about 70 to about 150° C. or heating to from about 70 to about 120° C. or heating to from about 70 to about 90° C.:

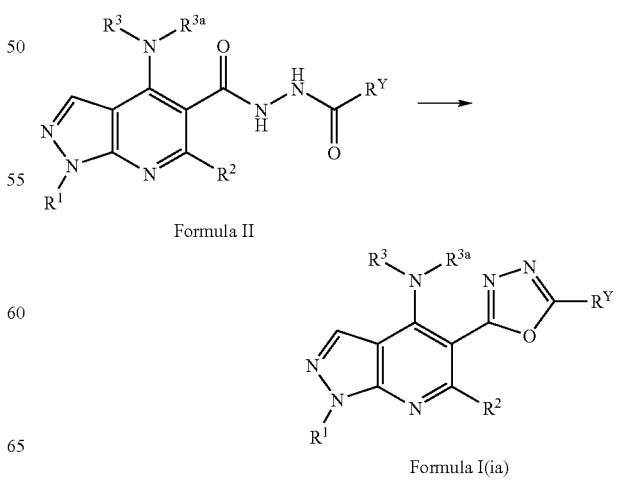

For the Formula II to Formula I(ia) cyclisation reaction, the conditions can for example be as described in (a) Examples 1-3 or 43 (POCl$_3$ and acetonitrile), or (b) in Examples 32, 34-37, 35 (alternative synthesis), 3840, 44, 66 or 97-125 (Burgess reagent, with THF and/or DMF).

Compounds of Formula II may themselves be prepared by reacting a compound of Formula III with a suitably substituted hydrazine derivative of formula R$^Y$CONHNH$_2$, under standard coupling conditions. For example a coupling reagent such as 1-(3-dimethylaminopropyl)-3-ethylcarbodiimide hydrochloride (EDC) may be used e.g. in the presence of hydroxybenzotriazole (HOBT), for example in a suitable solvent such as DMF:

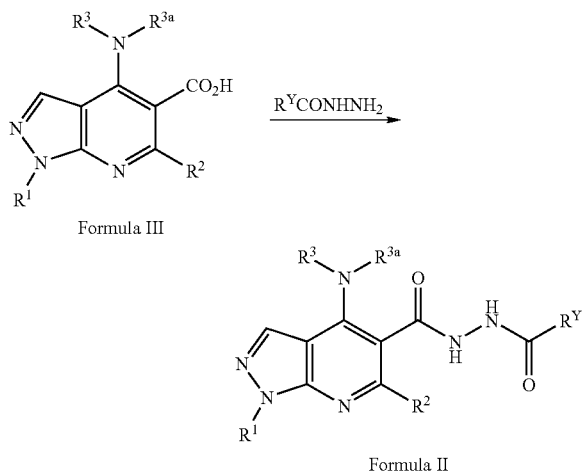

Where the required hydrazine derivative R$^Y$CONHNH$_2$ is not readily available, compounds of Formula II may alternatively be prepared by initially reacting a compound of Formula III with a carbazate ROCONHNH$_2$ such as t-butylcarbazate $^t$BuOCONHNH$_2$ under coupling conditions to form a compound of formula IV. For example a coupling reagent such as EDC may be used, e.g. in the presence of hydroxybenzotriazole, for example in a suitable solvent such as DMF:

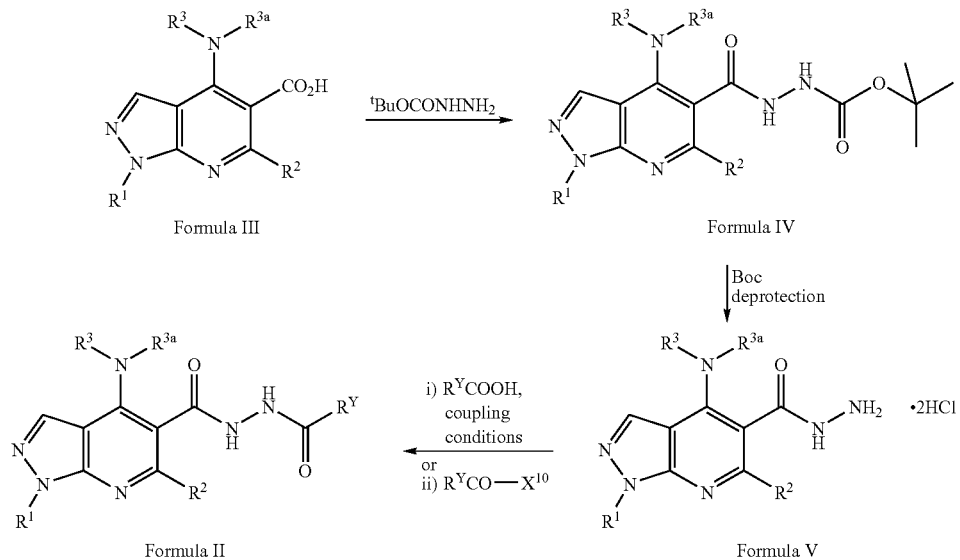

Subsequent Boc-deprotection of the resultant acid hydrazide derivative (compound of Formula IV) to afford a hydrazide derivative of Formula V, can be achieved using a dilute acid such as 2M hydrochloric acid in an organic solvent such as dioxane.

The compound of Formula V can be converted to the compound of Formula II (the desired hydrazide derivative). This can be achieved by reaction of the compound of Formula V with an acid of formula R$^Y$CO$_2$H under coupling conditions. For example a coupling agent such as EDC may be used e.g. in the presence of hydroxybenzotriazole (HOBT), for example in a suitable solvent such as DMF. Alternatively, an activated acid derivative of formula R$^Y$CO—X$^{10}$ where X is a leaving group such as chloro (acid chloride) or —O—CO—R$^{30}$ or —O—SO$_2$—R$^{30}$ (where R$^{30}$ can e.g. be R$^Y$ or alkyl or aryl such as methyl, t-butyl or p-methylphenyl) may be used to effect formation of a hydrazide of Formula II, through reaction with a hydrazide derivative of Formula V.

Compounds of Formula III can be prepared by hydrolysis of an ester of Formula VI (for example R$^4$ can be C$_{1-6}$alkyl such as Et), for example according to the method described by Yu et. al. in *J. Med. Chem.*, 2001, 44, 1025-1027. This hydrolysis procedure usually involves reaction with a base such as sodium hydroxide or potassium hydroxide in a solvent such as ethanol or dioxane (e.g. NaOH in EtOH), one or both solvents preferably containing some water:

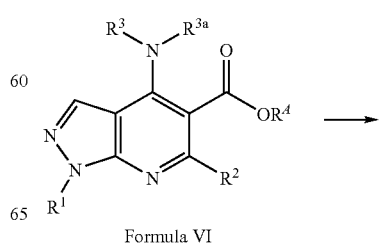

-continued

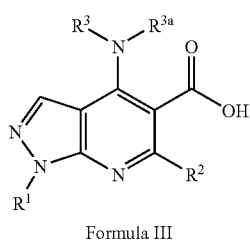

Formula III

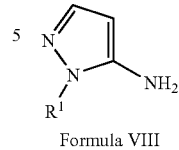

Formula VIII

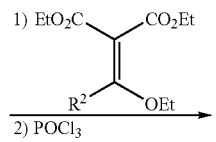

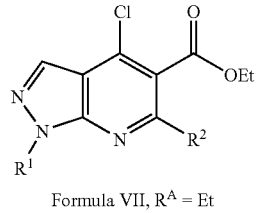

Formula VII, $R^A$ = Et

Compounds of Formula VI can be prepared, e.g. according to the method described by Yu et. al. in *J. Med. Chem.*, 2001, 44, 1025-1027, by reaction of a compound of Formula VII with an amine of Formula $R^3R^{3a}NH$. The reaction is best carried out in the presence of a base such as triethylamine or diisopropylethyl amine in a solvent such as ethanol or dioxane (e.g. $NEt_3$ in EtOH) and may require heating:

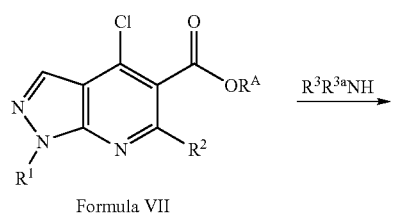

Formula VII

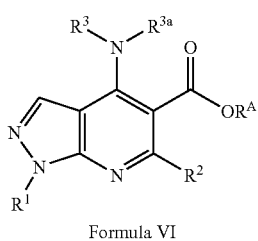

Formula VI

Many amines of Formula $R^3R^{3a}NH$, e.g. those amines wherein $R^3R^{3a}N$ are of sub-formulae (a) to (t2), are either commercially available, or syntheses therefor have been published and/or described herein, or they can be prepared from commercially available or synthesizable compounds e.g. from other amines of Formula $R^3R^{3a}NH$ or derivatives thereof. For amines $R^3R^{3a}NH$ whose preparations and/or specific commercial sources are described herein, see e.g. Intermediates 21, 21A, 25, 50, 54-57, and 140-163.

Compounds of Formula VII are also described in the above reference and can be prepared first by reaction of a compound of Formula VIII with, for example, diethyl (ethoxymethylene) malonate ($R^2$=H, to afford $R^4$=Et) or diethyl 2-(1-ethoxyethylidene)malonate ($R^2$=Me, to afford $R^4$=Et), e.g. with heating, followed by reaction with phosphorous oxychloride, again preferably with heating. See for example Intermediate 1 synthesis and G. Yu et. al., *J. Med. Chem.*, 2001, 44, 1025-1027 hereinafter, where $R^2$=H and $R^1$=ethyl; and see Intermediate 58 synthesis hereinafter where $R^2$=Me and $R^1$=ethyl:

Where, for example, the desired amino pyrazole of Formula VIII is not commercially available, preparation of the Formula VIII pyrazole can be achieved, for example using methods described by Dorgan et. al. in *J. Chem. Soc., Perkin Trans.* 1980, 1 (4), 938-42, involving reaction of cyanoethyl hydrazine with a suitable aldehyde $R^{1a}CHO$ in a solvent such as ethanol, with heating, followed by reduction, for example reduction with sodium in a solvent such as t-butanol. $R^{1a}$ should be chosen so as to contain one less carbon atom than $R^1$, for example $R^{1a}$=methyl will afford $R^1$=ethyl.

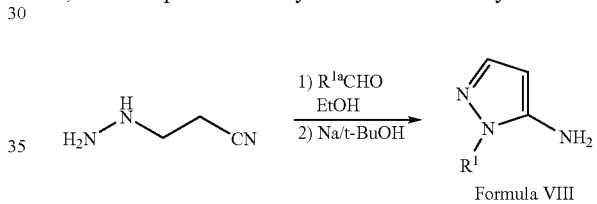

Formula VIII

Alternatively, e.g. where the desired amino pyrazole of Formula VIII is not commercially available, preparation of the compound of Formula VI can be achieved from the compound of Formula VII (e.g. Intermediate 1 wherein $R^1$=ethyl), using a generalised version of the reaction scheme shown in Example 43, especially that part relating to conversion of Intermediate 1 to Intermediate 38. In this method: the 4-chloro pyrazolopyridine of Formula VII (e.g. Intermediate 1) is optionally converted to the 4-alkoxy (e.g. $C_{1-4}$alkoxy such as ethoxy) pyrazolopyridine (e.g. Intermediate 35); the $R^1$ group is removed (to e.g. Intermediate 36 wherein $R^1$ is H rather than alkyl), the 4-amino $R^3R^{3a}N$ group is inserted by displacing the 4-chloro or 4-alkoxy group by reaction with $R^3R^{3a}NH$ (e.g. to Intermediate 37); and the pyrazolopyridine is alkylated at N-1 by reacting it with $R^1$—$X^{40}$ where $X^{40}$ is a group displaceable by the N-1 nitrogen of the pyrazolopyridine in order to re-insert the desired $R^1$ group (e.g. Intermediate 38 synthesis). $X^{40}$ can for example be a halogen, e.g. Cl, Br or I; or $X^{40}$ can be —O—$SO_2$—$R^{40}$ where $R^{40}$ is $C_{1-4}$alkyl, $C_{1-2}$fluoroalkyl, or phenyl optionally substituted by $C_{1-2}$alkyl.

Process B

Compounds of formula (I) which are compounds of Formula I(ia) (that is, compounds of formula (I) wherein Het is of sub-formula (ia)) can alternatively be prepared by reaction of a compound of Formula IX with an amine of formula $R^3R^{3a}NH$, preferably in a solvent (e.g. organic solvent) such as ethanol or acetonitrile, and/or preferably in the presence of a base such as DIPEA. Heating may be required to effect the conversion:

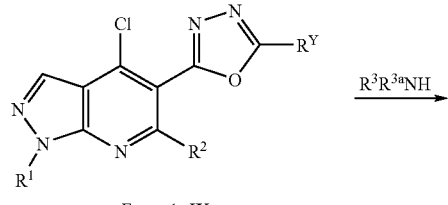

Formula IX

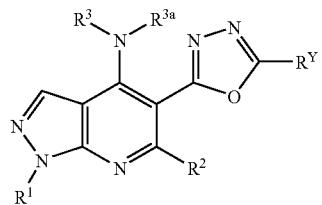

Formula I(ia)

For the reaction of a compound of Formula IX with an amine of formula $R^3R^{3a}NH$ to prepare the compound of Formula I(ia), the reaction conditions, e.g. solvents, mole ratios, temperatures and/or reaction times, can optionally be as described in Examples 9, 10-11 and/or 12-27.

The reaction of Formula IX with $R^3R^{3a}NH$ to give Formula I(ia) can be generalised for any compound of Formula (I), containing any Het group as defined herein, starting from a compound of Formula IXa:

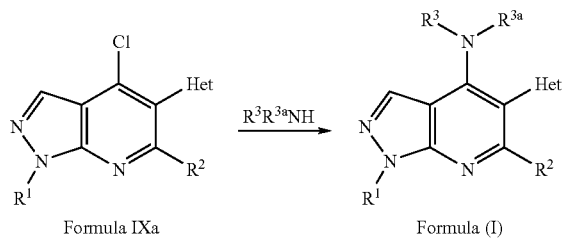

Formula IXa                Formula (I)

Compounds of Formula IX can themselves be prepared by cyclisation of a compound of Formula X, preferably in the presence of a dehydrating agent such as phosphorous oxychloride or Burgess reagent [(Methoxycarbonylsulphamoyl)triethylammonium hydroxide], in a suitable solvent (e.g. organic solvent, preferably anhydrous) such as acetonitrile (e.g. for $POCl_3$) or THF and/or DMF (e.g. for Burgess reagent). The reaction may require heating, for example heating to from about 70 to about 150° C. or heating to from about 70 to about 120° C. or heating to from about 70 to about 90° C.:

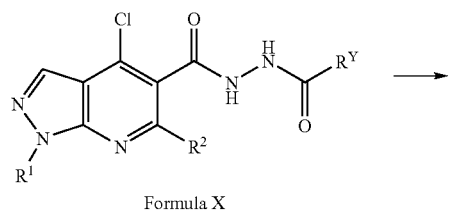

Formula X

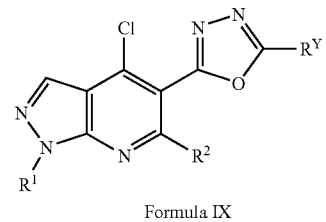

Formula IX

Compounds of Formula X can be prepared by initial activation of an acid of Formula XI, for example with an amide coupling reagent such as EDC/HOBT or with thionyl chloride, followed by reaction of the thus formed activated intermediate with an acid hydrazide of Formula $R^YCONHNH_2$:

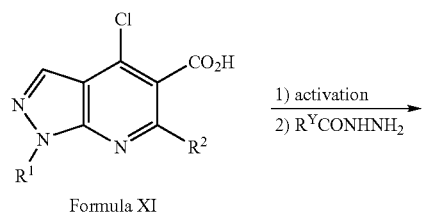

Formula XI

Formula X

Examples of reactions of the compound of Formula XI to Formula X and of the compound of Formula X to Formula IX are presented in Intermediates 12 to 15.

Acids of Formula XI can themselves be prepared by hydrolysis of an ester of Formula VII (e.g. as described in Process A) using a base such as potassium hydroxide in a solvent such as aqueous dioxane dioxane/water):

Formula VII                Formula XI

Process C

Compounds of Formula XII (that is, compounds of formula (I) wherein Het is of sub-formula (ib)) can be prepared by reaction of a compound of Formula II with a reagent capable of inserting sulfur, such as Lawesson's reagent, usually in a suitable solvent such as acetonitrile. The reaction may require heating:

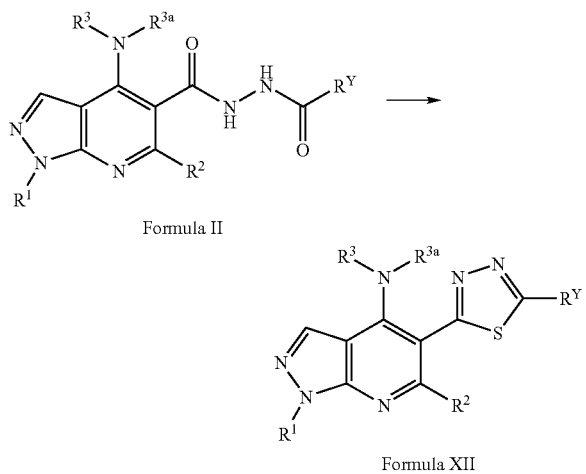

Formula II

Formula XII

The reaction conditions, e.g. solvents, mole ratios, temperatures and/or reaction times, can optionally be as described in Examples 4, 5 or 6.

Process D

Compounds of Formula XIII [which are compounds of formula (I) wherein Het is of sub-formula (ic)] can be prepared by reaction of a compound of Formula VI can be $C_{1-6}$alkyl such as Et) with an amidoxime of formula $R^XC(=NOH)NH_2$, preferably in the presence of a base such as sodium ethoxide and/or preferably in a suitable solvent (e.g. anhydrous and/or organic solvent) such as ethanol, and preferably in the presence of molecular sieves (e.g. 4 Angstrom and/or powdered molecular sieves) or under other conditions effective for removing water. The reaction mixture may optionally be heated, for example to reflux:

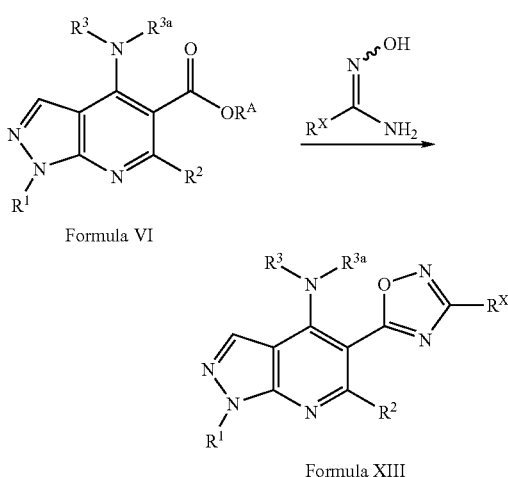

Formula VI

Formula XIII

The reaction conditions, e.g. solvents, mole ratios, temperatures and/or reaction times, can optionally be as described in Examples 7, 28-29, 30, 31, 48, 82-84, 92, 93 and/or 178-187.

Process E

Compounds of Formula XIV (which are compounds of formula (I) wherein Het is of sub-formula (if)) can be prepared by reaction of a compound of Formula XV with a suitable acetimidate $R^X$—$C(=NH)OR^E$, where $R^E$ is $C_{1-6}$alkyl e.g. methyl, (such as methyl acetimidate ($R^X$=Me)), preferably in the presence of a base (such as triethylamine or sodium ethoxide) and/or in a suitable solvent (e.g. anhydrous and/or organic solvent) such as ethanol:

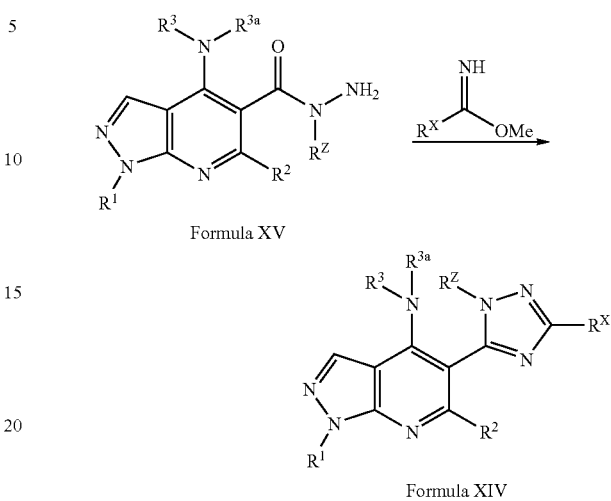

Formula XV

Formula XIV

Compounds of Formula XV may themselves be prepared by reaction of a compound of Formula III with a suitably substituted hydrazine derivative of Formula $R^ZNHNH_2$, under coupling conditions. For example a coupling agent such as EDC may be used, e.g. in the presence of hydroxybenzotriazole (HOBT), in a suitable solvent such as DMF:

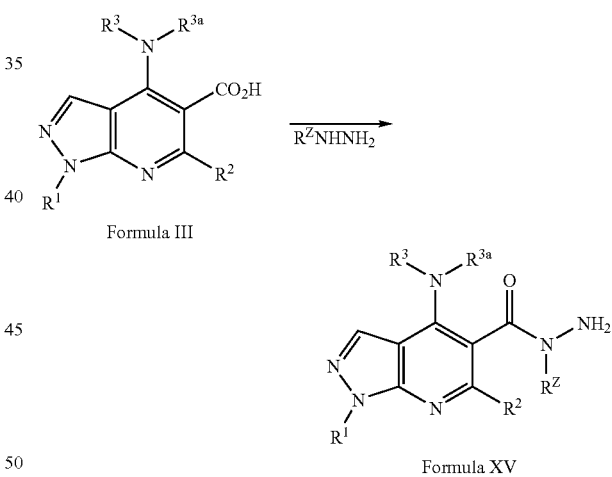

Formula III

Formula XV

Process F

To make a compound of formula (I) wherein Het is of sub-formula (id) (optionally substituted 1,3-oxazol-2-yl), methods known to the skilled person can be used.

For example, the 5-carboxylic acid compound of Formula III can be converted directly or indirectly to a compound of formula (I) wherein Het is of sub-formula (id) (i.e. to a 5-(optionally-substituted 1,3-oxazol-2-yl)-pyrazolopyridine). Alternatively or additionally, a compound of formula (I), wherein Het is of sub-formula (va) in which $R^{X1}$ and R are H and $R^{X1}$ is $R^X$ and $R^{Y1}$ is $R^Y$ [i.e. the corresponding 5-(optionally-substituted 4,5-dihydro-1,3-oxazol-2-yl)-pyrazolopyridine], can be dehydrogenated to a compound of formula (I) wherein Het is of sub-formula (id); e.g. by the method shown in Example 41 (DBU, CCl₄, CH₃CN, Pyridine) or a modification of this method or by an analogous method for example using an oxidising agent.

The dehydrogenation (oxidation) of the 4,5-dihydro-1,3-oxazol-2-yl compound of formula (I) (wherein Het is of sub-formula (va) in which $R^{X1}$ and $R^{Y1}$ are H and $R^{X1}$ is $R^X$ and $R^{Y1}$ is $R^Y$) to the corresponding 1,3-oxazol-2-yl compound of formula (I) wherein Het is of sub-formula (id) can be carried out using reagents and conditions known to the skilled man (see for example the following reviews: T. G. Gant et al., *Tetrahedron*, 1994, 50(8), 2297-2360; M. Reuman et al., *Tetrahedron*, 1985, 41(5), 837-860; and references cited therein). For this dehydrogenation reaction, preferably an oxidising agent is used such as nickel peroxide, manganese dioxide (MnO₂), or 2,3-dichloro-5,6-dicyano-1,4-benzoquinone (DDQ).

A compound of formula (I) wherein Het is of sub-formula (va) can be prepared by cyclisation of a compound of Formula XXVIII, for example in the presence of Burgess reagent and/or preferably in a suitable solvent (e.g. organic solvent, preferably anhydrous) such as THF.

prepared by reaction of a compound of the Formula XVII with an amine of Formula $R^{10}R^{11}NH$, under coupling conditions. Standard coupling conditions can be used known to the skilled person. For example a coupling agent such as TBTU may be used, preferably in the presence of hydroxybenzotriazole. However, it is more preferable that the coupling agent is oxalyl chloride, which in the reaction forms the corresponding acid chloride from the carboxylic acid of the compound of Formula XVII; in this embodiment it is preferable that the acid chloride is not isolated, i.e. the solvent in which it is formed is preferably not removed to a substantial extent. Preferably, whatever the coupling agent/coupling conditions, the reaction is carried out in the presence of a base such as diisopropylethylamine, and/or in a suitable solvent (e.g. organic solvent, preferably anhydrous) such as DMF and/or dicloromethane.

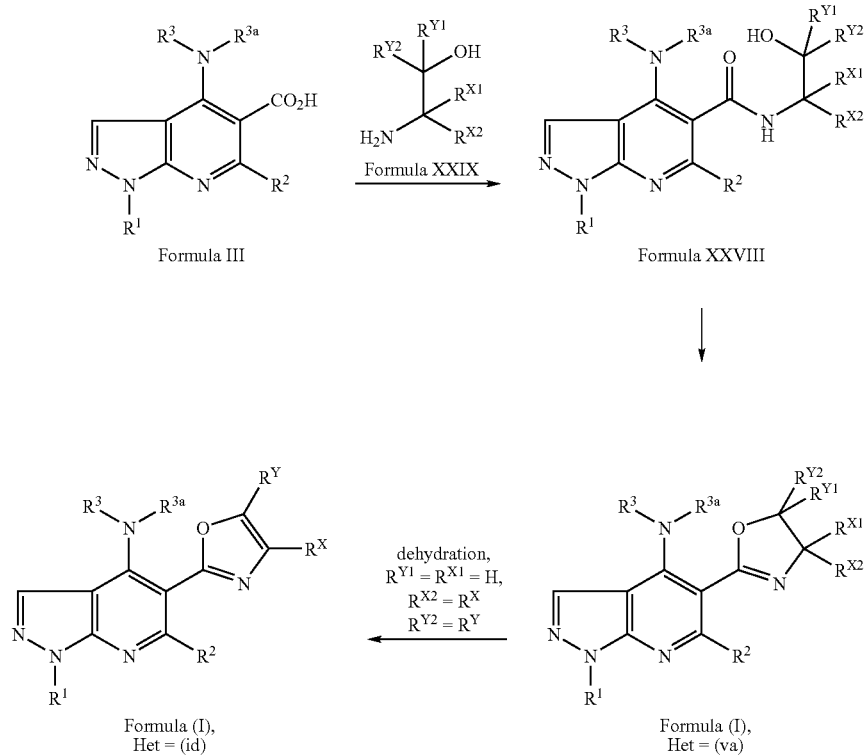

The compound of Formula XXVIII can be prepared from the compound of Formula III by reaction with the compound of Formula XXIX under coupling conditions (e.g. EDC with or without HOBT), optionally in the presence of a base such as Et₃N, and preferably in a suitable solvent such as DMF.

Process G

Compounds of the invention of Formula XVI (1,2,4-oxadiazoles), which are compounds of formula (I) wherein Het is of sub-formula (ic) and $R^X$ is —CH₂C(O)NR¹⁰R¹¹, can be

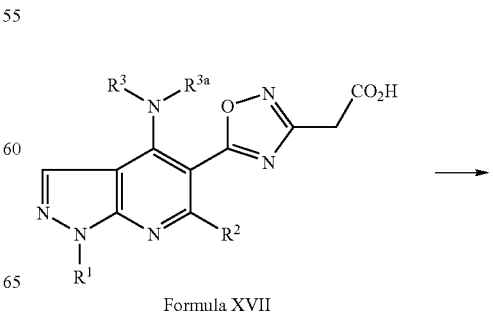

Formula XVII

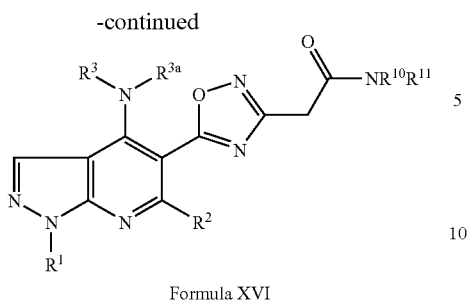

Formula XVI

The reaction conditions for the Formula XVII to Formula XVI reaction, e.g. solvents, mole ratios, temperatures and/or reaction times, can optionally be as described in Examples 85-90, 95-96 and/or 148-155.

Compounds of Formula XVII may themselves be prepared by reaction of a compound of Formula XVII ($R^G$ is preferably $^tBu$) with a hydrolysing agent (e.g. an acid such as trifluoroacetic acid) in a solvent such as dichloromethane:

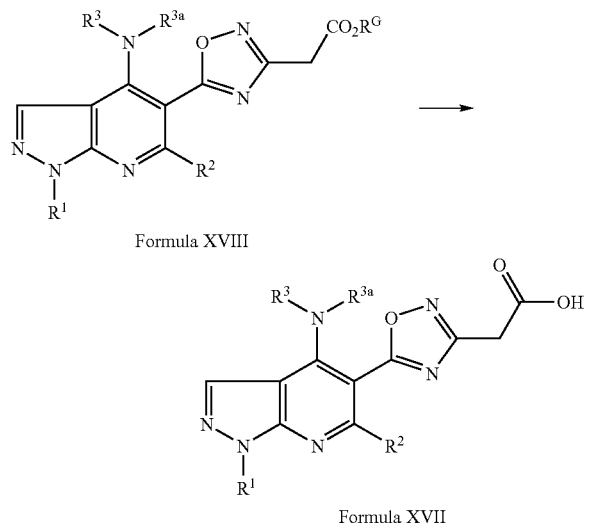

Formula XVIII

Formula XVII

Compounds of Formula XVIII can be prepared by reaction of a compound of Formula VI ($R^4$=H) with an amidoxime of formula $R^GOC(=O)CH_2C(=NOH)NH_2$ and a coupling agent, for example TBTU, preferably in the presence of hydroxybenzotriazole, preferably in the presence of a base such as diisopropylethylamine and/or in a suitable solvent such as DMF, followed by reaction with 1,1'-carbonyldiimidazole:

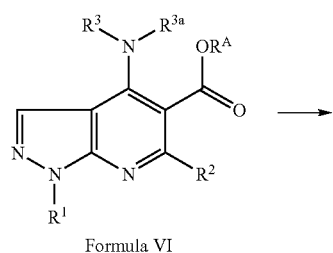

Formula VI

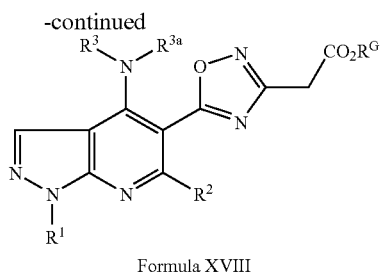

Formula XVIII

Process H

Compounds of Formula XIX, which are compounds of formula (I) wherein Het is of sub-formula (ic) and $R^X$ is —$CH_2$—$NR^6R^7$ wherein $R^7$ is $C(O)R^{17}$, may be prepared from compounds of Formula XX. For example, this can be by reaction of the compound of Formula XX with a carboxylic acid $R^{17}COOH$ in the presence of a coupling agent, for example TBTU, preferably with hydroxybenzotriazole, and preferably in the presence of a base such as diisopropylethylamine in a suitable solvent such as DMF. Alternatively or additionally, the compound of Formula XX can be reacted with an activated derivative of the carboxylic acid moiety of $R^{17}COOH$ (e.g. by reaction with an acid chloride $R^{17}C(O)Cl$), preferably in the presence of a base such as diisopropylethylamine and/or in a suitable solvent (e.g. organic) such as dichloromethane and/or chloroform.

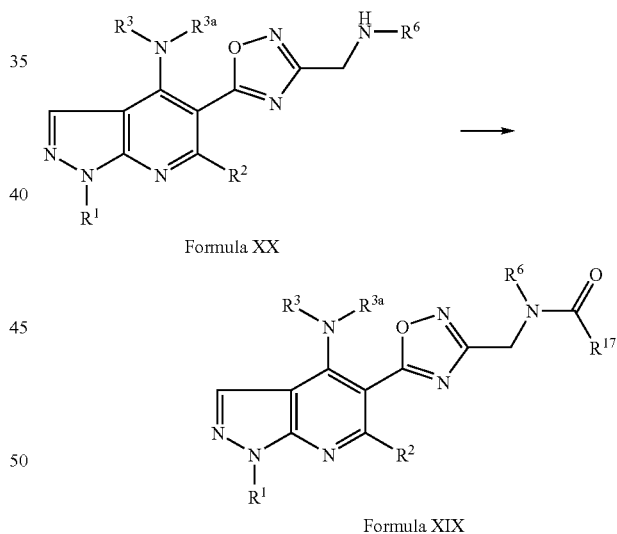

Formula XX

Formula XIX

The reaction conditions for the Formula XX to Formula XIX reaction, e.g. solvents, mole ratios, temperatures and/or reaction times, can optionally be as described in any of Examples 159-165.

Compounds of Formula XX, which are compounds of formula (I) wherein Het is of sub-formula (ic) and $R^X$ is —$CH_2$—$NR^6R^7$ wherein $R^7$ is H, may be prepared by deprotecting compounds of Formula XX wherein $R^H$ is benzyl or $C_{1-6}$alkyl such as $^tBu$, e.g. by reaction with an acid such as trifluoroacetic acid (e.g. where $R^H$ is $C_{1-6}$alkyl such as $^tBu$) or by hydrogenation (e.g. where $R^H$ is benzyl), preferably in a suitable solvent such as dichloromethane:

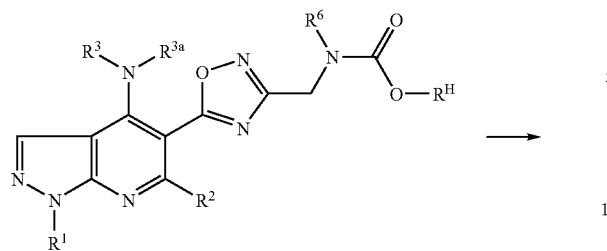

Formula XXI

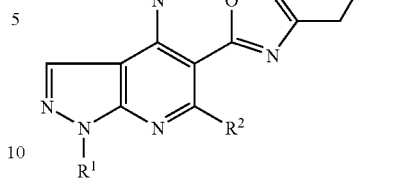

Formula XX

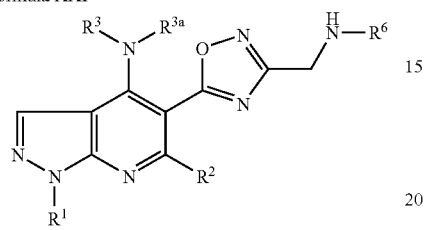

Formula XX

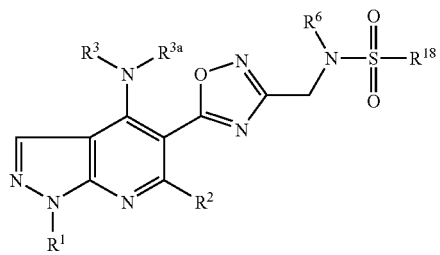

Formula XXII

Compounds of Formula XXI can be prepared by reaction of a compound of Formula VI (but wherein $R^A$ is OH) with an amidoxime of formula $R^HOC(=O)N(R^6)CH_2C(=NOH)NH_2$ and a coupling agent, for example TBTU, preferably in the presence of hydroxybenzotriazole, and preferably in the presence of a base such as diisopropylethylamine, and/or preferably in a suitable solvent such as DMF, followed by reaction with a base such as 1,8-diazabicyclo[5.4.0]undec-7-ene:

Formula VI

Formula XXI

Process I

Compounds of Formula XXII, which are compounds of formula (I) wherein Het is of sub-formula (ic) and $R^X$ is —$CH_2$—$NR^6R^7$ wherein $R^7$ is —$S(O)_2R^{18}$, may be prepared from compounds of Formula XX by reaction with a sulphonyl chloride $R^{18}S(O)_2Cl$, preferably in the presence of a base such as triethylamine and/or pyridine, and/or preferably in a suitable solvent (e.g. organic) such as dichloromethane and/or chloroform:

The reaction conditions, e.g. solvents, mole ratios, temperatures and/or reaction times, can optionally be as described in any of Examples 166-172.

Process J

Compounds of Formula XXIII are compounds of formula (I) wherein Het is of sub-formula (ic) and $R^X$ is —$CH_2$—$NR^6R^7$, wherein $R^6$ and $R^7$ together are —$(CH_2)_{n^5}$—$X^5$—$(CH_2)_{n^6}$— in which $n^5$ and $n^6$ independently are 2 or 3, and wherein the ring formed by $NR^6R^7$ is substituted by one oxo (=O) substituent at a carbon atom within $(CH_2)_{n^6}$ which carbon atom is bonded to the nitrogen.

Compounds of Formula XXIII can be prepared by reaction of a compound of the type Formula XX wherein $R^6$=H with acid chlorides of the type $X^J$—$(CH_2)_{n^5}$—$X^5$—$(CH_2)_{(n^6-1)}$—COCl, where $X^J$ is a leaving group, preferably in the presence of a base such as triethylamine and/or preferably in a suitable solvent, for example dichloromethane or tetrahydrofuran, preferably followed by treatment with a base such as sodium hydride in a suitable solvent such as DMF. The leaving group $X^J$ can for example be a halogen atom such as Cl, Br or I; or $X^J$ can for example be —O—$SO_2$—$R^J$ where $R^J$ is $C_{1-4}$alkyl, $C_{1-2}$fluoroalkyl, or phenyl optionally substituted by $C_{1-2}$alkyl e.g. 4-methylphenyl.

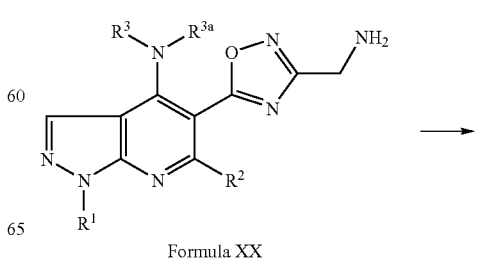

Formula XX

-continued

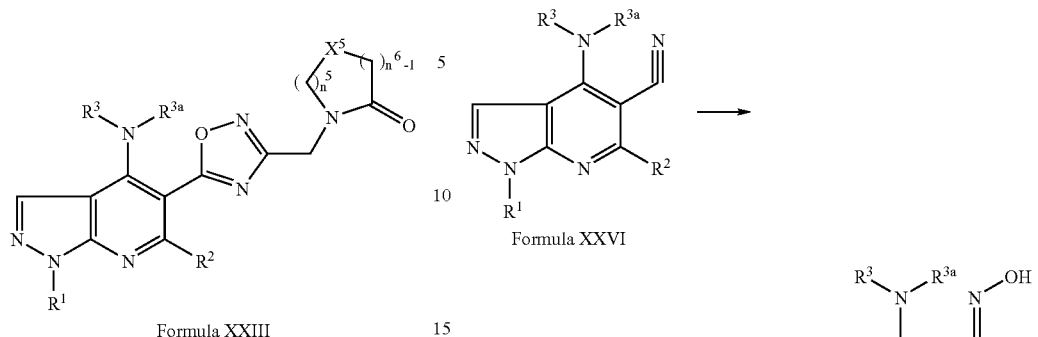

Formula XXIII

For examples of reaction conditions for the Formula XX to Formula XXII reaction, see for example Intermediates 119 and/or 120 and/or subsequent Examples 173 and/or 174.

Process K

Compounds of the type Formula XXIV, which are compounds of formula (I) wherein Het is of sub-formula (iia), can be prepared from compounds of the type Formula XXV by reaction with $R^Y C(O)X^K$ where $X^K$ is a leaving group, preferably in a solvent such as acetic acid, pyridine, diglyme and/or dichloromethane. $X^K$ can for example be chloro; or $R^Y C(O)X^K$ can be an anhydride such as $[R^Y(C=O)]_2O$; or $R^Y C(O)X^K$ can be an activated carboxylic acid derivative prepared from the reaction of $R^Y C(O)OH$ with a coupling reagent such as EDC or TBTU with or without the presence of HOBT.

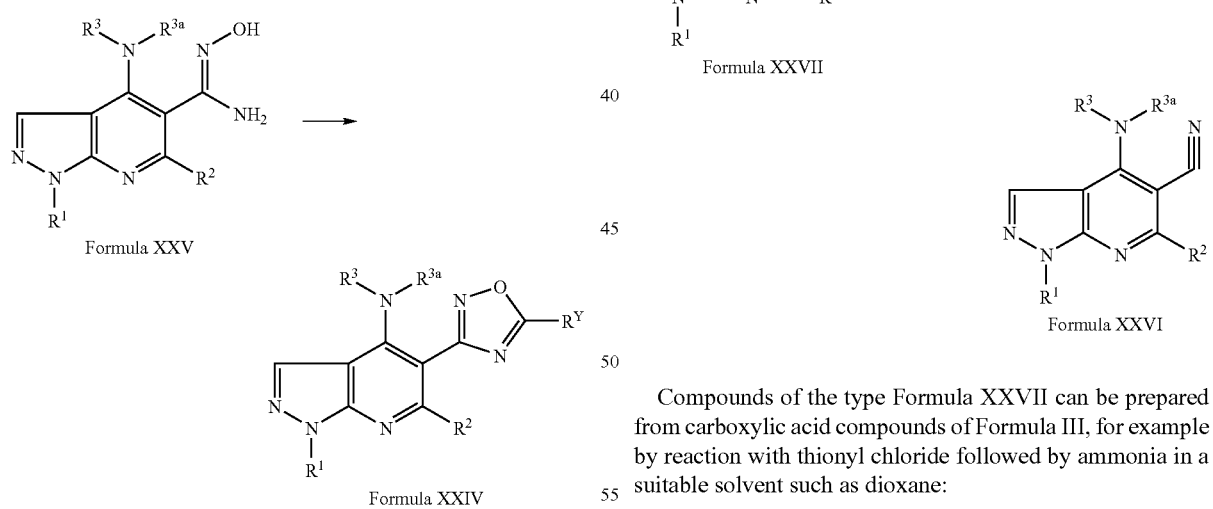

Formula XXV

Formula XXIV

For the Formula XXV to Formula XXIV reaction, the reaction conditions can for example be as described in Examples 188, 189 and/or 190.

Compounds of the type Formula XXV can be prepared from compounds of the type Formula XXVI by reaction with hydroxylamine or a hydroxylamine salt, preferably in the presence of a base such as potassium carbonate, sodium alkoxide or a tertiary amine, and/or preferably in a suitable solvent such as ethanol or methanol:

Formula XXVI

Formula XXV

Compounds of the type Formula XXVI may themselves be prepared from compounds of Formula XXVII by reaction with a dehydrating agent such as Burgess Reagent, preferably in a solvent, for example tetrahydrofuran:

Formula XXVII

Formula XXVI

Compounds of the type Formula XXVII can be prepared from carboxylic acid compounds of Formula III, for example by reaction with thionyl chloride followed by ammonia in a suitable solvent such as dioxane:

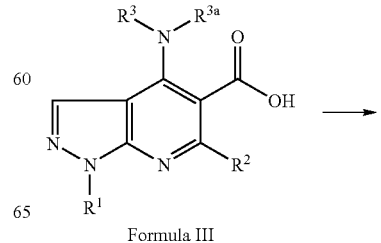

Formula III

-continued

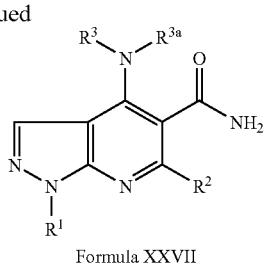

Formula XXVII

Process L—Conversion of a Compound of Formula (I) or a Salt Thereof into a Different Compound of Formula (I) or a Salt Thereof One compound of formula (I) or salt thereof can be converted into another compound of formula (I) or salt thereof. This conversion preferably comprises or is one or more of the following processes L1 to L10:

L1. An oxidation process. For example, the oxidation process can comprise or be oxidation of an alcohol to a ketone (e.g. using Jones reagent) or oxidation of an alcohol or a ketone to a carboxylic acid.

L2. A reduction process, for example reduction of a ketone or a carboxylic acid to an alcohol.

L3. Acylation, for example acylation of an amine or of a hydroxy group.

L4. Alkylation, for example alkylation of an amine or of a hydroxy group.

L5. Hydrolysis, e.g. hydrolysis of an ester to the corresponding carboxylic acid or salt thereof, for example in the presence of base (e.g. alkali-metal hydroxide, preferably also in the presence of water) or in the presence of acid (e.g. aqueous HCl, or HCl in an anhydrous organic solvent such as dioxane).

The hydrolysis can for example be hydrolysis of an ester compound, in which $R^X$, $R^{X2}$, $R^Y$ or $R^{Y2}$ is —$(CH_2)_n{}^{12}$—C(O)—$OR^{13}$ wherein $R^{13}$ is not a hydrogen atom (H), to the corresponding carboxylic acid wherein $R^{13}$ is a hydrogen atom (H). See for example Example 57 and Intermediate 83.

The hydrolysis can for example be hydrolysis of an ester compound, wherein $R^3$ is substituted by —C(O)$OR^{23}$ in which $R^{23}$ is $C_{1-2}$alkyl (e.g. $NHR^3$ or $NR^3R^{3a}$ is of sub-formula (p8)), to the corresponding carboxylic acid or salt thereof wherein $R^{23}$ is H (e.g. $NHR^3$ or $NR^3R^{3a}$ is of sub-formula (p7)).

L6. Deprotection, e.g. deprotection (e.g. deacylation or t-butyloxycarbonyl (BOC) removal or benzyloxycarbonyl removal) of an amine group.

L7. Formation of an ester or amide, for example from the corresponding carboxylic acid and/or an activated derivative of the carboxylic acid (e.g. acid chloride or acid anhydride or carboxylic acid activated by a coupling agent).

The amide formation can be formation of an amide compound, in which one or more of $R^X$, $R^{X2}$, $R^Y$ and $R^{Y2}$ is —$(CH_2)_n{}^{11}$—C(O)—$NR^{10}R^{11}$, —CH($C_{1-2}$alkyl)-C(O)—$NR^{10}R^{11}$, —$CMe_2$-C(O)—$NR^{10}R^{11}$ or cycloalkyl substituted by —C(O)—$NR^{10}R^{11}$, from the corresponding carboxylic acid and/or an activated derivative of the carboxylic acid. For examples of this amide formation, see Examples 58-59 and/or 126-147 for Het=sub-formula (id), and/or Process G herein for Het=sub-formula (ic) (e.g. Examples 85-90, 95-96 and/or 148-155).

The amide formation can alternatively be formation of an amide compound, in which one or more of $R^X$, $R^{X2}$, $R^Y$ and $R^{Y2}$ is —$(CH_2)_n{}^4$—$NR^6R^7$, —CH($C_{1-2}$alkyl)-$NR^6R^7$, —$CMe_2$-$NR^6R^7$ or cycloalkyl substituted by —$NR^6R^7$, wherein $R^6$ is $C(O)R^{17}$, from the corresponding carboxylic acid and/or an activated derivative of the carboxylic acid. For one example where Het is of sub-formula (ic) see Process H and/or Examples 159-165.

L8. Conversion of a ketone into the corresponding oxime or oxime ether. This can for example include conversion of an oxo (=O) substituent within $R^3$, e.g. within the $NHR^3$ or $NR^3R^{3a}$ sub-formula (O), into an hydroxyimino (—N—OH) or ($C_{1-4}$alkoxy)imino (=N—$OR^{26}$) substituent within $R^3$, e.g. within the $NHR^3$ or $NR^3R^{3a}$ sub-formula (o2), (o3), (o4) or (o5). This conversion can be carried out in the case of an oxime (hydroxyimino, =N—OH) by reacting hydroxylamine or a salt thereof (e.g. hydroxylamine hydrochloride) with the ketone, or in the case of an oxime ether ($C_{1-4}$alkoxy) imino, =N—$OR^{26}$) by reacting $C_{1-4}$alkoxyamine or a salt thereof (e.g. hydrochloride salt) with the ketone. The reaction is preferably carried out in the presence of a base such as anhydrous potassium carbonate or diisopropylethylamine and/or in a suitable solvent such as acetonitrile. The mixture can be heated e.g. to reflux.

L9. Sulfonylation, e.g. sulfonamide formation by reaction of an amine with a sulfonyl halide e.g. a sulfonyl chloride (e.g. see also Process I). and/or L10. Beckmann rearrangement of one compound of formula (I) into another compound of formula (I). Preferably, this uses cyanuric chloride (2,4,6-trichloro-1,3,5-triazine) together with a formamide such as DMF, e.g. at room temperature (see L. D. Luca, J. Org. Chem., 2002, 67, 6272-6274). The Beckmann rearrangement can for example comprise conversion of an (hydroxyimino)cycloalkyl compound of formula (I), e.g. wherein $NHR^3$ or $NR^3R^{3a}$ is of sub-formula (o2)

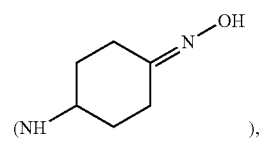

into a single-atom-ring-expanded lactam compound of formula (I), e.g. wherein $NHR^3$ or $NR^3R^{3a}$ is of sub-formula (m3)

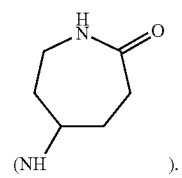

The present invention therefore also provides a method of preparing a compound of formula (I) or a salt thereof, comprising:

(a) cyclisation of a compound of formula II to a compound of formula (I) wherein Het is of sub-formula (ia) (that is: to a compound of Formula I(ia), i.e. to an optionally substituted 1,3,4-oxadiazol-2-yl derivative at the 5-position of the pyrazolopyridine ring system), for example in the presence of a dehydrating agent such as phosphorus oxychloride or Burgess reagent, or (b) reaction of a compound of formula IXa with an amine of formula $R^3R^{3a}NH$ to form a compound of formula (I), preferably in a solvent (e.g. organic solvent) and/or preferably in the presence of a base, or (c) cyclisation of a compound of formula II to a compound of formula (I) wherein Het is of sub-formula (ib) (i.e. to a compound of Formula XII i.e. to an optionally substituted 1,3,4-thiadiazol-2-yl derivative at the 5-position of the pyrazolopyridine ring system), for example in the presence of an agent capable of introducing sulfur such as Lawesson's reagent, or (d) reaction of a compound of formula VI, wherein $R^A$ is $C_{1-6}$alkyl such as Et, with an amidoxime of formula $R^XC(=NOH)NH_2$ or a salt thereof, preferably in the presence of a base such as sodium ethoxide and/or preferably in a suitable solvent (e.g. anhydrous and/or organic solvent) such as ethanol; or (e) reaction of a compound of formula XV with an acetimidate $R^X—C(=NH)OR^E$, where $R^E$ is $C_{1-6}$alkyl, to prepare a compound of formula (I) wherein Het is of sub-formula (if) (i.e. to a compound of Formula XIV, i.e. to an optionally substituted 1,2,4-triazol-3-yl or 5-yl derivative at the 5-position of the pyrazolopyridine ring system), preferably in the presence of a base (such as triethylamine or sodium ethoxide) and/or in a suitable solvent (e.g. anhydrous and/or organic solvent) such as ethanol; or (f)(i) converting directly or indirectly a compound of Formula III to a compound of formula (I) wherein Het is of sub-formula (id); and/or (f)(ii) dehydrogenating a compound of formula (I), wherein Het is of sub-formula (va) in which $R^{X1}$ and $R^{Y1}$ are H and $R^{X1}$ is $R^X$ and $R^{Y1}$ is $R^Y$, to a compound of formula (I) wherein Het is of sub-formula (id); or (f)(iii) cyclisation of a compound of Formula XXVIII, for example in the presence of Burgess reagent and/or preferably in a suitable solvent, to prepare a compound of formula (I) wherein Het is of sub-formula (va); or (g) reaction of a compound of the Formula XVII with an amine of Formula $R^{10}R^{11}NH$ under coupling conditions, to prepare a compound of formula (I) wherein Het is of sub-formula (ic) and $R^X$ is $—CH_2C(O)NR^{10}R^{11}$ (i.e. to prepare a compound of Formula XVI), the reaction preferably being carried out in the presence of a base such as diisopropylethylamine, and/or preferably in a suitable solvent (e.g. organic solvent, preferably anhydrous) such as DMF and/or dicloromethane, and/or preferably in the presence of oxalyl chloride; or (h) conversion of a compound of Formula XX into a compound of formula (I) wherein Het is of sub-formula (ic) and $R^X$ is $—CH_2—NR^6R^7$ wherein $R^7$ is $C(O)R^{17}$ (i.e. into a compound of Formula XIX), preferably either by reaction of the compound of Formula XX with a carboxylic acid $R^{17}COOH$ in the presence of a coupling agent, and/or by reaction of the compound of Formula XX with an activated derivative of the carboxylic acid moiety of $R^{17}COOH$ (e.g. $R^{17}C(O)Cl$), preferably in the presence of a base and/or a suitable solvent; or (i) reaction of a compound of Formula XX with a sulphonyl chloride $R^{18}S(O)_2Cl$ to prepare a compound of formula (I) wherein Het is of sub-formula (ic) and $R^X$ is $—CH_2—NR^6R^7$ wherein $R^7$ is $—S(O)_2R^{18}$ (i.e. to prepare a compound of Formula XXII), preferably in the presence of a base such as triethylamine and/or pyridine, and/or preferably in a suitable solvent such as dichloromethane and/or chloroform; or (j) reaction of a compound of Formula XX wherein $R^6=H$ with an acid chloride of formula $X^J—(CH_2)_{n^5}—X^5—(CH_2)_{(n^6-1)}—COCl$, where $X^J$ is a leaving group ($X^J$ preferably being a halogen atom or $—O—SO_2—R^J$ where $R^J$ is $C_{1-4}$alkyl, $C_{1-2}$fluoroalkyl, or phenyl optionally substituted by $C_{1-2}$alkyl), to prepare a compound of formula (I) wherein Het is of sub-formula (ic) and $R^X$ is $—CH_2—NR^6R^7$, wherein $R^6$ and $R^7$ together are $—(CH_2)_{n^5}—X^5—(CH_2)_{n^6}—$ in which $n^5$ and $n^6$ independently are 2 or 3, and wherein the ring formed by $NR^6R^7$ is substituted by one oxo (=O) substituent at a carbon atom within $(CH_2)_{n^6}$ which carbon atom is bonded to the nitrogen (i.e. to prepare a compound of Formula XXIII); the reaction preferably being in the presence of a base and/or in a suitable solvent, and/or preferably being followed by treatment with a base; or (k) reaction of a compound of Formula XXV with $R^YC(O)X^K$ where $X^K$ is a leaving group, to prepare a compound of formula (I) wherein Het is of sub-formula (iia) (i.e. to prepare a compound of Formula XXIV); or (L) conversion of a compound of formula (I) or a salt thereof into a different compound of formula (I) or a salt thereof;

and optionally converting the compound of formula (I) into a salt e.g. a pharmaceutically acceptable salt.

Salt formation processes may optionally be as described elsewhere herein.

Preferred features of methods (a), (b), (c), (d), (e), (f)(i), (f)(ii), (f)(iii), (g), (h), (i), (j), (k), and (L), independently of each other, are preferably as described above for Processes A, B, C, D, E, F, G, H, I, J, K, and L with all necessary changes being made. For example, the conversion process (L) preferably comprises or: is one or more of processes L1 to L10 described herein, e.g. hereinabove.

In any of the methods which involve reaction of a carboxylic acid and/or an activated carboxylic acid derivative with an amine to form an amide, the activated carboxylic acid derivative preferably comprises a $—C(O)X^{11}$ group in place of the COOH, wherein $X^{11}$ is a leaving group substitutable by an amine. For example $X^{11}$ can be Cl (wherein the activated derivative=the acid chloride) or $—OC(O)R$ (wherein the activated derivative=an anhydride). Alternatively, the activated carboxylic acid derivative can be an activated ester wherein the leaving group $X^{11}$ is

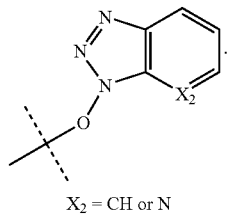

$X_2$ = CH or N

The latter activated carboxylic acid derivative can be formed from the carboxylic acid ($X^{11}=OH$) either:

(a) by reaction of the carboxylic acid with a carbodiimide such as EDC, which is 1-ethyl-3-(3'-dimethylaminopropyl) carbodiimide and is also 1-(3-dimethylaminopropyl)-3-ethylcarbodiimide, or a salt thereof e.g. hydrochloride salt, preferably followed by reaction of the resulting product with 1-hydroxybenzotriazole (HOBT); reaction (a) usually being carried out in the presence of a solvent (preferably anhydrous) such as dimethyl formamide (DMF) or acetonitrile and/or preferably under anhydrous conditions and/or usually at room temperature (e.g. about 20 to about 25° C.); or (b) by reaction with 2-(1H-benzotriazole-1-yl)-1,1,3,3-tetramethyluronium tetrafluoroborate (TBTU) or O-(7-Azabenzotriazol-1-yl)-N,N,N,N'-tetramethyluronium hexafluorophosphate (HATU), preferably in the presence of a base such as diisopropylethylamine ($^{i}Pr_2NEt=DIPEA$), and usually in the presence of a solvent such as dimethyl formamide (DMF) or acetonitrile and/or preferably under anhydrous conditions and/or usually at room temperature (e.g. about 20 to about 25° C.).

The present invention also provides: (m) a method of preparing a pharmaceutically acceptable salt of a compound of formula (I) comprising conversion of the compound of formula (I) or a salt thereof into the desired pharmaceutically acceptable salt thereof.

The present invention also provides a compound of formula (I) or a salt thereof, prepared by a method as defined herein.

Medical Uses

The present invention also provides a compound of formula (I) or a pharmaceutically acceptable salt thereof for use as an active therapeutic substance in a mammal such as a human. The compound or salt can be for use in the treatment and/or prophylaxis of any of the diseases/conditions described herein (e.g. for use in the treatment and/or prophylaxis of an inflammatory and/or allergic disease in a mammal) and/or for use as a phosphodiesterase inhibitor e.g. for use as a phosphodiesterase 4 (PDE4) inhibitor. "Therapy" may include treatment and/or prophylaxis.

Also provided is the use of a compound of formula (I) or a pharmaceutically acceptable salt thereof in the manufacture of a medicament (e.g. pharmaceutical composition) for the treatment and/or prophylaxis of any of the diseases/conditions described herein in a mammal such as a human, e.g. for the treatment and/or prophylaxis of an inflammatory and/or allergic disease in a mammal such as a human.

Also provided is a method of treatment and/or prophylaxis of any of the diseases/conditions described herein in a mammal (e.g. human) in need thereof, e.g. a method of treatment and/or prophylaxis of an inflammatory and/or allergic disease in a mammal (e.g. human) in need thereof, which method comprises administering to the mammal (e.g. human) a therapeutically effective amount of a compound of formula (I) as herein defined or a pharmaceutically acceptable salt thereof.

Phosphodiesterase 4 inhibitors are thought to be useful in the treatment and/or prophylaxis of a variety of diseases/conditions, especially inflammatory and/or allergic diseases, in mammals such as humans, for example: asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder such as Alzheimer's disease), depression, or pain. Ulcerative colitis and/or Crohn's disease are collectively often referred to as inflammatory bowel disease.

In the treatment and/or prophylaxis, the inflammatory and/or allergic disease is preferably chronic obstructive pulmonary disease (COPD), asthma, rheumatoid arthritis or allergic rhinitis in a mammal (e.g. human). More preferably, the treatment and/or prophylaxis is of COPD or asthma in a mammal (e.g. human).

PDE4 inhibitors are thought to be effective in the treatment of asthma (e.g. see M. A. Giembycz, *Drugs*, February 2000, 59(2), 193-212; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; and refs cited therein).

PDE4 inhibitors are thought to be effective in the treatment of COPD (e.g. see S. L. Wolda, *Emerging Drugs*, 2000, 5(3), 309-319; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; and refs cited therein). COPD is often characterised by the presence of airflow obstruction due to chronic bronchitis and/or emphysema (SL Wolda, *Emerging Drugs*, 2000, 5(3), 309-319).

PDE4 inhibitors are thought to be effective in the treatment of allergic rhinitis (e.g. see B. M. Schmidt et al., *J. Allergy & Clinical Immunology*, 108(4), 2001, 530-536).

PDE4 inhibitors are thought to be effective in the treatment of rheumatoid arthritis and multiple sclerosis (e.g. see H. J. Dyke et al., *Expert Opinion on Investigational Drugs*, January 2002, 11(1), 1-13; C. Burnouf et al., *Current Pharmaceutical Design*, 2002, 8(14), 1255-1296; and A. M. Doherty, *Current Opinion Chem. Biol.*, 1999, 3(4), 466-473; and refs cited therein). See e.g. A. M. Doherty, *Current Opinion Chem. Biol.*, 1999, 3(4), 466473 and refs cited therein for atopic dermatitis use.

PDE4 inhibitors have been suggested as having analgesic properties and thus being effective in the treatment of pain (A. Kumar et al., *Indian J. Exp. Biol.*, 2000, 38(1), 26-30).

In the invention, the treatment and/or prophylaxis can be of cognitive impairment e.g. cognitive impairment in a neurological disorder such as Alzheimer's disease. For example, the treatment and/or prophylaxis can comprise cognitive enhancement e.g. in a neurological disorder. See for example: H. T. Zhang et al. in: *Psychopharmacology*, June 2000, 150 (3), 311-316 and *Neuropsychopharmacology*, 2000, 23(2), 198-204; and T. Egawa et al., *Japanese J. Pharmacol.*, 1997, 75(3), 275-81.

PDE4 inhibitors such as rolipram have been suggested as having antidepressant properties (e.g. J. Zhu et al., *CNS Drug Reviews*, 2001, 7(4), 387-398; O'Donnell, *Expert Opinion on Investigational Drugs*, 2000, 9(3), 621-625; and H. T. Zhang et al., *Neuropsychopharmacology*, October 2002, 27(4), 587-595).

Pharmaceutical Compositions and Dosing

For use in medicine, the compounds of the present invention are usually administered as a pharmaceutical composition.

The present invention therefore provides in a further aspect a pharmaceutical composition comprising a compound of formula (I) or a pharmaceutically acceptable salt thereof and one or more pharmaceutically acceptable carriers and/or excipients.

The pharmaceutical composition can be for use in the treatment and/or prophylaxis of any of the conditions described herein.

The invention also provides a method of preparing a pharmaceutical composition comprising a compound of formula (I), as herein defined, or a pharmaceutically acceptable salt thereof, and one or more pharmaceutically acceptable carriers and/or excipients, the method comprising mixing the compound or salt with the one or more pharmaceutically acceptable carriers and/or excipients.

The invention also provides a pharmaceutical composition prepared by said method.

The compounds of formula (I) and/or the pharmaceutical composition may be administered, for example, by oral, parenteral (e.g. intravenous, subcutaneous, or intramuscular), inhaled or nasal administration. Accordingly, the pharmaceutical composition is preferably suitable for oral, parenteral (e.g. intravenous, subcutaneous, or intramuscular), inhaled or nasal administration. More preferably, the pharmaceutical composition is suitable for inhaled or oral administration, e.g. to a mammal such as a human. Inhaled administration involves topical administration to the lung e.g. by aerosol or dry powder composition. Oral administration to a human is most preferred.

A pharmaceutical composition suitable for oral administration can be liquid or solid; for example it can be a syrup, suspension or emulsion, a tablet, a capsule or a lozenge.

A liquid formulation will generally consist of a suspension or solution of the compound or pharmaceutically acceptable salt in a suitable pharmaceutically acceptable liquid carrier(s), for example an aqueous solvent such as water, ethanol or glycerine, or a non-aqueous solvent, such as polyethylene glycol or an oil. The formulation may also contain a suspending agent, preservative, flavouring and/or colouring agent.

In one preferable embodiment, the pharmaceutical composition is in unit dose form such as a tablet or capsule for oral administration, e.g. for oral administration to a human.

A pharmaceutical composition suitable for oral administration being a tablet can comprise one or more pharmaceutically acceptable carriers and/or excipients suitable for preparing tablet formulations. The carrier can for example be or include lactose, cellulose (for example microcrystalline cellulose), or mannitol. The tablet can also or instead contain one or more pharmaceutically acceptable excipients, for example a binding agent such as hydroxypropylmethylcellulose or povidone(polyvinylpyrollidone), a lubricant e.g. an alkaline earth metal stearate such as magnesium stearate, and/or a tablet disintegrant such as sodium starch glycollate, croscarmellose sodium, or crospovidone (cross-linked polyvinylpyrollidone). The pharmaceutical composition being a tablet can be prepared by a method comprising the steps of: (i) mixing the compound of formula (I), as herein defined, or a pharmaceutically acceptable salt thereof, with the one or more pharmaceutically acceptable carriers and/or excipients, (ii) compressing the resulting mixture (which is usually in powder form) into tablets, and (iii) optionally coating the tablet with a tablet film-coating material.

A pharmaceutical composition suitable for oral administration being a capsule can be prepared using encapsulation procedures. For example, pellets or powder containing the active ingredient can be prepared using a suitable pharmaceutically acceptable carrier and then filled into a hard gelatin capsule. Alternatively, a dispersion or suspension can be prepared using any suitable pharmaceutically acceptable carrier, for example an aqueous gum or an oil and the dispersion or suspension then filled into a soft gelatin capsule.

A parenteral composition can comprise a solution or suspension of the compound or pharmaceutically acceptable salt in a sterile aqueous carrier or parenterally acceptable oil. Alternatively, the solution can be lyophilised; the lyophilised parenteral pharmaceutical composition can be reconstituted with a suitable solvent just prior to administration.

Compositions for nasal or inhaled administration may conveniently be formulated as aerosols, drops, gels or dry powders.

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide, or an organic propellant such as a chlorofluorocarbon (CFC) or hydrofluorocarbon (HFC). Suitable CFC propellants include dichlorodifluoromethane, trichlorofluoromethane and dichlorotetrafluoroethane. Suitable HFC propellants include 1,1,1,2,3,3,3-heptafluoropropane and 1,1,1,2-tetrafluoroethane. The aerosol dosage forms can also take the form of a pump-atomiser.

Particle Size Reduction of Compound of Formula (I) or Salt Thereof

For pharmaceutical compositions suitable and/or adapted for inhaled administration, it is preferred that the compound or salt of formula (I) is in a particle-size-reduced form, and more preferably the size-reduced form is obtained or obtainable by micronisation. Micronisation usually involves subjecting the compound/salt to collisional and abrasional forces in a fast-flowing circular or spiral/vortex-shaped airstream often including a cyclone component. The preferable particle size (e.g. D50 value) of the size-reduced (e.g. micronised) compound or salt is about 0.5 to about 10 microns, e.g. about 1 to about 5 microns (e.g. as measured using laser diffraction). For example, it is preferable for the compound or salt of formula (I) to have a particle size defined by: a D10 of about 0.3 to about 3 microns (e.g. about 1 micron), and/or a D50 of about 1 to about 5 microns (e.g. about 2-5 or about 2-3 microns), and/or a D90 of about 2 to about 20 microns or about 3 to about 10 microns (e.g. about 5-8 or about 5-6 microns); for example as measured using laser diffraction. The laser diffraction measurement can use a dry method (suspension of compound/salt in airflow crosses laser beam) or a wet method [suspension of compound/salt in liquid dispersing medium, such as isooctane or (e.g. if compound soluble in isooctane) 0.1% Tween 80 in water, crosses laser beam]. With laser diffraction, particle size is preferably calculated using the Fraunhofer calculation; and/or preferably a Malvern Mastersizer or Sympatec apparatus is used for measurement.

An illustrative non-limiting example of a small-scale micronisation process is now given:

MICRONISATION EXAMPLE

Purpose: To micronize a compound of formula (I) or a salt thereof—in particular one of the Examples of the invention (described hereinafter)—usually in an amount of approximately 600-1000 mg, using a Jetpharma MC1 micronizer.

The parent (unmicronised) and micronised materials are analyzed for particle size by laser diffraction and crystallinity by PXRD.

Equipment and Material

| Equipment/material | Description and specification |
|---|---|
| Jetpharma MC1 Micronizer | Nitrogen supply: Air tank with 275 psi rate tubing |
| Analytical balance | Sartorius Analytical |
| Top loader balance | Mettler PM400 |
| Digital Caliper | VWR Electronic caliper |
| Vibrational spatula | Auto-spat Dispenser |
| Materials to be micronised | (not yet performed) |

The Jetpharma MC1 Micronizer comprises a horizontal disc-shaped milling housing having: a tubular compound inlet (e.g. angled at ca. 30 degrees to the horizontal) for entry of a suspension of unmicronised compound of formula (I) or salt in an gasflow, a separate gas inlet for entry of gases, a gas outlet for exit of gases, and a collection vessel for collecting micronised material. The milling housing has two chambers: an outer annular chamber in gaseous connection with the gas inlet the chamber being for receiving pressurised gas (e.g. air or nitrogen), an disc-shaped inner milling chamber within and coaxial with the outer chamber for micronising the input compound/salt, the two chambers being separated by an annular wall. The annular wall (ring R) has a plurality of narrow-bored holes connecting the inner and outer chambers and circumferentially-spaced-apart around the annular wall. The holes open into the inner chamber directed at an angle (directed part-way between radially and tangentially), and in use act as nozzles directing pressurised gas at high velocity from the outer chamber into the inner chamber and in an inwardly-spiral path (vortex) around the inner chamber (cyclone). The compound inlet is is gaseous communication with the inner chamber via a nozzle directed tangentially to the inner chamber, within and near to the annular wall. Upper and lower broad-diameter exit vents in the central axis of the the inner milling chamber connect to (a) (lower exit) the collection vessel which has no air outlet, and (b) (upper exit) the gas outlet which leads to a collection bag, filter and a gas exhaust. Inside the tubular compound inlet and longitudinally-movable within it is positioned a venturi inlet (V) for entry of gases. The compound inlet also has a bifurcation connecting to an upwardly-directed material inlet port for inputting material.

In use, the narrow head of the venturi inlet (V) is preferably positioned below and slightly forward of the material inlet port so that when the venturi delivers pressurised gas (eg air or nitrogen) the feed material is sucked into the gasstream thorough the compound inlet and accelerates it into the inner milling chamber tangentially at a subsonic speed. Inside the milling chamber the material is further accelerated to a supersonic speed by the hole/nozzle system around the ring (R) (annular wall) of the milling chamber. The nozzles are slightly angled so that the acceleration pattern of the material is in the form of an inwardly-directed vortex or cyclone. The material inside the milling chamber circulates rapidly and particle collisions occur during the process, causing larger particles to fracture into smaller ones. “Centrifugal” acceleration in the vortex causes the larger particles to remain at the periphery of the inner chamber while progressively smaller particles move closer to the center until they exit the milling chamber, generally through the lower exit, at low pressure and low velocity. The particles that exit the milling chamber are heavier than air and settle downward thorough the lower exit into the collection vessel, while the exhaust gas rises (together with a minority of small particles of micronised material) and escapes into the atmosphere at low pressure and low velocity.

Procedure:

The micronizer is assembled. The venturi protrusion distance from input port is adjusted to 1.0 cm respectively (e.g. so that the narrow head of the venturi inlet is positioned below and slightly forward of the material inlet port) and is measured with a micro-caliper to make sure that it is inserted correctly. The ring (R) and venturi (V) pressures are adjusted according to the values specified in the experimental design (refer to experimental section below) by adjusting the valves on the pressure gauges on the micronizer. The setup is checked for leakage by observing if there is any fluctuation in the reading of the pressure gauges.

Note that the venturi (V) pressure is kept at least 2 bars greater than the ring (R) pressure to prevent regurgitation of material, e.g. outwardly from the material inlet port.

Balance performance is checked with calibration weights. Specified amount of the parent material (see section on experimental run) is weighed into a plastic weigh boat. The material is then fed into the micronizer using a vibrational spatula (e.g. V-shaped in cross-section) at a specified feed rate. The material feeding time and equipment pressures are monitored during the micronization process.

Upon completion of the micronising run, the nitrogen supply is shut off and the collection bag is tapped to allow particles to settle into the recovery/collection vessel at the bottom of the micronizer. The collection bag is removed and set aside. The micronised powder in the recovery vessel (collection vessel) and the cyclone (above the recovery vessel) are collected separately into different weighed+labelled collection vials. The weight of the micronised material is recorded. The micronizer is disassembled and residual PDE4 compound on the micronizer inner surface is rinsed with 70/30 isopropyl alcohol/water and collected into a flask. The micronizer is then thoroughly cleaned by rinsing and wiping with suitable solvent and dried before subsequent runs are performed.

Preferred Experimental Parameters

Balance(s) Used: Sartorius analytical

Venturi outlet insertion depth: 10.0 mm

| Procedure no. | Material input amount (g) | Venturi (V)/ ring (R) Pressure (bar) | Intended feed-rate | Time needed to feed material (min + sec) | Actual feed-rate (g/min) |
|---|---|---|---|---|---|
| 1 | 0.8795 g | V = 10 bar<br>R = 6 bar | 200 mg/min | 4 min 51 sec | 0.181 g/min |

-continued

| Procedure no. | Material input amount (g) | Venturi (V)/ ring (R) Pressure (bar) | Intended feed-rate | Time needed to feed material (min + sec) | Actual feed-rate (g/min) |
|---|---|---|---|---|---|
| 2 | 0.9075 g | V = 8 bar<br>R = 5.5 bar | 200 mg/min | 4 min 43 sec | 192 mg/min |

The above preferred or optional parameters can be varied using the skilled person's knowledge.

Yield Calculations

% yield=[(Material from vessel+Material from cyclone)/Material input amount]×100

In general, very approximately 50-75% yields are achievable using this method.

Dry Powder Inhalable Compositions

For pharmaceutical compositions suitable and/or adapted for inhaled administration, it is preferred that the pharmaceutical composition is a dry powder inhalable composition. Such a composition can comprise a powder base such as lactose or starch, the compound of formula (I) or salt thereof (preferably in particle-size-reduced form, e.g. in micronised form), and optionally a performance modifier such as L-leucine, mannitol, trehalose and/or magnesium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometres) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

In the dry powder inhalable composition, preferably, the compound of formula (I) or salt thereof is present in about 0.1% to about 70% (e.g. about 1% to about 50%, e.g. about 5% to about 40%, e.g. about 20 to about 30%) by weight of the composition.

An illustrative non-limiting example of a dry powder inhalable composition follows:

Dry Powder Formulation Example—Dry Powder Lactose Blend Preparation

Using a size-reduced e.g. micronised form of the compound of formula (I) or salt thereof (e.g. as prepared in the Micronisation Example above), the dry powder blend is prepared by mixing the required amount of the compound/salt (e.g. 10 mg, 1% w/w) with inhalation-grade lactose containing 10% fines (e.g. 990 mg, 99% w/w) in a Teflon™ (polytetrafluoroethene) pot in a Mikro-dismembrator ball-mill (but without a ball bearing) at ¾ speed (ca. 2000-2500 rpm) for about 4 hours at each blend concentration. The Mikro-dismembrator (available from B. Braun Biotech International, Schwarzenberger Weg 73-79, D-34212 Melsungen, Germany; www.bbraunbiotech.com) comprises a base with an upwardly-projecting and sidewardly-vibratable arm to which is attached the Teflon™ pot. The vibration of the arm achieves blending.

Other blends: 10% w/w compound/salt (50 mg)+90% w/w lactose (450 mg, inhalation-grade lactose containing 10% fines).

Serial dilution of the 1% w/w blend can achieve e.g. 0.1% and 0.3% w/w blends.

Dry Powder Inhalation Devices

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose, e.g. of the dry powder composition, can be administered by inhalation via a device such as the DISKUS™ device, marketed by GlaxoSmithKhne. The DISKUS™ inhalation device is usually substantially as described in GB 2,242,134 A, and in such device at least one container for the pharmaceutical composition in powder form (the at least one container preferably being a plurality of sealed dose containers mounted longitudinally in a strip or ribbon) is defined between two members peelably secured to one another; the device comprises: means defining an opening station for the said at least one container; means for peeling the members apart at the opening station to open the container; and an outlet, communicating with the opened container, through which a user can inhale the pharmaceutical composition in powder form from the opened container.

Unit Dose Form and Dosing Regimens

Preferably the composition is in unit dose form such as a tablet or capsule for oral administration, e.g. for oral administration to a human.

In the pharmaceutical composition, a or each dosage unit for oral or parenteral administration preferably contains from 0.01 to 3000 mg, more preferably 0.5 to 1000 mg, of a compound of the formula (I) or a pharmaceutically acceptable salt thereof, calculated as the free base. A or each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

A pharmaceutically acceptable compound or salt of the invention is preferably administered to a mammal (e.g.

human) in a daily oral or parenteral dose of 0.001 mg to 50 mg per kg body weight per day (mg/kg/day), for example 0.01 to 20 mg/kg/day or 0.03 to 10 mg/kg/day or 0.1 to 2 mg/kg/day, of the compound of the formula (I) or a pharmaceutically acceptable salt thereof, calculated as the free base.

A pharmaceutically acceptable compound or salt of the invention is preferably administered to a mammal (e.g. human) in a daily nasal or inhaled dose of: 0.0001 to 5 mg/kg/day or 0.0001 to 1 mg/kg/day, e.g. 0.001 to 1 mg/kg/day or 0.001 to 0.3 mg/kg/day or 0.001 to 0.1 mg/kg/day or 0.005 to 0.3 mg/kg/day, of the compound of the formula (I) or a pharmaceutically acceptable salt thereof, calculated as the free base.

The pharmaceutically acceptable compounds or salts of the invention is preferably administered in a daily dose (for an adult patient) of, for example, an oral or parenteral dose of 0.01 mg to 3000 mg per day or 0.5 to 1000 mg per day e.g. 2 to 500 mg per day, or a nasal or inhaled dose of 0.001 to 300 mg per day or 0.001 to 50 mg per day or 0.01 to 30 mg per day or 0.01 to 5 mg per day or 0.02 to 2 mg per day, of the compound of the formula (I) or a pharmaceutically acceptable salt thereof, calculated as the free base.

Combinations

The compounds, salts and/or pharmaceutical compositions according to the invention may also be used in combination with another therapeutically active agent, for example, a $\beta_2$ adrenoreceptor agonist, an anti-histamine, an anti-allergic or an anti-inflammatory agent.

The invention thus provides, in a further aspect, a combination comprising a compound of formula (I) or a pharmaceutically acceptable salt thereof together with another therapeutically active agent, for example, a $\beta_2$-adrenoreceptor agonist, an anti-histamine, an anti-allergic, an anti-inflammatory agent or an antiinfective agent.

Preferably, the $\beta_2$-adrenoreceptor agonist is salmeterol (eg as racemate or a single enantiomer such as the R-enantiomer), salbutamol, formoterol, salmefamol, fenoterol or terbutaline, or a salt thereof (e.g. pharmaceutically acceptable salt thereof), for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 12-24 hour period such as salmeterol or formoterol. Preferably, the $\beta_2$-adrenoreceptor agonist is for inhaled administration, e.g. once per day and/or for simultaneous inhaled administration; and more preferably the $\beta_2$-adrenoreceptor agonist is in particle-size-reduced form e.g. as defined herein. Preferably, the $\beta_2$-adrenoreceptor agonist combination is for treatment and/or prophylaxis of COPD or asthma. Salmeterol or a pharmaceutically acceptable salt thereof, e.g. salmeterol xinofoate, is preferably administered to humans at an inhaled dose of 25 to 50 micrograms twice per day (measured as the free base). The combination with a $\beta_2$-adrenoreceptor agonist can be as described in WO 00/12078.

Preferred long acting $\beta_2$-adrenoreceptor agonists include those described in WO 02/066422A, WO 03/024439, WO 02/070490 and WO 02/076933.

Especially preferred long-acting $\beta_2$-adrenoreceptor agonists include compounds of formula (X) (described in WO 02/066422) (note that the R groups therein are defined independently of the corresponding R groups of formula (I)):

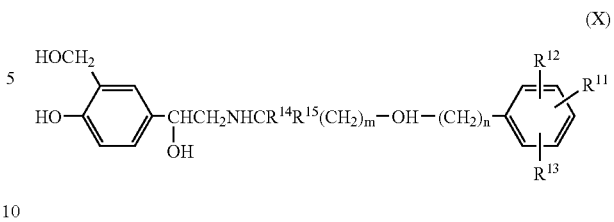

or a salt or solvate thereof, wherein in formula (X):
m is an integer of from 2 to 8;
n is an integer of from 3 to 11,
with the proviso that m+n is 5 to 19,
$R^{11}$ is $-XSO_2NR^{16}R^{17}$ wherein X is $-(CH_2)_p-$ or $C_{2-6}$ alkenylene;
$R^{16}$ and $R^{07}$ are independently selected from hydrogen, $C_{1-6}$alkyl, $C_{3-7}$cycloalkyl, $C(O)NR^{11}R^{19}$, phenyl, and phenyl ($C_{1-4}$alkyl)-,
or $R^{16}$ and $R^7$, together with the nitrogen to which they are bonded, form a 5-, 6-, or 7-membered nitrogen containing ring, and $R^{16}$ and $R^{17}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, $-CO_2R^{18}$, $-SO_2NR^{18}R^{19}$, $-CONR^{18}R^{19}$, $-NR^{18}C(O)R^{19}$, or a 5-, 6- or 7-membered heterocyclic ring;
$R^{18}$ and $R^{19}$ are independently selected from hydrogen, $C_{1-6}$alkyl, $C_{3-6}$cycloalkyl, phenyl, and phenyl ($C_{1-4}$alkyl)-; and
p is an integer of from 0 to 6, preferably from 0 to 4;
$R^{12}$ and $R^{13}$ are independently selected from hydrogen, $C_{1-6}$alkyls, $C_{1-6}$alkoxy, halo, phenyl, and $C_{1-6}$haloalkyl; and
$R^{14}$ and $R^{15}$ are independently selected from hydrogen and $C_{1-4}$alkyl with the proviso that the total number of carbon atoms in $R^{14}$ and $R^{15}$ is not more than 4.

Preferred $\beta_2$-adrenoreceptor agonists disclosed in WO 02/066422 include:
3-(4-{[6-({(2R)-2-hydroxy-2-[4-hydroxy-3-(hydroxymethyl)-phenyl]ethyl}amino)hexyl]oxy}butyl)benzenesulfonamide and
3-(3-{[7-({(2R)-2-hydroxy-2-[4-hydroxy-3-hydroxymethyl)phenyl]ethyl}-amino)heptyl]oxy}propyl)benzenesulfonamide.

A preferred $\beta_2$-adrenoreceptor agonist disclosed in WO 03/024439 is:
4-{(1R)-2-[(6-{2-[(2,6-dichlorobenzyl)oxy]ethoxy}hexyl) amino]-1-hydroxyethyl}-2-(hydroxymethyl)phenol.

A combination of a compound of formula (I) or salt together with an anti-histamine is preferably for oral administration (e.g. as a combined composition such as a combined tablet), and can be for treatment and/or prophylaxis of allergic rhinitis. Examples of anti-histamines include methapyrilene, or H1 antagonists such as cetirizine, loratadine (e.g. Clarityn™), desloratadine (e.g. Clarinex™) or fexofenadine (e.g. Allegra™).

The invention also provides, in a further aspect, a combination comprising a compound of formula (I) or a pharmaceutically acceptable salt thereof together with an anticholinergic compound, e.g. a muscarinic (M) receptor antagonist in particular an $M_1$, $M_2$, $M_1/M_2$, or $M_3$ receptor antagonist, more preferably a $M_3$ receptor antagonist, still more preferably a $M_3$ receptor antagonist which selectively antagonises (e.g. antagonises 10 times or more strongly) the $M_3$ receptor over the $M_1$ and/or $M_2$ receptor. For combinations of antiecholinergic compounds/muscarinic (M) receptor antagonists with PDE4 inhibitors, see for example WO 03/011274 A2 and WO 02/069945 A2/US 2002/0193393 A1 and US 2002/052312 A1, and some or all of these publications give examples of anticholinergic compounds/muscarinic receptor antagonists which may be used with the compounds of formula (I) or salts, and/or suitable pharmaceutical compositions. For example, the muscarinic receptor antagonist can comprise or be an ipratropium salt (e.g. ipratropium bromide), an oxitropium salt (e.g. oxitropium bromide), or more preferably a tiotropium salt (e.g. tiotropium bromide); see e.g. EP 418 716 A1 for tiotropium.

The anticholinergic compound or muscarinic (M) receptor antagonists e.g. $M_3$ receptor antagonist, is preferably for inhaled administration, more preferably in particle-size-reduced form e.g. as defined herein. More preferably, both the muscarinic (M) receptor antagonist and the compound of formula (I) or the pharmaceutically acceptable salt thereof are for inhaled administration. Preferably, the anticholinergic compound or muscarinic receptor antagonist and the compound of formula (I) or salt are for simultaneous administration. The muscarinic receptor antagonist combination is preferably for treatment and/or prophylaxis of COPD.

Other suitable combinations include, for example, a combination comprising a compound of formula (I) or a pharmaceutically acceptable salt thereof together with another anti-inflammatory agent such as an anti-inflammatory corticosteroid; or a non-steroidal anti-inflammatory drug NSAID) such as a leukotriene antagonist (e.g. montelukast), an iNOS inhibitor, a tryptase inhibitor, an elastase inhibitor, a beta-2 integrin antagonist, an adenosine 2a agonist, a $CCR^3$ antagonist, or a 5-lipoxogenase inhibitor; or an antiinfective agent (eg. an antibiotic or an antiviral). An iNOS inhibitor is preferably for oral administration. Suitable iNOS inhibitors (inducible nitric oxide synthase inhibitors) include those disclosed in WO 93/13055, WO 98/30537, WO 02/50021, WO 95/34534 and WO 99/62875. Suitable $CCR^3$ inhibitors include those disclosed in WO 02/26722.

In a combination comprising a compound of formula (I) or a pharmaceutically acceptable salt thereof together with an anti-inflammatory corticosteroid (which is preferably for treatment and/or prophylaxis of asthma, COPD or allergic rhinitis), then preferably the anti-inflammatory corticosteroid is fluticasone, fluticasone propionate (e.g. see U.S. Pat. No. 4,335,121), beclomethasone, beclomethasone 17-propionate ester, beclomethasone 17,21-dipropionate ester, dexamethasone or an ester thereof, mometasone or an ester thereof, ciclesonide, budesonide, flunisolide, or a compound as described in WO 02/12266 A1 (e.g. as claimed in any of claims 1 to 22 therein), or a pharmaceutically acceptable salt of any of the above. If the anti-inflammatory corticosteroid is a compound as described in WO 02/12266 A1, then preferably it is Example 1 therein {which is 6α,9α-difluoro-17α-[(2-furanylcarbonyl)oxy]-11β-hydroxy-16α-methyl-3-oxo-androsta-1,4-diene-17β-carbothioic acid S-fluoromethyl ester} or Example 41 therein {which is 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester}, or a pharmaceutically acceptable salt thereof. The anti-inflammatory corticosteroid is preferably for intranasal or inhaled administration. Fluticasone propionate is preferred and is preferably for inhaled administration to a human either (a) at a dose of 250 micrograms once per day or (b) at a dose of 50 to 250 micrograms twice per day.

Also provided is a combination comprising a compound of formula (I) or a pharmaceutically acceptable salt thereof together with β$_2$-adrenoreceptor agonist and an anti-inflammatory corticosteroid, for example as described in WO 03/030939 A1. Preferably this combination is for treatment and/or prophylaxis of asthma, COPD or allergic rhinitis. The β$_2$-adrenoreceptor agonist and/or the anti-inflammatory corticosteroid can be as described above and/or as described in WO 03/030939 A1. Most preferably, in this "triple" combination, the β$_2$-adrenoreceptor agonist is salmeterol or a pharmaceutically acceptable salt thereof (e.g. salmeterol xinafoate) and the anti-inflammatory corticosteroid is fluticasone propionate.

The combinations referred to above may conveniently be presented for use in the form of a pharmaceutical composition and thus a pharmaceutical composition comprising a combination as defined above together with one or more pharmaceutically acceptable carriers and/or excipients represent a further aspect of the invention.

The individual compounds of such combinations may be administered either sequentially or simultaneously in separate or combined pharmaceutical composition(s).

In one embodiment, the combination as defined herein can be for simultaneous inhaled administration and is disposed in a combination inhalation device. Such a combination inhalation device is another aspect of the invention. Such a combination inhalation device can comprise a combined pharmaceutical composition for simultaneous inhaled administration (e.g. dry powder composition), the composition comprising all the individual compounds of the combination, and the composition being incorporated into a plurality of sealed dose containers mounted longitudinally in a strip or ribbon inside the inhalation device, the containers being rupturable or peel-openable on demand; for example such inhalation device can be substantially as described in GB 2,242,134 A (DISKUS™) and/or as described above. Alternatively, the combination inhalation device can be such that the individual compounds of the combination are administrable simultaneously but are stored separately (or wholly or partly stored separately for triple combinations), e.g. in separate pharmaceutical compositions, for example as described in PCT/EP03/00598 filed on 22 Jan. 2003 (e.g. as described in the claims thereof e.g. claim 1).

The invention also provides a method of preparing a combination as defined herein, the method comprising either (a) preparing a separate pharmaceutical composition for administration of the individual compounds of the combination either sequentially or simultaneously, or (b) preparing a combined pharmaceutical composition for administration of the individual compounds of the combination simultaneously, wherein the pharmaceutical composition comprises the combination together with one or more pharmaceutically acceptable carriers and/or excipients.

The invention also provides a combination as defined herein, prepared by a method as defined herein.

Biological Test Methods

PDE 3, PDE 4B, PDE 4D, PDE 5, PDE 6 Primary Assay Methods

The activity of the compounds can be measured in the assay methods shown below.

Preferred compounds of the invention are selective PDE4 inhibitors, i.e. they inhibit PDE4 (e.g. PDE4B and/or PDE4D, preferably PDE4B) more strongly than they inhibit PDE3 and/or more strongly than they inhibit PDE5 and/or more strongly than they inhibit PDE6.

PDE Enzyme Sources and Literature References

Human recombinant PDE4B, in particular the 2B splice variant thereof (HSPDE4B2B), is disclosed in WO 94/20079 and also M. M. McLaughlin et al., "A low Km, rolipram-sensitive, cAMP-specific phosphodiesterase from human brain: cloning and expression of cDNA, biochemical characterisation of recombinant protein, and tissue distribution of mRNA", *J. Biol. Chem.,* 1993, 268, 6470-6476. Human recombinant PDE4B was expressed in the PDE-deficient yeast *Saccharomyces cerevisiae* strain GL62. 100,000×g supernatant fractions of yeast cell lysates were used for PDE4B assays and inhibitor studies.

Human recombinant PDE4D (HSPDE4D3A) is disclosed in P. A. Baecker et al., "Isolation of a cDNA encoding a human rolipram-sensitive cyclic AMP phoshodiesterase (PDE IV$_D$)", *Gene,* 1994, 138, 253-256.

Human recombinant PDE5 is disclosed in K. Loughney et al., "Isolation and characterisation of cDNAs encoding PDE5A, a human cGMP-binding, cGMP-specific 3',5'-cyclic nucleotide phosphodiesterase", *Gene,* 1998, 216, 139-147.

PDE3 was purified from bovine aorta as described by H. Coste and P. Grondin, "Characterisation of a novel potent and specific inhibitor of type V phosphodiesterase", *Biochem. Pharmacol.,* 1995, 50, 1577-1585.

PDE6 was purified from bovine retina as described by: P. Catty and P. Deterre, "Activation and solubilization of the retinal cGMP-specific phosphodiesterase by limited proteolysis", *Eur. J. Biochem.,* 1991, 199, 263-269; A. Tar et al. "Purification of bovine retinal cGMP phosphodiesterase", *Methods in Enzymology,* 1994, 238, 3-12; and/or D. Srivastava et al. "Effects of magnesium on cyclic GMP hydrolysis by the bovine retinal rod cyclic GMP phosphodiesterase", *Biochem. J.,* 1995, 308, 653-658.

Inhibition of PDE 3, PDE 4B, PDE 4D, PDE 5 or PDE 6 Activity: Radioactive Scintillation Proximity Assay (SPA)

The ability of compounds to inhibit catalytic activity at PDE4B or 4D (human recombinant), PDE3 (from bovine aorta) or PDE5 (human recombinant) or PDE6 (from bovine retina) was determined by Scintillation Proximity Assay (SPA) in 96-well format. Test compounds (preferably as a solution in DMSO, e.g. about 2 microlitre (ul) volume of DMSO solution) were preincubated at ambient temperature (room temperature, e.g. 19-23° C.) in Wallac Isoplates (code 1450-514) with PDE enzyme in 50 mM Tris-HCl buffer pH 7.5, 8.3 mM MgCl$_2$, 1.7 mM EGTA, 0.05% (w/v) bovine serum albumin for 10-30 minutes (usually 30 minutes). The enzyme concentration was adjusted so that no more than 20% hydrolysis of the substrate defined below occurred in control wells without compound, during the incubation. For PDE3, PDE4B and PDE4D assays, [5',8-$^3$H]Adenosine 3',5'-cyclic phosphate (Amersham Pharmacia Biotech, code TRK.559; or Amersham Biosciences UK Ltd, Pollards Wood, Chalfont St Giles, Buckinghamshire HP8 4SP, UK) was added to give 0.05 uCi per well and ~10 nM final concentration. For the PDE5 and PDE6 assay [8-$^3$H]Guanosine 3',5'-cyclic phosphate (Amersham Pharmacia Biotech, code TRK.392) was added to give 0.05 uCi per well and ~36 nM final concentration. Plates, preferably containing approx. 100 ul volume of assay mixture, were mixed on an orbital shaker for 5 minutes and incubated at ambient temperature for 1 hour. Phosphodiesterase SPA beads (Amersham Pharmacia Biotech, code RPNQ 0150) were added (~1 mg per well) to terminate the assay. Plates were sealed and shaken and allowed to stand at ambient temperature for 35 minutes to 1 hour (preferably 35 minutes) to allow the beads to settle. Bound radioactive product was measured using a WALLAC TRILUX 1450 Microbeta scintillation counter. For inhibition curves, 10 concentrations (1.5-M-30 uM) of each compound were assayed. Curves were analysed using ActivityBase and XLfit (ID Businesss Solutions Limited, 2 Ocean Court, Surrey Research Park, Guildford, Surrey GU2 7QB, United Kindgom) Results were expressed as pIC$_{50}$ values.

In an alternative to the above radioactive SPA assay, PDE4B or PDE4D inhibition can be measured in the following Fluorescence Polarisation (FP) assay:

Inhibition of PDE4B or PDE4D Activity: Fluorescence Polarisation (FP) Assay

The ability of compounds to inhibit catalytic activity at PDE4B (human recombinant) or PDE4D (human recombinant) was determined by IMAP Fluorescence Polarisation (FP) assay (IAP Explorer kit, available from Molecular Devices Corporation, Sunnydale, Calif., USA; Molecular Devices code: R8062) in 384-well format. The IMAP FP assay is able to measure PDE activity in an homogenous, non-radioactive assay format. The FP assay uses the ability of immobilised trivalent metal cations, coated onto nanoparticles (tiny beads), to bind the phosphate group of Fl-AMP that is produced on the hydrolysis of fluorescein-labelled (Fl) cyclic adenosine mono-phosphate (Fl-cAMP) to the non-cyclic Fl-AMP form. Fl-cAMP does not bind. Binding of Fl-AMP product to the beads (coated with the immobilised trivalent cations) slows the rotation of the bound Fl-AMP and leads to an increase in the fluorescence polarisation ratio of parallel to perpendicular light. Inhibition of the PDE reduces/inhibits this signal increase.

Test compounds (small volume, e.g. ca. 0.5 to 1 ul, preferably ca. 0.5 ul, of solution in DMSO) were preincubated at ambient temperature (room temperature, e.g. 19-23° C.) in black 384-well microtitre plates (supplier: NUNC, code 262260) with PDE enzyme in 10 mM Tris-HCl buffer pH 7.2, 10 mM MgCl$_2$, 0.1% (w/v) bovine serum albumin, and 0.05% NaN$_3$ for 10-30 minutes. The enzyme level was set by experimentation so that reaction was linear throughout the incubation. Fluorescein adenosine 3',5'-cyclic phosphate (from Molecular Devices Corporation, Molecular Devices code: R7091) was added to give about 40 nM final concentration (final assay volume usually ca. 20-40 ul, preferably ca. 20 ul). Plates were mixed on an orbital shaker for 10 seconds and incubated at ambient temperature for 40 minutes. IMAP binding reagent (as described above, from Molecular Devices Corporation, Molecular Devices code: R7207) was added (60 ul of a 1 in 400 dilution in binding buffer of the kit stock solution) to terminate the assay. Plates were allowed to stand at ambient temperature for 1 hour. The Fluorescence Polarisation (FP) ratio of parallel to perpendicular light was measured using an Analyst™ plate reader (from Molecular Devices Corporation). For inhibition curves, 10 concentrations (1.5 nM-30 uM) of each compound were assayed. Curves were analysed using ActivityBase and XLfit (ID Businesss Solutions Limited, 2 Ocean Court, Surrey Research Park, Guildford, Surrey GU2 7QB, United Kindgom). Results were expressed as pIC$_{50}$ values.

In the FP assay, all reagents were dispensed using Multidrop™ (available from Thermo Labsystems Oy, Ratastie 2, PO Box 100, Vantaa 01620, Finland).

For a given PDE4 inhibitor, the PDE4B (or PDE4D) inhibition values measured using the SPA and FP assays can differ slightly. However, in a regression analysis of 100 test compounds, the pIC$_{50}$ inhibition values measured using SPA and FP assays have been found generally to agree within 0.5 log units, for PDE4B and PDE4D (linear regression coefficient 0.966 for PDE4B and 0.971 for PDE4D; David R.

Mobbs et al., "Comparison of the IMAP Fluorescence Polarisation Assay with the Scintillation Proximity Assay for Phosphodiesterase Activity", poster to be presented at 2003 Molecular Devices UK & Europe User Meeting, 2 Oct. 2003, Down Hall, Harlow, Essex, United Kingdom).

Biological Data obtained for some of the Examples (PDE4B inhibitory activity, either as one reading or as an average of ca. 2-6 readings) are as follows, based on current measurements only. In each of the SPA and FP assays, absolute accuracy of measurement is not possible, and the readings given are accurate only up to about ±0.5 of a log unit, depending on the number of readings made and averaged:

| Example number | PDE4B pIC$_{50}$ (±about 0.5) |
|---|---|
| 6 | 8.1 |
| 10 | 8.2 |
| 12 | 7.9 |
| 14 | 7.6 |
| 23 | 8.1 |
| 24 | 8.2 |
| 35 | 7.5 |
| 42 | 8.3 |
| 7, 43, 48, 60, 61 and 64 | 6.6 to 7.2 |
| 2, 17, 26, 34, 38, 39, 44, 50, 59, 62, 63, 66, 71, 76, 77 and 84 | 7.5 to 9.1 |

Many, but not all, of the Examples have been tested for PDE4B inhibition. Of the Examples tested for PDE4B inhibition, some were tested by the radioactive SPA assay, some were tested by the FP assay.

Most or substantially all of Examples 1-45, 47-55, 57-81, 83 and 84 have PDE4B inhibitory activities in the range of pIC$_{50}$=about 6 (± about 0.5) to about 9.1 (±0.5).

The Examples wherein $R^3$=cyclohexyl (NHR$^3$ or NR$^3$R$^{3a}$=sub-formula (c)), tetrahydro-2H-pyran-4-yl (NHR$^3$ or NR$^3$R$^{3a}$=group (h)), or certain other types of substituted cyclohexyl or certain heterocycles, or Examples wherein NHR$^3$ or NR$^3$R$^{3a}$=sub-formula(s), usually or often (based on data for $R^1$=ethyl) have a higher level of selectivity for PDE4B over PDE5, as measured in the above enzyme inhibition assays, compared to the selectivities of comparable Examples wherein $R^3$=cyclopropyl (NHR$^3$ or NR$^3$R$^{3a}$=sub-formula (b)).

Emesis: Some known PDE4 inhibitors can cause emesis and/or nausea to greater or lesser extents (e.g. see Z. Huang et al., Current Opinion in Chemical Biology, 2001, 5: 432-438, see especially pages 433-434 and refs cited therein). Therefore, it would be preferable, but not essential, if a particular PDE4 inhibitory compound or salt of the invention were to cause only limited or manageable emetic side-effects. Emetic side-effects can for example be measured by the emetogenic potential of the compound or salt when administered to ferrets; for example one can measure the time to onset, extent, frequency and/or duration of vomiting, retching and/or writhing in ferrets after oral or parenteral administration of the compound or salt. See for example In vivo Assay 4 hereinafter for a measurement method for anti-inflammatory effect, emetic side-effects and therapeutic index (TI) in the ferret. See also for example A. Robichaud et al., "Emesis induced by inhibitors of [PDE IV] in the ferret", Neuropharmacology, 1999, 38, 289-297, erratum Neuropharmacology, 2001, 40, 465-465. However, optionally, emetic side-effects and therapeutic index (TI) in rats can be conveniently measured by monitoring the pica feeding behaviour of rats after administration of the compound or salt of the invention (see In Vivo Assay 2 below).

Other side effects: Some known PDE4 inhibitors can cause other side effects such as headache and other central nervous system (CNS—) mediated side effects; and/or gastrointestinal (GI) tract disturbances. Therefore, it would be preferable but not essential if a particular PDE4 inhibitory compound or salt of the invention were to cause only limited or manageable side-effects in one or more of these side-effect categories.

In Vivo Biological Assays

The in vitro enzymatic PDE4B inhibition assay described above should be regarded as being the primary test of biological activity. However, additional in vivo biological tests, which are optional and which are not an essential measure of efficacy or side-effects, are described below.

In Vivo Assay 1. LPS-induced Pulmonary Neutrophilia in Rats: Effect of Orally Administered PDE4 Inhibitors Pulmonary neutrophil influx has been shown to be a significant component to the family of pulmonary diseases like chronic obstructive pulmonary disease (COPD) which can involve chronic bronchitis and/or emphysema (G. F. Filley, Chest. 2000; 117(5); 251s-260s). The purpose of this neutrophilia model is to study the potentially anti-inflammatory effects in vivo of orally administered PDE4 inhibitors on neutrophilia induced by inhalation of aerosolized lipopolysaccharide (LPS), modelling the neutrophil inflammatory component(s) of COPD. See the literature section below for scientific background.

Male Lewis rats (Charles River, Raleigh, N.C., USA) weighing approximately 300-400 grams are pretreated with either (a) test compound suspended in 0.5% methylcellulose (obtainable from Sigma-Aldrich, St Louis, Mo., USA) in water or (b) vehicle only, delivered orally in a dose volume of 10 ml/kg. Generally, dose response curves are generated using the following doses of PDE4 inhibitors: 10.0, 2.0, 0.4, 0.08 and 0.016 mg/kg. Thirty minutes following pretreatment, the rats are exposed to aerosolized LPS (Serotype E. Coli 026:B6 prepared by trichloroacetic acid extraction, obtainable from Sigma-Aldrich, St Louis, Mo., USA), generated from a nebulizer containing a 100 µg/ml LPS solution. Rats are exposed to the LPS aerosol at a rate of 4 L/min for 20 minutes. LPS exposure is carried out in a closed chamber with internal dimensions of 45 cm length×24 cm width×20 cm height. The nebulizer and exposure chamber are contained in a certified fume hood. At 4 hours-post LPS exposure the rats are euthanized by overdose with pentobarbital at 90 mg/kg, administered intraperitoneally. Bronchoalveolar lavage (BAL) is performed through a 14 gauge blunt needle into the exposed trachea. Five, 5 ml washes are performed to collect a total of 25 ml of BAL fluid. Total cell counts and leukocyte differentials are performed on BAL fluid in order to calculate neutrophil influx into the lung. Percent neutrophil inhibition at each dose (cf. vehicle) is calculated and a variable slope, sigmoidal dose-response curve is generated, usually using Prism Graph-Pad. The dose-response curve is used to calculate an ED50 value (in mg per kg of body weight) for inhibition by the PDE4 inhibitor of the LPS-induced neutrophilia Results: Based on current measurements, the compounds of Examples 14, 17, 23, 35 and 38, administered orally in the above procedure, exhibited neutrophilia-inhibition ED50 values in the range of about 0.03 mg/kg to about 1 mg/kg, subject to testing inaccuracies.

Alternative method and results: In an alternative embodiment of the procedure, a single oral dose of 10 mg/kg or 1 mg/kg of the PDE4 inhibitor (or vehicle) is administered to the rats, and percent neutrophil inhibition is calculated and reported for that specific dose. In this embodiment, based on current measurements, the compounds of Examples 2, 14, 23 and 38, administered orally in this alternative procedure at a single dose of 10 mg/kg, exhibited percent neutrophilia-inhibition in the range of about 74% to about 86%, subject to testing inaccuracies.

Literature:

Filley G. F. Comparison of the structural and inflammatory features of COPD and asthma. *Chest.* 2000; 117(5) 251s-260s.

Howell R E, Jenkins L P, Fielding L E, and Grimes D. Inhibition of antigen-induced pulmonary eosinophilia and neutrophilia by selective inhibitors of phosphodiesterase types 3 and 4 in brown Norway rats. *Pulmonary Pharmacology.* 1995; 8: 83-89.

Spond J, Chapman R, Fine J, Jones H, Kreutner W, Kung T T, Minnicozzi M. Comparison of PDE 4 inhibitors, Rolipram and SB 207499 (Ariflo™), in a rat model of pulmonary neutrophilia. *Pulmonary Pharmacology and Therapeutics.* 2001; 14:157-164.

Underwood D C, Osborn R R, Bochnowicz S, Webb E F, Rieman D J, Lee J C, Romanic A M, Adams J L, Hay D W P, and Griswold D E. SB 239063, a p38 MAPK inhibitor, reduces neutrophilia, inflammatory cytokines, MMP-9, and fibrosis in lung. *Am J Physiol Lung Cell Mol Physiol.* 2000; 279: L895-L902.

In Vivo Assay 2. Rat Pica Model of Emesis

Background: Selective PDE4 inhibitors have been shown to inhibit inflammation in various in vitro and in vivo models by increasing intracellular levels of cAMP of many immune cells (e.g. lymphocytes, monocytes). However, a side effect of some PDE4 inhibitors in many species is emesis. Because many rat models of inflammation are well characterized, they have been used in procedures (see e.g. In Vivo Assay 1 above) to show beneficial anti-inflammatory effects of PDE 4 inhibitors. However rats have no emetic response (they have no vomit reflex), so that the relationship between beneficial anti-inflammatory effects of PDE 4 inhibitors and emesis is difficult to study directly in rats.

However, in 1991, Takeda et al. (see Literature section below) demonstrated that the pica feeding response is analogous to emesis in rats. Pica feeding is a behavioural response to illness in rats wherein rats eat non-nutritive substances such as earth or in particular clay (e.g. kaolin) which may help to absorb toxins. Pica feeding can be induced by motion and chemicals (especially chemicals which are emetic in humans), and can be inhibited pharmacologically with drugs that inhibit emesis in humans. The Rat Pica Model, In Vivo Assay 2, can determine the level of pica response of rats to PDE 4 inhibition at pharmacologically relevant doses in parallel to in vivo anti-inflammatory Assays in (a separate set of) rats (e.g. In Vivo Assay 1 above). Anti-inflammatory and pica assays in the same species together can provide data on the "therapeutic index" (TI) in the rat of the compounds/salts of the invention. The Rat TI can for example be calculated as the ratio of a) the potentially-emetic Pica Response ED50 dose from Assay 2 to b) the rat anti-inflammatory ED50 dose (e.g. measured by rat neutrophilia-inhibition in eg In Vivo Assay 1), with larger TI ratios possibly indicating lower emesis at many anti-inflammatory doses. This might allow a choice of a non-emetic or minimal-emetic pharmaceutical dose of the compounds or salts of the invention which has an anti-inflammatory effect. It is recognised however that achieving a low-emetic PDE4 inhibitory compound is not essential to the invention.

Procedure: On the first day of the experiment, the rats are housed individually in cages without bedding or "enrichment". The rats are kept off of the cage floor by a wire screen. Pre-weighed food cups containing standard rat chow and clay pellets are placed in the cage. The clay pellets, obtainable from Languna Clay Co, City of Industry, Calif., USA, are the same size and shape as the food pellets. The rats are acclimated to the clay for 72 hours, during which time the cups and food and clay debris from the cage are weighed daily on an electronic balance capable of measuring to the nearest 0.1 grams. By the end of the 72 hour acclimation period the rats generally show no interest in the clay pellets.

At the end of 72 hours the rats are placed in clean cages and the food cups weighed. Rats that are still consuming clay regularly are removed from the study. Immediately prior to the dark cycle (the time when the animals are active and should be eating) the animals are split into treatment groups and dosed orally with a dose of the compound/salt of the invention (different doses for different treatment groups) or with vehicle alone, at a dose volume of 2 ml/kg. In this oral dosing, the compound/salt is in the form of a suspension in 0.5% methylcellulose (obtainable Sigma-Aldrich, St. Louis, Mo., USA) in water. The food and clay cups and cage debris are weighed the following day and the total clay and food consumed that night by each individual animal is calculated.

A dose response is calculated by first converting the data into quantal response, where animals are either positive or negative for the pica response. A rat is "pica positive" if it consumes greater than or equal to 0.3 grams of clay over the mean of is usually calculated using logistic regression performed by the Statistica software statistical package. A Pica Response ED50 value in mg per kg of body weight can then be calculated.

The Pica Response ED50 value can be compared to the neutrophilia-inhibition ED50 values for the same compound administered orally to the rat (measurable by In Vivo Assay 1 above), so that a Therapeutic Index (TI) in rats can be calculated thus:

$$\text{Rat Therapeutic index } (TI) \text{ (50/50)} = \frac{\text{Pica Response } ED50 \text{ value}}{\text{rat neutrophilia-inhibition } ED50 \text{ value}}$$

In general, the Therapeutic Index (TI) calculated this way is often substantially different to, for example can often be substantially higher than, the TI (D20/D50) calculated in the ferret (see In vivo Assay 4 below).

Results: Using the above procedure, and according to current measurements, the compounds of Examples 14, 17, 23, 35 and 38 exhibited a Pica Response ED50 in the range of about 2 mg/kg to greater than about 50 mg/kg, subject to testing inaccuracies. Taking the specific Pica Response ED50 values for these compounds together with the specific rat neutrophilia-inhibition ED50 values measured in In Vivo Assay 1 for Examples 14, 17, 23, 35 and 38, the Rat Therapeutic Index (TI) for orally-administered Examples 14, 17, 23, 35 and 38 was calculated using the above equation as being in the range of from about 12 to about 470, according to current measurements, subject to testing inaccuracies.

Literature:

Beavo J A, Contini, M., Heaslip, R. J. Multiple cyclic nucleotide phosphodiesterases. *Mol Pharmacol.* 1994; 46:399-405.

Spond J, Chapman R, Fine J, Jones H, Kreutner W, Kung T T, Mirnicozzi M. Comparison of PDE 4 inhibitors, Rolipram and SB 207499 (Ariflo™), in a rat model of pulmonary neutrophilia *Pulmonary Pharmacology and Therapeutics.* 2001; 14:157-164.

Takeda N, Hasegawa S, Morita M, and Matsunaga T. Pica in rats is analogous to emesis: an animal model in emesis research. *Pharmacology, Biochemistry and Behavior.* 1991; 45:817-821.

Takeda N, Hasegawa S, Morita M, Horii A, Uno A, Yamatodani A and Matsunaga T. Neuropharmacological mechanisms of emesis. I. Effects of antiemetic drugs on motion- and apomorphine-induced pica in rats. *Meth Find Exp Clin Pharmacol.* 1995; 17(9) 589-596.

Takeda N, Hasegawa S, Morita M, Horii A, Uno A, Yamatodani A and Matsunaga T. Neuropharmacological mechanisms of emesis. II. Effects of antiemetic drugs on cisplatin-induced pica in rats. *Meth Find Exp Clin Pharmacol.* 1995; 17(9) 647-652.

In Vivo Assay 3. LPS Induced Pulmonary Neutrophilia in Rats: Effect of Intratracheally Administered PDE4 Inhibitors This assay is an animal model of inflammation in the lung—specifically neutrophilia induced by lipopolysaccharide (LPS)—and allows the study of putative inhibition of such neutrophilia (anti-inflammatory effect) by intratracheally (i.t.) administered PDE4 inhibitors. The PDE4 inhibitors are preferably in dry powder or wet suspension form. I.t. administration is one model of inhaled administration, allowing topical delivery to the lung.

Animals: Male CD (Sprague Dawley Derived) rats supplied by Charles River, Raleigh, N.C., USA are housed in groups of 5 rats per cage, acclimatised after delivery for at least 7 days with bedding/nesting material regularly changed, fed on SDS diet $R^1$ pelleted food given ad lib, and supplied with daily-changed pasteurised animal grade drinking water.

Device for dry powder administration: Disposable 3-way tap between dosing needle and syringe. A 3-way sterile tap (Vycon Ref 876.00) is weighed, the drug blend or inhalation grade lactose (vehicle control) is then added to the tap, the tap closed to prevent loss of drug, and the tap is re-weighed to determine the weight of drug in the tap. After dosing, the tap is weighed again to determine the weight of drug that had left the tap. The needle, a Sigma Z21934-7 syringe needle 19-gauge 152 mm (6 inches) long with luer hub, is cut by engineering to approximately 132 mm (5.2 inches), a blunt end is made to prevent them damaging the rat's trachea, and the needle is weighed prior to and after drug delivery to confirm that no drug is retained in the needles after dosing.

Device for wet suspension administration: This is the similar to the above but a blunt dosing needle, whose forward end is slightly angled to the needle axis, is used, with a flexible plastic portex canula inserted into the needle.

Drugs and Materials: Lipopolysaccharide (LPS) (Serotype:0127:B8) (L3129 Lot 61K4075) was dissolved in phosphate-buffered saline (PBS). PDE4 inhibitors are used in size-reduced (e.g. micronised) form, for example according to the Micronisation Example given above. For dry powder administration of the drug, the Dry Powder Formulation Example given above, comprising drug and inhalation-grade lactose, can be used. The inhalation-grade lactose usually used (Lot E98L4675 Batch 845120) has 10% fines (10% of material under 15 um particle size measured by Malvern particle size).

Wet suspensions of the drug can be prepared by added the required volume of vehicle to the drug, the vehicle being used being a mixture of saline/tween (0.2% tween 80). The wet suspension was sonicated for 10 minutes prior to use.

Preparation, and dosing with PDE 4 inhibitor: Rats are anaesthetised by placing the animals in a sealed Perspex chamber and exposing them to a gaseous mixture of isoflourane (4.5%), nitrous oxide (3 litres·minute$^{-1}$) and oxygen (1 litre·minute$^{-1}$). Once anaesthetised, the animals are placed onto a stainless steel i.t. dosing support table. They are positioned on their back at approximately a 35° angle. A light is angled against the outside of the throat to highlight the trachea. The mouth is opened and the opening of the upper airway visualised. The procedure varies for wet suspension and dry powder administration of PDE4 inhibitors as follows:

Dosing with a Wet suspension: A portex cannula is introduced via a blunt metal dosing needle that had been carefully inserted into the rat trachea. The animals are intratracheally dosed with vehicle or PDE4 inhibitor via the dosing needle with a new internal canula used for each different drug group. The formulation is slowly (10 seconds) dosed into the trachea using a syringe attached to the dosing needle.

Dosing with a Dry Powder: The three-way tap device and needle are inserted into the rat trachea up to a pre-determined point established to be located approximately 1 cm above the primary bifurcation. Another operator holds the needle at the specified position whilst 2×4 ml of air is delivered through the three-way tap by depressing the syringes (ideally coinciding with the animal inspiring), aiming to expel the entire drug quantity from the tap. After dosing, the needle and tap are removed from the airway and the tap is closed off to prevent any retained drug leaving the tap. After dosing with either wet suspension or dry powder, the animals are then removed from the table and observed constantly until they have recovered from the effects of anaesthesia. The animals are returned to the holding cages and given free access to food and water; they are observed and any unusual behavioural changes noted.

Exposure to LPS: About 2 hours after i.t. dosing with vehicle control or the PDE4 inhibitor, the rats are placed into sealed Perspex containers and exposed to an aerosol of LPS (nebuliser concentration 150 μg·ml$^{-1}$) for 15 minutes. Aerosols of LPS are generated by a nebuliser (DeVilbiss, USA) and this is directed into the Perspex exposure chamber. Following the 15-minute LPS-exposure period, the animals are returned to the holding cages and allowed free access to both food and water.

[In an alternative embodiment, the rats can exposed to LPS less than 2 hours after i.t. dosing. In another alternative embodiment, the rats can exposed to LPS more than 2 hours (e.g. ca. 4 or ca. 6 hours) after i.t. dosing by vehicle or PDE4 inhibitor, to test whether or not the PDE4 inhibitor has a long duration of action (which is not essential).]

Bronchoalveolar lavage: 4 hours after LPS exposure the animals are killed by overdose of sodium pentobarbitone (i.p.). The trachea is cannulated with polypropylene tubing and the lungs lavaged (washed out) with 3×5 mls of heparinised (25 units·ml$^{-1}$) phosphate buffered saline (PBS).

Neutrophil cell counts: The Bronchoalveolar lavage (BAL) samples are centrifuged at 1300 rpm for 7 minutes. The supernatant is removed and the resulting cell pellet resuspended in 1 ml PBS. A cell slide of the resuspension fluid is prepared by placing 100 μl of resuspended BAL fluid into cytospin holders and then spun at 5000 rpm for 5 minutes. The slides are allowed to air dry and then stained with Leishmans stain (20 minutes) to allow differential cell counting. The total cells are also counted from the resuspension. From these two counts, the total numbers of neutrophils in the BAL are determined. For a measure of PDE4-inhibitor-induced inhibition of neutrophilia, a comparison of the neutrophil count in rats treated with vehicle and rats treated with PDE4 inhibitors is conducted.

By varying the dose of the PDE4 inhibitor used in the dosing step (e.g. 0.2 or 0.1 mg of PDE4 inhibitor per kg of body weight, down to e.g. 0.01 mg/kg), a dose-response curve can be generated.

In vivo Assay 4. Evaluation of Therapeutic Index of Orally-administered PDE 4 Inhibitors in the Conscious Ferret 1.1 Materials The following materials are used for these studies:

PDE4 inhibitors are prepared for oral p.o.) administration by dissolving in a fixed volume (1 ml) of acetone and then adding cremophor to 20% of the final volume. Acetone is evaporated by directing a flow of nitrogen gas onto the solution. Once the acetone is removed, the solution is made up to final volume with distilled water. LPS is dissolved in phosphate buffered saline.

1.2 Animals

Male ferrets (Mustela Pulorius Furo, weighing 1-2 kg) are transported and allowed to acclimatise for not less than 7 days. The diet comprises SDS diet C pelleted food given ad lib with Whiskers™ cat food given 3 times per week. The animals are supplied with pasteurised animal grade drinking water changed daily.

1.3 Experimental Protocol(s)

1.3.1 Dosing with PDE4 Inhibitors

PDE4 inhibitors are administered orally (p.o.), using a dose volume of 1 ml/kg.

Ferrets are fasted overnight but allowed free access to water. The animals are orally dosed with vehicle or PDE 4 inhibitor using a 15 cm dosing needle that is passed down the back of the throat into the oesophagus. After dosing, the animals are returned to holding cages fitted with perspex doors to allow observation, and given free access to water. The animals are constantly observed and any emetic episodes (retching and vomiting) or behavioural changes are recorded. The animals are allowed access to food 60-90 minutes after p.o. dosing.

1.3.2 Exposure to LPS

Thirty minutes after oral dosing with compound or vehicle control, the ferrets are placed into sealed perspex containers and exposed to an aerosol of LPS (30 μg/ml) for 10 minutes. Aerosols of LPS are generated by a nebuliser (DeVilbiss, USA) and this is directed into the perspex exposure chamber. Following a 10-minute exposure period, the animals are returned to the holding cages and allowed free access to water, and at a later stage, food. General observation of the animals continues for a period of at least 2.5 hours post oral dosing. All emetic episodes and behavioural changes are recorded.

1.3.3 Bronchoalveolar Ravage and Cell Counts

Six hours after LPS exposure the animals are killed by overdose of sodium pentobarbitone administered intraperitoneally. The trachea is then cannulated with polypropylene tubing and the lungs lavaged twice with 20 ml heparinised (10 units/ml) phosphate buffered saline (PBS). The bronchoalveolar lavage (BAL) samples are centrifuged at 1300 rpm for 7 minutes. The supernatant is removed and the resulting cell pellet re-suspended in 1 ml PBS. A cell smear of re-suspended fluid is prepared and stained with Leishmans stain to allow differential cell counting. A total cell count is made using the remaining re-suspended sample. From this, the total number of neutrophils in the BAL sample is determined.

1.3.4 Pharmacodynamic Readouts

The following parameters are recorded:

a) % inhibition of LPS-induced pulmonary neutrophilia to determine the dose of PDE4 inhibitor which gives 50% inhibition (D50).

b) Emetic episodes—the number of vomits and retches are counted to determine the dose of PDE4 inhibitor that gives a 20% incidence of emesis (D20).

c) A therapeutic index (TI), using this assay, is then calculated for each PDE4 inhibitor using the following equation:

$$\text{Ferret Therapeutic Index } (TI)\,(D20/D50) = \frac{D20 \text{ incidence of emesis in ferret}}{D50 \text{ inhibition of neutrophilia in ferret}}$$

It is noted that the Ferret Therapeutic index (TI) (D20/D50) calculated using this in vivo Assay 4 is often substantially different to, and for example is often substantially lower than, the Rat TI (50/50) calculated using the rat oral inflammation and pica feeding Assays 1+2.

The calculation of TI using the known PDE4 inhibitor roflumilast in this Assay 4 is: D20 for emesis=0.46 mg/kg p.o., D50 for ferret neutroplilia=0.42 mg/kg p.o., Ferret TI=1.1.

All publications, including but not limited to patents and patent applications, cited in this specification are herein incorporated by reference as if each individual publication were specifically and individually indicated to be incorporated by reference herein as though fully set forth.

EXAMPLES

The various aspects of the invention will now be described by reference to the following examples. These examples are merely illustrative and are not to be construed as a limitation of the scope of the present invention. In this section, "Intermediates" represent syntheses of intermediate compounds intended for use in the synthesis of the "Examples".

Abbreviations Used Herein:
BEMP 2-t-butylimino-2-diethylamino-1,3-dimethylperhydro-1,3,2-diazaphosphazine
CDI 1,1'-carbonyldiimidazole
DBU 1,8-Diazabicyclo[5.4.0]undec-7-ene
DCM dichloromethane
DMF dimethyl formamide
DMSO dimethyl sulfoxide
EtOAc ethyl acetate
$Et_2O$ diethyl ether
EDC 1-(3-Dimethylaminopropyl)-3-ethylcarbodiimide hydrochloride
h hours
HOBT hydroxybenzotriazole=1-hydroxybenzotriazole
HATU O-(7-Azabenzotriazol-1-yl)-N,N,N',N'-tetramethyluronium hexafluorophosphate
HBTU O-(Benzotriazol-1-yl)-N,N,N',N'-tetramethyluronium hexafluorophosphate
HPLC High performance liquid chromatography
LCMS liquid chromatography/mass spectroscopy
MeCN acetonitrile
MeOH methanol
NMR nuclear magnetic resonance (in which: s=singlet, d=doublet, t=triplet, q=quartet, dd=doublet of doublets, m=multiplet, n H means that n is the number of protons)
DIPEA N,N-diisopropylethylamine ($^i Pr_2 NEt$)
SPE solid phase extraction TBTU O-(Benzotriazol-1-yl)-N,N,N',N'-tetramethyluronium tetrafluoroborate TMF Tetrahydrofuran $T_{RET}$ retention time (from LCMS)

TLC thin layer chromatography

Lawesson's reagent 2,4-bis(4-methoxyphenyl)-1,3-dithia-2,4-diphosphetane-2,4-disulphide Burgess Reagent (Methoxycarbonylsulphamoyl)triethylammonium hydroxide Room temperature=ambient temperature: this is usually in the range of about 15 to about 25° C. or about 20 to about 25° C.

Machine Methods Used Herein:

LCMS (Liquid Chromatography/Mass Spectroscopy)

Waters ZQ mass spectrometer operating in positive ion electrospray mode, mass range 100-1000 amu.

UV wavelength: 215-330 nM

Column: 3.3 cm×4.6 mm ID, 3 µm ABZ+PLUS

Flow Rate: 3 ml/min

Injection Volume: 5 µl

Solvent A: 95% acetonitrile+0.05% formic acid

Solvent B: 0.1% formic acid+10 mMolar ammonium acetate

Gradient: 0% A/0.7 min, 0-100% A/3.5 min, 100% A/1.1 min, 100-0% A/0.2 min

Mass Directed Autoprep HPLC

The prep column used was a Supelcosil ABZplus (10 cm×2.12 cm) (usually 10 cm×2.12 cm×5 µm).

UV wavelength: 200-320 nM

Flow: 20 ml/min

Injection Volume: 1 ml; or more preferably 0.5 ml

Solvent A: 0.1% formic acid (or 0.1% trifluoroacetic acid)

Solvent B: 95% acetonitrile+5% of (formic acid or trifluoroacetic acid); or more usually 99.95% acetonitrile+0.05% of (formic acid or trifluoroacetic acid)

Gradient: 100% A/1 min, 100-80% A/9 min, 80-1% A/3.5 min, 1% A/1.4 min, 1-100% A/0.1 min Microwave The CEM Discover Focused Microwave Synthesis system was used.

Intermediates and Examples

All reagents not detailed in the text below are commercially available from established suppliers such as Sigma-Aldrich. The addresses of the suppliers for some of the starting materials mentioned in the Intermediates and Examples below or the Assays above are as follows:

ABCR GmbH & CO. KG, P.O. Box 21 01 35, 76151 Karlsruhe, Germany

Aceto Color Intermediates (catalogue name), Aceto Corporation, One Hollow Lane, Lake Success, N.Y., 11042-1215, USA Acros Organics, A Division of Fisher Scientific Company, 500 American Road, Morris Plains, N.J. 07950, USA Apin Chemicals Ltd., 82 C Milton Park, Abingdon, Oxon OX14 4RY, United Kingdom Apollo Scientific Ltd., Unit 1A, Bingswood Industrial Estate, Whaley Bridge, Derbyshire SK23 7LY, United Kingdom Aldrich (catalogue name), Sigma-Aldrich Company Ltd., Dorset, United Kingdom, telephone: +44 1202 733114; Fax: +44 1202 715460; ukcustsv@eurnotes.sial.com; or Aldrich (catalogue name), Sigma-Aldrich Corp., P.O. Box 14508, St. Louis, Mo. 63178-9916, USA; telephone: 314-771-5765; fax: 314-771-5757; custserv@sial.com; or Aldrich (catalogue name), Sigma-Aldrich Chemie Gmbh, Munich, Germany; telephone: +49 89 6513 0; Fax: +49 89 6513 1169; deorders@eurnotes.sial.com.

Alfa Aesar, A Johnson Matthey Company, 30 Bond Street, Ward Hill, Mass. 01835-8099, USA Amersham Biosciences UK Ltd, Pollards Wood, Chalfont St Giles, Buckinghamshire HP8 4SP, United Kingdom Array Biopharma Inc., 1885 33rd Street, Boulder, Colo. 80301, USA AstaTech, Inc., 8301 Torresdale Ave., 19C, Philadelphia, Pa. 19136, USA Austin Chemical Company, Inc., 1565 Barclay Blvd., Buffalo Grove, Ill. 60089, USA Avocado Research, Shore Road, Port of Heysham Industrial Park, Heysham Lancashire LA3 2XY, United Kingdom Bayer A G, Business Group Basic and Fine Chemicals, D-51368 Leverkusen, Germany Berk Univar plc, Berk House, P.O. Box 56, Basing View, Basingstoke, Hants RG21 2E6, United Kingdom Butt Park Ltd., Braysdown Works, Peasedown St. John, Bath BA2 8LL, United Kingdom Chemical Building Blocks (catalogue name), Ambinter, 46 quai Louis Bleriot, Paris, F-75016, France ChemBridge Europe, 4 Clark's Hill Rise, Hampton Wood, Evesham, Worcestershire WR11 6FW, United Kingdom ChemService Inc., P.O. Box 3108, West Chester, Pa. 19381, USA Combi-Blocks Inc., 7949 Silverton Avenue, Suite 915, San Diego, Calif. 92126, USA Dyrnamit Nobel GmbH, Germany; also available from: Saville Whittle Ltd (UK agents of Dynamit Nobel), Vickers Street, Manchester M40 8EF, United Kingdom E. Merck, Germany; or E. Merck (Merck Ltd), Hunter Boulevard, Magna Park, Lutterworth, Leicestershire LE17 4XN, United Kingdom Esprit Chemical Company, Esprit Plaza, 7680 Matoaka Road, Sarasota, Fla. 34243, USA Exploratory Library (catalogue name), Ambinter, 46 quai Louis Bleriot, Paris, F-75016, France Fluka Chemie A G, Industriestrasse 25, P.O. Box 260, CH-9471 Buchs, Switzerland Fluorochem Ltd., Wesley Street, Old Glossop, Derbyshire SK13 7R$^Y$, United Kingdom ICN Biomedicals, Inc., 3300 Hyland Avenue, Costa Mesa, Calif. 92626, USA Interchim Intermediates (catalogue name), Interchim, 213 Avenue Kennedy, BP 1140, Montlucon, Cedex, 03103, France Key Organics Ltd., 3, Highfield Indusrial Estate, Camelford, Cornwall PL32 9QZ, United Kingdom Lancaster Synthesis Ltd., Newgate, White Lund, Morecambe, Lancashire LA3 3DY, United Kingdom Manchester Organics Ltd., Unit 2, Ashville Industrial Estate, Sutton Weaver, Runcorn, Cheshire WA7 3PF, United Kingdom Matrix Scientific, P.O. Box 25067, Columbia, S.C. 29224-5067, USA Maybridge Chemical Company Ltd., Trevillett, Tintagel, Cornwall PL34 0HW, United Kingdom Maybridge Reactive Intermediates (catalogue name), Maybridge Chemical Company Ltd., Trevillett, Tintagel, Cornwall PL34 0HW, United Kingdom MicroChemistry Building Blocks (catalogue name), MicroChemistry-RadaPharma, Shosse Entusiastov 56, Moscow, 111123, Russia Miteni S.p.A., Via Mecenate 90, Milano, 20138, Italy Molecular Devices Corporation, Sunnydale, Calif., USA N.D. Zelinsky Institute, Organic Chemistry, Leninsky prospect 47, 117913 Moscow B-334, Russia Optimer Building Block (catalogue name), Array BioPharma, 3200 Walnut Street, Boulder, Colo. 80301, USA Peakdale Molecular Ltd., Peakdale Science Park, Sheffield Road, Chapel-en-le-Frith, High Peak SK23 0PG, United Kingdom Pfaltz & Bauer, Inc., 172 East Aurora Street, Waterbury, Conn. 06708, USA Rare Chemicals (catalogue name), Rare Chemicals GmbH, Schulstrasse 6, 24214 Gettorf, Germany SALOR (catalogue name) (Sigma Aldrich Library of Rare Chemicals), Aldrich Chemical Company Inc, 1001 West Saint Paul Avenue, Milwaukee, Wis. 53233, USA Sigma (catalogue name), Sigma-Aldrich Corp., P.O. Box 14508, St. Louis, Mo. 63178-9916, USA; see "Aldrich" above for other non-US addresses and other contact details SIGMA-RBI, One Strathmore Road, Natick, Mass. 01760-1312, USA Synchem OHG Heinrich-Plett-Strasse 40, Kassel, D-34132, Germany Syngene International Pvt Ltd, Hebbagodi, Hosur Road, Bangalore, India.

TCI America, 9211 North Harborgate Street, Portland, Oreg. 97203, USA

TimTec Building Blocks A, TimTec, Inc., PO Box 8941, Newark, Del. 19714-8941, USA Trans World Chemicals, Inc., 14674 Southlawn Lane, Rockville, Md. 20850, USA Ubichem PLC, Mayflower Close, Chandlers Ford Industrial Estate, Eastleigh, Hampshire SO53 4AR, United Kingdom Ultrafine (UFC Ltd.), Synergy House, Guildhall Close, Manchester Science Park Manchester M15 6SY, United Kingdom

| Table of Intermediates | |
|---|---|
| Intermediate Number | Name |
| 1 | Ethyl 4-chloro-1-ethyl-1H-pyrazolo[3,4-b]pyridine-5-carboxylate |
| 2 | Ethyl 4-(cyclopentylamino)-1-ethyl-1H-pyrazolo[3,4-b]pyridine-5-carboxylate |
| 3 | 4-(Cyclopentylamino)-1-ethyl-1H-pyrazolo[3,4-b]pyridine-5-carboxylic acid |
| 4 | N'-Acetyl-4-(Cyclopentylamino)-1-ethyl-1H-pyrazolo[3,4-b]pyridine-5-carbohydrazide |
| 5 | 4-(Cyclopentylamino)-1-ethyl-N'-[(methylsulfonyl)acetyl]-1H-pyrazolo[3,4-b]pyridine-5-carbohydrazide |
| 6 | Ethyl 4-(4-fluorophenylamino)-1-ethyl-1H-pyrazolo[3,4-b]pyridine-5-carboxylate |
| 7 | 4-(Cyclopentylamino)-1-ethyl-N-[methyl]-1H-pyrazolo[3,4-b]pyridine-5-carbohydrazide |
| 8 | Methanesulfonyl acetic acid hydrazide |
| 9 | Acetamidoxime |
| 10 | 4-(Cyclopentylamino)-1-ethyl-N'-isobutyryl-1H-pyrazolo[3,4-b]pyridine-5-carbohydrazide |
| 11 | 4-Chloro-1-ethyl-1H-pyrazolo[3,4-b]pyridine-5-carboxylic acid |
| 12 | 4-Chloro-1-ethyl-5-(5-methyl-1,3,4-oxadiazol-2-yl)-1H-pyrazolo[3,4-b]pyridine |
| 13 | 4-Chloro-1-ethyl-5-(5-isopropyl-1,3,4-oxadiazol-2-yl)-1H-pyrazolo[3,4-b]pyridine |
| 14 | 5-(5-Tert-butyl-1,3,4-oxadiazol-2-yl)-4-chloro-1-ethyl-1H-pyrazolo[3,4-b]pyridine |
| 15 | 4-Chloro-1-ethyl-5-{5-[(methylsulfonyl)methyl]-1,3,4-oxadiazol-2-yl}-1H-pyrazolo[3,4-b]pyridine |
| 16 | Ethyl 1-ethyl-4-(tetrahydro-2H-pyran-4-ylamino)-1H-pyrazolo[3,4-b]pyridine-5-carboxylate |
| 17 | 1-Ethyl-4-(tetrahydro-2H-pyran-4-ylamino)-1H-pyrazolo[3,4-b]pyridine-5-carboxylic acid |
| 18 | Tert-butyl 2-{[1-ethyl-4-(tetrahydro-2H-pyran-4-ylamino)-1H-pyrazolo[3,4-b]pyridin-5-yl]carbonyl}hydrazinecarboxylate |
| 19 | 1-Ethyl-4-(tetrahydro-2H-pyran-4-ylamino)-1H-pyrazolo[3,4-b]pyridine-5-carbohydrazide dihydrochloride |
| 20 | N'-(Cyclopropylcarbonyl)-1-ethyl-4-(tetrahydro-2H-pyran-4-ylamino)-1H-pyrazolo[3,4-b]pyridine-5-carbohydrazide |
| 21 | Tetrahydro-2H-pyran-4-amine = 4-Aminotetrahydropyran |
| 21A | Tetrahydro-2H-pyran-4-amine hydrochloride = 4-aminotetrahydropyran hydrochloride |
| 22 | N'-Hydroxy-2-methoxyethanimidamide |
| 23 | 2-(Dimethylamino)-N'-hydroxyethanimidamide |
| 24 | N'-Hydroxy-2-morpholin-4-ylethanimidamide |
| 25 | 1-Acetyl-4-aminopiperidine hydrochloride |
| 26 | 3-Methyloxetane-3-carboxylic acid |
| 27 | (4-Methylpiperazin-1-yl)acetic acid |
| 28 | (Isopropylamino)(oxo)acetic acid |
| 29 | 1-Methyl-5-oxopyrrolidine-3-carboxylic acid |

-continued

Table of Intermediates

| Intermediate Number | Name |
|---|---|
| 30 | Tetrahydro-2H-pyran-4-carboxylic acid |
| 31 | Morpholin-4-ylacetic acid |
| 32 | Tert-butoxyacetic acid |
| 33 | Methyl (2S)-2-({[1-ethyl-4-(tetrahydro-2H-pyran-4-ylamino)-1H-pyrazolo[3,4-b]pyridin-5-yl]carbonyl}amino)-3-hydroxypropanoate |
| 34 | 1-Ethyl-N-(2-hydroxy-1-methylethyl)-4-(tetrahydro-2H-pyran-4-ylamino)-1H-pyrazolo[3,4-b]pyridine-5-carboxamide |
| 35 | Ethyl 4-ethoxy-1-ethyl-1H-pyrazolo[3,4-b]pyridine-5-carboxylate |
| 36 | Ethyl 4-ethoxy-1H-pyrazolo[3,4-b]pyridine-5-carboxylate |
| 37 | Ethyl 4-(tetrahydro-2H-pyran-4-ylamino)-1H-pyrazolo[3,4-b]pyridine-5-carboxylate |
| 38 | Ethyl 1-n-propyl-4-(tetrahydro-2H-pyran-4-ylamino)-1H-pyrazolo[3,4-b]pyridine-5-carboxylate |
| 39 | 1-n-Propyl-4-(tetrahydro-2H-pyran-4-ylamino)-1H-pyrazolo[3,4-b]pyridine-5-carboxylic acid |
| 40 | N'-Acetyl 1-n-propyl-4-(tetrahydro-2H-pyran-4-ylamino)-1H-pyrazolo[3,4-b]pyridine-5-carbohydrazide |
| 41 | Ethyl 4-[(1-acetyl-4-piperidinyl)amino]-1-ethyl-1H-pyrazolo[3,4-b]pyridine-5-carboxylate |
| 42 | 1-Ethyl-N-[(1R)-2-hydroxy-1-phenylethyl]-4-(tetrahydro-2H-pyran-4-ylamino)-1H-pyrazolo[3,4-b]pyridine-5-carboxamide |
| 43 | 1-Ethyl-N-[(1S)-2-hydroxy-1-phenylethyl]-4-(tetrahydro-2H-pyran-4-ylamino)-1H-pyrazolo[3,4-b]pyridine-5-carboxamide |
| 44 | 1-Ethyl-N-[(1S)-2-hydroxy-1-(phenylmethyl)ethyl]-4-(tetrahydro-2H-pyran-4-ylamino)-1H-pyrazolo[3,4-b]pyridine-5-carboxamide |
| 45 | 1-Ethyl-N-[(1R)-2-hydroxy-1-(phenylmethyl)ethyl]-4-(tetrahydro-2H-pyran-4-ylamino)-1H-pyrazolo[3,4-b]pyridine-5-carboxamide |
| 46 | 1-Ethyl-N-[(1S,2R)-2-hydroxy-1-phenylpropyl]-4-(tetrahydro-2H-pyran-4-ylamino)-1H-pyrazolo[3,4-b]pyridine-5-carboxamide |
| 47 | 1-Ethyl-N-[(2R)-2-hydroxy-2-phenylethyl]-4-(tetrahydro-2H-pyran-4-ylamino)-1H-pyrazolo[3,4-b]pyridine-5-carboxamide |
| 48 | 1-Ethyl-N-[(2S)-2-hydroxy-2-phenylethyl]-4-(tetrahydro-2H-pyran-4-ylamino)-1H-pyrazolo[3,4-b]pyridine-5-carboxamide |
| 49 | 1-Ethyl-N-(2-hydroxy-1,1-dimethylethyl)-4-(tetrahydro-2H-pyran-4-ylamino)-1H-pyrazolo[3,4-b]pyridine-5-carboxamide |
| 50 | N-methyltetrahydro-2H-pyran-4-amine |
| 51 | Ethyl 1-ethyl-4-[methyl(tetrahydro-2H-pyran-4-yl)amino]-1H-pyrazolo[3,4-b]pyridine-5-carboxylate |
| 52 | 1-Ethyl-4-[methyl(tetrahydro-2H-pyran-4-yl)amino]-1H-pyrazolo[3,4-b]pyridine-5-carboxylic acid |
| 53 | N'-Acetyl-1-ethyl-4-[methyl(tetrahydro-2H-pyran-4-yl)amino]-1H-pyrazolo[3,4-b]pyridine-5-carbohydrazide |
| 54 | trans-4-Aminocyclohexanol |
| 55 | Tetrahydro-2H-pyran-3-amine hydrochloride |
| 56 | 4-Aminocyclohexanone hydrochloride |
| 57 | N-Propyltetrahydro-2H-pyran-4-amine |
| 58 | Ethyl 4-chloro-1-ethyl-6-methyl-1H-pyrazolo[3,4-b]pyridine-5-carboxylate |
| 59 | Ethyl 1-ethyl-6-methyl-4-(tetrahydro-2H-pyran-4-ylamino)-1H-pyrazolo[3,4-b]pyridine-5-carboxylate |
| 60 | 1-Ethyl-6-methyl-4-(tetrahydro-2H-pyran-4-ylamino)-1H-pyrazolo[3,4-b]pyridine-5-carboxylic acid |
| 61 | N'-(2,2-Dimethylpropanoyl)-1-ethyl-6-methyl-4-(tetrahydro-2H-pyran-4-ylamino)-1H-pyrazolo[3,4-b]pyridine-5-carbohydrazide |
| 62 | 1,1-Dimethylethyl 2-{[1-ethyl-6-methyl-4-(tetrahydro-2H-pyran-4-ylamino)-1H-pyrazolo[3,4-b]pyridin-5-yl]carbonyl}hydrazinecarboxylate |
| 63 | 1-Ethyl-6-methyl-4-(tetrahydro-2H-pyran-4-ylamino)-1H-pyrazolo[3,4-b]pyridine-5-carbohydrazide hydrochloride |
| 64 | 1-Ethyl-6-methyl-4-(tetrahydro-2H-pyran-4-ylamino)-N'-(tetrahydro-2H-pyran-4-ylcarbonyl)-1H-pyrazolo[3,4-b]pyridine-5-carbohydrazide |
| 65 | N'-(Cyclobutylcarbonyl)-1-ethyl-4-(tetrahydro-2H-pyran-4-ylamino)-1H-pyrazolo[3,4-b]pyridine-5-carbohydrazide |
| 66 | 1-Ethyl-N'-[(5-oxo-2-pyrrolidinyl)carbonyl]-4-(tetrahydro-2H-pyran-4-ylamino)-1H-pyrazolo[3,4-b]pyridine-5-carbohydrazide (non-preferred name) |
| 67 | N-[2-(2-{[1-Ethyl-4-(tetrahydro-2H-pyran-4-ylamino)-1H-pyrazolo[3,4-b]pyridin-5-yl]carbonyl}hydrazino)-2-oxoethyl]acetamide (non-preferred name) |
| 68 | 1-Ethyl-N'-[(1-methyl-2-piperidinyl)carbonyl]-4-(tetrahydro-2H-pyran-4-ylamino)-1H-pyrazolo[3,4-b]pyridine-5-carbohydrazide |
| 69 | 1-Ethyl-N'-[(4-methyl-1,2,5-oxadiazol-3-yl)acetyl]-4-(tetrahydro-2H-pyran-4-ylamino)-1H-pyrazolo[3,4-b]pyridine-5-carbohydrazide |

-continued

Table of Intermediates

| Intermediate Number | Name |
|---|---|
| 70 | 1-Ethyl-N'-[(3-oxocyclopentyl)carbonyl]-4-(tetrahydro-2H-pyran-4-ylamino)-1H-pyrazolo[3,4-b]pyridine-5-carbohydrazide |
| 71 | 1-Ethyl-N'-(tetrahydro-3-furanylcarbonyl)-4-(tetrahydro-2H-pyran-4-ylamino)-1H-pyrazolo[3,4-b]pyridine-5-carbohydrazide |
| 72 | 1-ethyl-N'-[(2-oxo-1,3-thiazolidin-4-yl)carbonyl]-4-(tetrahydro-2H-pyran-4-ylamino)-1H-pyrazolo[3,4-b]pyridine-5-carbohydrazide |
| 73 | N'-[(2,2-Dimethylcyclopropyl)carbonyl]-1-ethyl-4-(tetrahydro-2H-pyran-4-ylamino)-1H-pyrazolo[3,4-b]pyridine-5-carbohydrazide |
| 74 | N-[2-(2-{[1-Ethyl-4-(tetrahydro-2H-pyran-4-ylamino)-1H-pyrazolo[3,4-b]pyridin-5-yl]carbonyl}hydrazino)-2-oxoethyl]-N-methylacetamide (non-preferred name) |
| 75 | 1-Ethyl-N'-(tetrahydro-2H-pyran-4-ylacetyl)-4-(tetrahydro-2H-pyran-4-ylamino)-1H-pyrazolo[3,4-b]pyridine-5-carbohydrazide |
| 76 | 1-Ethyl-N'-[(1-methylcyclobutyl)carbonyl]-4-(tetrahydro-2H-pyran-4-ylamino)-1H-pyrazolo[3,4-b]pyridine-5-carbohydrazide |
| 77 | 1-Ethyl-N'-[(3-methyl-5-isoxazolyl)carbonyl]-4-(tetrahydro-2H-pyran-4-ylamino)-1H-pyrazolo[3,4-b]pyridine-5-carbohydrazide |
| 78 | 1-Ethyl-N'-[(1-methyl-1H-pyrazol-5-yl)carbonyl]-4-(tetrahydro-2H-pyran-4-ylamino)-1H-pyrazolo[3,4-b]pyridine-5-carbohydrazide |
| 79 | N'-[(1-Acetyl-4-piperidinyl)carbonyl]-1-ethyl-4-(tetrahydro-2H-pyran-4-ylamino)-1H-pyrazolo[3,4-b]pyridine-5-carbohydrazide |
| 80 | (1E/Z)-N-hydroxy-2-(4-methyl-1-piperazinyl)ethanimidamide |
| 81 | 4-Fluoro-N-hydroxybenzenecarboximidamide |
| 82 | (1E/Z)-N-hydroxy-3-oxo-3-(1-pyrrolidinyl)propanimidamide |
| 83 | {5-[1-Ethyl-4-(tetrahydro-2H-pyran-4-ylamino)-1H-pyrazolo[3,4-b]pyridin-5-yl]-1,2,4-oxadiazol-3-yl}acetic acid |
| 84 | 1,1-Dimethylethyl {5-[1-ethyl-4-(tetrahydro-2H-pyran-4-ylamino)-1H-pyrazolo[3,4-b]pyridin-5-yl]-1,2,4-oxadiazol-3-yl}acetate |
| 85 | 1,1-Dimethylethyl (3E/Z)-3-(hydroxyamino)-3-iminopropanoate |
| 86 | N''-{1-Ethyl-4-(tetrahydro-2H-pyran-4-ylamino)-1H-pyrazolo[3,4-b]pyridin-5-yl]carbonyl}-N,N,N',N'-tetramethylcarbonohydrazonic diamide |
| 87 | Ethyl (2-methyl-1,3-thiazol-4-yl) acetate |
| 88 | 2-Methyl-1,3-thiazol-4-yl acetic acid |
| 89 | 1-Ethyl-4-(tetrahydro-2H-pyran-4-ylamino)-N'-(1H-1,2,3-triazol-1-ylacetyl)-1H-pyrazolo[3,4-b]pyridine-5-carbohydrazide |
| 90 | N'-[(2,4-Dimethyl-1,3-thiazol-5-yl)acetyl]-1-ethyl-4-(tetrahydro-2H-pyran-4-ylamino)-1H-pyrazolo[3,4-b]pyridine-5-carbohydrazide |
| 91 | 1-Ethyl-N'-(2-furanylacetyl)-4-(tetrahydro-2H-pyran-4-ylamino)-1H-pyrazolo[3,4-b]pyridine-5-carbohydrazide |
| 92 | 1-Ethyl-N'-(3-isoxazolylacetyl)-4-(tetrahydro-2H-pyran-4-ylamino)-1H-pyrazolo[3,4-b]pyridine-5-carbohydrazide |
| 93 | 1-Ethyl-N'-{[4-(methyloxy)phenyl]acetyl}-4-(tetrahydro-2H-pyran-4-ylamino)-1H-pyrazolo[3,4-b]pyridine-5-carbohydrazide |
| 94 | 1-Ethyl-4-(tetrahydro-2H-pyran-4-ylamino)-N'-(1H-tetrazol-1-ylacetyl)-1H-pyrazolo[3,4-b]pyridine-5-carbohydrazide |
| 95 | 1-Ethyl-N'-(5-isothiazolylacetyl)-4-(tetrahydro-2H-pyran-4-ylamino)-1H-pyrazolo[3,4-b]pyridine-5-carbohydrazide |
| 96 | 1-Ethyl-N'-[(3-methyl-5-isoxazolyl)acetyl]-4-(tetrahydro-2H-pyran-4-ylamino)-1H-pyrazolo[3,4-b]pyridine-5-carbohydrazide |
| 97 | N'-{[4-(Dimethylamino)phenyl]acetyl}-1-ethyl-4-(tetrahydro-2H-pyran-4-ylamino)-1H-pyrazolo[3,4-b]pyridine-5-carbohydrazide |
| 98 | 1-Ethyl-N'-[(2-methyl-1,3-thiazol-4-yl)acetyl]-4-(tetrahydro-2H-pyran-4-ylamino)-1H-pyrazolo[3,4-b]pyridine-5-carbohydrazide |
| 99 | 2-{1-[2-(2-{[1-Ethyl-4-(tetrahydro-2H-pyran-4-ylamino)-1H-pyrazolo[3,4-b]pyridin-5-yl]carbonyl}hydrazino)-2-oxoethyl]cyclopentyl}-N-methylacetamide |
| 100 | N-[2-(2-{[1-Ethyl-4-(tetrahydro-2H-pyran-4-ylamino)-1H-pyrazolo[3,4-b]pyridin-5-yl]carbonyl}hydrazino)-2-oxoethyl]cyclopropanecarboxamide (non-preferred name) |
| 101 | 1-Ethyl-N'-[(5-methyl-3-isoxazolyl)carbonyl]-4-(tetrahydro-2H-pyran-4-ylamino)-1H-pyrazolo[3,4-b]pyridine-5-carbohydrazide |
| 102 | 1-Ethyl-N'-[(5-methyl-3-isoxazolyl)acetyl]-4-(tetrahydro-2H-pyran-4-ylamino)-1H-pyrazolo[3,4-b]pyridine-5-carbohydrazide |
| 103 | 1-Ethyl-N'-[3-(4-methyl-1,3-thiazol-5-yl)propanoyl]-4-(tetrahydro-2H-pyran-4-ylamino)-1H-pyrazolo[3,4-b]pyridine-5-carbohydrazide |
| 104 | 1-Ethyl-N'-[(6-oxo-2-piperidinyl)carbonyl]-4-(tetrahydro-2H-pyran-4-ylamino)-1H-pyrazolo[3,4-b]pyridine-5-carbohydrazide |
| 105 | 1-Ethyl-N'-[(3-methyl-1H-1,2,4-triazol-5-yl)acetyl]-4-(tetrahydro-2H-pyran-4-ylamino)-1H-pyrazolo[3,4-b]pyridine-5-carbohydrazide |
| 106 | N'-[(3,5-Dimethyl-4-isoxazolyl)acetyl]-1-ethyl-4-(tetrahydro-2H-pyran-4-ylamino)-1H-pyrazolo[3,4-b]pyridine-5-carbohydrazide |

-continued

Table of Intermediates

| Intermediate Number | Name |
|---|---|
| 107 | N-[2-(2-{[1-Ethyl-4-(tetrahydro-2H-pyran-4-ylamino)-1H-pyrazolo[3,4-b]pyridin-5-yl]carbonyl}hydrazino)-1-methyl-2-oxoethyl]acetamide (non-preferred name) |
| 108 | N'-[(1-Acetyl-4-piperidinyl)acetyl]-1-ethyl-4-(tetrahydro-2H-pyran-4-ylamino)-1H-pyrazolo[3,4-b]pyridine-5-carbohydrazide |
| 109 | 1-Ethyl-N'-[(4-methylphenyl)acetyl]-4-(tetrahydro-2H-pyran-4-ylamino)-1H-pyrazolo[3,4-b]pyridine-5-carbohydrazide |
| 110 | 1-Ethyl-N'-[(4-methylphenyl)carbonyl]-4-(tetrahydro-2H-pyran-4-ylamino)-1H-pyrazolo[3,4-b]pyridine-5-carbohydrazide |
| 111 | N'-[(3,4-Dimethylphenyl)carbonyl]-1-ethyl-4-(tetrahydro-2H-pyran-4-ylamino)-1H-pyrazolo[3,4-b]pyridine-5-carbohydrazide |
| 112 | N'-[(2,4-Dimethylphenyl)carbonyl]-1-ethyl-4-(tetrahydro-2H-pyran-4-ylamino)-1H-pyrazolo[3,4-b]pyridine-5-carbohydrazide |
| 113 | N'-[(2,4-Dimethylphenyl)acetyl]-1-ethyl-4-(tetrahydro-2H-pyran-4-ylamino)-1H-pyrazolo[3,4-b]pyridine-5-carbohydrazide |
| 114 | N'-[(4-Bromophenyl)acetyl]-1-ethyl-4-(tetrahydro-2H-pyran-4-ylamino)-1H-pyrazolo[3,4-b]pyridine-5-carbohydrazide |
| 115 | 4-Fluoro-N-hydroxybenzenecarboximidamide |
| 116 | 1,1-Dimethylethyl [(2Z)-2-(hydroxyamino)-2-iminoethyl]carbamate |
| 117 | 1,1-Dimethylethyl ({5-[1-ethyl-4-(tetrahydro-2H-pyran-4-ylamino)-1H-pyrazolo[3,4-b]pyridin-5-yl]-1,2,4-oxadiazol-3-yl}methyl)carbamate |
| 118 | 5-[3-(Aminomethyl)-1,2,4-oxadiazol-5-yl]-1-ethyl-N-(tetrahydro-2H-pyran-4-yl)-1H-pyrazolo[3,4-b]pyridine-4-amine |
| 119 | 4-Chloro-N-({5-[1-ethyl-4-(tetrahydro-2H-pyran-4-ylamino)-1H-pyrazolo[3,4-b]pyridin-5-yl]-1,2,4-oxadiazol-3-yl}methyl)butanamide |
| 120 | 5-Chloro-N-({5-[1-ethyl-4-(tetrahydro-2H-pyran-4-ylamino)-1H-pyrazolo[3,4-b]pyridin-5-yl]-1,2,4-oxadiazol-3-yl}methyl)pentanamide |
| 121 | (1E/Z)-N-hydroxy-2-(4-morpholinyl)propanimidamide |
| 122 | (1E/Z)-2-cyclohexyl-N-hydroxyethanimidamide |
| 123 | 1,1-Dimethylethyl 4-[(2Z)-2-(hydroxyamino)-2-iminoethyl]-1-piperidinecarboxylate |
| 124 | 1,1-Dimethylethyl 4-({5-[1-ethyl-4-(tetrahydro-2H-pyran-4-ylamino)-1H-pyrazolo[3,4-b]pyridin-5-yl]-1,2,4-oxadiazol-3-yl}methyl)-1-piperidinecarboxylate |
| 125 | 1-Ethyl-5-[3-(4-piperidinylmethyl)-1,2,4-oxadiazol-5-yl]-N-(tetrahydro-2H-pyran-4-yl)-1H-pyrazolo[3,4-b]pyridin-4-amine hydrochloride |
| 126 | N-Hydroxy-1-(phenylsulfonyl)cyclopropanecarboximidamide |
| 127 | (1E/Z)-N-Hydroxy-2-phenylethanimidamide |
| 128 | (1E/Z)-N-Hydroxy-2-phenylpropanimidamide |
| 129 | (1E/Z)-N-Hydroxy-2-[4-(methyloxy)phenyl]ethanimidamide |
| 130 | (1E/Z)-N-Hydroxy-2-[3-(methyloxy)phenyl]ethanimidamide |
| 131 | (1E/Z)-2-[4-(Dimethylamino)phenyl]-N-hydroxyethanimidamide |
| 132 | (1E/Z)-2-[3-(Dimethylamino)phenyl]-N-hydroxyethanimidamide |
| 133 | (1E/Z)-N-Hydroxy-2-(phenyloxy)ethanimidamide |
| 134 | (1E/Z)-N-hydroxy-2-(5,6,7,8-tetrahydro[1,2,4]triazolo[4,3-a]pyridin-3-yl)ethanimidamide |
| 135 | (1E/Z)-N-Hydroxy-2-(4-phenyl-1-piperazinyl)ethanimidamide |
| 136 | 1-Ethyl-4-(tetrahydro-2H-pyran-4-ylamino)-1H-pyrazolo[3,4-b]pyridine-5-carboxamide |
| 137 | 1-Ethyl-4-(tetrahydro-2H-pyran-4-ylamino)-1H-pyrazolo[3,4-b]pyridine-5-carbonitrile |
| 138 | 1-Ethyl-N-hydroxy-4-(tetrahydro-2H-pyran-4-ylamino)-1H-pyrazolo[3,4-b]pyridine-5-carboximidamide |
| 139 | 1-Ethyl-N-[4-(hydroxymethyl)tetrahydro-2H-pyran-4-yl]-4-(tetrahydro-2H-pyran-4-ylamino)-1H-pyrazolo[3,4-b]pyridine-5-carboxamide |

Intermediate 1: Ethyl 4-chloro-1-ethyl-1H-pyrazolo [3,4-b]pyridine-5-carboxylate Prepared from commercially available 5-amino-1-ethyl pyrazole as described by G. Yu et. al. in *J. Med Chem.*, 2001, 44, 1025-1027:

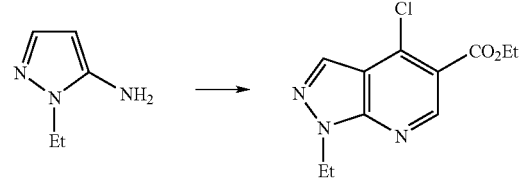

Intermediate 2: Ethyl 4-(cyclopentylamino)-1-ethyl-1H-pyrazolo[3,4-b]pyridine-5-carboxylate

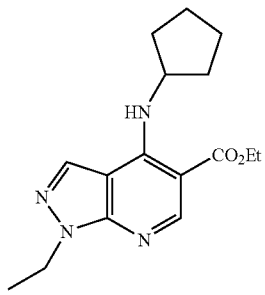

Intermediate 1 (0.051 g) and cyclopentyl amine (0.019 g) were suspended in ethanol (2 ml) and triethylamine (0.14 ml) was added. The mixture was stirred under nitrogen and heated at 80° C. for 16 h. After cooling to room temperature, ethanol was removed by evaporation under a stream of nitrogen and the residue partitioned between DCM and water. The organic layer was loaded directly onto an SPE cartridge (silica, 5 g) and eluted sequentially with; (i) DCM, (ii) DCM:Et$_2$O (2:1), (iii) DCM:Et$_2$O (1:1), (iv) Et$_2$O, (v) EtOAc and (vi) MeOH. Fractions containing desired material were combined and concentrated in vacuo to afford Intermediate 2 (0.074 g). LCMS showed MH$^+$303; T$_{RET}$=3.45 min

Intermediate 3: 4-(Cyclopentylamino)-1-ethyl-1H-pyrazolo[3,4-b]pyridine-5-carboxylic acid

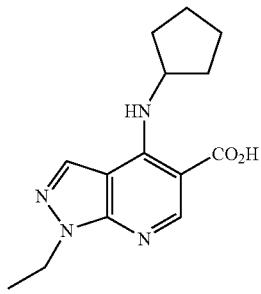

A solution of Intermediate 2 (2.2 g) in ethanol: water (95:5, 16.85 ml) was treated with sodium hydroxide (1.2 g) and heated at 50° C. for 16 h. The mixture was concentrated in vacuo and the residue re-dissolved in water (0.85 ml). The solution was acidified to pH4 using acetic acid and the resultant white precipitate was collected by filtration and dried under vacuum to afford Intermediate 3 (1.9 g). LCMS showed MH$^+$=275; T$_{RET}$=2.65 min

Intermediate 4: N'-Acetyl-4-(Cyclopentylamino)-1-ethyl-1H-pyrazolo[3,4-b]pyridine-5-carbohydrazide

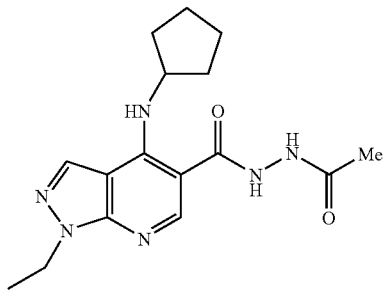

Intermediate 3 (0.066 g), EDC (0.06 g) and HOBT (0.035 g) were suspended in DMF (2 ml) and the mixture was stirred for 15 minutes. Acetic hydrazide (0.02 g) was then added and the mixture stirred under nitrogen for 18 h. Solvents were removed by concentration in vacuo and the residue partitioned between DCM and water. The layers were separated and the organic phase was washed with saturated aqueous sodium bicarbonate solution, then concentrated and applied to an SPE cartridge (aminopropyl, 1 g) which was eluted with methanol. Concentration in vacuo afforded Intermediate 4 (0.043 g). LCMS showed MH$^+$=331; T$_{RET}$=2.38 min.

Intermediate 5: 4-(Cyclopentylamino)-1-ethyl-N'-[(methylsulfonyl)acetyl]-1H-pyrazolo[3,4-b]pyridine-5-carbohydrazide

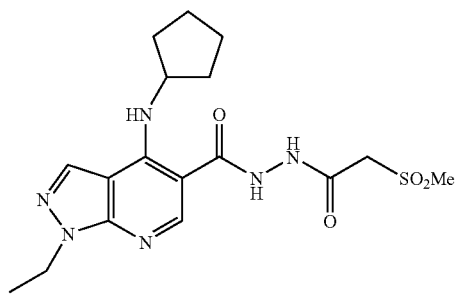

Intermediate 3 (0.12 g), EDC (0.12 g) and HOBT (0.072 g) were suspended in DMF (2 ml) and stirred for 15 minutes. Intermediate 8 (0.082 g) was then added and the mixture stirred under nitrogen for 18 h. Reaction was incomplete so a further portion of Intermediate 8 was added (0.040 g) and stirring continued for a further 66 h. Solvents were removed in vacuo and the residue partitioned between DCM and water. The aqueous phase was further extracted with DCM and the combined organic layers applied to an SPE cartridge (silica, 5 g) which was eluted sequentially with a gradient of Et$_2$O:MeOH (1:0, 9:1, 8:2, 7:3 and 6:4). Fractions containing desired material were combined and concentrated in vacuo to afford Intermediate 5 (0.154 g). LCMS showed MH$^+$=409; T$_{RET}$=2.42 min.

Intermediate 6: Ethyl 4-(4-fluorophenylamino)-1-ethyl-1H-pyrazolo[3,4-b]pyridine-5-carboxylate

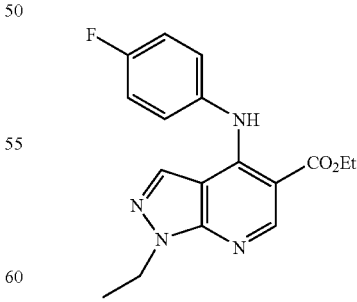

Intermediate 1 (0.051 g) and 4-fluoroaniline (0.024 g) were suspended in ethanol (2 ml) and triethylamine (0.14 ml) was added. The mixture was stirred under nitrogen and heated at 80° C. for 16 h. After cooling to room temperature, ethanol was removed by evaporation under a stream of nitrogen and the residue partitioned between DCM and water. The organic layer was loaded directly onto an SPE cartridge (silica, 5 g) and eluted sequentially with; (i) DCM, (ii) DCM: Et$_2$O (2:1), (iii) DCM:Et$_2$O (1:1), (iv) Et$_2$O, (v) EtOAc, (vi) MeOH. Fractions containing desired material were combined and concentrated in vacuo to afford Intermediate 6 (0.077 g). LCMS showed MH$^+$=328; T$_{RET}$=3.36 min.

Intermediate 7: 4-(Cyclopentylamino)-1-ethyl-N-[methyl]-1H-pyrazolo[3,4-b]pyridine-5-carbohydrazide

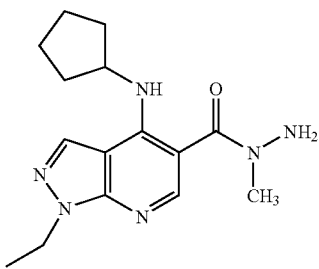

Intermediate 3 (0.10 g) was dissolved in DMF (2 ml) and treated with HBTU (0.136 g) and DIPEA (0.116 g). A separate portion of Intermediate 3 (0.10 g) was dissolved in DMF (2 ml) and treated with EDC (0.096 g) and HOBT (0.058 g). The resultant suspensions were both stirred under nitrogen for 15 min, then methyl hydrazine (0.017 g) added to each and stirring continued under nitrogen for 18 h. The mixtures were independently concentrated in vacuo and the residues partitioned between DCM and water. The organic layers were concentrated and each applied to an SPE cartridge (aminopropyl, 2 g) which was eluted with methanol, followed by 10% ammonia in methanol. The two portions of Intermediate 7 thus afforded were combined (0.16 g). LCMS showed MH$^+$=303; T$_{RET}$=2.22 min.

Intermediate 8: Methanesulfonyl Acetic Acid Hydrazide

Prepared from commercially available ethyl methylsulphonyl acetate as described by D. E. Bays et. al. in EP 50407:

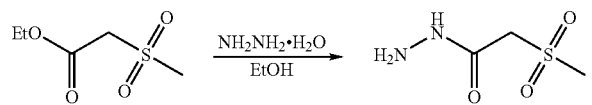

Intermediate 9: Acetamidoxime

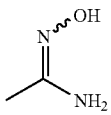

Can be prepared from aqueous hydroxylamine and acetonitrile as described by J. J. Sahbari et. al. in WO 00/032565.

Intermediate 10: 4-(Cyclopentylamino)-1-ethyl-N'-isobutyryl-1H-pyrazolo[3,4-b]pyridine-5-carbohydrazide

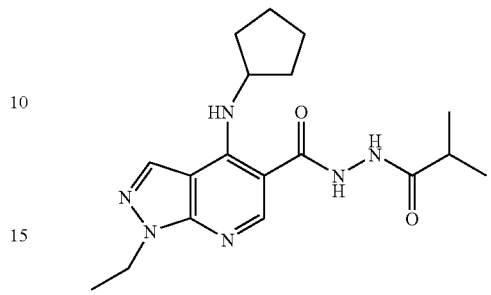

Intermediate 3 (0.060 g), EDC (0.06 g) and HOBT (0.035 g) were suspended in DMF (2 ml) and stirred under nitrogen for 15 minutes. Isobutyric acid hydrazide (0.027 g) was then added and the mixture stirred under nitrogen for 18 h. Solvents were removed in vacuo and the residue partitioned between DCM and water. The organic phase was washed with saturated aqueous sodium bicarbonate solution, then concentrated in vacuo and applied to an SPE cartridge (aminopropyl, 1 g) which was eluted with methanol. Concentration in vacuo afforded Intermediate 10. LCMS showed MH$^+$=359; T$_{RET}$=2.70 min.

Intermediate 11: 4-Chloro-1-ethyl-1H-pyrazolo[3,4-b]pyridine-5-carboxylic acid

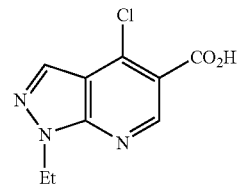

A solution of Intermediate 1 (3.5 g) in dioxane (28 ml) was treated with potassium hydroxide (6.3 g) as a solution in water (20 ml). The mixture was stirred for 2 h, then concentrated in vacuo, acidified to pH 3 with 2M aqueous hydrochloric acid and extracted with ethyl acetate. The layers were separated, the organic layer dried over sodium sulphate, then concentrated in vacuo to afford Intermediate 11 as a white solid (2.4 g). LCMS showed MH$^+$=226; T$_{RET}$=2.62 min.

Intermediate 12: 4-Chloro-1-ethyl-5-(5-methyl-1,3,4-oxadiazol-2-yl)-1H-pyrazolo[3,4-b]pyridine

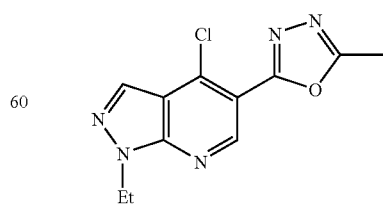

Intermediate 11 (0.4 g) was dissolved in thionyl chloride (3 ml) and the mixture was heated at reflux (95° C.) with stirring for 1 h. After cooling to room temperature, excess thionyl chloride was removed by evaporation under reduced pressure and the resultant solid dissolved in anhydrous acetonitrile (2 ml). This solution was added to a solution of acetic hydrazide (0.145 g) and diisopropylethylamine (0.465 ml) in anhydrous acetonitrile (2 ml), and the mixture stirred for a further 2 h. The mixture was concentrated in vacuo and the residue treated directly with phosphorus oxychloride (4 ml). The resultant solution was stirred and heated at reflux (120° C.) for 0.5 h, then allowed to cool and purified by Biotage (silica, 40 g), eluting with cyclohexane:EtOAc (1:1) to afford Intermediate 12 (0.32 g). LCMS showed MH$^+$=264; T$_{RET}$=2.55 min.

Intermediate 13: 4-Chloro-1-ethyl-5-(5-isopropyl-1, 3,4-oxadiazol-2-yl)-1H-pyrazolo[3,4-b]pyridine

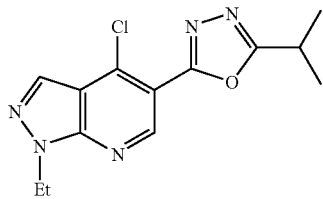

Intermediate 11 (0.05 g) was dissolved in thionyl chloride (1 ml) and the mixture was heated at reflux (95° C.) with stirring for 1 h. After cooling to room temperature, excess thionyl chloride was removed by evaporation under reduced pressure and the resultant solid dissolved in anhydrous acetonitrile (0.5 ml). This solution was added to a solution of isobutyric acid hydrazide (0.025 g) and diisopropylethylamine (0.058 ml) in anhydrous acetonitrile (1 ml), and the mixture stirred for a further 1.5 h. The mixture was concentrated in vacuo and the residue treated directly with phosphorus oxychloride (2 ml). The resultant solution was stirred and heated at reflux (120° C.) for 2 h, then allowed to cool and concentrated in vacuo. The residue was applied to an SPE cartridge (silica, 5 g) which was eluted sequentially with a gradient of EtOAc:cyclohexanI (i) 1:16, (ii) 1:8, (iii) 1:4, (iv) 1:2, (v) 1:1 and (vi) 1:0. Fractions containing desired material were combined and concentrated in vacuo to afford Intermediate 13 (0.049 g). LCMS showed MH$^+$=292; T$_{RET}$=2.96 min.

Intermediate 14: 5(5-Tert-butyl-1,3,4-oxadiazol-2-yl)-4-chloro-1-ethyl-1H-pyrazolo[3,4-b]pyridine

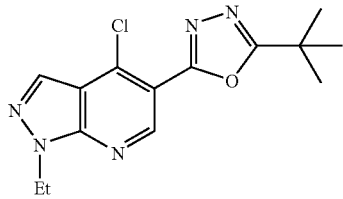

Intermediate 11 (0.40 g) was dissolved in thionyl chloride (3 ml) and the mixture was heated at reflux (95° C.) with stirring for 1 h. After cooling to room temperature, excess thionyl chloride was removed by evaporation under reduced pressure and the resultant solid dissolved in anhydrous acetonitrile (2 ml). This solution was added to a solution of pivalic acid hydrazide (0.228 g) and diisopropylethylamine (0.465 ml) in anhydrous acetonitrile (2 ml), and the mixture stirred for a further 1.5 h. The mixture was concentrated in vacuo and the residue treated directly with phosphorus oxychloride (5 ml). The resultant solution was stirred and heated at reflux (120° C.) for 1.5 h, then allowed to cool, concentrated in vacuo and purified by Biotage (silica, 40 g), eluting with petroleum ether (40/60): EtOAc (1:1) to afford Intermediate 14 (0.388 g). LCMS showed MH$^+$=306; T$_{RET}$=3.14 min.

Intermediate 15: 4-Chloro-1-ethyl-5-{5-[(methylsulfonyl)methyl]-1,3,4-oxadiazol-2-yl}-1H-pyrazolo[3,4-b]pyridine

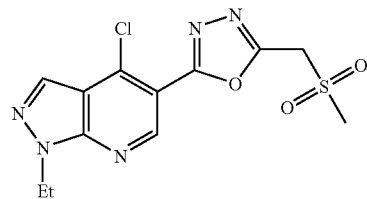

Intermediate 11 (0.68 g) was dissolved in thionyl chloride (4 ml) and the mixture was heated at reflux (95° C.) with stirring for 1 h. After cooling to room temperature, excess thionyl chloride was removed by evaporation under reduced pressure and the resultant solid dissolved in anhydrous acetonitrile (3 ml). This solution was added dropwise over 5 minutes to a solution of Intermediate 8 (0.504 g) and diisopropylethylamine (0.787 ml) in anhydrous acetonitrile (12 ml), and the mixture then stirred for a further 1 h. The mixture was concentrated in vacuo and the residue treated directly with phosphorus oxychloride (8 ml). The resultant solution was stirred and heated at reflux (120° C.) for 2.5 h, then allowed to cool, concentrated in vacuo and purified by Biotage (silica, 40 g), eluting first with petroleum ether (40/60): EtOAc (2:1), then with petroleum ether (40/60): EtOAc (1:1). Fractions containing desired material were combined, concentrated in vacuo and the residue further purified by trituration with diethyl ether to afford Intermediate 15 (0.41 g). LCMS showed MH$^+$=342; T$_{RET}$=2.46 min.

Intermediate 16: Ethyl 1-ethyl-4-(tetrahydro-2H-pyran-4-ylamino)-1H-pyrazolo[3,4-b]pyridine-5-carboxylate

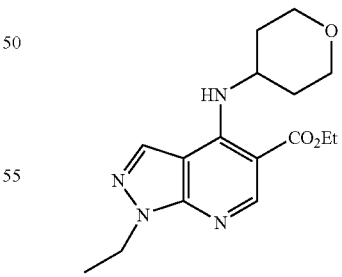

Intermediate 1 (0.20 g) and triethylamine (0.55 ml) were suspended in ethanol (8 ml) and 4-aminotetrahydropyran (Intermediate 21, 0.088 g) was added. The mixture was stirred under nitrogen, heated at 80° C. for 16 h, then concentrated in vacuo. The residue was partitioned between DCM and water. The layers were separated and the organic layer was loaded directly onto an SPE cartridge (silica, 5 g) which was eluted sequentially with; (i) DCM, (ii) DCM:Et$_2$O (2:1), (iii) DCM:Et$_2$O (1:1), (iv) Et$_2$O and (v) EtOAc. Fractions containing desired material were combined and concentrated in vacuo to afford Intermediate 16 (0.21 g). LCMS showed MH$^+$=319; T$_{RET}$=2.93 min.

Intermediate 17: 1-Ethyl-4-(tetrahydro-2H-pyran-4-ylamino)-1H-pyrazolo[3,4-b]pyridine-5-carboxylic acid

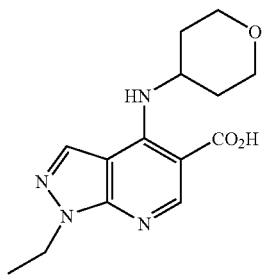

A solution of Intermediate 16 (0.21 g) in ethanol:water (95:5, 10 ml) was treated with sodium hydroxide (0.12 g). The mixture was heated at 50° C. for 8 h, then concentrated in vacuo, dissolved in water and acidified to pH 4 with acetic acid. The resultant white solid was removed by filtration and dried under vacuum to afford Intermediate 17 as an off-white solid (0.16 g). LCMS showed MH$^+$=291; T$_{RET}$=2.11 min.

An alternative preparation of Intermediate 17 is as follows:

A solution of Intermediate 16 (37.8 g) in ethanol:water (4:1, 375 ml) was treated with sodium hydroxide (18.9 g). The mixture was heated at 50° C. for 5 hours, then concentrated in vacuo, dissolved in water and acidified to pH 2 with aqueous hydrochloric acid (2M). The resultant white solid was removed by filtration and dried under vacuum to afford Intermediate 17 as an off-white solid (29.65 g). LCMS showed MH$^+$=291; T$_{RET}$=2.17 min.

Intermediate 18: Tert-butyl 2-{[1-ethyl-4-(tetrahydro-2H-pyran-4-ylamino)-1H-pyrazolo[3,4-b]pyridin-5-yl]carbonyl}hydrazinecarboxylate

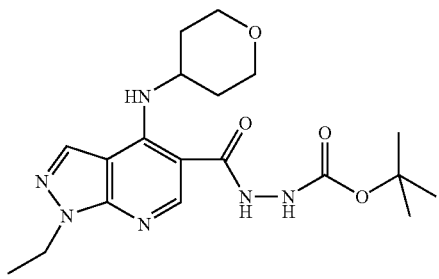

A suspension of Intermediate 17 (1.48 g), EDC (1.34 g) and HOBT (0.83 g) in DMF (20 ml) was stirred at room temperature for 30 min. t-Butyl carbazate (0.68 g) was then added and stirring continued under nitrogen for a further 66 h. The mixture was concentrated in vacuo and the residue divided into two portions for purification. Each portion was applied to an SPE cartridge (aminopropyl, 10 g) which was eluted with methanol and the combined eluents were concentrated in vacuo. Further purification was carried out by Biotage (silica, 40 g), eluting with cyclohexane:ethyl acetate (1:4). Fractions containing desired material were combined and concentrated in vacuo to afford Intermediate 18 (1.39 g). LCMS showed MH$^+$=405; T$_m$=2.64 min.

Intermediate 19: 1-Ethyl-4-(tetrahydro-2H-pyran-4-ylamino)-1H-pyrazolo[3,4-b]pyridine-5-carbohydrazide dihydrochloride

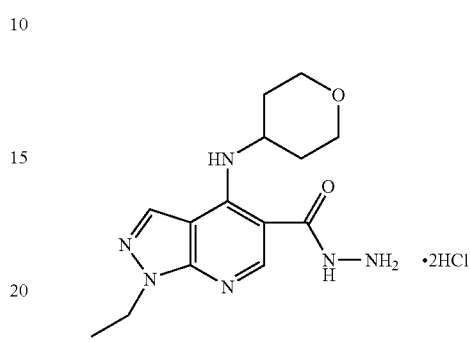

Intermediate 18 (1.39 g) was treated with a 4M solution of hydrochloric acid in dioxane (8 ml) and the mixture stirred under nitrogen for 1 h. Concentration in vacuo afforded Intermediate 19 as a white solid (1.17 g). LCMS showed MH$^+$=305; T$_{RET}$=2.04 min.

Intermediate 20: N'-(Cyclopropylcarbonyl)-1-ethyl-4-(tetrahydro-2H-pyran-4-ylamino)-1H-pyrazolo[3,4-b]pyridine-5-carbohydrazide

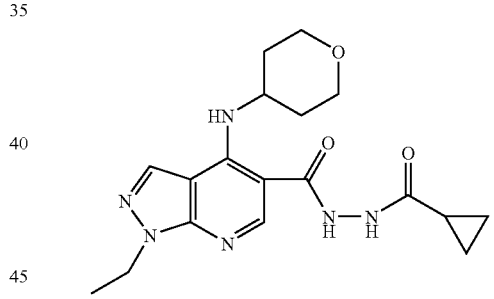

A solution of Intermediate 19 (0.045 g) in THF (2 ml) was treated with DIPEA (0.045 ml), then with cyclopropylcarbonyl chloride (0.013 g) and stirred at room temperature for 16 h. The mixture was concentrated in vacuo and the residue partitioned between dichloromethane and water. The layers were separated and the organic layer concentrated in vacuo, then applied to an SPE cartridge (aminopropyl, 1 g). The column was eluted with methanol to afford Intermediate 20 as a white solid (0.02 g). LCMS showed MH$^+$=373; T$_{RET}$=2.15 min.

Intermediate 21: 4-Aminotetrahydropyran

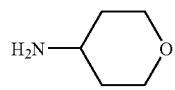

Commercially available from Combi-Blocks Inc., 7949 Silverton Avenue, Suite 915, San Diego, Calif. 92126. CAS (Chemical Abstracts) Registry Number 38041-19-9.

Intermediate 21A: Tetrahydro-2H-pyran-4-amine hydrochloride=4-Aminotetrahydropyran hydrochloride

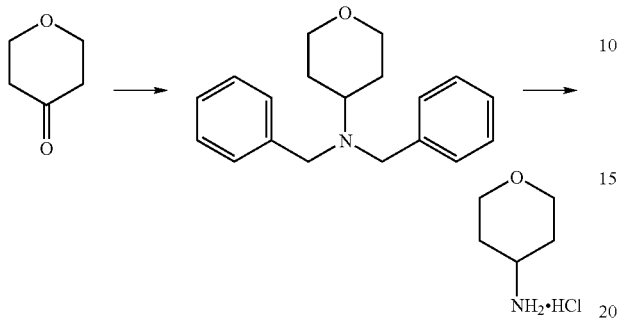

Step 1: N,N-dibenzyltetrahydro-2H-pyran-4-amine

Dibenzylamine (34.5 g) and acetic acid (6.7 ml) were added to a stirred solution of tetrahydro-4H-pyran-4-one (16.4 g, commercially available from e.g. Aldrich) in dichloromethane (260 ml) at 0° C. to 5° C. After 2.5 h at 0° C. to 5° C., sodium triacetoxyborohydride (38.9 g) was added portionwise, and the mixture was allowed to warm to room temperature. After stirring at room temperature overnight, the reaction mixture was washed successively with 2M-sodium hydroxide (200 ml and 50 ml), water (2×50 ml) and brine (50 ml), then dried and evaporated to give a yellow oil (45 g). This oil was stirred with methanol (50 ml) at 4° C. for 30 min to give the product as a white solid (21.5 g). LCMS showed MH$^+$=282; T$_{RET}$=1.98 min.

Step 2: Tetrahydro-2H-pyran-4-amine hydrochloride

N,N-dibenzyltetrahydro-2H-pyran-4-amine (20.5 g) was dissolved in ethanol (210 ml) and hydrogenated over 10% palladium on carbon catalyst (4 g) at 100 psi for 72 h at room temperature. The reaction mixture was filtered and the filtrate was adjusted to pH 1 with 2M-hydrogen chloride in diethyl ether. Evaporation of solvents gave a solid which was triturated with diethyl ether to give the product as a white solid (9.23 g). $^1$H NMR (400 MHz, d$_6$-DMSO, δ ppm) 8.24 (br. s, 3H), 3.86 (dd, 12, 4 Hz, 2H), 3.31 (dt, 2, 12 Hz, 2H), 3.20 (m, 1H), 1.84 (m, 2H), 1.55 (dq, 4, 12 Hz, 2H).

Intermediate 22:
N'-Hydroxy-2-methoxyethanimidamide

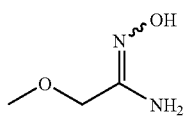

A solution of methoxyacetonitrile (12.26 g) in ethanol (220 ml) was treated with hydroxylamine hydrochloride (11.95 g) followed by potassium carbonate (22.9 g) and heated under reflux for 2 days. The mixture was concentrated in vacuo, then partitioned between ethylacetate and water. The organic layer was concentrated in vacuo to afford Intermediate 22 as a colourless liquid (7.6 g). $^1$H NMR (CDCl$_3$) 7.16 (3H, s), 7.67 (s, 2H), 9.32 (brs, 2H), 13.08 (1H, s).

Intermediate 23:
2-(Dimethylamino)-N'-hydroxyethanimidamide

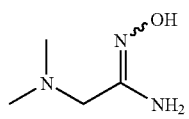

Can be prepared in an analogous manner to Intermediate 9, starting from dimethylamino acetonitrile.

Intermediate 24:
N'-Hydroxy-2-morpholin-4-ylethanimidamide

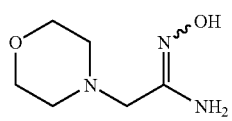

Can be prepared in an analogous manner to Intermediate 9, staring from morpholino acetonitrile (itself commercially available from TCI America, 9211 North Harborgate Street, Portland, Oreg. 97203, USA).

Intermediate 25: 1-Acetyl-4-aminopiperidine hydrochloride

Prepared from commercially available N1-benzyl-4-aminopiperidine as described by Yamada et. al. *In WO* 00/42011:

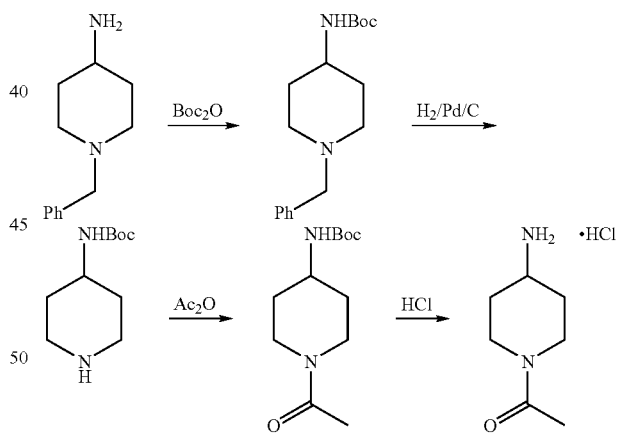

Intermediate 26: 3-Methyloxetane-3-carboxylic acid

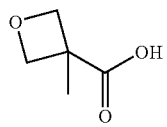

Can be prepared by oxidation of 3-Methyl-3-oxetanemethanol (commercially available from e.g. Fluka, CAS (Chemical Abstracts) Registry Number 3143-02-0) according to the procedure described by H. Fiege et. al. in DE3618142.

Intermediate 27: (4-Methylpiperazin-1-yl)acetic acid

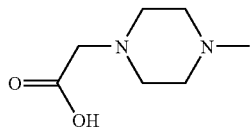

Commercially available from ChemPacific USA Sales Marketing and Research Center, 6200 Freeport Centre, Baltimore, Md. 21224, USA (CAS Registry Number 54699-92-2).

Intermediate 28: (Isopropylamino)(oxo)acetic acid

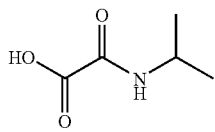

Commercially available from Austin Chemical Company, Inc., 1565 Barclay Blvd., Buffalo Grove, Ill. 60089, USA. CAS (Chemical Abstracts) Registry Number 3338-22-5.

Intermediate 29: 1-Methyl-5-oxopyrrolidine-3-carboxylic acid

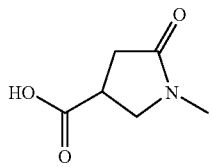

Commercially available from MicroChemistry-RadaPharma, Shosse Entusiastov 56, Moscow 111123, Russia. CAS (Chemical Abstracts) Registry Number 42346-68-9.

Intermediate 30: Tetrahydro-2H-pyran-4-carboxylic acid

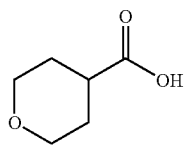

Commercially available from Combi-Blocks Inc., 7949 Silverton Avenue, Suite 915, San Diego, Calif. 92126, USA. CAS (Chemical Abstracts) Registry Number 5337-03-1.

Intermediate 31: Morpholin-4-ylacetic acid

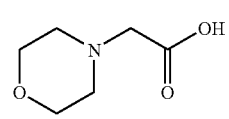

Can be prepared from ethyl bromoacetate as described by Z. Dega-Szafran et. al. in *J. Molecular Structure*, 2001, 560, 261-273.

Intermediate 32: Tert-butoxyacetic acid

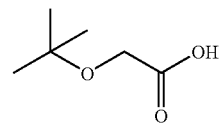

A suspension of sodium t-butoxide (24.1 g) in t-butanol (150 ml) was cooled in a water bath and treated drop-wise with a solution of chloroacetic acid (11.4 g) in t-butanol (30 ml). The mixture was heated under reflux for 5 h then concentrated in vacuo. The resultant white solid was dried in vacuo for 16 h then water (10 ml) was added and the mixture was filtered. The filtrate was treated with diethyl ether (150 ml), then cooled in an ice bath, stirred and acidified to pH1 with 2N sulphuric acid. The layers were separated and the aqueous layer was further extracted with diethyl ether. The combined organic extracts were dried MgSO$_4$) and concentrated in vacuo to afford Intermediate 32 (11.1 g). $^1$H NMR (400 MHz, CDCl$_3$, δ ppm) 1.27 (9H, s), 4.04 (2H, s).

Intermediate 33: Methyl(2S)-2-({[1-ethyl-4-(tetrahydro-2H-pyranylamino)-1H-pyrazolo[3,4-b]pyridin-5-yl]carbonyl}amino)-3-hydroxypropanoate

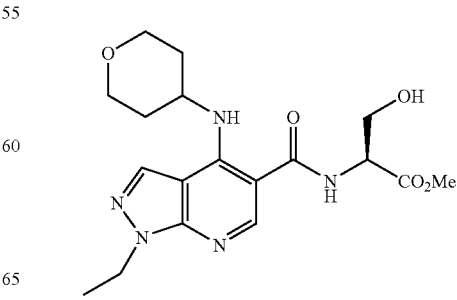

Reaction scheme:

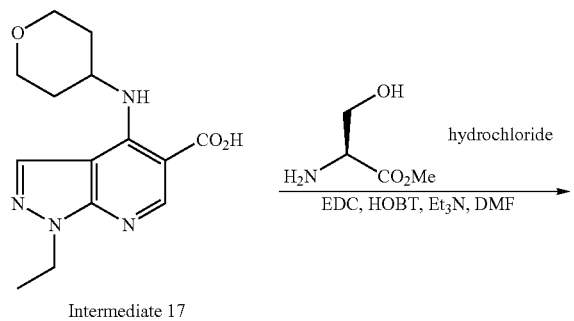

Intermediate 17

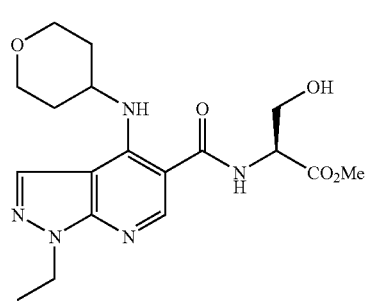

Intermediate 17 (0.1 g, 0.34 mmol), EDC (0.066 g, 0.34 mmol) and HOBT (0.05 g, 0.37 mmol) were suspended in DMF (2 ml) and stirred at room temperature under nitrogen for 15 mins. L-Serine methyl ester hydrochloride (0.054 g, 0.34 mmol) and triethylamine (0.036 g, 0.36 mmol) were added and the mixture stirred at room temperature under nitrogen for 18 hours. Solvents were removed in vacuo and the residue was partitioned between DCM and water. The organic layer was concentrated in vacuo and applied to an SPE cartridge (aminopropyl, 5 g), which was eluted with methanol. Concentration in vacuo afforded an impure residue which was further purified by SPE cartridge (silica, 5 g), eluting with ethyl acetate followed by 5% methanol/ethyl acetate. The desired fractions were concentrated in vacuo to afford Intermediate 33 (0.055 g). LCMS showed MH$^+$=393; T$_{RET}$=2.22 min.

Intermediate 34: 1-Ethyl-N-(2-hydroxy-1-methyl-ethyl)(tetrahydro-2H-pyran-4 ylamino)-1H-pyrazolo[3,4-b]pyridine-5-carboxamide

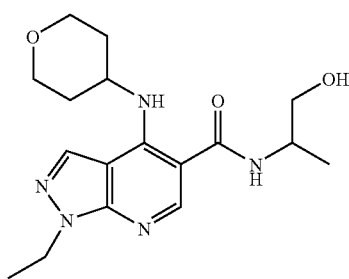

Intermediate 17 (0.1 g, 0.34 mmol), EDC (0.066 g, 0.34 mmol) and HOBT (0.05 g, 0.37 mmol) were suspended in DMF (2 ml) and stirred at room temperature under nitrogen for 15 min. 2-aminopropan-1-ol (0.026 g, 0.34 mmol) and triethylamine (0.036 g, 0.36 mmol) were added and the mixture was stirred at room temperature under nitrogen for 6 hours. Solvents were removed in vacuo and the residue partitioned between DCM and water. The organic layer was concentrated and applied to an SPE cartridge (aminopropyl, 5 g), which was eluted with methanol. Concentration in vacuo afforded Intermediate 34 (0.095 g). LCMS showed MH$^+$=348, T$_{RET}$=2.15 min.

Intermediate 35: Ethyl 4-ethoxy-1-ethyl-1H-pyrazolo[3,4-b]pyridine-5-carboxylate

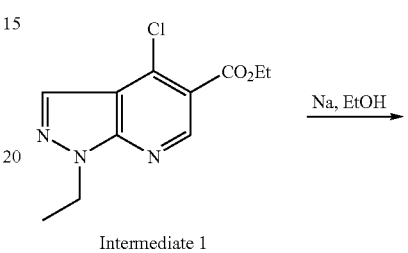

Intermediate 1

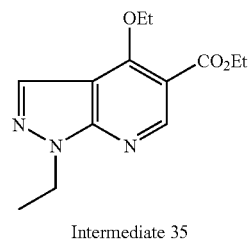

Intermediate 35

Sodium (0.55 g, 23.7 mmol) was added portionwise to anhydrous ethanol (25 ml) at 20° C. under an atmosphere of nitrogen. After stirring for 1 hour the solution was added to Intermediate 1 (4.622 g, 18.22 mmol) and the reaction mixture heated at reflux for 2 hours. The mixture was evaporated in vacuo and the residue partitioned between dichloromethane and water. The organic phase was washed with brine, dried (Na$_2$SO$_4$) and evaporated in vacuo. The residue was purified on SPE cartridges (silica, 4×20 g) eluting with dichloromethane, ethyl acetate:petroleum ether (1:4, 1:2 then 1:1) followed by ethyl acetate). Appropriate fractions were combined and evaporated in vacuo to afford Intermediate 35 as white solid (4.33 g). LCMS showed MH$^+$=264, T$_{RET}$=2.77 min.

Intermediate 36: Ethyl 4-ethoxy-1H-pyrazolo[3,4-b]pyridine-5-carboxylate

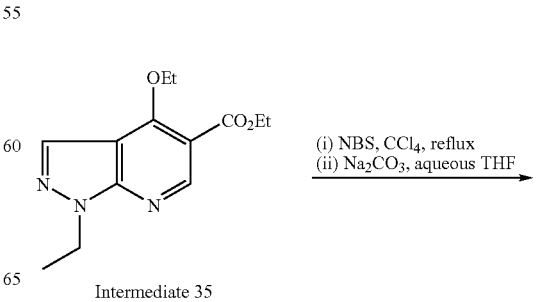

Intermediate 35

-continued

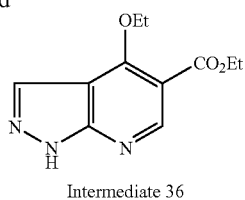

Intermediate 36

A mixture of Intermediate 35 (1.0 g, 3.8 mmol) and N-bromosuccinimide (1.49 g, 8.4 mmol) in carbon tetrachloride (35 ml) was heated at reflux for 3 hours. The reaction mixture was cooled in an ice-bath and the precipitate filtered. The filtrate was concentrated in vacuo and the residue dissolved in tetrahydrofuran (12.5 ml). Water (3.5 ml) and saturated sodium carbonate solution (3 ml) were added and the mixture stirred at 20° C. for 18 hours. The reaction was diluted with water and extracted with ethyl acetate. The combined organic phases were dried $Na_2SO_4$) and evaporated in vacuo. The residue was purified on an SPE cartridge (silica, 20 g) eluting with dichloromethane, chloroform, then chloroform:methanol (99:1, 49:1, 19:1 then 9:1). Appropriate fractions were combined and evaporated in vacuo to afford Intermediate 36 as an off-white solid (0.45 g). LCMS showed $MH^+$+236, $T_{RET}$=2.46 min.

Intermediate 37: Ethyl 4-(tetrahydro-2H-pyran-4-ylamino)-1H-pyrazolo[3,4-b]pyridine-5-carboxylate

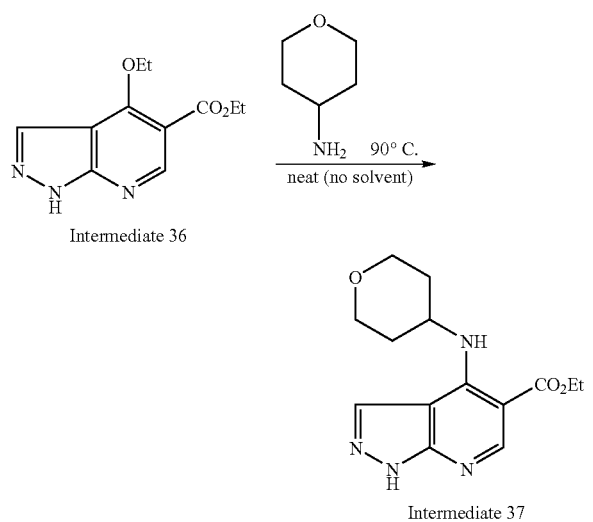

Method 1: Intermediate 36 (0.035 g) was placed in a Reactivial™ and treated with 4-aminotetrahydropyran (0.05 ml). The mixture was heated at 90° C. for 1.5 hours, then allowed to cool to room temperature and partitioned between chloroform (2 ml) and water (1 ml). The layers were separated and the organic phase was concentrated. The crude product was purified by mass directed autoprep HPLC to afford Intermediate 37 as an off-white solid (0.011 g). LCMS showed $MH^+$=291; $T_{RET}$=2.08 min.

Alternative Method 2: Intermediate 36 (2 g) was suspended in 4-aminotetrahydropyran (2 g), and the mixture was heated at 90° C. for 6 hours. The residual mixture was allowed to cool to room temperature and partitioned between chloroform (50 ml) and water (50 ml). The phases were separated and the organic phase was evaporated to dryness. The residue was triturated with $Et_2O$ (30 ml) and the insoluble solid was collected and dried to afford Intermediate 37 as a cream solid (2.24 g). LCMS showed $MH^+$=291; $T_{RET}$=2.19 min.

Intermediate 38: Ethyl 1-n-propyl-4-(tetrahydro-2H-pyran-4-ylamino)-1H-pyrazolo[3,4-b]pyridine-5-carboxylate

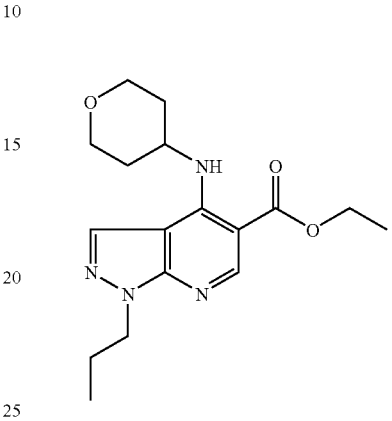

Sodium hydride (0.067 g, 60% dispersion in oil) was added to a stirred solution of Intermediate 37 (0.47 g) in DMF (19 ml), followed by n-propyl iodide (0.17 ml). The mixture was stirred at 23° C. for 16 hours, then concentrated, diluted with chloroform (30 ml) and washed with 1:1 water:brine solution (30 ml), separated and the organic layer concentrated. The residue was purified on a SPE cartridge (silica, 10 g) eluting with 10 ml volumes of dichloromethane, 1:1 diethyl ether: cyclohexane, and diethyl ether. The combined 1:1 diethyl ether: cyclohexane, and diethyl ether, fractions were concentrated to give Intermediate 38 as a clear gum (0.23 g). LCMS showed $MH^+$=333; $T_{RET}$=3.14 min.

Intermediate 39: 1-n-Propyl-4-(tetrahydro-2H-pyran-4-ylamino)-1H-pyrazolo[3,4-b]pyridine-5-carboxylic acid

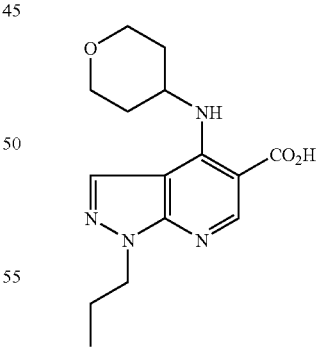

2M-Sodium hydroxide solution (0.7 ml) was added to a stirred suspension of Intermediate 38 (0.23 g) in ethanol (5 ml) and water (1.5 ml). After stirring overnight at room temperature, a further quantity of 2M-sodium hydroxide solution (0.7 ml) was added, and the reaction mixture was heated at 43° C. for 2.5 hours. The reaction solution was concentrated, diluted with water (5 ml) and acidified with 2M-hydrochloric acid. The resulting precipitate was collected by filtration, washed with water and dried to give Intermediate 39 as a white solid (0.14 g). LCMS showed MH$^+$=305; T$_{RET}$=2.42 min.

Intermediate 40: N'-Acetyl 1-n-propyl-4-(tetrahydro-2H-pyran-4-ylamino)-1H-pyrazolo[3,4-b]pyridine-5-carbohydrazide

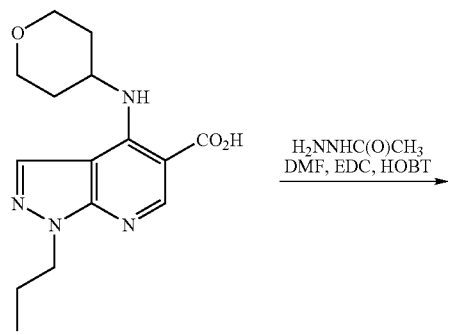

Intermediate 39

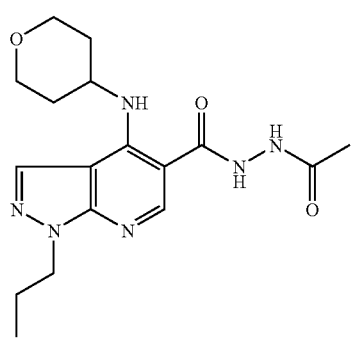

Intermediate 40

Intermediate 40 can be made from Intermediate 39 in a similar way to the process described for Intermediate 4, for example using a similar or the same number of moles of reagents and/or volumes of solvents.

Intermediate 41: Ethyl 4-[(1-acetyl-4-piperidinyl)amino]-1-ethyl-1H-pyrazolo[3,4-b]pyridine-5-carboxylate

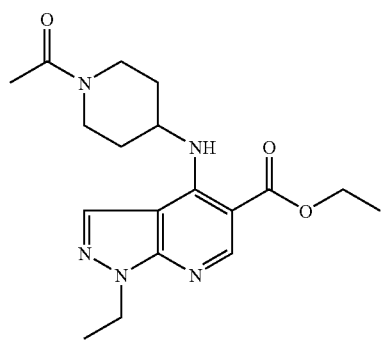

Intermediate 1 (0.079 g, 0.56 mmol), Intermediate 25 (0.129 g, 0.51 mmol) and diisopropylethylamine (0.45 ml, 2.55 mmol) in acetonitrile (2 ml) were heated at 85° C. for 36 hours. The reaction mixture was concentrated in vacuo and the residue partitioned between DCM and water. The phases were separated using a hydrophobic frit (Whatman). The organic phase was evaporated in vacuo and the residue applied to an SPE cartridge (silica, 5 g). The cartridge was eluted with EtOAc and then DCM/MeOH (1:1). Fractions containing the desired material were combined and concentrated in vacuo to afford Intermediate 41 (0.1 g). LCMS showed MH$^+$=360; T$_{RET}$=2.63 min.

Intermediate 42: 1-Ethyl-N-[(1R)-2-hydroxy-1-phenylethyl]-4-(tetrahydro-2H-pyran-4-ylamino)-1H-pyrazolo[3,4-b]pyridine-5-carboxamide

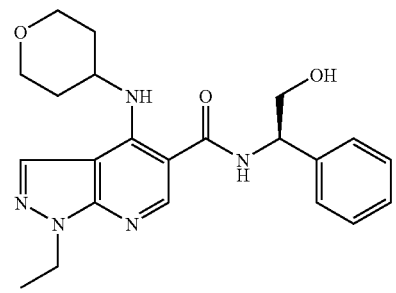

Intermediate 17 (0.25 g, 0.86 mmol), EDC (0.23 g, 1.2 mmol) and HOBT (0.139 g, 1.03 mmol) were suspended in DMF (5 ml) and the suspension was stirred at room temperature. After 25 min, (2R)-2-Amino-2-phenylethanol (0.13 g, 0.95 mmol, commercially available from Aldrich) was added, and the mixture was stirred at room temperature for 20 hours. Solvents were removed in vacuo and the residue was dissolved in DCM (50 ml) and washed successively with water (25 ml) and 5% sodium hydrogen carbonate solution (25 ml). The organic layer was dried over anhydrous sodium sulphate and concentrated in vacuo. The residue was dissolved in dichloromethane (5 ml) and applied to a SPE cartridge (silica, 10 g), which was eluted with a gradient of ethyl acetate—petroleum ether (1:2, 1:1 and 1:0). Fractions containing the desired material were combined and concentrated in vacuo to afford Intermediate 42 as a white foam (0.318 g). LCMS showed MH$^+$=410; T$_{RET}$=2.55 min.

Intermediate 43: 1-Ethyl-N-[(1S)-2-hydroxy-1-phenylethyl]-4-(tetrahydro-2-pyran-4-ylamino)-1H-pyrazolo[3,4-b]pyridine-5-carboxamide

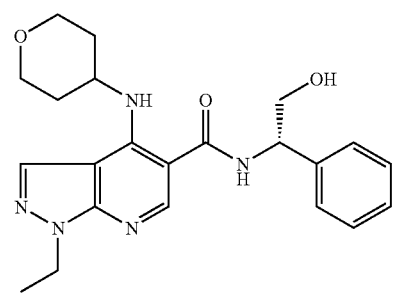

Intermediate 43 was prepared from Intermediate 17 and (2S)-2-amino-2-phenylethanol (commercially available from Lancaster Synthesis) using an analogous method to that for Intermediate 42. LCMS showed MH$^+$=410; T$_{RET}$=2.55 min.

Intermediate 44 1-Ethyl-N-[(1S)-2-hydroxy-1-(phenylmethyl)ethyl]-4-(tetrahydro-2H-pyran-4-ylamino)-1H-pyrazolo[3,4-b]pyridine-5-carboxamide

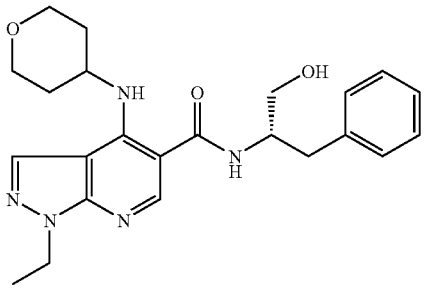

Intermediate 44 was prepared from Intermediate 17 and (2S)-2-amino-3-phenyl-1-propanol (commercially available from Aldrich) using an analogous method to that for Intermediate 42. LCMS showed MH$^+$=424; T$_{RET}$=2.60 min.

Intermediate 45: 1-Ethyl-N-[(1R)-2-hydroxy-1-(phenylmethyl)ethyl]-4-(tetrahydro-2H-pyran 4-ylamino)-1H-pyrazolo[3,4-b]pyridine-5-carboxamide

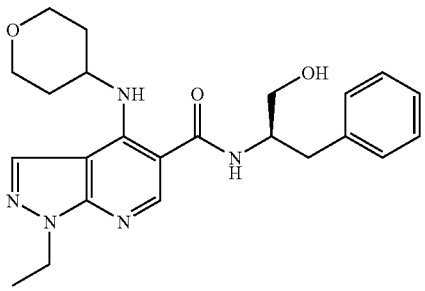

Intermediate 45 was prepared from Intermediate 17 and (2R)-2-amino-3-phenyl-1-propanol (commercially available from Aldrich) using an analagous method to that for Intermediate 42. LCMS showed MH$^+$=424; T$_{RET}$=2.59 min.

Intermediate 46: 1-Ethyl-N-[(1S,4R)-2-hydroxy-1-phenylpropyl]-4-(tetrahydro-2H-pyran-4-ylamino)-1H-pyrazolo[3,4-b]pyridine-5-carboxamide

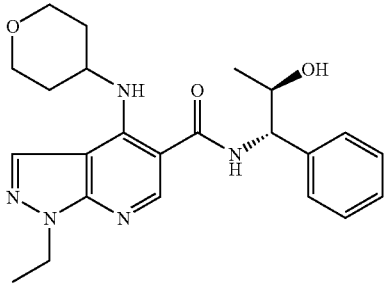

Intermediate 46 was prepared from Intermediate 17 and (1S,2R)-1-amino-1-phenyl-2-propanol hydrochloride (commercially available from Arch Corporation, 100 Jersey Avenue, Building D, New Brunswick, N.J. 08901, USA) using an analogous method to that for Intermediate 42. LCMS showed MH$^+$=424; T$_{RET}$=2.5 8 min.

Intermediate 47: 1-Ethyl-N-[(2R)-2-hydroxy-2-phenylethyl]-4-(tetrahydro-2H-pyran-4-ylamino)-H-pyrazolo[3,4-b]pyridine-5-carboxamide

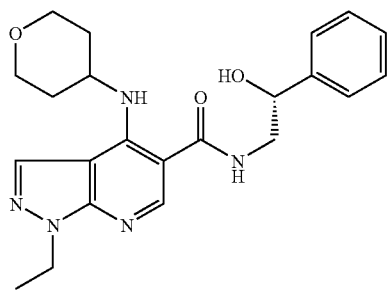

Intermediate 47 was prepared from Intermediate 17 and (1R)-2-amino-1-phenylethanol (commercially available from Aldrich) using an analogous method to that for Intermediate 42. LCMS showed MH$^+$=410; T$_{RET}$=2.62 min.

Intermediate 48: 1-Ethyl-N-[(2S)-2-hydroxy-2-phenylethyl]-4-(tetrahydro-2H-pyran-4-ylamino)-1H-pyrazolo[3,4-b]pyridine-5-carboxamide

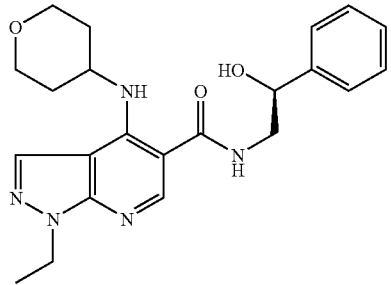

Intermediate 48 was prepared from Intermediate 17 and (1S)-2-amino-1-phenylethanol (commercially available from Fluka) using an analogous method to that for Intermediate 42. LCMS showed MH$^+$=410; T$_{RET}$=2.62 min.

Intermediate 49: 1-Ethyl-N-(2-hydroxy-1,1-dimethylethyl)-4-(tetrahydro-2H-pyran-4-ylamino)-1H-pyrazolo[3,4-b]pyridine-5-carboxamide

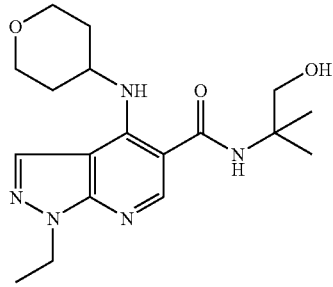

Intermediate 49 was prepared from Intermediate 17 and 2-amino-2-methyl-1-propanol (commercially available from Aldrich) using an analogous method to that for Intermediate 42. LCMS showed MH$^+$=362; T$_{RET}$=2.28 min.

Intermediate 50: N-methyltetrahydro-2H-pyran-4-amine

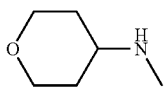

Can be prepared from tetrahydro-4H-pyran-4-one (commercially available from e.g. Sigma Aldich; CAS (Chemical Abstracts) Registry Number 29943-42-8) according to the procedure described by H. Hashimoto et al. in *Organic Process Research and Development* 2002, 6, 70.

Intermediate 51: Ethyl 1-ethyl-4-[methyl(tetrahydro-2H-pyran-4-yl)amino]-1H-pyrazolo[3,4-b]pyridine-5-carboxylate

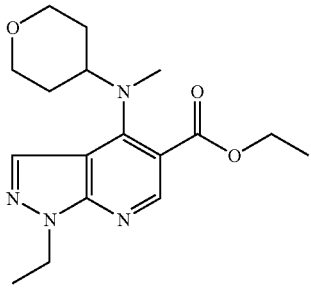

Intermediate 1 (1.2 g, 4.76 mmol), Intermediate 50 (0.79 g, 5.2 mmol) and diisopropylethylamine (4 ml, 24 mmol) in MeCN (8 ml) was heated at 70° C. for 24 hours. The solvent was removed in vacuo and the residue partitioned between DCM and water. The organic phase was concentrated in vacuo and the residue chromatographed on silica (50 g) eluting with cyclohexane:ethyl acetate (2:1 followed by 1:1 then 1:2). Appropriate fractions were combined and evaporated to give Intermediate 51 as a brown oil (1.21 g). LCMS showed $MH^+=334$; $T_{RET}=2.61$ min.

Intermediate 52: 1-Ethyl-4-[methyl(tetrahydro-2H-pyran-4-yl)amino]-1H-pyrazolo[3,4-b]pyridine-5-carboxylic acid

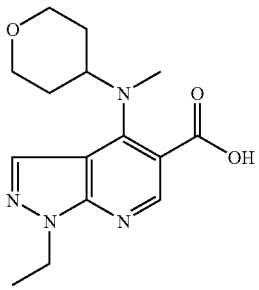

Sodium hydroxide (0.43 g, 10.8 mmol) was added to a solution of Intermediate 51 in ethanol (10 ml, 95%). The reaction mixture was heated at 50° C. for 18 hours. The solvent was evaporated in vacuo and the residue dissolved in water and acidified to pH 3 by the addition of aqueous hydrochloric acid. The solution was extracted with DCM. The organic phase was separated using a hydrophobic frit (Whatman PTFE Folter Media with Polypropylene Housing 5 μM pore size) and the solvent evaporated in vacuo to give Intermediate 52 as a white solid (0.65 g). LCMS showed $MH^+=305$; $T_{RET}=1.97$ min.

Intermediate 53: N'-Acetyl-1-ethyl [methyl(tetrahydro-2H-pyran-4-yl)amino]-1H-pyrazolo[3,4-b]pyridine-5-carbohydrazide

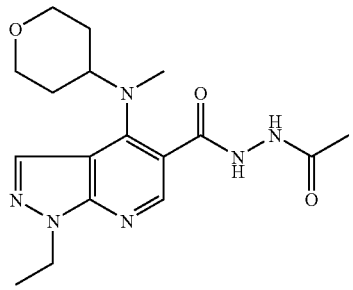

Intermediate 53 was prepared from Intermediate 52 using an analogous method to that for Intermediate 4. LCMS showed $MH^+=361$; $T_{RET}=1.91$ min.

Intermediate 54: trans-4-Aminocyclohexanol

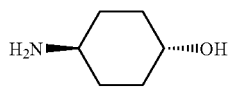

Commercially available from e.g. Acros. CAS (Chemical Abstracts) Registry Number 27489-62-9.

Intermediate 55: Tetrahydro-2H-pyran-3-amine hydrochloride

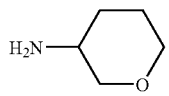

Prepared as described in *Anales De Quimica*, 1988, 84, 148.

Intermediate 56: 4-Aminocyclohexanone hydrochloride

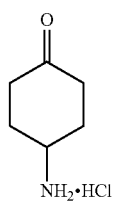

A solution of hydrogen chloride in dioxan (0.5 ml, 2.0 mmol, 4M) was added to a stirred solution of tert-butyl 4-oxocyclohexylcarbamate (0.043 g, 0.20 mmol, commercially available from Astatech Inc., Philadelphia, USA) in dioxan (0.5 ml) and the mixture was stirred at room temperature. After 1 h, the reaction mixture was evaporated to give Intermediate 56 as a cream solid (34 mg). $^1$H NMR (400 MHz in d$_6$-DMSO, 27° C., δ ppm) 8.09 (br. s, 3H), 3.51 (tt, 11, 3.5 Hz, 1H), 2.45 (m, 2H, partially obscured), 2.29 (m, 2H), 2.16 (m, 2H), 1.76 (m, 2H).

Intermediate 57: N-Propyltetrahydro-2H-pyran-4-amine

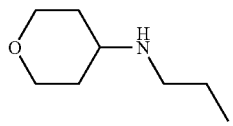

Can be prepared from tetrahydro-4H-pyran-4-one (commercially available from e.g. Sigma Aldich CAS 29943-42-8) as described by C. Zagar in WO 99/07702.

Intermediate 58: Ethyl 4-chloro-1-ethyl-6-methyl-1H-pyrazolo[3,4-b]pyridine-5 carboxylate

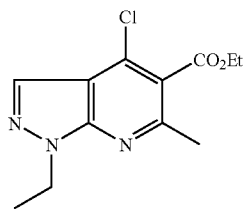

A mixture of 5-amino-1-ethylpyrazole (1.614 g, 14.5 mmol) and diethyl 2-(1-ethoxyethylidene)malonate (3.68 g, 16.0 mmol, as described by P. P. T. Sah, J. Amer. Chem. Soc., 1931, 5, 1836) was heated at 150° C. under Dean Stark conditions for 5 hours. Phosphorous oxychloride (25 ml) was carefully added to the mixture and the resulting solution was heated at 130° C. under reflux for 18 hours. The mixture was concentrated in vacuo, then the residual oil was carefully added, with cooling, to water (100 ml). The resulting mixture was extracted with DCM (3×100 ml) and the combined organic extracts were dried over anhydrous sodium sulphate and concentrated in vacuo. The residual oil was purified by Biotage chromatography (silica, 90 g) eluting with ethyl acetate-petrol (1:19). Fractions containing the desired product were combined and concentrated in vacuo to afford Intermediate 58 (1.15 g). LCMS showed MH$^+$=268; T$_{RET}$=3.18 min.

Intermediate 59: Ethyl 1-ethyl-6-methyl-4-(tetrahydro-2H-pyran-4-ylamino)-1H-pyrazolo[3,4-b]pyridine-5-carboxylate

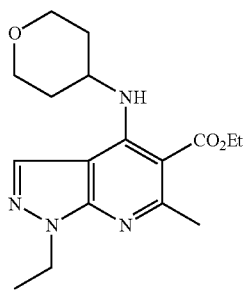

4-Aminotetrahydropyran hydrochloride (Intermediate 21, 0.413 g, 3.0 mmol) was added to a mixture of Intermediate 58 (0.268 g, 1.0 mmol) and N,N-diisopropylethylamine (0.87 ml, 5.0 mmol) in acetonitrile (3 ml). The resulting mixture was heated at 85° C. for 24 hours. Volatiles were removed in vacuo and the residue was dissolved in chloroform (1.5 ml) and applied to a SPE cartridge (silica, 5 g). The cartridge was eluted successively with Et$_2$O, EtOAc and EtOAc-MeOH (9/1). Fractions containing the desired product were combined and concentrated in vacuo to give the desired product contaminated with starting material (Intermediate 51). Further purification using a SPE cartridge (silica, 5 g) eluting with ethyl acetate-cyclohexane (1:3) afforded Intermediate 59 (0.248 g). LCMS showed MH$^+$=333; T$_{RET}$=2.75 min.

Intermediate 60: 1-Ethyl-6-methyl-4-(tetrahydro-2H-pyran-4-ylamino)-1H-pyrazolo[3,4-b]pyridine-5-carboxylic acid

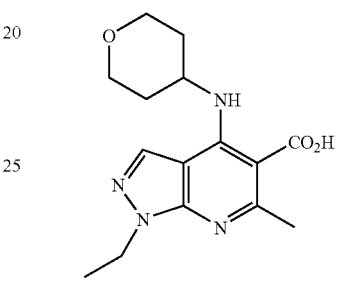

2M-Sodium hydroxide solution (0.75 ml, 1.5 mmol) was added to Intermediate 59 (0.248 g, 0.75 mmol) in ethanol (2 ml), and the mixture was heated at reflux for 16 hours. The reaction mixture was concentrated, diluted with water (1 ml) and acidified with 2M-hydrochloric acid (0.75 ml) to precipitate a solid which was collected by filtration to afford Intermediate 60 (0.168 g). LCMS showed MH$^+$=305; T$_{RET}$=1.86 min.

Intermediate 61: N'-(2,2-Dimethylpropanoyl-ethyl-6-methyl-4-(tetrahydro-2H-pyran-4-ylamino)-1H-pyrazolo[3,4-b]pyridine-5-carbohydrazide

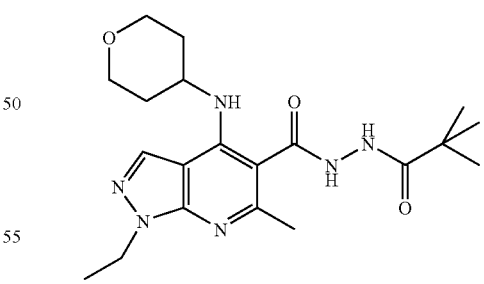

Intermediate 60 (0.255 g, 0.84 mmol), EDC (0.225 g, 1.17 mmol) and HOBT (0.136 g, 1.0 mmol) in DMF (5 ml) was stirred at 20° C. for 75 minutes. Pivalic acid hydrazide (0.107 g, 0.92 mmol) was added and stirring continued for 18 hours. The reaction mixture was concentrated in vacuo and the residue partitioned between DCM and water. The organic phase was washed with aqueous sodium hydrogen carbonate then evaporated in vacuo to afford Intermediate 61 as a white solid (0.27 g).). LCMS showed MH$^+$=403; T$_{RET}$=2.13 min.

Intermediate 62: 1,1-Dimethylethyl 2-{[1-ethyl-6-methyl-4-(tetrahydro-2H-pyran-4-ylamino)-1H-pyrazolo[3,4-b]pyridin-5-yl]carbonyl}hydrazinecarboxylate

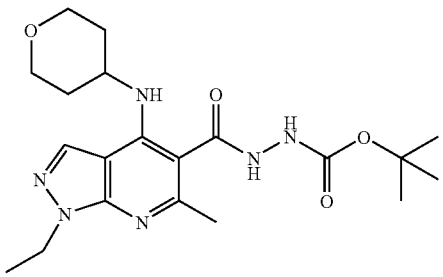

Intermediate 60 (0.253 g, 0.83 mmol), EDC (0.223 g, 1.17 mmol) and HOBT (0.135 g, 1.0 mmol) in DMF (5 ml) was stirred at 20° C. for 30 minutes. t-Butyl carbazate (0.110 g, 0.83 mmol) was added and stirring continued for 18 hours. The reaction mixture was concentrated in vacuo and the residue dissolved in DMF (5 ml) additional EDC (0.159 g0) and HOBT (0.112 g) added. After 30 minutes t-butyl carbazate (0.019 g) was added and stirring continued for 18 hours. The reaction was concentrated in vacuo and the residue partitioned between DCM and water. The organic phase was washed with aqueous sodium hydrogen carbonate then evaporated in vacuo. The material was applied to a SPE cartridge (silica, 10 g) and eluted with cyclohexane:ethyl acetate (1:1 followed by 2:1) to afford Intermediate 62 as a white solid (0.19 g). LCMS showed MH$^+$=419; T$_{RET}$=2.35 min.

Intermediate 63: 1-Ethyl-6-methyl-4-(tetrahydro-2H-pyran-4-ylamino)-1H-pyrazolo[3,4-b]pyridine-5-carbohydrazide hydrochloride

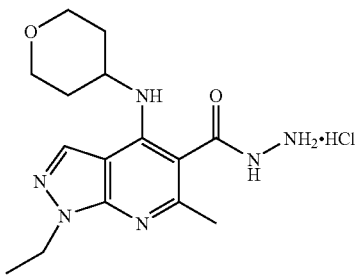

Intermediate 62 (0.19 g, 0.46 mmol) was dissolved in 4M hydrogen chloride in dioxane (5 ml) and the reaction mixture stirred overnight at 20° C. Concentration in vacuo afforded Intermediate 63 as a white solid (0.161 g). LCMS showed MH$^+$=319; T$_{RET}$=1.72 min.

Intermediate 64: 1-Ethyl-6-methyl-4-(tetrahydro-2H-pyran-4-ylamino)-M-(tetrahydro-2H-pyran-4-ylcarbonyl)-1H-pyrazolo[3,4-b]pyridine-5-carbohydrazide

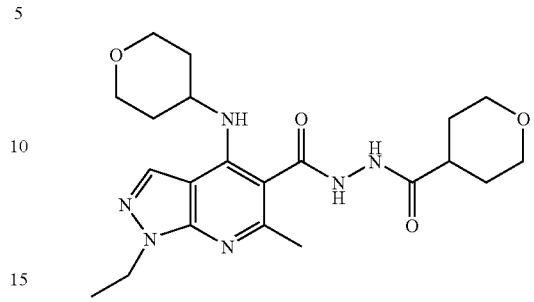

Intermediate 30 (0.06 g, 0.45 mmol) and TBTU (0.146 g, 0.45 mmol) in DMF (5 ml) was stirred at 20° C. for 30 minutes. A mixture of Intermediate 63 (0.16 g, 0.45 mmol) and diisopropylethylamine (0.32 ml, 1.82 mmol) in DMF (1 ml) was added and the reaction mixture stirred overnight under nitrogen. The reaction was concentrated in vacuo and the residue partitioned between DCM and water. The phases were separated using a hydrophobic frit (Whatman PTFE Folter Media with Polypropylene Housing 5 µM pore size) and the organic phase evaporated in vacuo. The residue was applied to an SPE cartridge (aminopropyl, 10 g) and eluted with MeOH. Appropriate fractions were concentrated in vacuo then applied to an additional SPE cartridge (silica, 2 g) which was eluted sequentially with a gradient of MeOH in DCM (i) 2%, (ii) 4%, (iii) 6% and (iv) 10%. Fractions containing the desired material were combined and concentrated in vacuo to afford Intermediate 64 as a white solid (0.048 g). LCMS showed MH$^+$=431; T$_{RET}$=1.87 min.

Intermediate 65: N'-(Cyclobutylcarbonyl)-1-ethyl(tetrahydro-2H-pyran-4-ylamino)-1H-pyrazolo[3,4-b]pyridine-5-carbohydrazide

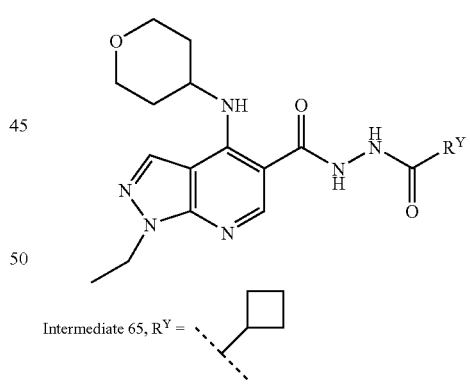

TBTU (0.050 g, 0.15 mmol) and diisopropylethylamine (0.04 ml, 0.26 mmol) in DMF (0.5 ml) was added to cyclobutylcarboxylic acid (R$^Y$COOH, 0.015 g, 0.15 mmol). The reaction mixture was stirred for 40 minutes at 20° C. A mixture of Intermediate 19 (0.045 g, 0.13 mmol) and diisopropylethylamine (0.04 ml, 0.26 mmol) in DMF (0.5 ml) was added and the reaction mixture stirred for 18 h. The solvent was removed in vacuo and the residue applied to a SPE cartridge (aminopropyl, 2 g). The cartridge was eluted with methanol to afford Intermediate 65 (0.052 g). LCMS showed MH$^+$=387; T$_{RET}$=2.28 min.

Similarly prepared using the same or similar numbers of moles of reagents and/or volumes of solvents were the following:

| R<sup>Y</sup>COOH | Source of Acid | MH+ | T<sub>RET</sub> (min) |
|---|---|---|---|
| Intermediate 66 (5-oxopyrrolidine-2-carboxylic acid) | Sigma-Aldrich | 416 | 2.03 |
| Intermediate 67 (N-acetylglycine) | Sigma-Aldrich | 404 | 2.01 |
| Intermediate 68 (1-methylpiperidine-2-carboxylic acid) | HCl Salt: Maybridge, or DE10008089 | 430 | 1.89 |
| Intermediate 69 (4-methyl-1,2,5-oxadiazol-3-yl acetic acid) | Interchim Intermediates | 429 | 2.35 |
| Intermediate 70 (3-oxocyclopentanecarboxylic acid) | Sigma-Aldrich, or J. Org. Chem., 1997, 62, 5144 | 415 | 2.12 |
| Intermediate 71 (tetrahydrofuran-3-carboxylic acid) | Sigma-Aldrich | 403 | 2.11 |
| Intermediate 72 (2-oxothiazolidine-4-carboxylic acid) | Sigma-Aldrich | 434 | 2.15 |
| Intermediate 73 (2,2-dimethylcyclopropanecarboxylic acid) | ChemPacific | 401 | 2.46 |
| Intermediate 74 (N-methyl-N-acetylglycine) | Sigma-Aldrich | 418 | 2.06 |
| Intermediate 75 (2-(tetrahydropyran-4-yl)acetic acid) | Astatech, or J. Med. Chem., 1993, 36, 2300 | 431 | 2.18 |
| Intermediate 76 (1-methylcyclobutanecarboxylic acid) | Synthesis, 1971, 258; or WO 03/082190 | 401 | 2.35 |
| Intermediate 77 (3-methylisoxazole-5-carboxylic acid) | Eur. J. Med. Chem., 1992 37, 581 | 414 | 2.30 |
| Intermediate 78 (1-methyl-1H-pyrazole-5-carboxylic acid) | Indian J. Chemistry, 2002, 41B, 1093 | 413 | 2.24 |
| Intermediate 79 (1-acetylpiperidine-4-carboxylic acid) | Lancaster Synthesis | 458 | 2.18 |

Intermediate 80: (1E/Z)-N-hydroxy-2-(4-methyl-1-piperazinyl)ethanimidamide (4-Methyl-1-piperazinyl)acetonitrile (1.08 g, 7.7 mmol) (*J. Med. Chem.*, 1999, 42, 2870) was added to a suspension of potassium carbonate (3.2 g, 23.1 mmol) and hydroxylamine hydrochloride (1.06 g, 15.4 mmol) in ethanol (10 ml). The reaction mixture was heated at reflux for 9 hours then allowed to cool. The reaction was filtered and the solvent evaporated in vacuo to afford Intermediate 80 (1.53 g). $^1$H NMR (400 MHz in d$_6$-DMSO, 27° C., δ ppm) 9.02 (br s, 1H), 5.17 (br s, 2H), 2.78 (s, 2H), 2.31 (br s, 8H), 2.13 (s, 3H).

Intermediate 81: 4-Fluoro-N-hydroxybenzenecarboximidamide

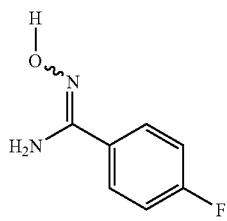

Commercially available from Sigma-Aldrich, CAS (Chemical Abstracts) Registry Number 22179-78-8.

Intermediate 82: (1E/Z)-N-hydroxy-3-oxo-3-(1-pyrrolidinyl)propanimidamide

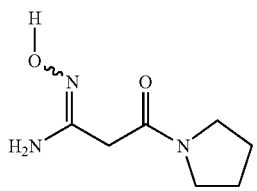

Commercially available from the Maybridge Chemical Company, CAS (Chemical Abstracts) Registry Number 57399-51-6.

Intermediates 83 and 84

The structures of Intermediates 83 and 84 and their preparation are as follows:

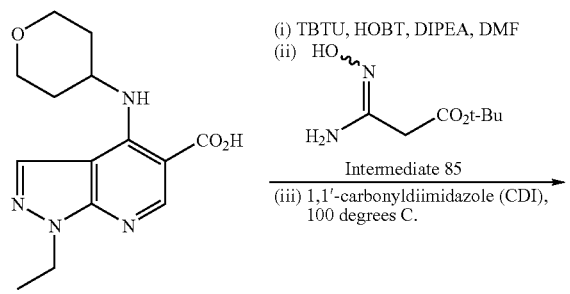

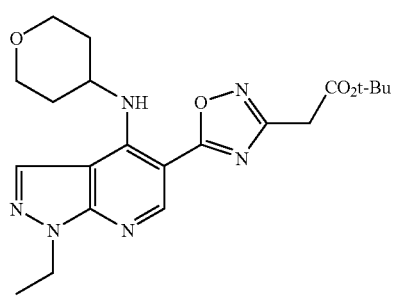

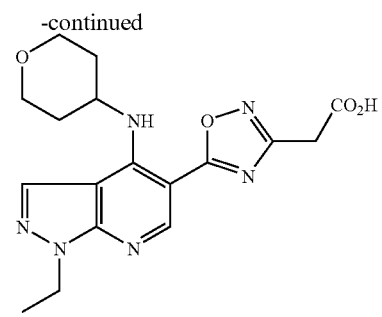

Intermediate 83

Intermediate 83: {5-[1-Ethyl-4-(tetrahydro-2H-pyran 4-ylamino)-H-pyrazolo[3,4-b]pyridin-5-yl]-1,2,4-oxadiazol-3-yl}acetic acid

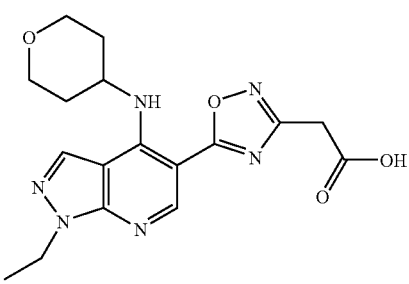

Anhydrous hydrogen chloride in dioxane (8 ml, 4M solution) was added to Intermediate 84 (0.807 g, 1.88 mol). The reaction mixture was stirred overnight at room temperature then evaporated in vacuo. The residue was suspended in ether and the mixture filtered to give Intermediate 83 as a brown solid (0.525 g). LCMS showed $MH^+$=373; $T_{RET}$=2.62 min.

Intermediate 84: 1,1-Dimethylethyl {5-[1-ethyl-4-(tetrahydro-2H-pyran-4-ylamino)-1H-pyrazolo[3,4-b]pyridin-5-yl]-1,2,4-oxadiazol-3-yl}acetate

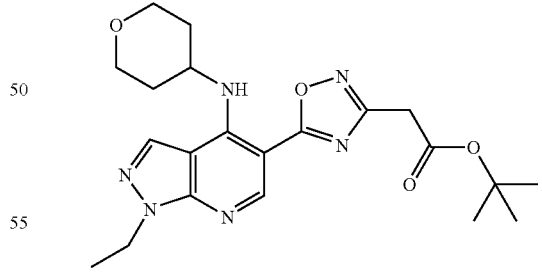

Diisopropyethylamine (8.3 ml, 47.5 mmol) was added to a mixture of Intermediate 17 (2.76 g, 9.5 mmol), TBTU (3.050 g, 9.5 mmol) and hydroxybenzotriazole (1.28 g, 9.5 mmol) in N,N-dimethylformamide (40 ml) at room temperature. After stirring for 10 minutes Intermediate 85 (2.318 g, 13.3 mmol) was added. The reaction mixture was stirred for 50 minutes then 1,1'-carbonyldiimidazole (1.54 g, 9.5 mmol) was added and the reaction heated at 100° C. for 16 hours. The solvent was removed in vacuo and the residue partitioned between dichloromethane and water. The organic phase was washed with aqueous sodium hydrogen carbonate (5%) then dried (Na$_2$SO$_4$) and evaporated in vacuo. The residue was purified by chromaography using the Biotage system (10 g, silica) eluting with cyclohexane:ethyl acetate (1:1). Intermediate 84 was obtained a brown solid (0.97 g). LCMS showed MH$^+$=429 T$_{RET}$=3.26 min.

Intermediate 85: 1,1-Dimethylethyl(3E/Z)-3-(hydroxyamino)-3-iminopropanoate

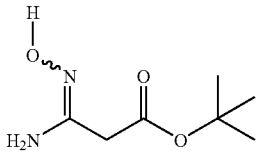

The reaction scheme was as follows:

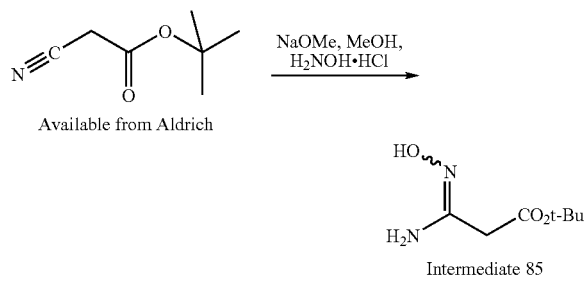

A solution of sodium methoxide in methanol (50 ml, 0.5M) was added to hydroxylamine hydrochloride (1.78 g, 25.62 mmol) at room temperature. After stirring for 15 minutes the solution was filtered and the filtrate added to t-butyl cyanoacetate (3.0 g, 21.25 mmol, available from Aldrich). The solution was refluxed for 1.75 hours then cooled and evaporated in vacuo. The residue was partitioned between ethyl acetate and water. The aqueous phase was extracted with ethyl acetate and the combined organic phases washed with brine, dried (MgSO$_4$) and evaporated in vacuo. The residue was suspended in cyclohexane: ether (1:1) then filtered to give Intermediate 85 as a white solid (1.883 g). $^1$H NMR (400 MHz in CDCl$_3$, 27° C., δ ppm) 8.34 (br s, 1H), 5.05 (br s, 2H), 3.09 (s, 2H), 1.47 (s, 9H).

Intermediate 86: N''-{[1-Ethyl-4-(tetrahydro-2H-pyran-4-ylamino)-1H-pyrazolo[3,4-b]pyridin-5-yl]carbonyl}-N,N,N',N'-tetramethylcarbonohydrazonic diamide

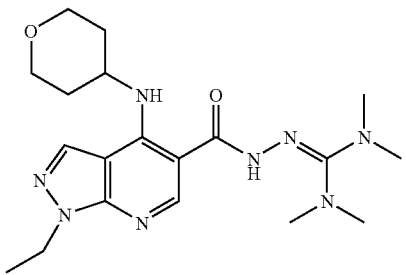

Intermediate 19 (0.1 g, 0.29 mmol), TBTU (0.094 g, 0.29 mmol) and diisopropylethylamine (0.204 ml, 1.17 mmol) in N,N-dimethylformamide (1 ml) were stirred at room temperature for 1 hour. The solvent was evaporated in vacuo and the residue dissolved in methanol and applied to an SPE cartridge (aminopropyl, 5 g). The cartridge was eluted with methanol and appropriate factions evaporated in vacuo to give Intermediate 86 as a yellow solid (0.113 g). LCMS showed MH$^+$=403; T$_{RET}$=1.99 min.

Intermediate 87: Ethyl(2-methyl-1,3-thiazol-4-yl)acetate

Prepared as described by K. Arakawa et. al., Chem Pharm Bull, 1912, 20 (5), 1041

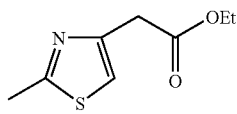

Intermediate 88: 2-Methyl-1,3-thiazol-4-yl acetic acid

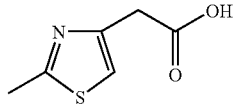

To a solution of Intermediate 87 (6 g, 32.4 mmol) in dioxan (15 ml) was added a solution of lithium hydroxide monohydrate (1.53 g, 36.4 mmol) in water (15 ml). The mixture was stirred for 17 h, then washed with diethyl ether (20 ml), then with ethyl acetate (20 ml) and acidified with concentrated hydrochloric acid under ethyl acetate (50 ml). The combined aqueous phases were adjusted to pH 2.7 by addition of sodium bicarbonate and extracted with further ethyl acetate (2×50 ml). The combined organic phases were washed with water (20 ml) and saturated brine (20 ml), then concentrated in vacuo to afford Intermediate 88 as a white solid (1.69 g). $^1$H NMR (400 MHz in CDCl$_3$, 27° C., δ ppm) 2.74 (s, 3H), 3.85 (s, 2H), 5.8-6.2 (br, s, 1H), 7.02 (s, 1H).

Intermediate 89: 1-Ethyl-4-(tetrahydro-2H-pyran-4-ylamino)-N'-(1H-1,2,3-triazol-1-ylacetyl)-1H-pyrazolo[3,4-b]pyridine-5-carbohydrazide

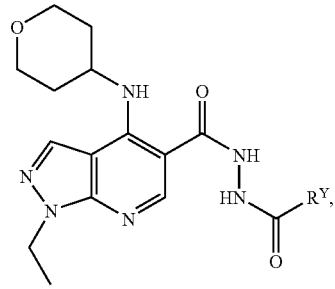

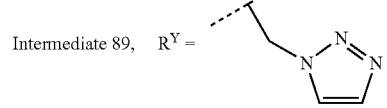

General Procedure for Intermediates 89 to 114:

A mixture of carboxylic acid R$^Y$CO$_2$H (0.2 mmol), diisopropylethylamine (0.105 ml, 0.6 mmol) and TBTU (0.071 g, 0.22 mmol) in N,N-dimethylformamide (0.5 ml) was allowed to stand for 10 minutes. A mixture of Intermediate 19 (0.2 mmol) and diisopropylethylamine (0.035 ml, 0.2 mmol) in N,N-dimethylformamide (0.5 ml) was added. After agitation the reactions were allowed to stand for 16 hours. The solvent was removed in vacuo and residue was applied to an SPE cartridge (aminopropyl, 0.5 g). The cartridge was eluted with chloroform, ethyl acetate:chloroform (1:1), ethyl acetate, ethyl acetate:methanol (9:1, 2 ml). Appropriate fractions were evaporated in vacuo to afford the Intermediates below.

| Intermediate Number | R$^Y$ | Source of Carboxylic acid R$^Y$CO$_2$H | MH$^+$ | T$_{RET}$ (min) |
|---|---|---|---|---|
| 89 | [1,2,3-triazolylmethyl] | ChemPacific Ltd | 413 | 2.17 |
| 90 | [2,4-dimethylthiazolylmethyl] | SPECS Fleminglaan 162289 CP Rijswijk The Netherlands | 457 | 2.3 |
| 91 | [furan-2-ylmethyl] | Advanced Synthesis P.O. Box 437920 San Ysidro, California 92173 United states | 412 | 2.4 |
| 92 | [isoxazol-3-ylmethyl] | Microchemistry Ltd, Shosse Entusiastov 56, Moscow 1111123, Russia | 413 | 2.25 |
| 93 | [4-methoxybenzyl] | Aldrich | 452 | 2.59 |
| 94 | [tetrazolylmethyl] | Maybridge Chemical Company Ltd., Trevillett, Tintagel, Cornwall PL340HW, United Kingdom | 414 | 2.2 |
| 95 | [isothiazol-5-ylmethyl] | Described by R. Raap et. al., US3271407A | 429 | 2.33 |
| 96 | [3-methylisoxazol-5-ylmethyl] | Aldrich | 427 | 2.32 |
| 97 | [4-(dimethylamino)benzyl] | Aldrich | 465 | 2.21 |
| 98 | [2-methylthiazol-4-ylmethyl] | Intermediate 88 | 443 | 2.33 |
| 99 | [1-(N-methylcarbamoylmethyl)cyclopentylmethyl] | Peakdale Molecular Ltd, Peakdale Science Park, Sheffield Road, Chapel-en-le-Frith, High Peak SK23 0PG, UK | 485 | 2.47 |
| 100 | [2-(cyclopropylcarbonylamino)ethyl] | J. Chem. Soc., Perkin Trans II, 1993, 4, 741-8 | 429 | 2.19 |
| 101 | [5-methylisoxazol-3-ylmethyl] | Lancaster Synthesis | 413 | 2.42 |
| 102 | [5-methylisoxazol-3-ylethyl] | J. Chem. Soc. Perkin Trans. 1, 1976, 9, 994-7 | 427 | 2.35 |
| 103 | [4-methylthiazol-5-ylethyl] | Microchemistry Ltd, Shosse Entusiastov 56, Moscow 1111123, Russia | 457 | 2.32 |
| 104 | [6-oxopiperidin-2-yl] | Microchemistry Ltd, Shosse Entusiastov 56, Moscow 1111123, Russia | 429 | 2.13 |
| 105 | [3-methyl-1H-1,2,4-triazol-5-ylmethyl] | Microchemistry Ltd, Shosse Entusiastov 56, Moscow 1111123, Russia | 427 | 2.11 |

-continued

| Intermediate Number | R$^Y$ | Source of Carboxylic acid R$^Y$CO$_2$H | MH$^+$ | T$_{RET}$ (min) |
|---|---|---|---|---|
| 106 | (5-methyl-3-methylisoxazol-4-yl)methyl | Microchemistry Ltd, Shosse Entusiastov 56, Moscow 1111123, Russia | 441 | 2.35 |
| 107 | N-acetyl-isopropylamino | Sigma Chemical Company | 417 | 2.11 |
| 108 | (1-acetylpiperidin-4-yl)methyl | T. J. Guzi et al., WO 03/022835 | 471 | 2.22 |
| 109 | 4-methylbenzyl | Aldrich | 437 | 2.7 |
| 110 | 4-methylphenyl | Aldrich | 423 | 2.6 |
| 111 | 3,4-dimethylbenzyl | Aldrich | 437 | 2.8 |
| 112 | 2,4-dimethylbenzyl | Aldrich | 437 | 2.7 |
| 113 | 2,4-dimethylbenzyl | ACB Blocks Ltd or Described by Rzeszotarski, W. J. in WO 93/05772 | 451 | 2.7 |
| 114 | 4-bromobenzyl | Aldrich | 501/503 | 2.8 |

Intermediate 115: 4-(Aminomethyl)benzamide

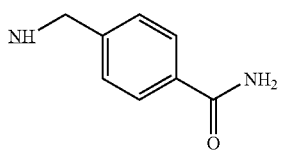

Can be prepared according to the procedure described by L. W. Jones et. al. WO 02/085860.

Intermediate 116: 1,1-Dimethylethyl [(2Z)-2-(hydroxyamino)-2-iminoethyl]carbamate

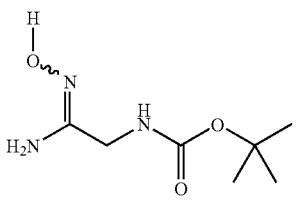

Prepared from commercially available N-(tert-Butoxycarbonyl)-2-aminoacetonitrile as described by M. Schwarz et. al. WO 02/102799.

Intermediate 117: 1,1-Dimethylethyl({5-[1-ethyl-4-(tetrahydro-2H-pyran-4-S ylamino)-1H-pyrazolo[3,4-b]pyridin-5-yl]-1,2,4-oxadiazol-3-yl}methyl)carbamate

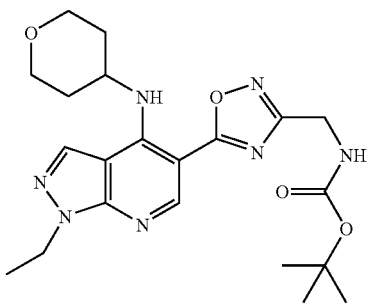

Diisopropylethylamine (6.0 ml, 34.4 mmol) was added to a stirred mixture of Intermediate 17 (2.0 g, 6.89 mmol), TBTU (2.212 g, 6.89 mmol) and HOBT (0.931 g, 6.89 mmol) in dry dimethylformamide (45 ml). After 10 min, the resulting clear solution was treated with Intermediate 116 (1.89 g, 10 mmol). The reaction mixture was stirred at room temperature for 2 h. DBU (5.14 ml, 34.5 mmol) was added, and the reaction mixture was heated at 80° C. After 3.5 h at 80° C., the reaction mixture was evaporated in vacuo, and the residue was dissolved in dichloromethane (150 ml) and washed successively with 5% sodium hydrogen carbonate (50 ml) and water (50 ml). The organic solution was dried over anhydrous sodium sulphate and evaporated to give the crude product. Purification by Biotage chromatography (silica, 100 g) eluting with ethyl acetate-petroleum ether (1:1) afforded Intermediate 117 as a white solid (2.70 g). LCMS showed MH$^+$=444, T$_{RET}$=3.06 min.

Intermediate 118: 5-[3-(Aminomethyl)-1,2,4-oxadiazol-5-yl]-1-ethyl-N-(tetrahydro-2H-pyran-4-yl)-1H-pyrazolo[3,4-b]pyridin-4-amine

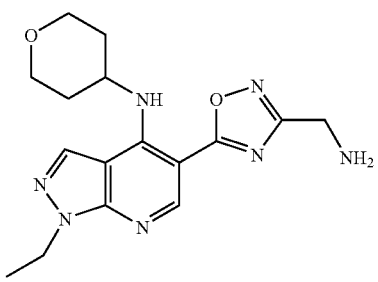

Trifluoroacetic acid (5 ml) was added to a stirred solution of Intermediate 117 (1.774 g, 4.0 mmol) in dry dichloromethane (20 ml) at 0° C. After 2 h, the reaction mixture was neutralised by careful addition of 5% sodium hydrogen carbonate solution (150 ml) and solid sodium hydrogen carbonate. The resulting mixture was extracted with chloroform (2×100 ml). The combined organic extracts were dried over anhydrous sodium sulphate and evaporated to afford Intermediate 118 as a white solid (1.358 g). LCMS showed MH$^+$=344, T$_{RET}$=1.95 min.

Intermediate 119: 4-Chloro-N-({5-[1-ethyl-4-(tetrahydro-2H-pyran-4-ylamino)-1H-pyrazolo[3,4-b]pyridin-5-yl]-1,2,4-oxadiazol-3-yl}methyl)butanamide

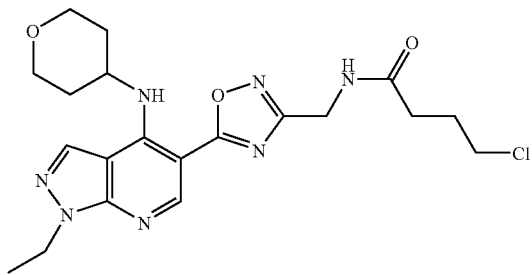

4-chlorobutanoyl chloride (0.12 mmol) was added to a stirred solution of Intermediate 118 (0.1 mmol) and diisopropylethylamine (0.3 mmol) in chloroform (1 ml) at room temperature. After stirring at room temperature for 16 h, the reaction mixture was applied to a SPE cartridge (aminopropyl, 2 g) and the cartridge was eluted sequentially with chloroform, ethyl acetate and methanol. Fractions containing the desired product were combined and blown down under nitrogen. The resulting residue was further purified on a SPE cartridge (silica, 1 g) eluting with a gradient of 30-100% ethyl acetate in petroleum ether to afford Intermediate 119 as a white solid (45 mg).). LCMS showed MH$^+$=448, T$_{RET}$=2.77 min.

Intermediate 120: 5-Chloro-N-({5-[1-ethyl-4-(tetrahydro-2H-pyran-4-ylamino)-1H-pyrazolo[3,4-b]pyridin-5-yl]-1,2,4-oxadiazol-3-yl}methyl)pentanamide

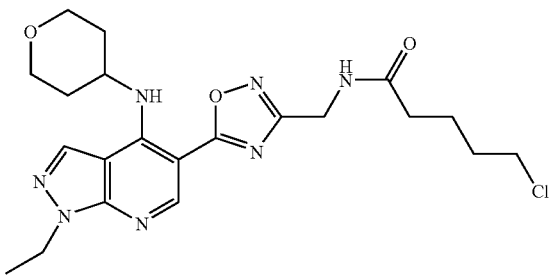

5-chloropentanoyl chloride (0.12 mmol) was added to a stirred solution of Intermediate 118 (0.1 mmol) and diisopropylethylamine (0.3 mmol) in chloroform (1 ml) at room temperature. After stirring at room temperature for 16 h, the reaction mixture was applied to a SPE cartridge (aminopropyl, 2 g) and the cartridge was eluted sequentially with chloroform, ethyl acetate and methanol. Fractions containing the desired product were combined and blown down under nitrogen. The resulting residue was further purified on a SPE cartridge (silica, 1 g) eluting with a gradient of 30-100% ethyl acetate in petroleum ether to afford Intermediate 120 as a white solid (46 mg). LCMS showed MH$^+$=462, T$_{RET}$=2.86 min.

Intermediate 121: (1E/Z)-N-hydroxy-2-(4-morpholinyl)propanimidamide

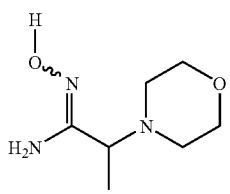

Prepared from α-methyl-4-morpholineacetonitrile using a similar process to that described for any of Intermediates 9, 22 or 80 using similar or the same number of moles of reagents and/or volumes of solvents. $^1$H NMR (27° C., d-4-MeOH) 3.70-3.60 (m, 5H), 3.13-3.07 (m, 2H), 2.83-2.76 (m, 2H), 1.84 (d, J=5 Hz, 3H)

α-Methyl-4-morpholineacetonitrile can be prepared according to the procedure described by H. R. Henze et. al. J. Am. Chem. Soc 1957, 79, 6230.

Intermediate 122: (1E/Z)-2-cyclohexyl-N-hydroxyethanimidamide

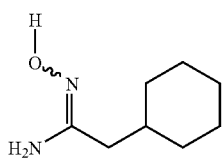

Can be prepared from cyclohexylacetic acid (commercially available from e.g. Aldrich) according to the procedure described by T. R. Alessi et al. in U.S. Pat. No. 4,895,860.

Intermediate 123: 1,1-Dimethylethyl 4-[(2Z)-2-(hydroxyamino)-2-iminoethyl]-1-piperidinecarboxylate

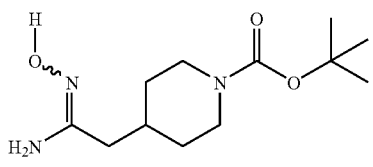

Prepared from 1,1-dimethylethyl 4-(cyanomethyl)-1-piperidinecarboxylate using a similar process to that described for any of Intermediates 9, 22 or 80 using similar or the same number of moles of reagents and/or volumes of solvents.

1,1-dimethylethyl 4-(cyanomethyl)-1-piperidinecarboxylate can be prepared from commercially available 1,1-dimethylethyl 4-oxo-1-piperidinecarboxylate according to the procedure described by A. M. Wilson in WO 00/006159.

Intermediate 124: 1,1-Dimethylethyl 4-({5-[1-ethyl-4-(tetrahydro-2H-pyran-4-ylamino)-1H-pyrazolo[3,4-b]pyridin-5-yl]-1,2,4-oxadiazol-3-yl}methyl)-1-piperidinecarboxylate

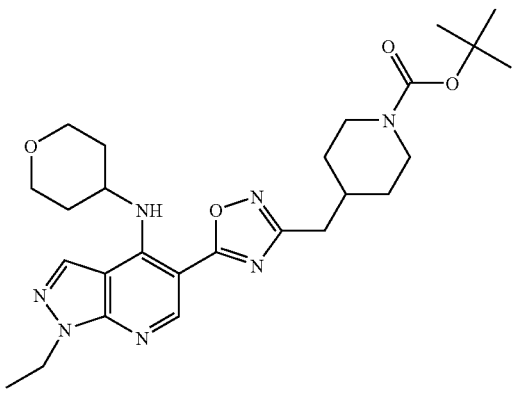

A mixture of Intermediate 16 (0.064 g, 0.2 mmol), Intermediate 80 (0.257 g, 1 mmol), a solution of sodium ethoxide in EtOH (0.19 ml, 21% solution) and powdered 4A molecular sieves (0.38 g) in EtOH (2 ml) were stirred at 82° C. under an atmosphere of nitrogen for 18 hours. Additional sodium ethoxide in ethanol (0.19 ml, 21% solution), molecular sieves (0.38 g) and ethanol (4 ml) were added and the reaction heated for a further 72 hours. The reaction mixture was filtered, the solvent was evaporated in vacuo and the residue was applied to an SPE cartridge (silica, 2 g). The cartridge was eluted with cyclohexane:ethyl acetate (4:1, 2:1, 1:1), then ethyl acetate to afford Intermediate 124 as a colourless oil (0.052 g). LCMS showed MH$^+$=512; T$_{RET}$=3.51 min.

Intermediate 125: 1-Ethyl-5-[3-(4-piperidinylmethyl)-1,2,4-oxadiazol-5-yl]-N-(tetrahydro-2H-pyran-4-yl)-1H-pyrazolo[3,4-b]pyridin-4-amine hydrochloride

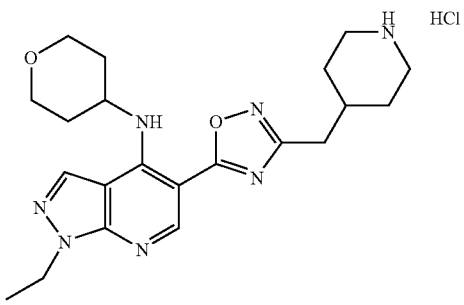

A solution of hydrogen chloride in dioxane (1 ml) was added to Intermediate 124 (0.052 g, 0.1 mmol) and the reaction mixture stirred at 20° C. for 2 hours. The solution was evaporated in vacuo to afford Intermediate 125 as a yellow solid (0.047 g). LCMS showed MH$^+$=412; T$_{RET}$=2.21 min.

Intermediate 126: N-Hydroxy-1-(phenylsulfonyl)cyclopropanecarboximidamide

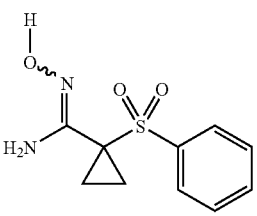

Prepared from 1-(phenylsulphonyl)cyclopropoanecarbonitrile (commercially available from Menai Organics Ltd, Menai Technology Centre, Deiniol Roas, Bangor, Gwynedd, Wales, LL57 UP, United Kingdom or described in Bull. Chem. Soc. Jpn. 1985 58(2), 765) using a similar process to that described for any of Intermediates 9, 22 or 80 using similar or the same number of moles of reagents and/or volumes of solvents. LCMS showed MH$^+$=241; T$_{RET}$=1.71 min.

Intermediate 127: (1E/Z)-N-Hydroxy-2-phenylethanimidamide

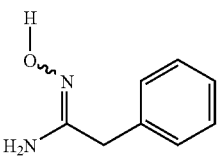

Commercially available from Maybridge Chemical Company Ltd, Trevillett, Tintagel, Cornwall, PL34 0HW, United Kingdom.

Intermediate 128: (1E/Z)-N-Hydroxy-2-phenylpropanimidamide

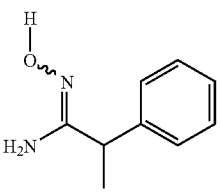

Can be prepared from α-methylphenylacetonitirile according to the procedure described by J. Rheineimer EP 323864.

Intermediate 129: (1E/Z)-N-Hydroxy-2-[4-(methyloxy)phenyl]ethanimidamide

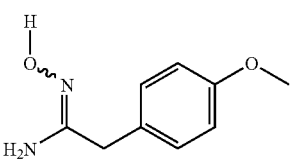

Commercially available from Exploratory Library, Ambinter, 46 quai Louis Bleriot, Paris, F-75016, France.

Intermediate 130: (1E/Z)-N-Hydroxy-2-[3-(methyloxy)phenyl]ethanimidamide

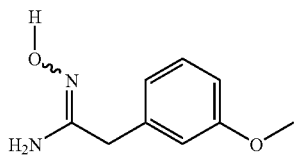

Can be prepared from according to the procedure described by S. Borg et. Al European J. Med. Chem. 1993, 28(10) 801.

Intermediate 131: (1E/Z)-2-[4-(Dimethylamino)phenyl]-N-hydroxyethanimidamide

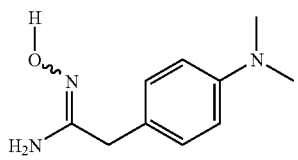

Prepared from 4-(dimethylamino)benzeneacetonitrile (described by Borovicka et al. Collect. Czech. Chem. Commun 1955, 20, 437) using a similar process to that described for any of Intermediates 9, 22 or 80 using similar or the same number of moles of reagents and/or volumes of solvents. LCMS showed MH$^+$=194; T$_{RET}$=0.38 min.

Intermediate 132: (1E/Z)-2-[3-(Dimethylamino)phenyl]-N-hydroxyethanimidamide

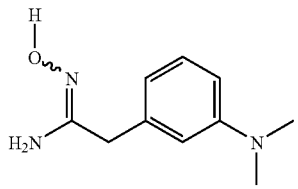

Prepared from 3-(dimethylamino)benzeneacetonitrile (described by M. L. Sznaidman et al. Bioorganic Medicinal Chemistry Letters 1996, 6(5), 565) using a similar process to that described for any of Intermediates 9, 22 or 80 using similar or the same number of moles of reagents and/or volumes of solvents. LCMS showed MH$^+$=194; T$_{RET}$=0.46 min Intermediate 133: (1E/Z)-N-Hydroxy-2-(phenyloxy)ethanimidamide

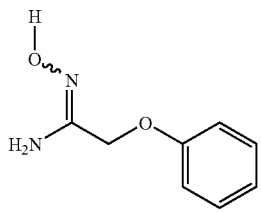

Commercially available from Pfaltz & Bauer Inc.

Intermediate 134: (1E/Z)-N-hydroxy-2-(5,6,7,8-tetrahydro[1,2,4]triazolo[4,3-a]pyridin-3-yl)ethanimidamide

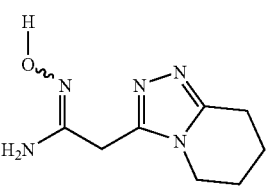

Prepared from 5,6,7,8-tetrahydro-1,2,4-triazolo[4,3-a]pyridine-3-acetonitrile (commercially available from Interchim, 213 Avenue Kennedy, BP 1140, Montlucon, Cedex 03103, France or Exploratory Library, Ambinter, 46 quai Louis Bleriot, Paris, F-75016, France) using a similar process to that described for any of Intermediates 9, 22 or 80 using similar or the same number of moles of reagents and/or volumes of solvents. LCMS showed MH$^+$=198; T$_{RET}$=0.32 min.

Intermediate 135: (1E/Z)-N-Hydroxy-2-(4-phenyl-1-piperazinyl)ethanimidamide

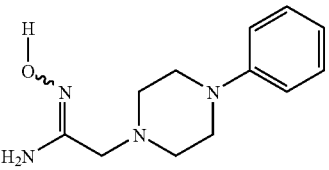

Prepared from 4-phenyl-1-piperazineacetonitrile (commercially available from Interchim, 213 Avenue Kennedy, BP 1140, Montlucon, Cedex 03103, France or Exploratory Library, Ambinter, 46 quai Louis Bleriot, Paris, F-75016, France) using a similar process to that described for any of Intermediates 9, 22 or 80 using similar or the same number of moles of reagents and/or volumes of solvents. LCMS showed MH$^+$=235; T$_{RET}$=1.09 min.

Intermediate 136: 1-Ethyl-4-(tetrahydro-2H-pyran-4-ylamino)-1H-pyrazolo[3,4-b]pyridine-5-carboxamide

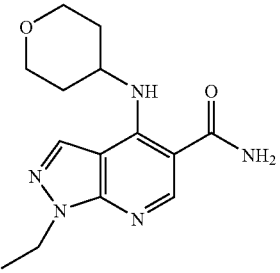

A solution of Intermediate 17 (3.263 g, 11.25 mmol) in thionyl chloride (17 ml) was heated at 60° C. for 2 hours. The solution was concentrated in vacuo and then co-evaporated with dichloromethane. The residue was suspended in a solution of ammonia in dioxane (45 ml, 0.5M solution) and the resultant mixture stirred for 18 hours. After concentration in vacuo the residue was re-suspended in ammonia in dioxane (45 ml, 0.5M) and stirred for a further 16 hours. The solvent was removed in vacuo and the solid suspended in a mixture of dichloromethane (40 ml) and water (40 ml). The solid was filtered, washed with water and dried in vacuo over $P_2O_5$ to afford Intermediate 136 as a cream solid (2.50 g). LCMS showed $MH^+$=290; $T_{RET}$=2.12 min Intermediate 137: 1-Ethyl-4-(tetrahydro-2H-pyran-4-ylamino)-1H-pyrazolo[3,4-b]pyridine-5-carbonitrile

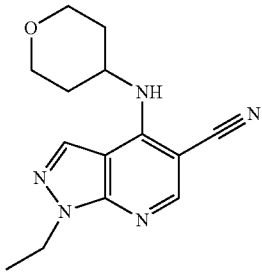

Burgess Reagent 4.53 g, 19.0 mmol) was added to a suspension of Intermediate 136 (5.0 g, 17.3 mmol) in THF (80 ml). The reaction mixture was stirred at room temperature for 18 hours then a further portion of Burgess Reagent (0.9 g, 1.8 mmol) was added and stirring continued for 5 hours. The reaction mixture was concentrated in vacuo and the residue partitioned between dichloromethane and water. The organic phase was washed with water, dried and evaporated in vacuo to afford Intermediate 137 as an off-white solid (4.43 g). LCMS showed $MH^+$=272; $T_{RET}$=2.40 min Intermediate 138: 1-Ethyl-N-hydroxy-4-(tetrahydro-2H-pyran-4-ylamino)-1H-pyrazolo[3,4-b]pyridine-5-carboximidamide

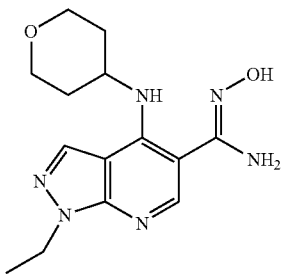

Intermediate 137 (3.50 g, 12.9 mmol), hydroxylamine hydrochloride (3.30 g, 47.8 mmol) and sodium hydrogencarbonate (4.01 g, 47.8 mmol) in EtOH (45 ml) were heated at 45° C. for 1.5 hours then at 50° C. for 2.5 hours. The suspension was concentrated in vacuo and the solid stirred in dichloromethane (80 ml) for 0.5 hours. The mixture was filtered and the solid stirred in EtOH, the resultant mixture was filtered and the filtrate evaporated. The solid was then washed with dichloromethane three time to afford Intermediate 138 as a white solid (1.62 g). LCMS showed $MH^+$=305; $T_{RET}$=1.85 min Intermediate 139: 1-Ethyl-N-[4-(hydroxymethyl) tetrahydro-2H-pyran-4-yl]-4-(tetrahydro-2H-pyran-4-ylamino)-1H-pyrazolo[3,4-b]pyridine-5-carboxamide

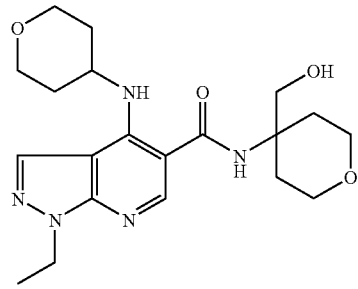

Intermediate 139 was prepared from Intermediate 17 and (4-aminotetrahydro-2H-pyran-4-yl)methanol (commercially available from PharmaCore Inc., 4170 Mendenhall Oaks Pkwy, Suite 140, High point, N.C., USA) using an analogous method to that for Intermediate 42. LCMS showed $MH^+$=404, $T_{RET}$=2.19 min.

Intermediate 140: (R)-(+)-3-Amino tetrahydrofuran 4-toluenesulphonate

Commercially available from Fluka Chemie AG, Germany (CAS 111769-27-8)

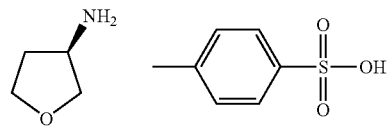

Intermediate 141: (S)-(−)-3-Amino tetrahydrofuran 4-toluenesulphonate

Commercially available from E. Merck, Germany, or from E. Merck (Merck Ltd), Hunter Boulevard, Magna Park, Lutterworth, Leicestershire LE17 4XN, United Kingdom (CAS 104530-80-5)

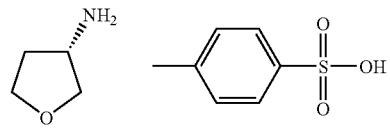

Intermediate 142: Tetrahydro-2H-thiopyran-4-amine

Prepared from commercially available tetrahydrothiopyran-4-one as described by Subramanian et. al., *J. Org. Chem.*, 1981, 46, 4376-4383. Subsequent preparation of the hydrochloride salt can be achieved by conventional means.

143

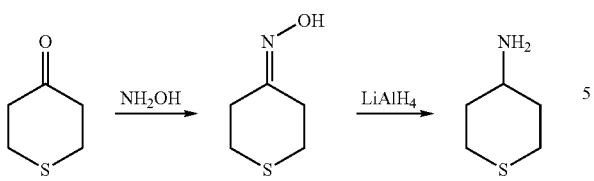

Intermediate 143: Tetrahydro-3-thiopheneamine

Prepared in an analogous manner to Intermediate 142 from commercially available tetrahydrothiophene-4-one. The oxime formation is described by Grigg et. al., *Tetrahedron*, 1991, 47, 4477-4494 and the oxime reduction by Unterhalt et. al., *Arch. Pharm.*, 1990, 317-318.

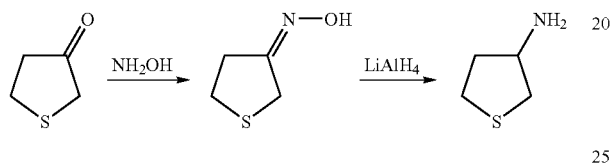

Intermediate 144: Tetrahydro-3-thiopheneamine 1,1-dioxide hydrochloride

Commercially available from Sigma Aldrich Library of Rare Chemicals (SALOR) (CAS-6338-70-1). Preparation of the hydrochloride salt of the amine can be achieved by conventional means.

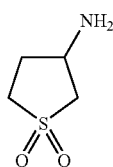

Intermediate 145:
Tetrahydro-2H-thiopyran-4-amine-1,1-dioxide hydrochloride

Prepared in an analogous manner to Intermediate 11 from commercially available tetrahydrothiophene-4-one. Oxidation to 1,1-dioxo-tetrahydro-1λ⁶-thiopyran-4-one is described by Rule et. al., in *J. Org. Chem.*, 1995, 60, 1665-1673. Oxime formation is described by Truce et. al., in *J. Org. Chem.*, 1957, 617, 620 and oxime reduction by Barkenbus et. al., *J. Am. Chem. Soc.*, 1955, 77, 3866. Subsequent preparation of the hydrochloride salt of the amine can be achieved by conventional means.

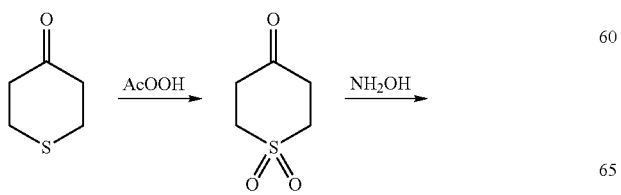

144

-continued

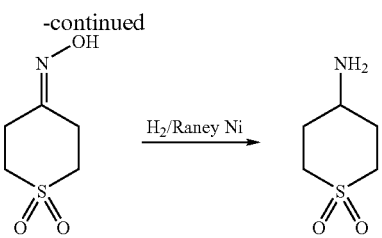

Intermediate 146:
1,1-Dimethylethyl(4,4-difluorocyclohexyl)carbamate

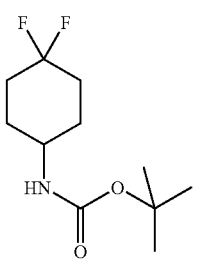

(Diethylamino)sulphur trifluoride (DAST), (0.06 ml, 0.47 mmol), was added to a stirred solution of 1,1-dimethylethyl (4-oxocyclohexyl)carbamate, (250 mg, 1.17 mmol, commercially available from AstaTech Inc., Philadelphia, USA) in anhydrous dichloromethane (5 ml) and the mixture was stirred under nitrogen at 20° C. After 22 h, the reaction mixture was cooled to 0° C., treated with saturated sodium hydrogen carbonate solution (4 ml), and then allowed to warm to ambient temperature. The phases were separated by passage through a hydrophobic frit and the aqueous phase was further extracted with DCM (5 ml). The combined organic phases were concentrated in vacuo to give an orange solid (369 mg) which was further purified by chromatography using a SPE cartridge (silica, 10 g), eluting with DCM to afford Intermediate 62 (140 mg) containing 20% of 1,1-dimethylethyl(4-fluoro-3-cyclohexen-1-yl)carbamate. ¹H NMR (400 MHz in CDCl₃, 27° C., δ ppm)

Minor component: δ5.11 (dm, 16 Hz, 1H), 4.56 (br, 1H), 3.80 (br, 1H) 2.45-1.45 (m's, 6H excess), 1.43 (s, 9H). Major component: δ4.43 (br, 1H), 3.58 (br, 1H), 2.45-1.45 (m's, 8H excess), 1.45 (s, 9H).

Intermediate 147: (4,4-Difluorocyclohexyl)amine hydrochloride

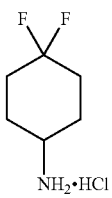

A solution of hydrogen chloride in dioxane (4M, 1.6 ml) was added at 20° C. to a stirred solution of Intermediate 146 (140 mg, 0.6 mmol), in dioxane (1.6 ml). After 3 h, the reaction mixture was concentrated in vacuo to afford Intermediate 147 (96.5 mg) containing 4-fluoro-3-cyclohexen-1- amine. $^1$H NMR (400 MHz in d$_6$-DMSO, 27° C., δ ppm) Minor component: δ8.22 (br, 3H excess), 5.18 (dm, 16 Hz, 1H), 3.28-3.13 (m, 1H excess), 2.41-1.53 (m's, 6H excess). Major component: δ8.22 (br, 3H excess), 3.28-3.13 (m, 1H excess), 2.41-1.53 (m's, 8H excess). Impurities are also present.

Intermediates 148 to 163: different types of R$^3$R$^{3a}$NH

| Intermediate Number | R$^3$R$^{3a}$NH | Source of R$^3$R$^{3a}$NH |
|---|---|---|
| 148 | (3-amino-cyclohexan-1-ol) | J. Chem. Soc., Perkin Trans. 1, 1994, 537 |
| 148A | as Intermediate 148, but racemic cis-isomer, i.e. racemic cis-(3-hydroxy-cyclohex-1-yl)-amine | J. Chem. Soc., Perkin Trans 1, 1994, 537 |
| 149 | (4-amino-cyclohexan-1-ol) | Aldrich; or TCI-America |
| 150 | (3-amino-cyclopentan-1-ol) | U.S. Pat. No. 4,219,660 |
| 151 | cyclobutylamine | Aldrich |
| 152 | cycloheptylamine | Aldrich |
| 153 | 4-methyl-cyclohexylamine | Aldrich |
| 154 | 3-methyl-cyclohexylamine | Pfaltz-Bauer |
| 155 | 1-methyl-cyclohexylamine | J. Org. Chem., 1985, 50(11), 1859 |
| 156 | (3-amino-pyrrolidin-2-one) | WO 99/12933 |
| 157 | (3-amino-pyrrolidine-2,5-dione) | EP 1188744 |
| 158 | (3-Aminoazepan-2-one) | Sigma-Aldrich Company Ltd |
| 159* | trans-1,4-diaminocyclohexane | J. Med. Chem., 1994, 37(17), 2360 |
| 160* | cis-1,4-diaminocyclohexane | Aldrich |
| 161* | 1,2-diaminocyclohexane | Aldrich |
| 162* | 1,2-diaminocyclohexane | Aldrich |
| 163* | 1,3-diaminocyclohexane | Peakdale Molecular Ltd |

*For R$^3$R$^{3a}$NH in Intermediates 159–163, R$^3$R$^{3a}$NH is the cis or trans isomer, if shown. For Intermediates 161–163, R$^3$R$^{3a}$NH is usually the 3-amino- or 2-amino-cyclohex-1-ylamine in a racemic form.

Table of Examples

| Example Number | Name |
|---|---|
| 1 | N-Cyclopentyl-1-ethyl-5-(5-methyl-1,3,4-oxadiazol-2-yl)-1H-pyrazolo[3,4-b]pyridin-4-amine |
| 2 | N-Cyclopentyl-1-ethyl-5-{5-[(methylsulfonyl)methyl]-1,3,4-oxadiazol-2-yl}-1H-pyrazolo[3,4-b]pyridin-4-amine |
| 3 | N-Cyclopentyl-1-ethyl-5-(5-isopropyl-1,3,4-oxadiazol-2-yl)-1H-pyrazolo[3,4-b]pyridin-4-amine |

-continued

Table of Examples

| Example Number | Name |
|---|---|
| 4 | N-Cyclopentyl-1-ethyl-5-(5-methyl-1,3,4-thiadiazol-2-yl)-1H-pyrazolo[3,4-b]pyridin-4-amine |
| 5 | N-Cyclopentyl-1-ethyl-5-{5-[(methylsulfonyl)methyl]-1,3,4-thiadiazol-2-yl}-1H-pyrazolo[3,4-b]pyridin-4-amine |
| 6 | N-Cyclopentyl-1-ethyl-5-(5-isopropyl-1,3,4-thiadiazol-2-yl)-1H-pyrazolo[3,4-b]pyridin-4-amine |
| 7 | 1-Ethyl-N-(4-fluorophenyl)-5-(3-methyl-1,2,4-oxadiazol-5-yl)-1H-pyrazolo[3,4-b]pyridin-4-amine |
| 8 | N-Cyclopentyl-5-(1,3-dimethyl-1H-1,2,4-triazol-5-yl)-1-ethyl-1H-pyrazolo[3,4-b]pyridin-4-amine |
| 9 | 1-Ethyl-5-(5-isopropyl-1,3,4-oxadiazol-2-yl)-N-tetrahydro-2H-pyran-4-yl-1H-pyrazolo[3,4-b]pyridin-4-amine |
| 10 | N-Cyclohexyl-1-ethyl-5-(5-isopropyl-1,3,4-oxadiazol-2-yl)-1H-pyrazolo[3,4-b]pyridin-4-amine |
| 11 | 1-Ethyl-N-isobutyl-5-(5-isopropyl-1,3,4-oxadiazol-2-yl)-1H-pyrazolo[3,4-b]pyridin-4-amine |
| 12 | 1-Ethyl-N-isobutyl-5-(5-methyl-1,3,4-oxadiazol-2-yl)-1H-pyrazolo[3,4-b]pyridin-4-amine |
| 13 | N-Cyclohexyl-1-ethyl-5-(5-methyl-1,3,4-oxadiazol-2-yl)-1H-pyrazolo[3,4-b]pyridin-4-amine |
| 14 | 1-Ethyl-5-(5-methyl-1,3,4-oxadiazol-2-yl)-N-tetrahydro-2H-pyran-4-yl-1H-pyrazolo[3,4-b]pyridin-4-amine<br>also named: 1-Ethyl-5-(5-methyl-1,3,4-oxadiazol-2-yl)-N-(tetrahydro-2H-pyran-4-yl)-1H-pyrazolo[3,4-b]pyridin-4-amine |
| 15 | N-[(1R)-1,2-dimethylpropyl]-1-ethyl-5-(5-methyl-1,3,4-oxadiazol-2-yl)-1H-pyrazolo[3,4-b]pyridin-4-amine |
| 16 | N-[(1S)-1,2-dimethylpropyl]-1-ethyl-5-(5-methyl-1,3,4-oxadiazol-2-yl)-1H-pyrazolo[3,4-b]pyridin-4-amine |
| 17 | 5-(5-Tert-butyl-1,3,4-oxadiazol-2-yl)-1-ethyl-N-tetrahydro-2H-pyran-4-yl-1H-pyrazolo[3,4-b]pyridin-4-amine<br>also named: 5-[5-(1,1-Dimethylethyl)-1,3,4-oxadiazol-2-yl]-1-ethyl-N-(tetrahydro-2H-pyran-4-yl)-1H-pyrazolo[3,4-b]pyridin-4-amine |
| 18 | 5-(5-Tert-butyl-1,3,4-oxadiazol-2-yl)-N-cyclohexyl-1-ethyl-1H-pyrazolo[3,4-b]pyridin-4-amine |
| 19 | 5-(5-Tert-butyl-1,3,4-oxadiazol-2-yl)-N-cyclopentyl-1-ethyl-1H-pyrazolo[3,4-b]pyridin-4-amine |
| 20 | 5-(5-Tert-butyl-1,3,4-oxadiazol-2-yl)-1-ethyl-N-isobutyl-1H-pyrazolo[3,4-b]pyridin-4-amine |
| 21 | 5-(5-Tert-butyl-1,3,4-oxadiazol-2-yl)-N-[(1S)-1,2-dimethylpropyl]-1-ethyl-1H-pyrazolo[3,4-b]pyridin-4-amine |
| 22 | 5-(5-Tert-butyl-1,3,4-oxadiazol-2-yl)-N-[(1R)-1,2-dimethylpropyl]-1-ethyl-1H-pyrazolo[3,4-b]pyridin-4-amine |
| 23 | 1-Ethyl-5-{5-[(methylsulfonyl)methyl]-1,3,4-oxadiazol-2-yl}-N-tetrahydro-2H-pyran-4-yl-1H-pyrazolo[3,4-b]pyridin-4-amine |
| 24 | N-Cyclohexyl-1-ethyl-5-{5-[(methylsulfonyl)methyl]-1,3,4-oxadiazol-2-yl}-1H-pyrazolo[3,4-b]pyridin-4-amine |
| 25 | 1-Ethyl-N-isobutyl-5-{5-[(methylsulfonyl)methyl]-1,3,4-oxadiazol-2-yl}-1H-pyrazolo[3,4-b]pyridin-4-amine |
| 26 | N-[(1S)-1,2-dimethylpropyl]-1-ethyl-5-{5-[(methylsulfonyl)methyl]-1,3,4-oxadiazol-2-yl}-1H-pyrazolo[3,4-b]pyridin-4-amine |
| 27 | N-[(1R)-1,2-dimethylpropyl]-1-ethyl-5-{5-[(methylsulfonyl)methyl]-1,3,4-oxadiazol-2-yl}-1H-pyrazolo[3,4-b]pyridin-4-amine |
| 28 | 1-Ethyl-5-(3-methyl-1,2,4-oxadiazol-5-yl)-N-tetrahydro-2H-pyran-4-yl-1H-pyrazolo[3,4-b]pyridin-4-amine |
| 29 | 1-Ethyl-5-[3-(methoxymethyl)-1,2,4-oxadiazol-5-yl]-N-tetrahydro-2H-pyran-4-yl-1H-pyrazolo[3,4-b]pyridin-4-amine |
| 30 | 5-{3-[(Dimethylamino)methyl]-1,2,4-oxadiazol-5-yl}-1-ethyl-N-tetrahydro-2H-pyran-4-yl-1H-pyrazolo[3,4-b]pyridin-4-amine |
| 31 | 1-Ethyl-5-[3-(morpholin-4-ylmethyl)-1,2,4-oxadiazol-5-yl]-N-tetrahydro-2H-pyran-4-yl-1H-pyrazolo[3,4-b]pyridin-4-amine |
| 32 | 5-(5-Cyclopropyl-1,3,4-oxadiazol-2-yl)-1-ethyl-N-tetrahydro-2H-pyran-4-yl-1H-pyrazolo[3,4-b]pyridin-4-amine |
| 33 | N-(1-Acetylpiperidin-4-yl)-1-ethyl-5-(5-methyl-1,3,4-oxadiazol-2-yl)-1H-pyrazolo[3,4-b]pyridin-4-amine |
| 34 | 1-Ethyl-5-[5-(3-methyloxetan-3-yl)-1,3,4-oxadiazol-2-yl]-N-tetrahydro-2H-pyran-4-yl-1H-pyrazolo[3,4-b]pyridin-4-amine |
| 35 | 1-Ethyl-5-{5-[(4-methylpiperazin-1-yl)methyl]-1,3,4-oxadiazol-2-yl}-N-tetrahydro-2H-pyran-4-yl-1H-pyrazolo[3,4-b]pyridin-4-amine<br>also named: 1-Ethyl-5-{5-[(4-methyl-1-piperazinyl)methyl]-1,3,4-oxadiazol-2-yl}-N-(tetrahydro-2H-pyran-4-yl)-1H-pyrazolo[3,4-b]pyridin-4-amine |
| 36 | 5-[1-Ethyl-4-(tetrahydro-2H-pyran-4-ylamino)-1H-pyrazolo[3,4-b]pyridin-5-yl]-N-isopropyl-1,3,4-oxadiazole-2-carboxamide |
| 37 | 4-{5-[1-Ethyl-4-(tetrahydro-2H-pyran-4-ylamino)-1H-pyrazolo[3,4-b]pyridin-5-yl]-1,3,4-oxadiazol-2-yl}-1-methylpyrrolidin-2-one |

-continued

Table of Examples

| Example Number | Name |
|---|---|
| 38 | 1-Ethyl-N-tetrahydro-2H-pyran-4-yl-5-(5-tetrahydro-2H-pyran-4-yl-1,3,4-oxadiazol-2-yl)-1H-pyrazolo[3,4-b]pyridin-4-amine<br>also named: 1-Ethyl-N-(tetrahydro-2H-pyran-4-yl)-5-[5-(tetrahydro-2H-pyran-4-yl)-1,3,4-oxadiazol-2-yl]-1H-pyrazolo[3,4-b]pyridin-4-amine |
| 39 | 1-Ethyl-5-[5-(morpholin-4-ylmethyl)-1,3,4-oxadiazol-2-yl]-N-tetrahydro-2H-pyran-4-yl-1H-pyrazolo[3,4-b]pyridin-4-amine<br>also named: 1-Ethyl-5-[5-(morpholin-4-ylmethyl)-1,3,4-oxadiazol-2-yl]-N-(tetrahydro-2H-pyran-4-yl)-1H-pyrazolo[3,4-b]pyridin-4-amine |
| 40 | 5-[5-(Tert-butoxymethyl)-1,3,4-oxadiazol-2-yl]-1-ethyl-N-tetrahydro-2H-pyran-4-yl-1H-pyrazolo[3,4-b]pyridin-4-amine |
| 40A | Methyl 2-[1-ethyl-4-(tetrahydro-2H-pyran-4-ylamino)-1H-pyrazolo[3,4-b]pyridin-5-yl]-4,5-dihydro-1,3-oxazole-4-carboxylate |
| 41 | Methyl 2-[1-ethyl-4-(tetrahydro-2H-pyran-4-ylamino)-1H-pyrazolo[3,4-b]pyridin-5-yl]-1,3-oxazole-4-carboxylate |
| 42 | 1-Ethyl-5-(4-methyl-4,5-dihydro-1,3-oxazol-2-yl)-N-(tetrahydro-2H-pyran-4-yl)-1H-pyrazolo[3,4-b]pyridin-4-amine |
| 43 | 1-(n-Propyl)-5-(5-methyl-1,3,4-oxadiazol-2-yl)-N-(tetrahydro-2H-pyran-4-yl)-1H-pyrazolo[3,4-b]pyridin-4-amine |
| 44 | 1-Ethyl-5-[5-(tetrahydrofuran-2-yl)-1,3,4-oxadiazol-2-yl]-N-(tetrahydro-2H-pyran-4-yl)-1H-pyrazolo[3,4-b]pyridin-4-amine |
| 45 | 1-Ethyl-5-[5-(dimethylamino)-1,3,4-oxadiazol-2-yl]-N-(tetrahydro-2H-pyran-4-yl)-1H-pyrazolo[3,4-b]pyridin-4-amine |
| 46 | 1-Ethyl-5-(5-methyl-1,2,4-triazol-3-yl)-N-(tetrahydro-2H-pyran-4-yl)-1H-pyrazolo[3,4-b]pyridin-4-amine |
| 47 | N-(1-Acetylpiperidin-4-yl)-1-ethyl-5-(3-methyl-1,2,4-oxadiazol-5-yl)-1H-pyrazolo[3,4-b]pyridin-4-amine |
| 48 | N-(1-Acetylpiperidin-4-yl)-1-ethyl-5-[3-(morpholin-4-ylmethyl)-1,2,4-oxadiazol-5-yl]-1H-pyrazolo[3,4-b]pyridin-4-amine |
| 49 | 1-Ethyl-5-[(4R)-4-phenyl-4,5-dihydro-1,3-oxazol-2-yl]-N-(tetrahydro-2H-pyran-4-yl)-1H-pyrazolo[3,4-b]pyridin-4-amine |
| 50 | 1-Ethyl-5-[(4S)-4-phenyl-4,5-dihydro-1,3-oxazol-2-yl]-N-(tetrahydro-2H-pyran-4-yl)-1H-pyrazolo[3,4-b]pyridin-4-amine |
| 51 | 1-Ethyl-5-[(4S)-4-(phenylmethyl)-4,5-dihydro-1,3-oxazol-2-yl]-N-(tetrahydro-2H-pyran-4-yl)-1H-pyrazolo[3,4-b]pyridin-4-amine |
| 52 | 1-Ethyl-5-[(4R)-4-(phenylmethyl)-4,5-dihydro-1,3-oxazol-2-yl]-N-(tetrahydro-2H-pyran-4-yl)-1H-pyrazolo[3,4-b]pyridin-4-amine |
| 53 | 1-Ethyl-5-[(4S,5R)-5-methyl-4-phenyl-4,5-dihydro-1,3-oxazol-2-yl]-N-(tetrahydro-2H-pyran-4-yl)-1H-pyrazolo[3,4-b]pyridin-4-amine |
| 54 | 1-Ethyl-5-[(5R)-5-phenyl-4,5-dihydro-1,3-oxazol-2-yl]-N-(tetrahydro-2H-pyran-4-yl)-1H-pyrazolo[3,4-b]pyridin-4-amine |
| 55 | 1-Ethyl-5-[(5S)-5-phenyl-4,5-dihydro-1,3-oxazol-2-yl]-N-(tetrahydro-2H-pyran-4-yl)-1H-pyrazolo[3,4-b]pyridin-4-amine |
| 56 | 5-(4,4-Dimethyl-4,5-dihydro-1,3-oxazol-2-yl)-1-ethyl-N-(tetrahydro-2H-pyran-4-yl)-1H-pyrazolo[3,4-b]pyridin-4-amine |
| 57 | 2-[1-Ethyl-4-(tetrahydro-2H-pyran-4-ylamino)-1H-pyrazolo[3,4-b]pyridin-5-yl]-1,3-oxazole-4-carboxylic acid |
| 58 | 2-[1-Ethyl-4-(tetrahydro-2H-pyran-4-ylamino)-1H-pyrazolo[3,4-b]pyridin-5-yl]-N-(1-methylethyl)-1,3-oxazole-4-carboxamide |
| 59 | 1-Ethyl-5-[4-(4-morpholinylcarbonyl)-1,3-oxazol-2-yl]-N-(tetrahydro-2H-pyran-4-yl)-1H-pyrazolo[3,4-b]pyridin-4-amine |
| 60 | 1-Ethyl-N-methyl-5-(5-methyl-1,3,4-oxadiazol-2-yl)-N-(tetrahydro-2H-pyran-4-yl)-1H-pyrazolo[3,4-b]pyridin-4-amine |
| 61 | trans-4-{[1-Ethyl-5-(5-methyl-1,3,4-oxadiazol-2-yl)-1H-pyrazolo[3,4-b]pyridin-4-yl]amino}cyclohexanol |
| 62 | 1-Ethyl-5-(5-methyl-1,3,4-oxadiazol-2-yl)-N-(tetrahydro-2H-pyran-3-yl)-1H-pyrazolo[3,4-b]pyridin-4-amine |
| 63 | 4-{[1-Ethyl-5-(5-methyl-1,3,4-oxadiazol-2-yl)-1H-pyrazolo[3,4-b]pyridin-4-yl]amino}cyclohexanone |
| 64 | 1-Ethyl-5-(5-methyl-1,3,4-oxadiazol-2-yl)-N-n-propyl-N-(tetrahydro-2H-pyran-4-yl)-1H-pyrazolo[3,4-b]pyridin-4-amine |
| 65 | 5-[5-(1,1-Dimethylethyl)-1,3,4-oxadiazol-2-yl]-1-ethyl-6-methyl-N-(tetrahydro-2H-pyran-4-yl)-1H-pyrazolo[3,4-b]pyridin-4-amine |
| 66 | 1-Ethyl-6-methyl-N-(tetrahydro-2H-pyran-4-yl)-5-[5-(tetrahydro-2H-pyran-4-yl)-1,3,4-oxadiazol-2-yl]-1H-pyrazolo[3,4-b]pyridin-4-amine |
| 67 | 5-(5-Cyclobutyl-1,3,4-oxadiazol-2-yl)-1-ethyl-N-(tetrahydro-2H-pyran-4-yl)-1H-pyrazolo[3,4-b]pyridin-4-amine |
| 68 | 5-{5-[1-Ethyl-4-(tetrahydro-2H-pyran-4-ylamino)-1H-pyrazolo[3,4-b]pyridin-5-yl]-1,3,4-oxadiazol-2-yl}-2-pyrrolidinone |
| 69 | N-({5-[1-Ethyl-4-(tetrahydro-2H-pyran-4-ylamino)-1H-pyrazolo[3,4-b]pyridin-5-yl]-1,3,4-oxadiazol-2-yl}methyl)acetamide |
| 70 | 1-Ethyl-5-[5-(1-methyl-2-piperidinyl)-1,3,4-oxadiazol-2-yl]-N-(tetrahydro-2H-pyran-4-yl)-1H-pyrazolo[3,4-b]pyridin-4-amine |
| 71 | 1-Ethyl-5-{5-[(4-methyl-1,2,5-oxadiazol-3-yl)methyl]-1,3,4-oxadiazol-2-yl}-N-(tetrahydro-2H-pyran-4-yl)-1H-pyrazolo[3,4-b]pyridin-4-amine |

-continued

Table of Examples

| Example Number | Name |
|---|---|
| 72 | 3-{5-[1-Ethyl-4-(tetrahydro-2H-pyran-4-ylamino)-1H-pyrazolo[3,4-b]pyridin-5-yl]-1,3,4-oxadiazol-2-yl}cyclopentanone |
| 73 | 1-Ethyl-5-[5-(tetrahydro-3-furanyl)-1,3,4-oxadiazol-2-yl]-N-(tetrahydro-2H-pyran-4-yl)-1H-pyrazolo[3,4-b]pyridin-4-amine |
| 74 | (4S)-4-{5-[1-Ethyl-4-(tetrahydro-2H-pyran-4-ylamino)-1H-pyrazolo[3,4-b]pyridin-5-yl]-1,3,4-oxadiazol-2-yl}-1,3-thiazolidin-2-one |
| 75 | 5-[5-(2,2-Dimethylcyclopropyl)-1,3,4-oxadiazol-2-yl]-1-ethyl-N-(tetrahydro-2H-pyran-4-yl)-1H-pyrazolo[3,4-b]pyridin-4-amine |
| 76 | N-({5-[1-Ethyl-4-(tetrahydro-2H-pyran-4-ylamino)-1H-pyrazolo[3,4-b]pyridin-5-yl]-1,3,4-oxadiazol-2-yl}methyl)-N-methylacetamide |
| 77 | 1-Ethyl-N-(tetrahydro-2H-pyran-4-yl)-5-[5-(tetrahydro-2H-pyran-4-ylmethyl)-1,3,4-oxadiazol-2-yl]-1H-pyrazolo[3,4-b]pyridin-4-amine |
| 78 | 1-Ethyl-5-[5-(1-methylcyclobutyl)-1,3,4-oxadiazol-2-yl]-N-(tetrahydro-2H-pyran-4-yl)-1H-pyrazolo[3,4-b]pyridin-4-amine |
| 79 | 1-Ethyl-5-[5-(3-methyl-5-isoxazolyl)-1,3,4-oxadiazol-2-yl]-N-(tetrahydro-2H-pyran-4-yl)-1H-pyrazolo[3,4-b]pyridin-4-amine |
| 80 | 1-Ethyl-5-[5-(1-methyl-1H-pyrazol-5-yl)-1,3,4-oxadiazol-2-yl]-N-(tetrahydro-2H-pyran-4-yl)-1H-pyrazolo[3,4-b]pyridin-4-amine |
| 81 | 5-[5-(1-Acetyl-4-piperidinyl)-1,3,4-oxadiazol-2-yl]-1-ethyl-N-(tetrahydro-2H-pyran-4-yl)-1H-pyrazolo[3,4-b]pyridin-4-amine |
| 82 | 1-Ethyl-5-{3-[(4-methyl-1-piperazinyl)methyl]-1,2,4-oxadiazol-5-yl}-N-(tetrahydro-2H-pyran-4-yl)-1H-pyrazolo[3,4-b]pyridin-4-amine |
| 83 | 1-Ethyl-5-[3-(4-fluorophenyl)-1,2,4-oxadiazol-5-yl]-N-(tetrahydro-2H-pyran-4-yl)-1H-pyrazolo[3,4-b]pyridin-4-amine |
| 84 | 1-Ethyl-5-{3-[2-oxo-2-(1-pyrrolidinyl)ethyl]-1,2,4-oxadiazol-5-yl}-N-(tetrahydro-2H-pyran-4-yl)-1H-pyrazolo[3,4-b]pyridin-4-amine |
| 85 | 2-{5-[1-Ethyl-4-(tetrahydro-2H-pyran-4-ylamino)-1H-pyrazolo[3,4-b]pyridin-5-yl]-1,2,4-oxadiazol-3-yl}-N-phenylacetamide |
| 86 | 2-{5-[1-Ethyl-4-(tetrahydro-2H-pyran-4-ylamino)-1H-pyrazolo[3,4-b]pyridin-5-yl]-1,2,4-oxadiazol-3-yl}-N-(1-phenylethyl)acetamide |
| 87 | 1-Ethyl-5-{3-[2-oxo-2-(1-piperidinyl)ethyl]-1,2,4-oxadiazol-5-yl}-N-(tetrahydro-2H-pyran-4-yl)-1H-pyrazolo[3,4-b]pyridin-4-amine |
| 88 | 2-{5-[1-Ethyl-4-(tetrahydro-2H-pyran-4-ylamino)-1H-pyrazolo[3,4-b]pyridin-5-yl]-1,2,4-oxadiazol-3-yl}-N-(phenylmethyl)acetamide |
| 89 | 2-{5-[1-Ethyl-4-(tetrahydro-2H-pyran-4-ylamino)-1H-pyrazolo[3,4-b]pyridin-5-yl]-1,2,4-oxadiazol-3-yl}-N,N-dimethylacetamide |
| 90 | N-Ethyl-2-{5-[1-ethyl-4-(tetrahydro-2H-pyran-4-ylamino)-1H-pyrazolo[3,4-b]pyridin-5-yl]-1,2,4-oxadiazol-3-yl}acetamide |
| 92 | 1-Ethyl-5-{3-[1-(4-morpholinyl)ethyl]-1,2,4-oxadiazol-5-yl}-N-(tetrahydro-2H-pyran-4-yl)-1H-pyrazolo[3,4-b]pyridin-4-amine |
| 93 | 5-[3-(Cyclohexylmethyl)-1,2,4-oxadiazol-5-yl]-1-ethyl-N-(tetrahydro-2H-pyran-4-yl)-1H-pyrazolo[3,4-b]pyridin-4-amine |
| 95 | 1-Ethyl-5-{3-[2-oxo-2-(1-piperidinyl)ethyl]-1,2,4-oxadiazol-5-yl}-N-(tetrahydro-2H-pyran-4-yl)-1H-pyrazolo[3,4-b]pyridin-4-amine |
| 96 | 1-ethyl-5-{3-[2-(4-methyl-1-piperazinyl)-2-oxoethyl]-1,2,4-oxadiazol-5-yl}-N-(tetrahydro-2H-pyran-4-yl)-1H-pyrazolo[3,4-b]pyridin-4-amine |
| 97 | 1-Ethyl-N-(tetrahydro-2H-pyran-4-yl)-5-[5-(1H-1,2,3-triazol-1-ylmethyl)-1,3,4-oxadiazol-2-yl]-1H-pyrazolo[3,4-b]pyridin-4-amine |
| 98 | 5-{5-[(2,4-Dimethyl-1,3-thiazol-5-yl)methyl]-1,3,4-oxadiazol-2-yl}-1-ethyl-N-(tetrahydro-2H-pyran-4-yl)-1H-pyrazolo[3,4-b]pyridin-4-amine formate |
| 99 | 1-Ethyl-5-[5-(2-furanylmethyl)-1,3,4-oxadiazol-2-yl]-N-(tetrahydro-2H-pyran-4-yl)-1H-pyrazolo[3,4-b]pyridin-4-amine formate |
| 100 | 1-Ethyl-5-[5-(3-isoxazolylmethyl)-1,3,4-oxadiazol-2-yl]-N-(tetrahydro-2H-pyran-4-yl)-1H-pyrazolo[3,4-b]pyridin-4-amine formate |
| 103 | 1-ethyl-5-(5-{[4-(methyloxy)phenyl]methyl}-1,3,4-oxadiazol-2-yl)-N-(tetrahydro-2H-pyran-4-yl)-1H-pyrazolo[3,4-b]pyridin-4-amine trifluoroacetate |
| 104 | 1-Ethyl-N-(tetrahydro-2H-pyran-4-yl)-5-[5-(1H-tetrazol-1-ylmethyl)-1,3,4-oxadiazol-2-yl]-1H-pyrazolo[3,4-b]pyridin-4-amine formate |
| 105 | 1-Ethyl-5-[5-(5-isothiazolylmethyl)-1,3,4-oxadiazol-2-yl]-N-(tetrahydro-2H-pyran-4-yl)-1H-pyrazolo[3,4-b]pyridin-4-amine |
| 106 | 1-Ethyl-5-{5-[(3-methyl-5-isoxazolyl)methyl]-1,3,4-oxadiazol-2-yl}-N-(tetrahydro-2H-pyran-4-yl)-1H-pyrazolo[3,4-b]pyridin-4-amine formate |
| 107 | 5-(5-{[4-(Dimethylamino)phenyl]methyl}-1,3,4-oxadiazol-2-yl)-1-ethyl-N-(tetrahydro-2H-pyran-4-yl)-1H-pyrazolo[3,4-b]pyridin-4-amine (1:1) |
| 108 | 1-Ethyl-5-{5-[(2-methyl-1,3-thiazol-4-yl)methyl]-1,3,4-oxadiazol-2-yl}-N-(tetrahydro-2H-pyran-4-yl)-1H-pyrazolo[3,4-b]pyridin-4-amine formate |
| 109 | 2-[1-({5-[1-ethyl-4-(tetrahydro-2H-pyran-4-ylamino)-1H-pyrazolo[3,4-b]pyridin-5-yl]-1,3,4-oxadiazol-2-yl}methyl)cyclopentyl]-N-methylacetamide trifluoroacetate |

-continued

Table of Examples

| Example Number | Name |
|---|---|
| 111 | N-({5-[1-Ethyl-4-(tetrahydro-2H-pyran-4-ylamino)-1H-pyrazolo[3,4-b]pyridin-5-yl]-1,3,4-oxadiazol-2-yl}methyl)cyclopropanecarboxamide |
| 112 | 1-Ethyl-5-{5-[(5-methyl-3-isoxazolyl)methyl]-1,3,4-oxadiazol-2-yl}-N-(tetrahydro-2H-pyran-4-yl)-1H-pyrazolo[3,4-b]pyridin-4-amine formate |
| 113 | 1-Ethyl-5-{5-[(5-methyl-3-isoxazolyl)methyl]-1,3,4-oxadiazol-2-yl}-N-(tetrahydro-2H-pyran-4-yl)-1H-pyrazolo[3,4-b]pyridin-4-amine |
| 114 | 1-Ethyl-5-{5-[2-(4-methyl-1,3-thiazol-5-yl)ethyl]-1,3,4-oxadiazol-2-yl}-N-(tetrahydro-2H-pyran-4-yl)-1H-pyrazolo[3,4-b]pyridin-4-amine formate |
| 117 | 5-{5-[(3,5-Dimethyl-4-isoxazolyl)methyl]-1,3,4-oxadiazol-2-yl}-1-ethyl-N-(tetrahydro-2H-pyran-4-yl)-1H-pyrazolo[3,4-b]pyridin-4-amine trifluoroacetate |
| 118 | N-(1-{5-[1-Ethyl-4-(tetrahydro-2H-pyran-4-ylamino)-1H-pyrazolo[3,4-b]pyridin-5-yl]-1,3,4-oxadiazol-2-yl}ethyl)acetamide |
| 119 | 5-{5-[(1-acetyl-4-piperidinyl)methyl]-1,3,4-oxadiazol-2-yl}-1-ethyl-N-(tetrahydro-2H-pyran-4-yl)-1H-pyrazolo[3,4-b]pyridin-4-amine trifluoroacetate |
| 120 | 1-Ethyl-5-{5-[(4-methylphenyl)methyl]-1,3,4-oxadiazol-2-yl}-N-(tetrahydro-2H-pyran-4-yl)-1H-pyrazolo[3,4-b]pyridin-4-amine |
| 121 | 1-Ethyl-5-[5-(4-methylphenyl)-1,3,4-oxadiazol-2-yl]-N-(tetrahydro-2H-pyran-4-yl)-1H-pyrazolo[3,4-b]pyridin-4-amine |
| 122 | 5-[5-(3,4-Dimethylphenyl)-1,3,4-oxadiazol-2-yl]-1-ethyl-N-(tetrahydro-2H-pyran-4-yl)-1H-pyrazolo[3,4-b]pyridin-4-amine |
| 123 | 5-[5-(2,4-Dimethylphenyl)-1,3,4-oxadiazol-2-yl]-1-ethyl-N-(tetrahydro-2H-pyran-4-yl)-1H-pyrazolo[3,4-b]pyridin-4-amine |
| 125 | 5-{5-[(4-Bromophenyl)methyl]-1,3,4-oxadiazol-2-yl}-1-ethyl-N-(tetrahydro-2H-pyran-4-yl)-1H-pyrazolo[3,4-b]pyridin-4-amine |
| 126 | 2-[1-Ethyl-4-(tetrahydro-2H-pyran-4-ylamino)-1H-pyrazolo[3,4-b]pyridin-5-yl]-N-(phenylmethyl)-1,3-oxazole-4-carboxamide |
| 127 | 2-[1-Ethyl-4-(tetrahydro-2H-pyran-4-ylamino)-1H-pyrazolo[3,4-b]pyridin-5-yl]-N-{[4-(methyloxy)phenyl]methyl}-1,3-oxazole-4-carboxamide |
| 128 | 2-[1-Ethyl-4-(tetrahydro-2H-pyran-4-ylamino)-1H-pyrazolo[3,4-b]pyridin-5-yl]-N-[(2-methylphenyl)methyl]-1,3-oxazole-4-carboxamide |
| 129 | 2-[1-Ethyl-4-(tetrahydro-2H-pyran-4-ylamino)-1H-pyrazolo[3,4-b]pyridin-5-yl]-N-[(4-methylphenyl)methyl]-1,3-oxazole-4-carboxamide |
| 130 | 2-[1-Ethyl-4-(tetrahydro-2H-pyran-4-ylamino)-1H-pyrazolo[3,4-b]pyridin-5-yl]-N-[(3-methylphenyl)methyl]-1,3-oxazole-4-carboxamide |
| 131 | N-[(4-Chlorophenyl)methyl]-2-[1-ethyl-4-(tetrahydro-2H-pyran-4-ylamino)-1H-pyrazolo[3,4-b]pyridin-5-yl]-1,3-oxazole-4-carboxamide |
| 132 | N-[(2,3-Dimethylphenyl)methyl]-2-[1-ethyl-4-(tetrahydro-2H-pyran-4-ylamino)-1H-pyrazolo[3,4-b]pyridin-5-yl]-1,3-oxazole-4-carboxamide |
| 133 | N-[(3,5-Dimethylphenyl)methyl]-2-[1-ethyl-4-(tetrahydro-2H-pyran-4-ylamino)-1H-pyrazolo[3,4-b]pyridin-5-yl]-1,3-oxazole-4-carboxamide |
| 134 | N-[(3,4-Dimethylphenyl)methyl]-2-[1-ethyl-4-(tetrahydro-2H-pyran-4-ylamino)-1H-pyrazolo[3,4-b]pyridin-5-yl]-1,3-oxazole-4-carboxamide |
| 135 | 2-[1-Ethyl-4-(tetrahydro-2H-pyran-4-ylamino)-1H-pyrazolo[3,4-b]pyridin-5-yl]-N-(1-phenylethyl)-1,3-oxazole-4-carboxamide |
| 136 | 2-[1-Ethyl-4-(tetrahydro-2H-pyran-4-ylamino)-1H-pyrazolo[3,4-b]pyridin-5-yl]-N-{(1R)-1-[4-(methyloxy)phenyl]ethyl}-1,3-oxazole-4-carboxamide |
| 137 | 2-[1-Ethyl-4-(tetrahydro-2H-pyran-4-ylamino)-1H-pyrazolo[3,4-b]pyridin-5-yl]-N-[(1R)-1-phenylpropyl]-1,3-oxazole-4-carboxamide |
| 138 | 2-[1-Ethyl-4-(tetrahydro-2H-pyran-4-ylamino)-1H-pyrazolo[3,4-b]pyridin-5-yl]-N-(4-methylphenyl)-1,3-oxazole-4-carboxamide |
| 139 | 2-[1-Ethyl-4-(tetrahydro-2H-pyran-4-ylamino)-1H-pyrazolo[3,4-b]pyridin-5-yl]-N-({4-[(methylsulfonyl)amino]phenyl}methyl)-1,3-oxazole-4-carboxamide |
| 140 | 2-[1-Ethyl-4-(tetrahydro-2H-pyran-4-ylamino)-1H-pyrazolo[3,4-b]pyridin-5-yl]-N-{[4-(methylsulfonyl)phenyl]methyl}-1,3-oxazole-4-carboxamide |
| 141 | N-(1-Acetyl-4-piperidinyl)-2-[1-ethyl-4-(tetrahydro-2H-pyran-4-ylamino)-1H-pyrazolo[3,4-b]pyridin-5-yl]-1,3-oxazole-4-carboxamide |
| 142 | 2-[1-Ethyl-4-(tetrahydro-2H-pyran-4-ylamino)-1H-pyrazolo[3,4-b]pyridin-5-yl]-N-(tetrahydro-2H-pyran-4-yl)-1,3-oxazole-4-carboxamide |
| 143 | 2-[1-Ethyl-4-(tetrahydro-2H-pyran-4-ylamino)-1H-pyrazolo[3,4-b]pyridin-5-yl]-N-(tetrahydro-2-furanylmethyl)-1,3-oxazole-4-carboxamide |

Table of Examples

| Example Number | Name |
|---|---|
| 144 | 2-[1-Ethyl-4-(tetrahydro-2H-pyran-4-ylamino)-1H-pyrazolo[3,4-b]pyridin-5-yl]-N-[2-(4-methyl-1-piperazinyl)ethyl]-1,3-oxazole-4-carboxamide |
| 145 | N-[1-(Aminomethyl)cyclohexyl]-2-[1-ethyl-4-(tetrahydro-2H-pyran-4-ylamino)-1H-pyrazolo[3,4-b]pyridin-5-yl]-N-methyl-1,3-oxazole-4-carboxamide |
| 146 | N-(2,6-Dimethylphenyl)-2-[1-ethyl-4-(tetrahydro-2H-pyran-4-ylamino)-1H-pyrazolo[3,4-b]pyridin-5-yl]-1,3-oxazole-4-carboxamide |
| 147 | N-{[4-(Aminocarbonyl)phenyl]methyl}-2-[1-ethyl-4-(tetrahydro-2H-pyran-4-ylamino)-1H-pyrazolo[3,4-b]pyridin-5-yl]-1,3-oxazole-4-carboxamide |
| 148 | 2-{5-[1-Ethyl-4-(tetrahydro-2H-pyran-4-ylamino)-1H-pyrazolo[3,4-b]pyridin-5-yl]-1,2,4-oxadiazol-3-yl}-N-(tetrahydro-2H-pyran-4-yl)acetamide |
| 149 | 5-{3-[2-(2,6-Dimethyl-4-morpholinyl)-2-oxoethyl]-1,2,4-oxadiazol-5-yl}-1-ethyl-N-(tetrahydro-2H-pyran-4-yl)-1H-pyrazolo[3,4-b]pyridin-4-amine |
| 150 | 1-Ethyl-5-{3-[2-(4-methyl-1-piperidinyl)-2-oxoethyl]-1,2,4-oxadiazol-5-yl}-N-(tetrahydro-2H-pyran-4-yl)-1H-pyrazolo[3,4-b]pyridin-4-amine |
| 152 | 2-{5-[1-Ethyl-4-(tetrahydro-2H-pyran-4-ylamino)-1H-pyrazolo[3,4-b]pyridin-5-yl]-1,2,4-oxadiazol-3-yl}-N-[1-methyl-2-(methyloxy)ethyl]acetamide |
| 153 | 5-{3-[2-(3,5-Dimethyl-1-piperidinyl)-2-oxoethyl]-1,2,4-oxadiazol-5-yl}-1-ethyl-N-(tetrahydro-2H-pyran-4-yl)-1H-pyrazolo[3,4-b]pyridin-4-amine |
| 154 | 1-Ethyl-5-{3-[2-(3-methyl-1-piperidinyl)-2-oxoethyl]-1,2,4-oxadiazol-5-yl}-N-(tetrahydro-2H-pyran-4-yl)-1H-pyrazolo[3,4-b]pyridin-4-amine |
| 155 | 2-{5-[1-Ethyl-4-(tetrahydro-2H-pyran-4-ylamino)-1H-pyrazolo[3,4-b]pyridin-5-yl]-1,2,4-oxadiazol-3-yl}-N-3-pyridinylacetamide |
| 157 | 6-{5-[1-Ethyl-4-(tetrahydro-2H-pyran-4-ylamino)-1H-pyrazolo[3,4-b]pyridin-5-yl]-1,3,4-oxadiazol-2-yl}-2-piperidinone |
| 158 | 1-Ethyl-5-{5-[(3-methyl-1H-1,2,4-triazol-5-yl)methyl]-1,3,4-oxadiazol-2-yl}-N-(tetrahydro-2H-pyran-4-yl)-1H-pyrazolo[3,4-b]pyridin-4-amine |
| 159 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)acetamide |
| 160 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)benzamide |
| 161 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-phenylacetamide |
| 162 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-methylpropanamide |
| 163 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)-3-methylbutanamide |
| 164 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)cyclohexanecarboxamide |
| 165 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-furancarboxamide |
| 166 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)methanesulfonamide |
| 167 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)benzenesulfonamide |
| 168 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)-1-phenylmethanesulfonamide |
| 169 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-propanesulfonamide |
| 170 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)-1-propanesulfonamide |
| 171 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)cyclopropanesulfonamide |
| 172 | N-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-thiophenesulfonamide |
| 173 | 1-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-pyrrolidinone |
| 174 | 1-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-piperidinone |
| 175 | 5-{3-[(1-Acetyl-4-piperidinyl)methyl]-1,2,4-oxadiazol-5-yl}-1-ethyl-N-(tetrahydro-2H-pyran-4-yl)-1H-pyrazolo[3,4-b]pyridin-4-amine |
| 176 | 1-Ethyl-5-(3-{[1-(3-methylbutanoyl)-4-piperidinyl]methyl}-1,2,4-oxadiazol-5-yl)-N-(tetrahydro-2H-pyran-4-yl)-1H-pyrazolo[3,4-b]pyridin-4-amine |
| 177 | 1-Ethyl-5-(3-{[1-(methylsulfonyl)-4-piperidinyl]methyl}-1,2,4-oxadiazol-5-yl)-N-(tetrahydro-2H-pyran-4-yl)-1H-pyrazolo[3,4-b]pyridin-4-amine |

Table of Examples

| Example Number | Name |
|---|---|
| 178 | 1-Ethyl-5-{3-[1-(phenylsulfonyl)cyclopropyl]-1,2,4-oxadiazol-5-yl}-N-(tetrahydro-2H-pyran-4-yl)-1H-pyrazolo[3,4-b]pyridin-4-amine |
| 179 | 1-Ethyl-5-[3-(phenylmethyl)-1,2,4-oxadiazol-5-yl]-N-(tetrahydro-2H-pyran-4-yl)-1H-pyrazolo[3,4-b]pyridin-4-amine |
| 180 | 1-Ethyl-5-[3-(1-phenylethyl)-1,2,4-oxadiazol-5-yl]-N-(tetrahydro-2H-pyran-4-yl)-1H-pyrazolo[3,4-b]pyridin-4-amine |
| 181 | 1-Ethyl-5-(3-{[4-(methyloxy)phenyl]methyl}-1,2,4-oxadiazol-5-yl)-N-(tetrahydro-2H-pyran-4-yl)-1H-pyrazolo[3,4-b]pyridin-4-amine |
| 182 | 5-(3-{[4-(Dimethylamino)phenyl]methyl}-1,2,4-oxadiazol-5-yl)-1-ethyl-N-(tetrahydro-2H-pyran-4-yl)-1H-pyrazolo[3,4-b]pyridin-4-amine |
| 183 | 5-(3-{[3-(Dimethylamino)phenyl]methyl}-1,2,4-oxadiazol-5-yl)-1-ethyl-N-(tetrahydro-2H-pyran-4-yl)-1H-pyrazolo[3,4-b]pyridin-4-amine |
| 184 | 5-(3-{[4-(Dimethylamino)phenyl]methyl}-1,2,4-oxadiazol-5-yl)-1-ethyl-N-(tetrahydro-2H-pyran-4-yl)-1H-pyrazolo[3,4-b]pyridin-4-amine |
| 185 | 1-Ethyl-5-{3-[(phenyloxy)methyl]-1,2,4-oxadiazol-5-yl}-N-(tetrahydro-2H-pyran-4-yl)-1H-pyrazolo[3,4-b]pyridin-4-amine |
| 186 | 1-ethyl-N-(tetrahydro-2H-pyran-4-yl)-5-[3-(5,6,7,8-tetrahydro[1,2,4]triazolo[4,3-a]pyridin-3-ylmethyl)-1,2,4-oxadiazol-5-yl]-1H-pyrazolo[3,4-b]pyridin-4-amine |
| 187 | 1-Ethyl-5-{3-[(4-phenyl-1-piperazinyl)methyl]-1,2,4-oxadiazol-5-yl}-N-(tetrahydro-2H-pyran-4-yl)-1H-pyrazolo[3,4-b]pyridin-4-amine |
| 188 | 1-Ethyl-5-(5-ethyl-1,2,4-oxadiazol-3-yl)-N-(tetrahydro-2H-pyran-4-yl)-1H-pyrazolo[3,4-b]pyridin-4-amine |
| 189 | 5-(5-{[4-(Dimethylamino)phenyl]methyl}-1,2,4-oxadiazol-3-yl)-1-ethyl-N-(tetrahydro-2H-pyran-4-yl)-1H-pyrazolo[3,4-b]pyridin-4-amine |
| 190 | 1-Ethyl-5-(5-{[4-(methyloxy)phenyl]methyl}-1,2,4-oxadiazol-3-yl)-N-(tetrahydro-2H-pyran-4-yl)-1H-pyrazolo[3,4-b]pyridin-4-amine |
| 191 | 5-(3,8-Dioxa-1-azaspiro[4.5]dec-1-en-2-yl)-1-ethyl-N-(tetrahydro-2H-pyran-4-yl)-1H-pyrazolo[3,4-b]pyridin-4-amine |

Example 1

N-Cyclopentyl-1-ethyl-5-(5-methyl-1,3,4-oxadiazol-2-yl)-1H-pyrazolo[3,4-b]pyridin-4-amine

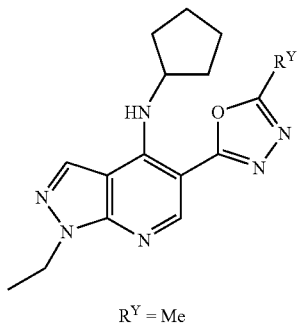

$R^Y$ = Me

Intermediate 4 (0.043 g) was dissolved in acetonitrile (2 ml) then treated with phosphorous oxychloride (0.101 g) and stirred under nitrogen and heated at 90° C. for 2 h. The mixture was concentrated in vacuo and the residue partitioned between DCM and saturated aqueous sodium bicarbonate solution. The organic layer was concentrated in vacuo and applied to an SPE cartridge (aminopropyl, 1 g), which was eluted with methanol. Concentration in vacuo afforded Example 1 (0.032 g). LCMS showed $MH^+$=313; $T_{RET}$=3.13 min.

Similarly prepared, for example without limitation using the same or similar number of moles of reagents and/or volumes of solvents, but with an extended reaction time (see table) was:

| | $R^Y$ | Starting material | Reaction time | $MH^+$ ion | $T_{RET}$ (min) |
|---|---|---|---|---|---|
| Example 2 | ~CH₂S(O)₂CH₃ | Intermediate 5 | 3 h | 391 | 2.88 |

Example 3

N-Cyclopentyl-1-ethyl-5-(5-isopropyl-1,3,4-oxadiazol-2-yl)-1H-pyrazolo[3,4-b]pyridin-4-amine

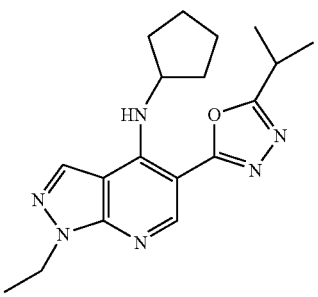

Intermediate 10 was dissolved in acetonitrile (2 ml) then treated with phosphorous oxychloride (0.101 g) and stirred under nitrogen at 90° C. for 3.5 h. The mixture was concentrated in vacuo and the residue partitioned between DCM and saturated aqueous sodium bicarbonate solution. The organic layer was concentrated in vacuo and the residue applied to a SPE cartridge (silica, 5 g), which was eluted with cyclohexane:Et$_2$O (1:2). Fractions containing desired material were combined and concentrated in vacuo to afford Example 3 (0.034 g). LCMS showed MH$^+$=341; T$_{RET}$=3.39 min.

Example 4

N-Cyclopentyl-1-ethyl-5(5-methyl-1,3,4-thiadiazol-2-yl)-1H-pyrazolo[3,4-b]pyridin-4-amine

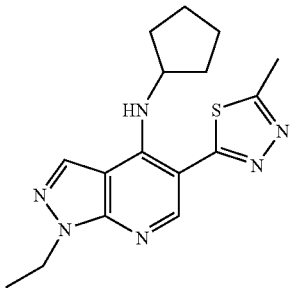

A solution of Intermediate 4 (0.09 g) in acetonitrile (5 ml) was stirred under nitrogen and treated with Lawesson's reagent (0.116 g). The mixture was heated at 65° C. for 16 h, then concentrated in vacuo. The residue was applied to an SPE cartridge (silica, 5 g) and eluted with a gradient of cyclohexane:Et$_2$O (1:2 then 1:3, 1:4, 1:5, 0:1). Fractions containing desired material were combined and concentrated in vacuo. Further purification was achieved using mass directed autoprep HPLC to afford Example 4 (0.002 g). LCMS showed MH$^+$=339; T$_{RET}$=3.23 min.

Example 5

N-Cyclopentyl-1-ethyl-5-{5-[(methylsulfonyl)methyl]-1,3,4-thiadiazol-2-yl}-1H-pyrazolo[3,4-b]pyridin-4-amine

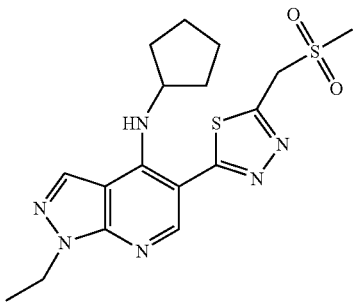

A solution of Intermediate 5 (0.07 g) in acetonitrile (3 ml) was stirred under nitrogen and treated with Lawesson's reagent (0.085 g). The mixture was heated at 65° C. for 136 h, then concentrated in vacuo. The residue was partitioned between DCM and water and the organic layer concentrated in vacuo. Further purification was achieved using mass directed autoprep HPLC to afford Example 5 (0.008 g). LCMS showed MH$^+$=407; T$_{RET}$=2.98 min.

Example 6

N-Cyclopentyl-1-ethyl-5-(5-isopropyl-1,3,4-thiadiazol-2-yl)-1H-pyrazolo[3,4-b]pyridin-4-amine

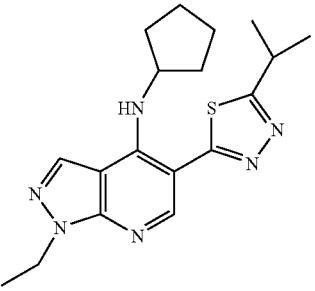

Intermediate 10 was dissolved in acetonitrile (5 ml) then treated with Lawesson's reagent (0.125 g) and heated under nitrogen at 65° C. for 66 h. Volatiles were removed in vacuo and the residue was purified by mass directed autoprep HPLC to afford Example 6. LCMS showed MH$^+$=357; T$_{RET}$=3.59 min.

Example 7

1-Ethyl-N-(4-fluorophenyl)-5-(3-methyl-1,2,4-oxadiazol-5-yl)-1H-pyrazolo[3,4-b]pyridin-4-amine

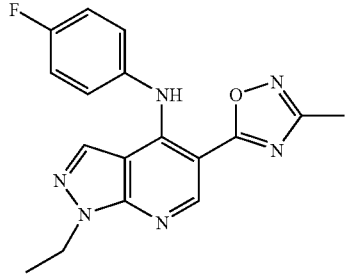

A solution of Intermediate 6 (0.04 g) in ethanol (1 ml) was stirred over powdered 4A molecular sieves (0.290 g) and treated with Intermediate 9 (0.045 g), followed by sodium ethoxide (0.020 g). The mixture was heated under reflux for 18 h, then cooled and filtered. Following concentration of the filtrate in vacuo, the residue was applied to an SPE cartridge (silica, 5 g) which was eluted with cyclohexane:Et$_2$O (1:1). Fractions containing desired material were combined and concentrated in vacuo to afford Example 7 (0.017 g). LCMS showed MH$^+$=339; T$_{RET}$=3.23 min.

Example 8

N-Cyclopentyl-5-(1,3-dimethyl-1H-1,2,4-triazol-5-yl)-1-ethyl-1H-pyrazolo[3,4-b]pyridin-4-amine

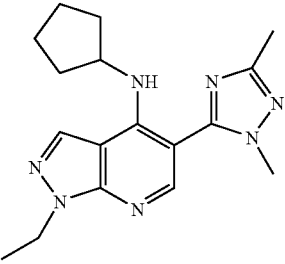

A solution of Intermediate 7 (0.06 g) in ethanol (2 ml) was treated with triethylamine (0.101 g), followed by methyl acetimidate hydrochloride (0.033 g) and the mixture heated under reflux (80° C.) for 42 h. Reaction was incomplete so a further portion of methyl acetimidate hydrochloride (0.033 g) was added and stirring continued under reflux for 6 days. The mixture was concentrated in vacuo and the residue partitioned between DCM and 2M aqueous HCl. The organic layer was concentrated in vacuo and purified by mass directed autoprep to afford Example 8 (0.003 g). LCMS showed MH$^+$=326; T$_{RET}$=2.66 min.

Example 9

1-Ethyl-5-(5-isopropyl-1,3,4-oxadiazol-2-yl)-N-tetrahydro-2H-pyran-4-yl-1H-pyrazolo[3,4-b]pyridin-4-amine

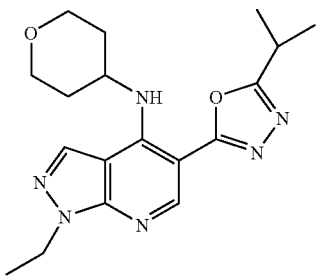

Intermediate 13 (0.016 g) was dissolved in anhydrous acetonitrile (1 ml). 4-Aminotetrahydropyran hydrochloride (Intermediate 21A, 0.008 g) was then added, followed by diisopropylethyl amine (0.05 ml) and the mixture was stirred under nitrogen at 75° C. for 19 h. A further portion of 4-aminotetrahydropyran (0.002 g) was added and stirring continued at 85° C. for 16 h. The mixture was concentrated in vacuo and partitioned between DCM and water. The organic phase was concentrated in vacuo and applied to an SPE cartridge (silica, 1 g), which was eluted sequentially with a gradient of EtOAc:cyclohexane (i) 1:8, (ii) 1:4, (iii) 1:2, (iv) 1:1 and (v) 1:0. Fractions containing desired material were combined and concentrated in vacuo to afford Example 9 (0.013 g). LCMS showed MH$^+$=357; T$_{RET}$=2.89 min.

Example 10

N-cyclohexyl-1-ethyl-5-(5-isopropyl-1,3,4-oxadiazol-2-yl)-1H-pyrazolo[3,4-b]pyridin-4-amine

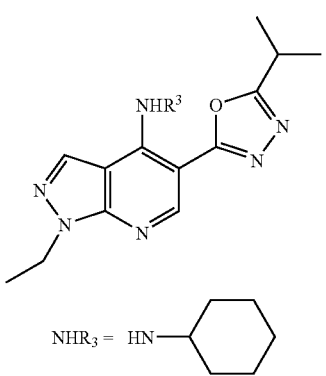

Intermediate 13 (0.016 g, 0.055 mmol) was dissolved in anhydrous acetonitrile (1 ml). Cyclohexyl amine (0.007 ml, 0.061 mmol) was then added, followed by diisopropylethyl amine (0.05 ml, 0.29 mmol) and the mixture was stirred under nitrogen at 75° C. for 16 h. The mixture was concentrated in vacuo and partitioned between DCM and water. The organic phase was concentrated in vacuo and applied to an SPE cartridge (silica, 1 g), which was eluted sequentially with a gradient of EtOAc:cyclohexane (i) 1:16, (ii) 1:8, (iii) 1:4, (iv) 1:2 and (v) 1:1. Fractions containing desired material were combined and concentrated in vacuo to afford Example 10 (0.015 g). LCMS showed MH$^+$=355; T$_{RET}$=3.59 min.

Similarly prepared using the same or similar number of moles of reagents and volumes of solvents was the following:

|  | NR$^3$R$^{3a}$ | Starting amine | MH$^+$ ion | T$_{RET}$(min) |
| --- | --- | --- | --- | --- |
| Example 11 | 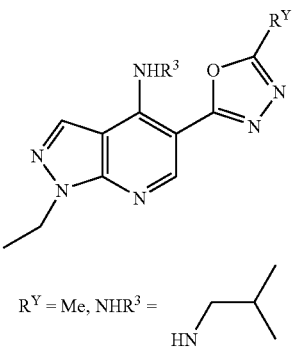 | Isobutyl amine | 329 | 3.40 |

Example 12

1-Ethyl-N-isobutyl-5-(5-methyl-1,3,4-oxadiazol-2-yl)-1H-pyrazolo[3,4-b]pyridin-4-amine Example 12

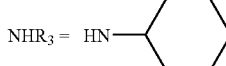

R$^Y$ = Me, NHR$^3$ =

Intermediate 12 (0.026 g, 0.1 mmol) was dissolved in ethanol (1.5 ml) and treated with a solution of isobutylamine (0.007 g, 0.1 mmol), also in ethanol (1 ml). The mixture was then treated with diisopropylethyl amine (0.075 ml, 0.4 mmol, 4 mole equivalents) and stirred at 75° C. for 16 h The mixture was concentrated in vacuo and applied to an SPE cartridge (silica, 0.5 g) which was eluted sequentially with (i) chloroform, (ii) Et$_2$O and (iii) methanol. Fractions containing desired material were combined and concentrated in vacuo to afford Example 12 (0.024 g). LCMS showed MH$^+$=301; T$_{RET}$=2.90 min Similarly prepared using the same or similar number of moles of reagents and volumes of solvents were the following:

| | R$^Y$ | NR$^3$R$^{3a}$ | Starting material | Amine reagent | MH$^+$ ion | T$_{RET}$(min) |
|---|---|---|---|---|---|---|
| Example 13 | Me | HN—cyclohexyl | Intermediate 12 | Cyclohexylamine | 327 | 3.12 |
| Example 14 | Me | HN—tetrahydropyran-4-yl | Intermediate 12 | 4-Amino tetrahydropyran | 329 | 2.49 |
| Example 15 | Me | (R)-3-methyl-2-butyl-HN | Intermediate 12 | (R)-(−)-3-methyl-2-butyl-amine | 315 | 3.00 |
| Example 16 | Me | (S)-3-methyl-2-butyl-HN | Intermediate 12 | (S)-(−)-3-methyl-2-butyl-amine | 315 | 3.00 |
| Example 17 | $^t$Bu | HN—tetrahydropyran-4-yl | Intermediate 14 | 4-Amino tetrahydropyran | 371 | 2.99 |
| Example 18 | $^t$Bu | HN—cyclohexyl | Intermediate 14 | Cyclohexylamine | 369 | 3.64 |
| Example 19 | $^t$Bu | HN—cyclopentyl | Intermediate 14 | Cyclopentylamine | 355 | 3.48 |
| Example 20 | $^t$Bu | HN—isobutyl | Intermediate 14 | Isobutylamine | 343 | 3.43 |
| Example 21 | $^t$Bu | (S)-3-methyl-2-butyl-HN | Intermediate 14 | (S)-(−)-3-methyl-2-butyl-amine | 357 | 3.53 |
| Example 22 | $^t$Bu | (R)-3-methyl-2-butyl-HN | Intermediate 14 | (R)-(−)-3-methyl-2-butyl-amine | 357 | 3.53 |
| Example 23 | CH$_2$SO$_2$Me | HN—tetrahydropyran-4-yl | Intermediate 15 | 4-Amino tetrahydropyran | 407 | 2.44 |
| Example 24 | CH$_2$SO$_2$Me | HN—cyclohexyl | Intermediate 15 | Cyclohexylamine | 405 | 3.00 |
| Example 25 | CH$_2$SO$_2$Me | HN—isobutyl | Intermediate 15 | Isobutylamine | 379 | 2.81 |
| Example 26 | CH$_2$SO$_2$Me | (S)-3-methyl-2-butyl-HN | Intermediate 15 | (S)-(−)-3-methyl-2-butyl-amine | 393 | 2.90 |

-continued

| | R$^Y$ | NR$^3$R$^{3a}$ | Starting material | Amine reagent | MH$^+$ ion | T$_{RET}$(min) |
|---|---|---|---|---|---|---|
| Example 27 | 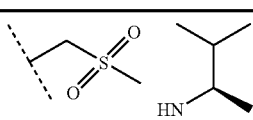 | | Intermediate 15 | (R)-(−)-3-methyl-2-butyl-amine | 393 | 2.91 |

Example 14

1-Ethyl-5-(5-methyl-1,3,4-oxadiazol-2-yl)-N-(tetrahydro-2H-pyran-4-yl)-1H-pyrazolo[3,4-b]pyridin-4-amine

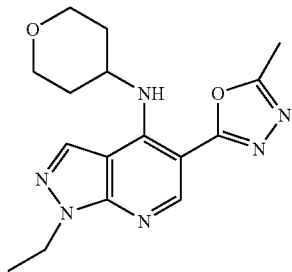

Example 17

5-[5-(1,1-Dimethylethyl)-1,3,4-oxadiazol-2-yl]-1-ethyl-N-(tetrahydro-2H-pyran-4-yl)-1H-pyrazolo[3,4-b]pyridin-4-amine

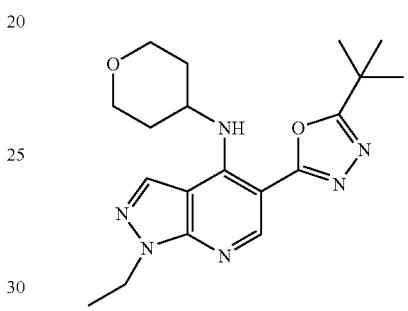

An alternative method of preparing Example 14 is now described:

EDC (0.823 g, 5.3 mmol) and HOBT (0.614 g, 4.55 mmol) were added to Intermediate 17 (10.10 g, 3.80 mmol) in N,N'-dimethylformamide (10 ml). The mixture was stirred for 1.5 hours then acetic hydrazide (0.421 g, 5.7 mmol) (commercially available e.g. from Aldrich) was added and the reaction mixture stirred at 20° C. for 48 hours. The reaction mixture was evaporated and the residue partitioned between chloroform and water. The aqueous phase was extracted with chloroform and the combined organic phases were washed with saturated aqueous sodium chloride solution then dried (Na$_2$SO$_4$) and evaporated. Phosphorus oxychloride (10 ml) was added to the residue and the mixture heated at 120° C. for 0.5 hours. The reaction mixture was evaporated in vacuo and the residue applied to an SPE cartridge (silica, 20 g). The cartridge was eluted with dichloromethane, cyclohexane:ethyl acetate (2:1 then 1:1), ethyl acetate, chloroform:methanol (19:1 followed by 9:1). Fractions containing the required compounds were combined and evaporated in vacuo. The residue was then chromatographed on the Biotage (silica, 50 g) using cyclohexane:ethyl acetate (2:1 then 1:1), ethyl acetate followed by ethyl acetate:ethanol (19:1, 9:1 then 9:2). The residue was partitioned between dichloromethane and aqueous sodium hydrogencarbonate solution. The organic phase was dried (Na$_2$SO$_4$) and evaporated in vacuo to give Example 14 as a pale yellow solid (0.93 g). LCMS showed MH$^+$=329, T$_{RET}$=2.54 min. $^1$H NMR (400 MHz in CDCl$_3$, 27° C., δ ppm) 9.12 (br m, 1H), 8.72 (s, 1H), 8.01 (s, 1H), 4.52 (q, 2H), 4.24 (m, 1H), 4.08 (m, 2H), 3.67 (m, 2H), 2.65 (s, 3H), 2.20 (m, 2H), 1.86 (m, 2H), 1.53 (t, 3H).

An alternative method of preparing Example 17 is now described:

EDC (1.30 g, 6.76 mmol) and HOBT (0.782 g, 5.80 mmol) were added to Intermediate 17 (1.40 g, 4.83 mmol) in N,N'-dimethylformamide (20 ml). The mixture was stirred for 0.5 hours then pivalic acid hydrazide (0.616 g, 5.3 mmol) (commercially available from Fluorochem Ltd, Wesley Stree, Glossop, Derbyshire SK13 9R$^Y$, United Kingdom or can be prepared according to the procedure by K Obmoto et al. in *J. Med. Chem.*, 2001, 44(8), 1268) was added and the reaction mixture stirred at 20° C. for 18 hours. The reaction mixture was evaporated and the residue partitioned between dichloromethane and water. The organic phase was washed with water, saturated aqueous sodium hydrogen carbonate solution followed by saturated aqueous sodium chloride solution then evaporated in vacuo. Phosphorus oxychloride (10 ml) was added to the residue and the mixture heated at 120° C. for 3 hours. The reaction mixture was evaporated in vacuo and the residue partitioned between dichloromethane and water. The organic phase was washed with aqueous sodium hydrogen carbonate solution then dried and evaporated in vacuo. The residue was applied to an SPE cartridge and eluted with cyclohexane:ethyl acetate (3:1 followed by 7:3). The solvent was evaporated in vacuo to give Example 17 as a white solid (0.65 g). LCMS showed MH$^+$=371, T$_{RET}$=3.05 min. $^1$H NMR (400 MHz in CDCl$_3$, 27° C., δ ppm) 9.18 (br m, 1H), 8.75 (s, 1H), 8.01 (s, 1H), 4.52 (q, 2H), 4.25 (m, 1H), 4.08 (m, 2H), 3.67 (m, 2H), 2.20 (m, 2H), 1.84 (m, 2H), 1.57-1.49 (m, 12H).

Example 28

1-Ethyl-5-(3-methyl-1,2,4-oxadiazol-5-yl)-N-tetrahydro-2H-pyran-4-yl-1H-pyrazolo[3,4-b]pyridin-4-amine

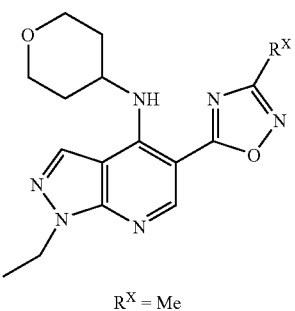

Example 28

$R^X$ = Me

A solution of Intermediate 16 (0.05 g, 0.157 mmol) in ethanol (2 ml) was stirred over powdered 4 Å molecular sieves (0.30 g) and treated with a solution of Intermediate 9 (0.059 g, 0.8 mmol) and sodium ethoxide (0.027 g, 0.4 mmol) in ethanol (1 ml). The mixture was heated at reflux for 18 h under nitrogen, then cooled and filtered. Following concentration of the filtrate in vacuo, the residue was applied to an SPE cartridge (silica, 5 g) which was eluted with cyclohexane:EtOAc (1:1). Fractions containing desired material were combined and concentrated in vacuo to afford Example 28 (0.024 g). LCMS showed MH$^+$=329; $T_{RET}$=2.86 min.

Similarly prepared using the same or similar number of moles of reagents and volumes of solvents were the following:

|  | $R^X$ | Starting Amidoxime | MH$^+$ ion | $T_{RET}$ (min) |
| --- | --- | --- | --- | --- |
| Example 29 | CH$_2$OMe | Intermediate 22 | 359 | 2.78 |

Example 30

5-{3-[(Dimethylamino)methyl]-1,2,4-oxadiazol-5-yl}-1-ethyl-N-tetrahydro-2H-pyran-4-yl-1H-pyrazolo[3,4-b]pyridin-4-amine

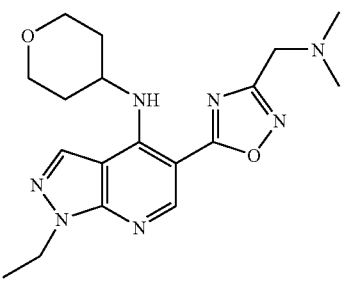

A solution of Intermediate 16 (0.05 g) in ethanol (2 ml) was stirred over powdered 4 Å molecular sieves (0.30 g) and treated with a solution of Intermediate 23 (0.094 g) and sodium ethoxide (0.027 g) in ethanol (1 ml). The mixture was heated at reflux for 18 h under nitrogen, then cooled and filtered. Following concentration of the filtrate in vacuo, the residue was applied to an SPE cartridge (silica, 5 g) which was eluted with 2-5% methanol in DCM. Fractions containing desired material were combined and concentrated in vacuo, then applied to a further SPE cartridge (aminopropyl, 1 g) which was eluted with methanol to afford Example 30 (0.02 g). LCMS showed MH$^+$=372; $T_{RET}$=2.10 min.

Example 31

1-Ethyl-5-[3-(morpholin-4-ylmethyl)-1,2,4-oxadiazol-5-yl]-N-tetrahydro-2H-pyran-4-yl-1H-pyrazolo[3,4-b]pyridin-4-amine

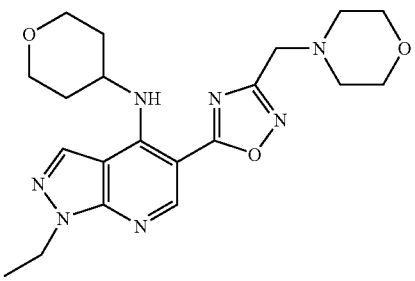

A solution of Intermediate 16 (0.05 g) in ethanol (2 ml) was stirred over powdered 4 Å molecular sieves (0.30 g) and treated with a solution of Intermediate 24 (0.128 g) and sodium ethoxide (0.027 g) in ethanol (1 ml). The mixture was heated at reflux for 18 h under nitrogen, then cooled and filtered. Following concentration of the filtrate in vacuo, the residue was applied to an SPE cartridge (silica, 5 g) which was eluted with 2-5% methanol in DCM. Fractions containing desired material were combined and concentrated in vacuo to afford Example 31 (0.025 g). LCMS showed MH$^+$=415; $T_{RET}$=2.46 min.

Example 32

5-(5-Cyclopropyl-1,3,4-oxadiazol-2-yl)-1-ethyl-N-tetrahydro-2H-pyran-4-yl-1H-pyrazolo[3,4-b]pyridin-4-amine

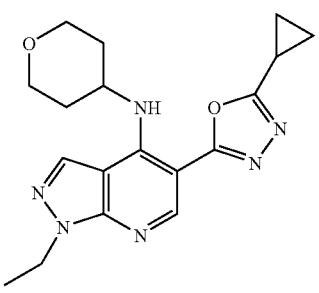

A solution of Intermediate 20 (0.020 g) in THF (0.2 ml) was treated with Burgess reagent (0.026 g) and heated in a microwave at 120° C. (100 W) for 5 min. The mixture was concentrated by evaporation under a stream of nitrogen and the residue applied to an SPE cartridge (silica, 1 g) which was eluted with 2% methanol in DCM to afford Example 32 as a white solid (0.014 g). LCMS showed MH⁺=355; $T_{RET}$=2.78 min.

Example 33

N-(1-Acetylpiperidin-4-yl)-1-ethyl-5-(5-methyl-1,3,4-oxadiazol-2-yl)-1H-pyrazolo[3,4-b]pyridin-4-amine

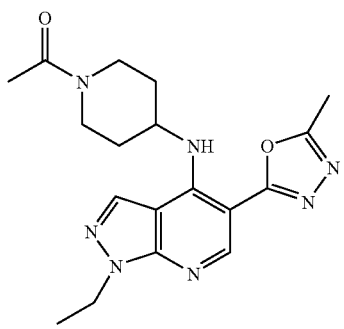

Intermediate 12 (0.03 g) was dissolved in acetonitrile (2 ml) and treated with DIPEA (0.1 ml) and Intermediate 25 (0.022 g). The mixture was stirred at 85° C. for 18 h then concentrated in vacuo and partitioned between DCM and water. The layers were separated and the organic layer concentrated in vacuo, then purified by mass directed autoprep HPLC to afford Example 33 (0.01 g). LCMS showed MH⁺=370; $T_{RET}$=2.48 min.

Example 34

1-Ethyl-5-[5(3-methyloxetan-3-yl)-1,3,4-oxadiazol-2-yl]-N-tetrahydro-2H-pyran-4-yl-1H-pyrazolo[3,4-b]pyridin-4-amine

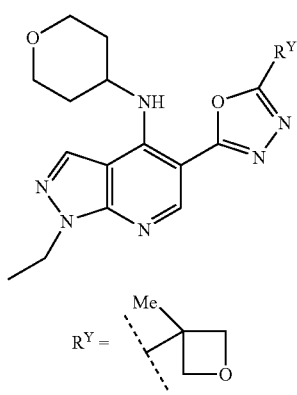

A solution of Intermediate 19 (0.05 g, 0.133 mmol), TBTU (0.045 g, 0.14 mmol) and DIPEA (0.1 ml, ca. 0.5 mmol) in DMW (1 ml) is stirred at room temperature under nitrogen for 5 min. A solution of Intermediate 26 (0.024 g, 0.21 mmol) in DMF (1 ml) is then added and stirring continued for 18 h. Reaction can be found to be incomplete after this time so a further portion of Intermediate 26 (0.012 g, 0.10 mmol) is added and stirring continued under nitrogen for a further 18 h. The mixture is concentrated in vacuo then the residue applied to an SPE cartridge (aminopropyl, 2 g), which is eluted with methanol (2×3 ml). Fractions containing desired material are concentrated in vacuo.

The partially purified intermediate is taken forward without further characterisation and si dissolved in THF (0.5 ml) then treated with Burgess reagent (0.025 g, ca. 0.1 mmol). The mixture is heated under microwave conditions at 120° C. (120 W) for 5 min. The mixture is then concentrated in vacuo and purified by mass directed autoprep HPLC to afford Example 34.

According to an alternative and more preferred embodiment, the reaction was performed as follows. A solution of carboxylic acid Intermediate 26 (0.024 g, 0.21 mmol), TBTU (0.045 g, 0.14 mmol) and DIPEA (0.1 ml, ca. 0.5 mmol) in DMF (1 ml) was stirred at room temperature under nitrogen for 5 min. A solution of Intermediate 19 (0.05 g, 0.133 mmol) in DMF (1 ml) was then added and stirring continued for 18 h. Reaction was found to be incomplete after this time so a further portion of Intermediate 26 (0.012 g, 0.10 mmol) was added and stirring continued under nitrogen for a further 18 h. The mixture was concentrated in vacuo then the residue applied to an SPE cartridge (aminopropyl, 2 g), which was eluted with methanol (2×3 ml). Fractions containing desired material were concentrated in vacuo. The partially purified intermediate was taken forward without further characterisation and was dissolved in THF (0.5 ml) then treated with Burgess reagent (0.025 g, ca. 0.1 mmol). The mixture was heated under microwave conditions at 120° C. (120 W) for 5 min. The mixture was then concentrated in vacuo and purified by mass directed autoprep HPLC to afford Example 34 (0.006 g). LCMS showed MH⁺=385; $T_{RET}$=2.65 min.

Similarly prepared, via the original or alternative embodiment described above, and using the same or similar number of moles of reagents and volumes of solvents, were the following:

| | $R^Y$ | Starting Carboxylic Acid (instead of Intermediate 26) | MH⁺ ion | $T_{RET}$ (min) |
|---|---|---|---|---|
| Example 35 | ⟶N(piperazine)N— | Intermediate 27 | 427 | 2.14 |
| Example 36 | ⟶C(=O)NH-iPr | Intermediate 28 | 400 | 2.87 |
| Example 37 | ⟶(1-methylpyrrolidin-2-one-4-yl) | Intermediate 29 | 412 | 2.39 |

Example 35

1-Ethyl-5-{5-[(4-methyl-1-piperazinyl)methyl]-1,3,4-oxadiazol-2-yl}-N-(tetrahydro-2H-pyran-4-yl)-1H-pyrazolo[3,4-b]pyridin-4-amine

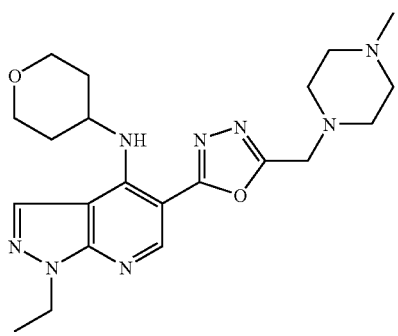

An alternative method of preparing Example 35 is now described:

A solution of Intermediate 27 (0.463 g, 2.93 mmol), TBTU (0.941 g, 2.93 mmol) and DIPEA (1.53 ml, 8.79 mmol) in dry dimethylformamide (7 ml) was stirred at room temperature for 5 min. A solution of Intermediate 19 (1.0 g, 2.93 mmol) in dry dimethylformamide (5 ml) was then added and stirring was continued for 1 h. The mixture was concentrated in vacuo, and the residue was dissolved in methanol (6 ml) and applied equally to two SPE cartridges (aminopropyl, 10 g). The cartridges were eluted with methanol. The product-containing fractions were combined and evaporated to give a yellow oil (1.56 g) which was dissolved in dichloromethane (10 ml) and applied to a SPE cartridge (silica, 10 g). The cartridge was eluted with chloroform-methanol-triethylamine (9/0.2/0.1). Fractions containing the desired product were combined and evaporated to give a pale yellow foam (1.17 g). This product was suspended in dry tetrahydrofuran (45 ml) and treated with Burgess reagent (1.244 g, 5.22 mmol) at room temperature under nitrogen. The resulting solution was heated at 70° C. After 2 h, the reaction mixture was evaporated and the residual oil was dissolved in dichloromethane (5 ml) and applied to a SPE cartridge (silica, 20 g). The cartridge was eluted with chloroform-methanol-triethylamine (9/0.2/0.1). Fractions containing the desired material were combined and evaporated to give a cream solid. Further purification by passage through a SCX cartridge (20 g) eluting with methanol followed by 10% ammonia in methanol afforded Example 35 as a buff coloured solid (0.72 g). LCMS showed MH$^+$=427, T$_{RET}$=2.02 min. $^1$H NMR (400 MHz in CDCl$_3$, 27° C., δ ppm) 9.11 (d, 7 Hz, 1H), 8.76 (s, 1H), 8.01 (s, 1H), 4.52 (q, 2H), 4.24 (m, 1H), 4.08 (m, 2H), 3.93 (s, 2H) 3.66 (m, 2H), 2.8-2.5 (br m's, 4H), 2.31 (s, 3H), 2.20 (m, 2H), 1.85 (m, 2H), 1.52 (t, 3H).

Example 38

1-Ethyl-N-(tetrahydro-2H-pyran-4-yl)-5-[5-(tetrahydro-2H-pyran-4-yl)-1,3,4-oxadiazol-2-yl]-1H-pyrazolo[3,4-b]pyridin-4-amine Example 38

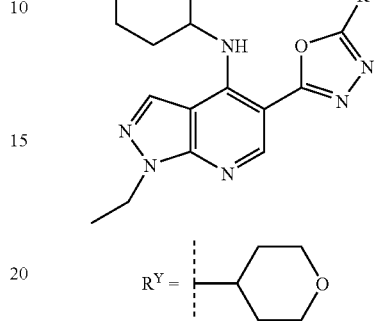

A solution of Intermediate 19 (0.05 g, 0.133 mmol), TBTU (0.045 g, 0.14 mmol) and DIPEA (0.1 ml, ca. 0.5 mmol) in DMF (1 ml) is stirred at room temperature under nitrogen for 5 min. A solution of Intermediate 30 (0.018 g, 0.14 mmol) in DMF (1 ml) is then added and stirring continued for 18 h. Reaction can be found to be incomplete after this time so a further portion of Intermediate 30 (0.009 g, 0.07 mmol) is added and stirring continued under nitrogen for a further 18 h. The mixture is concentrated in vacuo then the residue applied to an SPE cartridge (aminopropyl, 2 g), which is eluted with methanol (2×3 ml). Fractions containing desired material are concentrated in vacuo. The partially purified intermediate is taken forward without further characterisation and is dissolved in THF (0.5 ml) then treated with Burgess reagent (0.025 g, ca. 0.1 mmol). The mixture is heated under microwave conditions at 120° C. (120 W) for 5 min. Reaction can appear incomplete so a further portion of Burgess Reagent (0.012 g, ca. 0.05 mmol) is added and the mixture heated under microwave conditions at 140° C. (120 W) for a further 10 min. The mixture is then concentrated in vacuo and purified by mass directed autoprep HPLC to afford Example 38.

According to an alternative and more preferred embodiment, the reaction was performed as follows. A solution of carboxylic acid Intermediate 30 (0.018 g, 0.14 mmol), TBTU (0.045 g, 0.14 mmol) and DIPEA (0.1 ml, ca. 0.5 mmol) in DMF (1 ml) was stirred at room temperature under nitrogen for 5 min. A solution of Intermediate 19 (0.05 g, 0.133 mmol) in DMF (1 ml) was then added and stirring continued for 18 h. Reaction was found to be incomplete after this time so a further portion of Intermediate 30 (0.009 g, 0.07 mmol) was added and stirring continued under nitrogen for a further 18 h. The mixture was concentrated in vacuo then the residue applied to an SPE cartridge (aminopropyl, 2 g), which was eluted with methanol (2×3 ml). Fractions containing desired material were concentrated in vacuo. The partially purified intermediate was taken forward without further characterisation and was dissolved in THF (0.5 ml) then treated with Burgess reagent (0.025 g, ca. 0.1 mmol). The mixture was heated under microwave conditions at 120° C. (120 W) for 5 min. Reaction appeared incomplete so a further portion of Burgess Reagent (0.012 g, ca. 0.05 mmol) is added and the mixture heated under microwave conditions at 140° C. (120 W) for a further 10 min. The mixture was then concentrated in vacuo and purified by mass directed autoprep HPLC to afford Example 38 (0.006 g). LCMS showed MH$^+$=399; T$_{RET}$=2.64 min.

Similarly prepared, via the original or alternative embodiment described above, and using the same or similar number of moles of reagents and volumes of solvents, were the following:

|  | R$^Y$ | Starting Carboxylic Acid (instead of Intermediate 30) | MH$^+$ ion | T$_{RET}$ (min) |
|---|---|---|---|---|
| Example 39 | -CH₂-N(morpholine) | Intermediate 31 | 414 | 2.44 |
| Example 40 | CH₂O$^t$Bu | Intermediate 32 | 401 | 2.98 |

Example 38

1-Ethyl-N-(tetrahydro-2H-pyran-4-yl)-5-[5-(tetrahydro-2H-pyran-4-yl)-1,3,4-oxadiazol-2-yl]-1H-pyrazolo[3,4-b]pyridin-4-amine

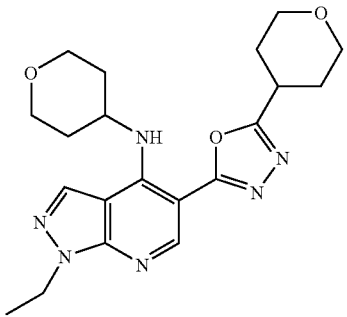

An alternative method of preparing Example 38 is now described:

A mixture of Intermediate 30 (0.325 g, 2.5 mmol), TBTU (0.803 g, 2.5 mmol) and DIPEA (1.75 ml, 10.04 mmol) in N,N-dimethylformamide (10 ml) was stirred at 20° C. for 20 minutes. A suspension of Intermediate 19 (1.024 g, 3.00 mmol) in N,N-dimethylformamide was added and the reaction mixture stirred for 18 hours. The solvent was evaporated and the residue applied to SPE cartridges (2×50 g, aminopropyl). The cartridges were eluted with dichloromethane:methanol (0-100% methanol over 17 minutes at 25 ml/min). Appropriate fractions were evaporated in vacuo and the residue dissolved in tetrahydrofuran (10 ml). Burgess Reagent (0.746 g, 3.13 mmol) was added and the reaction mixture was heated at reflux for 2.5 hours. Additional Burgess Reagent (0.284 g) was added and heating continued for 1.5 hours. The solvent was evaporated in vacuo. The residue was applied to an SPE cartridge (silica, 100 g) and eluted with cyclohexane:ethyl acteate (gradient of 0 to 100% ethyl acetate over 25 minutes at 25 ml/min) followed by ethyl acetate then ethyl acetate:methanol (4:1). Appropriate fractions were combined and evaporated to give Example 38 as a white solid (0.503 g). LCMS showed MH$^+$=399, T$_{RET}$=2.67 min. $^1$H NMR (400 MHz in CDCl$_3$, 27° C., δ ppm) 9.14 (br m, 1H), 8.72 (s, 1H), 8.01 (s, 1H), 4.52 (q, 21), 4.24 (m, 2H), 4.10 (m, 4H), 3.64 (m, 4H), 3.27 (m, 1H), 2.25-1.96 (m, 61), 1.85 (m, 2H), 1.53 (t, 3H).

Example 40A

Methyl 2-[1-ethyl-4-(tetrahydro-2H-pyran-4-ylamino)-1H-pyrazolo[3,4-b]pyridin-5-yl]4,5-dihydro-1,3-oxazole carboxylate

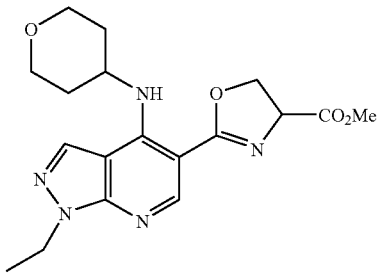

Intermediate 33 (0.055 g, 0.14 mmol) and Burgess reagent (0.037 g, 0.16 mmol) were suspended in THF (2 ml) and heated at reflux for 4 hours. Solvents were removed in vacuo and the residue applied to an SPE cartridge (silica, 2 g), which was eluted with cyclohexane:ethyl acetate (1:2). Concentration in vacuo afforded Example 40A (0.03 g). LCMS showed MH$^+$=374, T$_{RET}$=2.78 min.

Example 41

Methyl 2-[1-ethyl-4-(tetrahydro-2H-pyran-4-ylamino)-1H-pyrazolo[3,4-b]pyridin-5-yl]-1,3-oxazole-4-carboxylate

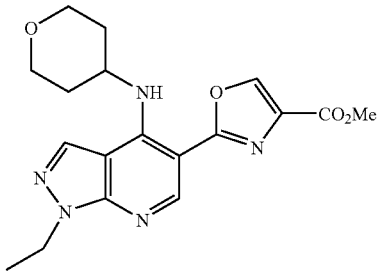

The compound of Example 41 was synthesised using the following route, reagents and solvents:

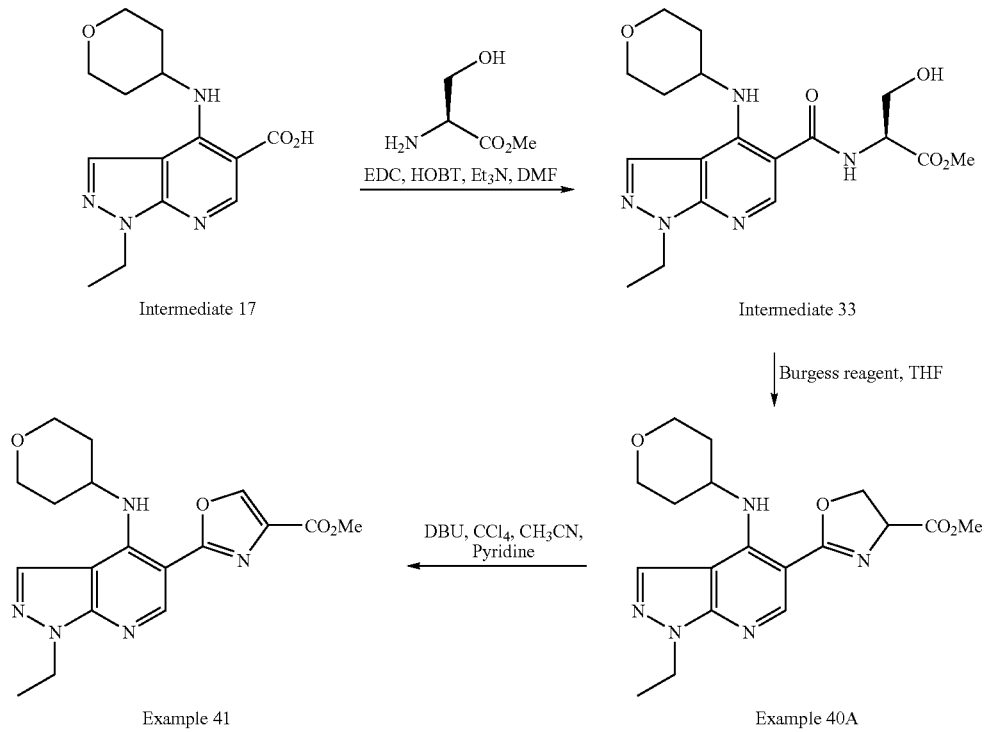

Intermediate 17

Intermediate 33

Example 41

Example 40A

In one embodiment, a suitable detailed procedure for the first two steps is given above in "Intermediate 33" and "Example 40A". In one embodiment, a suitable detailed procedure for synthesising Example 41 from Example 40A is as follows:

Example 40A (0.023 g, 0.062 mmol) and DBU (0.028 g, 0.18 mmol) were dissolved in carbon tetrachloride/acetonitrile/pyridine (2:3:3, 1.6 ml) and stirred at room temperature under nitrogen for 48 hours. Solvents were removed in vacuo and the residue was purified by mass directed autoprep HPLC to afford Example 41 (0.0017 g). LCMS showed MH$^+$=372, T$_{RET}$=9.24 min.

Example 42

1-Ethyl-5-(4-methyl-4,5-dihydro-1,3-oxazol-2-yl)-N-(tetrahydro-2H-pyran-4-yl)-1H-pyrazolo[3,4-b]pyridin-4-amine

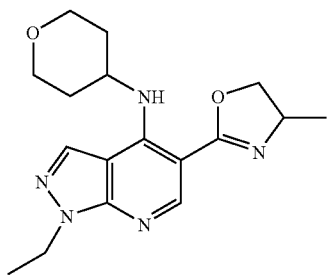

Intermediate 34 (0.095 g, 0.27 mmol) and Burgess reagent (0.071 g, 0.30 mmol) were dissolved in THF (2 ml) and heated at reflux for 4 hours. Solvents were removed in vacuo and the residue applied to an SPE (silica, 5 g), which was eluted with ethyl acetate to afford Example 42 (0.045 g). LCMS showed MH$^+$=330, T$_{RET}$=2.84 min.

Example 43

1-n-Propyl-5-(5-methyl-1,3,4-oxadiazol-2-yl)-N-(tetrahydro-2H-pyran-4-yl)-1H-pyrazolo[3,4-b]pyridin-4-amine

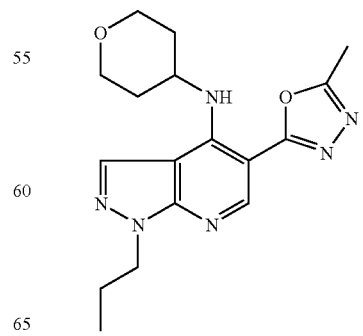

Example 43 was synthesised according to the following reaction scheme:
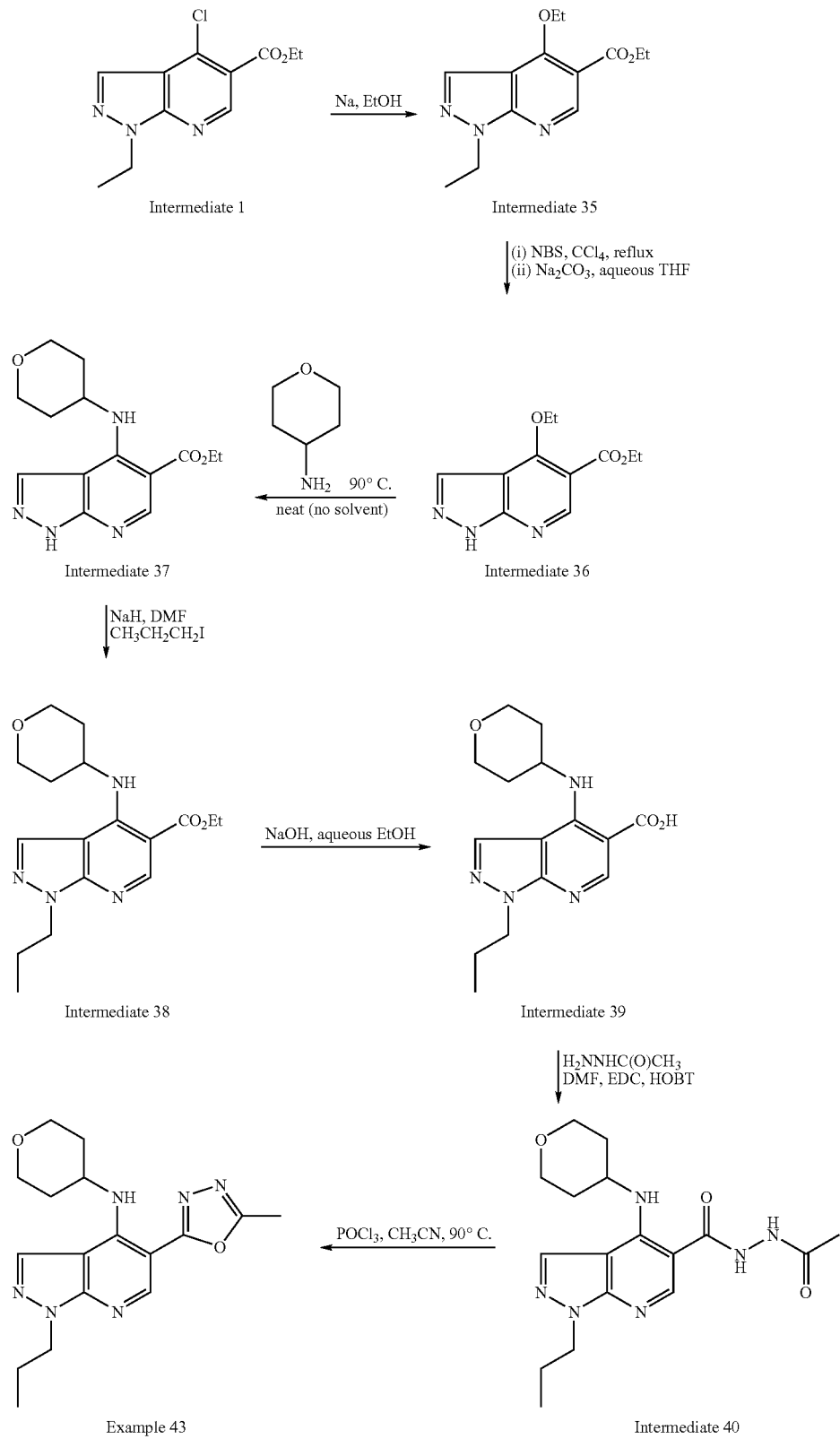

Detailed conditions which can be used for the first six reactions from Intermediate 1 to Intermediate 40 are given in the "Intermediate" syntheses hereinabove for Intermediates 35, 36, 37, 38, 39 and 40.

Example 43 can be made from Intermediate 40 using a similar process to that described for Example 1, 2, 3, using a similar or the same number of moles of reagents and/or volumes of solvents. LCMS showed MH$^+$=343, T$_{RET}$=2.70 min.

Example 44

1-Ethyl-5-[5-(tetrahydrofuran-2-yl)-1,3,4-oxadiazol-2-yl]-N-(tetrahydro-2H-pyran-4-yl)-1H-pyrazolo[3,4-b]pyridin-4-amine

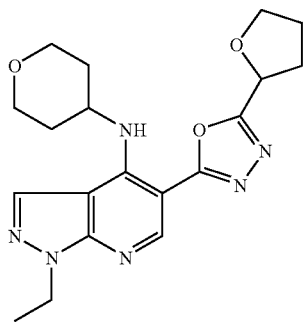

A solution of Tetrahydro-2-furoic acid=2-(tetrahydrofuran)carboxylic acid (commercially available from Sigma-Aldrich) (0.012 ml, 0.12 mmol), TBTU (0.039 g, 0.12 mmol) and DIPEA (0.084 ml, 0.48 mmol) in DMF (2 ml) was stirred at room temperature under nitrogen. Intermediate 19 (0.045 g, 0.12 mmol) was added and the reaction stirred for 2 days. The mixture was concentrated in vacuo then the residue applied to an SPE cartridge (aminopropyl, 5 g), which was eluted with methanol. Fractions containing the desired material were concentrated in vacuo. Half of the partially purified material was dissolved in THF (0.1 ml) and treated with Burgess reagent (0.015 g, 0.06 mmol). The mixture was heated under microwave conditions at 120° C. (100 W) for 5 minutes. The mixture was then concentrated in vacuo and applied to an SPE cartridge (silica, 0.5 g). The cartridge was eluted with dichloromethane:methanol (19:1), fractions containing the desired material were concentrated in vacuo. The sample was then partitioned between dichloromethane and water, the organic phase was evaporated to give Example 44 (0.0065 g). LCMS showed MH$^+$=385, T$_{RET}$=2.69 min.

Example 45

1-Ethyl-5-[5-(dimethylamino)-1,3,4-oxadiazol-2-yl]-N-(tetrahydro-2H-pyran-4-yl)-1H-pyrazolo[3,4-b]pyridin-4-amine

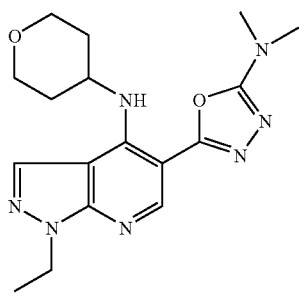

Intermediate 86 (0.113 g, 0.28 mmol) and Burgess Reagent (0.133 g, 0.56 mmol) in THF (1 ml) were heated in the microwave 5 minutes at 120° C. SmithCreator Microwave. The sample was evaporated in vacuo and the residue purified by mass directed autoprep HPLC . . . LCMS showed MH$^+$=358; T$_{RET}$=2.57 min Example 46

1-Ethyl-5-(5-methyl-1,2,4-triazol-3-yl)-N-(tetrahydro-2H-pyran-4-yl)-1H-pyrazolo[3,4-b]pyridin-4-amine

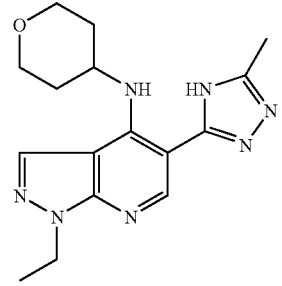

A solution of the Intermediate 19 (0.1 g, 0.29 mmol), diisopropylethylamine (0.3 ml, 1.74 mmol) and methyl acetimidate hydrochloride (0.095 g, 0.87 mmol, commercially available from Aldrich) in ethanol (3 ml) was heated under reflux. After 17 h, the reaction mixture was evaporated to an oily residue which was partitioned between dichloromethane (10 ml) and water (2 ml). The phases were separated and the organic phase was dried over anhydrous sodium sulphate and evaporated to a waxy solid (0.053 g). Purification of a portion of this solid (0.025 g) by mass directed autoprep HPLC afforded Example 46 (0.005 g). LCMS showed MH$^+$=328; T$_{RET}$=2.25 min.

Example 47

N-(1-Acetylpiperidin-4-yl)-1-ethyl-5-(3-methyl-1,2,4-oxadiazol-5-yl)-1H-pyrazolo[3,4-b]pyridin-4-amine

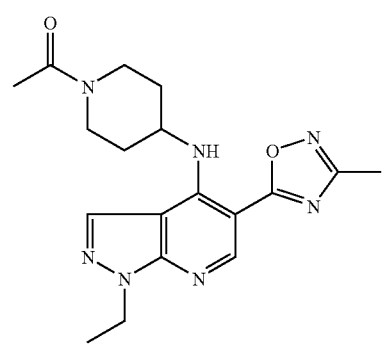

A mixture of Intermediate 41 (0.049 mg, 0.14 mmol), Intermediate 9 (0.051 g, 0.68 mmol), sodium ethoxide (0.13 ml, 21% solution in ethanol, commercially available from Aldrich) and powdered 4 Å molecular sieves (0.3 g) in ethanol (2 ml) were heated at 80° C. for 16 hours under nitrogen. The mixture was cooled and filtered and the filtrate concentrated in vacuo. The residue was applied to an SPE cartridge (silica, 5 g) and eluted with cyclohexane, cyclohexane:ethyl acetate (1:1) and then ethyl acetate. The desired fractions were combined and evaporated to give Example 47 (0.005 g). LCMS showed MH⁺=370; $T_{RET}$=2.77 min Example 48

N-(1-Acetylpiperidin-4-yl)-1-ethyl-5-[3-(morpholin-4-ylmethyl)-1,2,4-oxadiazol-5-yl]-1H-pyrazolo[3,4-b]pyridin-4-amine

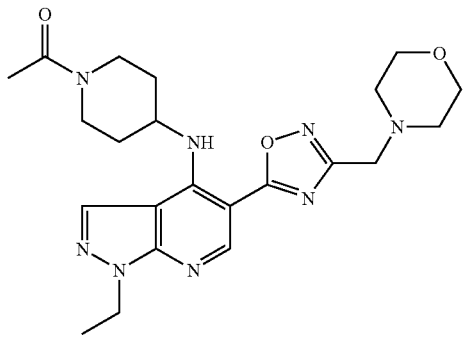

Example 48 was prepared from Intermediate 41 and Intermediate 24 using an analogous method to that for Example 47. LCMS showed MH⁺=455; $T_{RET}$=2.59 min.

Example 49

1-Ethyl-5-[(4R)-4-phenyl-4,5-dihydro-1,3-oxazol-2-yl]-N-(tetrahydro-2H-pyran-4-yl)-1H-pyrazolo[3,4-b]pyridin-4-amine

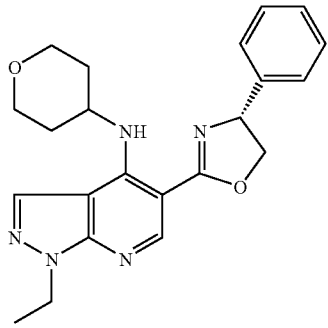

Burgess reagent (0.189 g, 0.79 mmol) was added portionwise, over 3 min, to a stirred solution of Intermediate 42 (0.293 g, 0.72 mmol) in dry tetrahydrofuran (13 ml) at room temperature under nitrogen. The resulting solution was heated at 70° C. under nitrogen for 4 h. The reaction mixture was evaporated to give an off-white solid which was dissolved in dichloromethane (5 ml) and applied to a SPE cartridge (silica, 10 g). The cartridge was eluted sequentially with a gradient of ethyl acetate-petroleum ether (1:8, 1:4, 1:2, 1:1, 1:0). Fractions containing the desired product were combined and evaporated to afford Example 49 as a white crystalline solid (0.169 g). LCMS showed MH⁺=392; $T_{RET}$=3.31 min.

Example 50

1-Ethyl-5-[(4S)-4-phenyl-4,5-dihydro-1,3-oxazol-2-yl]-N-(tetrahydro-2-pyran 1-yl)-1H-pyrazolo[3,4-b]pyridin-4-amine

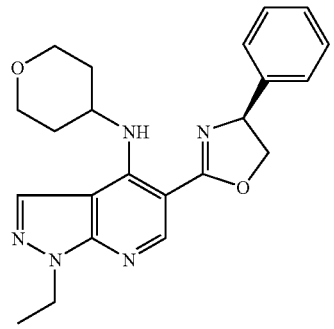

Example 50 was prepared from Intermediate 43 using an analogous method to that for Example 49. LCMS showed MH⁺=392; $T_{RET}$=3.32 min.

Example 51

1-Ethyl-5-[(4S)-4-phenylmethyl)-4,5-dihydro-1,3-oxazol-2-yl]-N-(tetrahydro-2H-pyran-4-yl)-1H-pyrazolo[3,4-b]pyridin-4-amine

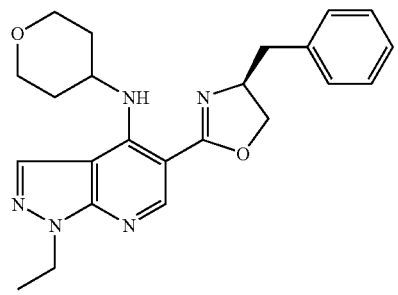

Example 51 was prepared from Intermediate 44 using an analogous method to that for Example 49. LCMS showed MH⁺=406; $T_{RET}$=3.38 min Example 52

1-Ethyl-5-[(4R)-4-(phenylmethyl)-4,5-dihydro-1,3-oxazol-2-yl]-N-(tetrahydro-2H-pyran-4-yl)-1H-pyrazolo[3,4-b]pyridin-4-amine

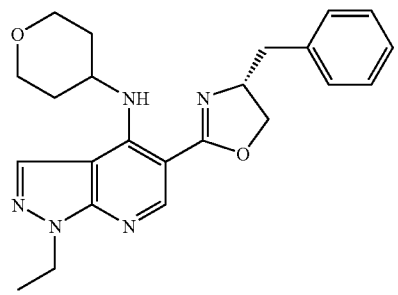

Example 52 was prepared from Intermediate 45 using an analogous method to that for Example 49. LCMS showed MH$^+$=406; T$_{RET}$=3.38 min.

Example 53

1-Ethyl-5-[(4S,5R)-5-methyl-4-phenyl-4,5-dihydro-1,3-oxazol-2-yl]-N-(tetrahydro-2H-pyran-4-yl)-1H-pyrazolo[3,4-b]pyridin-4-amine

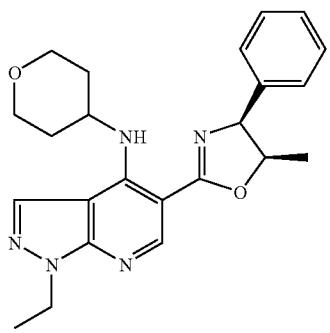

Example 53 was prepared from Intermediate 46 using an analogous method to that for Example 49. LCMS showed MH$^+$=406; T$_{RET}$=3.37 min.

Example 54

1-Ethyl-5-[(5R)-5-phenyl-4,5-dihydro-1,3-oxazol-2-yl]-N-(tetrahydro-2H-pyran-4-yl)-1H-pyrazolo[3,4-b]pyridin-4-anine

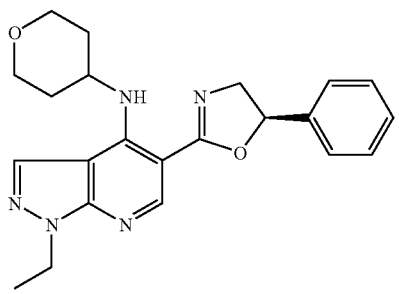

Example 54 was prepared from Intermediate 47 using an analogous method to that for Example 49. LCMS showed MH$^+$=392; T$_{RET}$=3.29 min.

Example 55

1-Ethyl-5-[(5S)-5-phenyl-4,5-dihydro-1,3-oxazol-2-yl]-N-(tetrahydro-2H-pyran-4-yl)-1H-pyrazolo[3,4-b]pyridin-4 amine

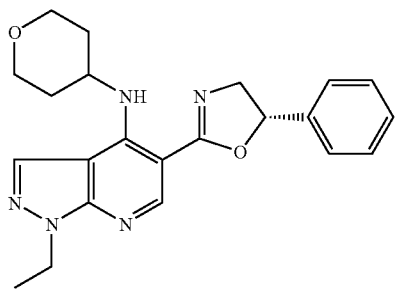

Example 55 was prepared from Intermediate 48 using an analogous method to that for Example 49. LCMS showed MH$^+$=392; T$_{RET}$=3.29 min.

Example 56

5-(4,4-Dimethyl-4,5-dihydro-1,3-oxazol-2-yl)-1-ethyl-N-(tetrahydro-2H-pyran-4-yl)-1H-pyrazolo[3,4-b]pyridin-4-amine

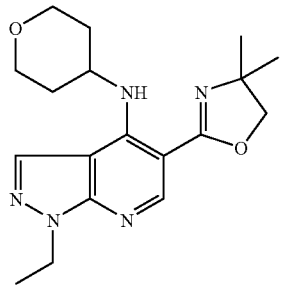

Example 56 was prepared from Intermediate 49 using an analogous method to that for Example 49. LCMS showed MH$^+$=344; T$_{RET}$=2.95 min.

Example 57

2-[1-Ethyl-4-(tetrahydro-2H-pyran-4-ylamino)-1H-pyrazolo[3,4-b]pyridin-5-yl]-1,3-oxazole-4-carboxylic acid

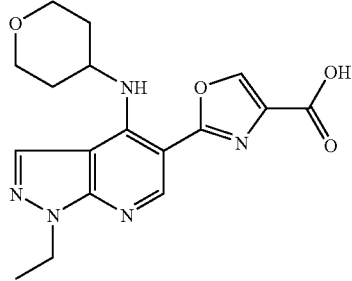

A solution of lithium hydroxide (0.12 g, 5.2 mmol) in water (6 ml) was added to a suspension of Example 41 (0.48 g, 1.3 mmol) in methanol (20 ml) and the resultant mixture heated at 50° C. for 2 hours. The solvent was evaporated in vacuo and the residue dissolved in water (50 ml), cooled in an ice bath and acidified to pH 3 by the addition of aqueous hydrochloric acid. The precipitate was filtered, washed with water and dried in vacuo at 40° C. to give Example 57 as a white solid (0.3 g). LCMS showed MH$^+$=358; T$_{RET}$=2.62 min

Example 58

2-[1-Ethyl-4-(tetrahydro-2H-pyran-4-ylamino)-1H-pyrazolo[3,4-b]pyridin-5-yl]-N-(1-methylethyl)-1,3-oxazole-4-carboxamide Example 58

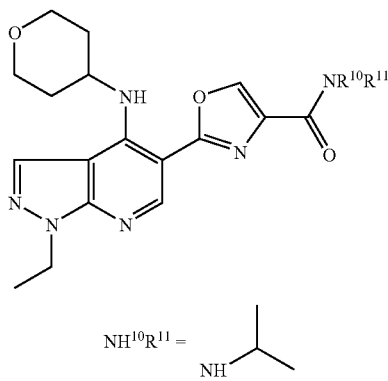

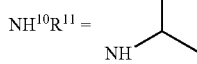

A mixture of Example 57 (0.05 g, 0.14 mmol), HOBT (0.023 g, 0.17 mmol), EDC (0.038 g, 0.2 mmol) in DMF (2 ml) were stirred at 20° C. for 20 minutes. Isopropylamine (0.013 ml, 0.15 mmol) was added and the reaction mixture stirred overnight. The solvent was concentrated in vacuo and the residue dissolved in DCM. The organic phase was washed with water then aqueous sodium hydrogen carbonate solution. The aqueous phases were extracted with DCM and the combined organic phases concentrated in vacuo. The residue was applied to an SPE cartridge (aminopropyl, 2 g) and eluted with MeOH, appropriate fractions were combined and evaporated in vacuo. The residue was further purified by chromatography on SPE (silica, 0.5 g) eluting with cyclohexane:ethyl acetate (2:1 followed by 1:1) to give Example 58 as a white solid (0.012 g). LCMS showed $MH^+=399$; $T_{RET}=2.78$ min Similarly prepared using the same or similar numbers of moles of reagents and/or volumes of solvents was the following:

| | $NR^{10}R^{11}$ | Starting amine | $MH^+$ | $T_{RET}$(min) |
|---|---|---|---|---|
| Example 59 | | Morpholine | 426 | 2.56 |

Example 60

1-Ethyl-N-methyl-5-(5-methyl-1,3,4-oxadiazol-2-yl)-N-(tetrahydro-2H-pyran-4-yl)-1H-pyrazolo[3,4-b]pyridin-4-amine

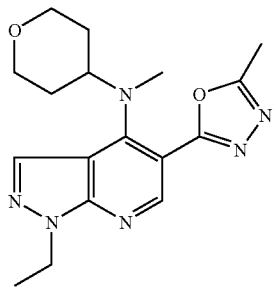

Intermediate 53 (0.076 g, 0.21 mmol) in phosphorous oxychloride (3 ml) was heated at 120° C. for 3 hours then evaporated in vacuo. The residue was partitioned between DCM and water and the organic phase concentrated in vacuo. The residue was purified by mass directed autoprep HPLC to afford Example 60 (0.027 g). LCMS showed $MH^+=343$; $T_{RET}=2.34$ min

Example 61 trans-4-[{1-Ethyl-5-(5-methyl-1,3,4-oxadiazol-2-yl)-1H-pyrazolo[3,4-b]pyridin-4-yl]amino}cyclohexanol Example 61

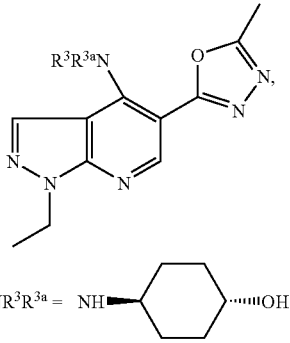

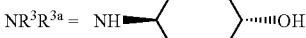

Intermediate 54 (0.072 g, 0.63 mmol), Intermediate 12 (0.150 g, 0.57 mmol) and diisopropylethylamine (0.51 ml) in acetonitrile (3 ml) were heated at 85° C. for 18 hours then evaporated in vacuo. The residue was partitioned between DCM and water and the organic phase concentrated in vacuo. The residue was purified by mass directed autoprep HPLC to afford Example 61 (0.004 g). LCMS showed $MH^+=343$; $T_{RET}=2.48$ min Similarly prepared using the same or similar numbers of moles of reagents and/or volumes of solvents were the following:

| | $NR^3R^{3a}$ | Amine $R^3R^{3a}NH$ (instead of Intermediate 54) | $MH^+$ | $T_{RET}$ (min) |
|---|---|---|---|---|
| Example 62 | NH—⟨pyran⟩ | Intermediate 55 | 329 | 2.59 |
| Example 63 | NH—⟨cyclohexanone⟩=O | Intermediate 56 | 341 | 2.53 |
| Example 64 | N—⟨ethyl-pyran⟩ | Intermediate 57 | 371 | 2.60 |

Example 65

5-[5-(1,1-Dimethylethyl)-1,3,4-oxadiazol-2-yl]-1-ethyl-6-methyl-N-(tetrahydro-2H-pyran-4-yl)-1H-pyrazolo[3,4-b]pyridin-4-amine

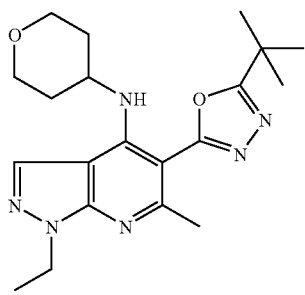

Intermediate 61 (0.266 g, 0.56 mmol) in phosphorous oxychloride (10 ml) was heated at 120° C. for 1.5 hours then evaporated in vacuo. The residue was partitioned between DCM and water and the organic phase concentrated in vacuo. The residue was purified on an SPE cartridge (silica, 5 g) eluting with cyclohexane:ethyl acetate (2:1, 1:1 then 2:3) to afford Example 65 (0.042 g). LCMS showed $MH^+$=385; $T_{RET}$=3.05 min.

Example 66

1-Ethyl-6-methyl-N-(tetrahydro-2H-pyran-4-yl)-5-[5-(tetrahydro-2H-pyran-4-yl)-1,3,4-oxadiazol-2-yl]-1H-pyrazolo[3,4-b]pyridin-4-amine

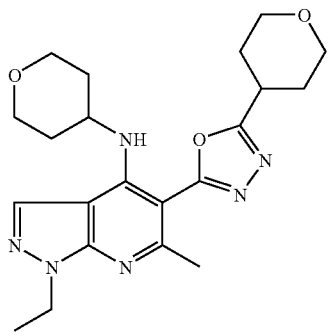

Intermediate 64 (0.05 g, 0.11 mol) and Burgess Reagent (0.053 g, 0.22 mol) in a mixture of THF/DMF (1 ml, 1:1) were heated under microwave conditions at 120° C. (120 W) for 5 minutes. The reaction mixtures were heated at 150° C. for four 10 minutes intervals with an additional portion of Burgess reagent (0.025 g) being added after the first and third period of additional microwave heating. The reaction mixture was concentrated in vacuo and purified by SPE (silica, 0.5 g) eluting with cyclohexane, cyclohexane:ethyl acetate (2:3 then 1:4) then ethyl acetate. Fractions containing the desired material were evaporated in vacuo to afford Example 66 (0.010 g). LCMS showed $MH^+$=413; $T_{RET}$=2.63 min.

Example 67

5-(5-Cyclobutyl-1,3,4-oxadiazol-2-yl)-1-ethyl-N-(tetrahydro-2H-pyran-4-yl)-1H-pyrazolo[3,4-b]pyridin-4-amine Example 67

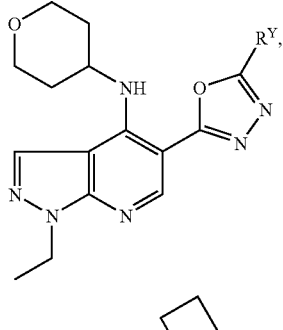

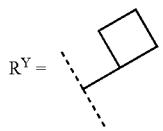

Intermediate 65 (0.05 g, 0.13 mmol) and Burgess Reagent (0.07 g, 0.3 mmol) in THF (2 ml) was heated at 80° C. for 7 hours. The reaction mixture was concentrated in vacuo and a further portion of Burgess Reagent (0.07 g, 0.3 mmol) in THF (0.5 ml) was added and the reaction mixture refluxed for 18 hours. The reaction was concentrated in vacuo and partitioned between DCM and water. The phases were separated using a hydrophobic frit (Whatman PTFE Filter Media with Polypropylene Housing 5 µM pore size). The organic phase was concentrated in vacuo and the residue purified by mass directed autoprep HPLC to afford Example 67 (0.018 g). LCMS showed $MH^+$=369; $T_{RET}$=3.03 min.

Similarly prepared using the same or similar numbers of moles of reagents and/or volumes of solvents were the following:

| | $R^Y$ | Starting Intermediate | $MH^+$ | $T_{RET}$(min) |
|---|---|---|---|---|
| Example 68 | 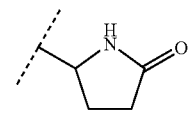 | Intermediate 66 | 398 | 2.34 |
| Example 69 | 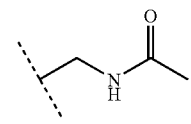 | Intermediate 67 | 386 | 2.29 |
| Example 70 | 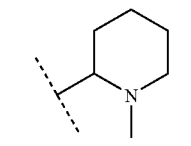 | Intermediate 68 | 412 | 2.03 |

-continued

| | R^Y | Starting Intermediate | MH+ | T_RET(min) |
|---|---|---|---|---|
| Example 71 | | Intermediate 69 | 411 | 2.92 |
| Example 72 | | Intermediate 70 | 397 | 2.67 |
| Example 73 | | Intermediate 71 | 385 | 2.65 |
| Example 74 | | Intermediate 72 | 416 | 2.59 |
| Example 75 | | Intermediate 73 | 383 | 3.22 |
| Example 76 | | Intermediate 74 | 400 | 2.38 |
| Example 77 | | Intermediate 75 | 413 | 2.79 |
| Example 78 | | Intermediate 76 | 383 | 3.22 |
| Example 79 | | Intermediate 77 | 396 | 2.88 |
| Example 80 | | Intermediate 78 | 395 | 2.91 |

Example 77

1-Ethyl-N-(tetrahydro-2H-pyran-4-yl)-5-[1(tetrahydro-2H-pyran-4-ylmethyl)-1,3,4-oxadiazol-2-yl]-1H-pyrazolo[3,4-b]pyridin amine

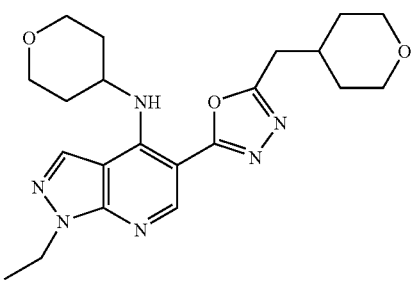

Alternative Procedure:

Burgess Reagent (0.168 g, 0.74 mmol) was added to a solution of Intermediate 75 (0.141 g, 0.33 mmol) in tetrahydrofuran (2 ml). The reaction mixture was heated at reflux for 1.5 hours then evaporated. The residue was applied to an SPE cartridge (silica, 10 g) and eluted with cyclohexane:ethyl acteate (gradient of 0 to 100% ethyl acetate over 15 minutes at 15 ml/min) followed by ethyl acetate then ethyl acetate:methanol (4:1). Appropriate fractions were combined and evaporated to give Example 77 as a white solid (0.099 g). LCMS showed MH+=413, T_RET=2.72 min. $^1$H NMR (400 MHz in CDCl$_3$, 27° C., δ ppm) 9.12 (br m, 1H), 8.72 (s, 1H), 8.01 (s, 1H), 4.52 (q, 2H), 4.245 (m, 1H), 4.08 (m, 21), 4.00 (m, 2H), 3.67 (m, 2H), 3.44 (m, 2H), 2.91 (m, 2H), 2.20 (m, 3H), 1.93-1.70 (m, 4H), 1.57-1.40 (m, 5H).

Example 81

5-[5-(1-Acetyl-4-piperidinyl)-1,3,4-oxadiazol-2-yl]-1-ethyl-N-(tetrahydro-2H-pyran-4-yl)-1H-pyrazolo[3,4-b]pyridin-4-amine

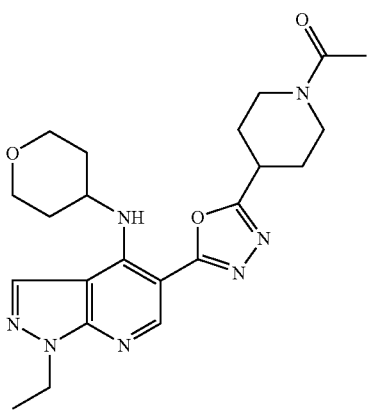

Intermediate 79 (0.18 mmol) and Burgess Reagent (0.14 g, 0.6 mmol) in THF (0.75 ml) was heated at 80° C. under an atmosphere of nitrogen for 16 hours. The reaction was concentrated using a stream of nitrogen and the residue dissolved in DCM (8 ml). The solution was stirred with water and the phases separated using a hydrophobic frit (Whatman). The organic phase was concentrated in vacuo and the material was purified by mass directed auotprep HPLC to afford Example 81 (0.005 g). LCMS showed MH+=440; $T_{RET}$=2.52 min.

Example 82

1-Ethyl-5-{3-[(4-methyl-1-piperazinyl)methyl]-1,2,4-oxadiazol-5-yl}-N-(tetrahydro-2H-pyranyl)-1H-pyrazolo[3,4-b]pyridin-4-amine Example 82

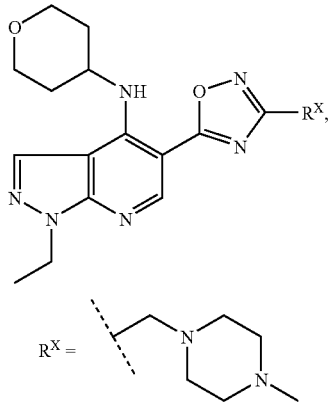

A mixture of Intermediate 16 (0.064 g, 0.2 mmol), Intermediate 80 (0.172 g, 1 mmol), a solution of sodium ethoxide in EtOH (0.19 ml, 21% solution) and powdered 4 Å molecular sieves (0.38 g) in EtOH (2 ml) were stirred at 82° C. under an atmosphere of nitrogen for 18 hours. The reaction mixture was filtered, the solvent was evaporated in vacuo and the residue was applied to an SPE cartridge (silica, 2 g). The cartridge was eluted with (i) cyclohexane, (ii) cyclohexane:ethyl acetate (4:1, 3:2, 1:1, 2:3, 1:4), (iii) EtOAc, (iv) MeOH and (v) 10% aqueous $NH_3$ solution in MeOH to afford Example 82 as a white solid (0.038 g). LCMS showed MH+=427; $T_{RET}$=2.10 min.

Similarly prepared from Intermediate 16, using the same or similar numbers of moles of reagents and/or volumes of solvents, were the following:

| | $R^X$ | Starting Intermediate (instead of Intermediate 80) | MH+ | $T_{RET}$(min) |
|---|---|---|---|---|
| Example 83 | (4-fluorophenyl) | Intermediate 81 | 398 | 2.34 |
| Example 84 | (pyrrolidinyl ketone) | Intermediate 82 | 426 | 2.6 |

Examples 85 to 96

Various 5-{3-[substituted]-1,2,4-oxadiazol-5-yl}-1-ethyl-N-(tetrahydro-2H-pyran-4-yl)-1H-pyrazolo[3,4-b]pyridin-4-amines Examples 85 to 96 can be prepared from Intermediate 16 using a similar processes to those described for any of Examples 28-31 or 82-84, using a similar or the same number of moles of reagents and/or volumes of solvents.

Alternatively, Examples 85 to 90 and Examples 95 to 96 (all amides) can be prepared from the corresponding carboxylic acid compound Intermediate 83, by activating the carboxylic acid moiety (e.g. using a coupling agent such as EDC, HATU or more preferably TBTU) and reacting the activated carboxylic acid with the appropriate amine $R^{10}R^{11}NH$. This reaction, preferred reagents, and the structure of Intermediate 83 is shown in the following scheme (Intermediate 83 has the same structure as Example 84 but the 1,2,4-oxadiazole side-chain $R^X$ is —$CH_2$—C(O)OH):

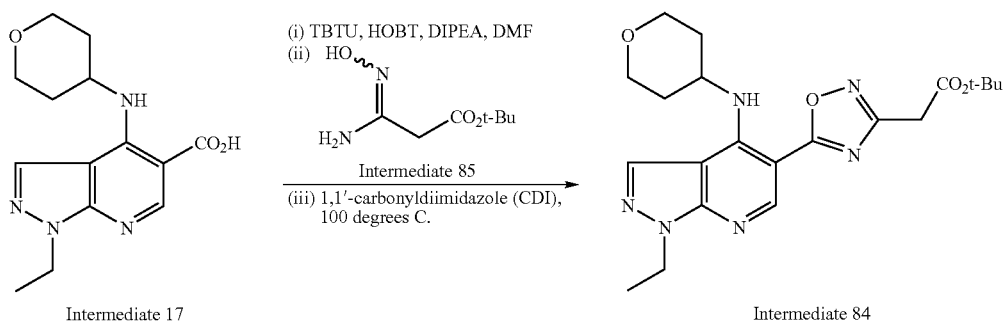

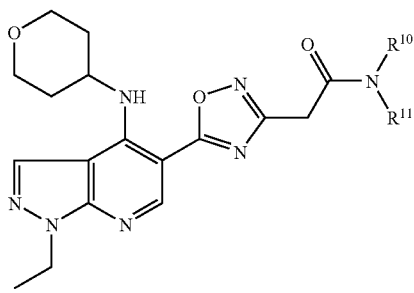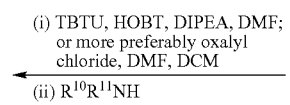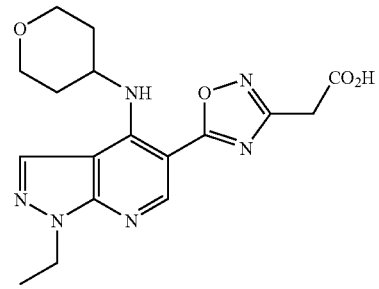

Intermediate 85-91 and 95-96 → Intermediate 83

(i) TBTU, HOBT, DIPEA, DMF; or more preferably oxalyl chloride, DMF, DCM
(ii) $R^{10}R^{11}NH$ As shown in the scheme above, Intermediate 83 can be prepared by hydrolysis of the corresponding t-butyl ester compound Intermediate 84 (wherein the 1,2,4-oxadiazole side-chain $R^X$ is $-CH_2-C(O)-O-{}^tBu$). Intermediate 84 can be prepared from Intermediate 17 and Intermediate 85 as shown in the scheme above. The preparation of Intermediate 85 has been shown earlier.

In an alternative embodiment, Examples 85 to 90 and Examples 95 to 96 can be prepared from reaction of carboxylic acid Intermediate 83 with $R^{10}R^{11}NH$ as shown above, but the Intermediate 83 (wherein the 1,2,4-oxadiazole side-chain $R^X$ is $-CH_2-C(O)OH$) might be preparable from Example 84, by hydrolysing the amide bond within $R^X$ in Example 84 to form the carboxylic acid Intermediate 83.

The example numbers and corresponding structures of Examples 85 to 96 are as follows:

Example 85

2-{5-[1-Ethyl-4-(tetrahydro-2H-pyran-4-ylamino)-1H-pyrazolo[3,4-b]pyridin-5-yl]-1,2,4-oxadiazol-3-yl}-N-phenylacetamide Example 85

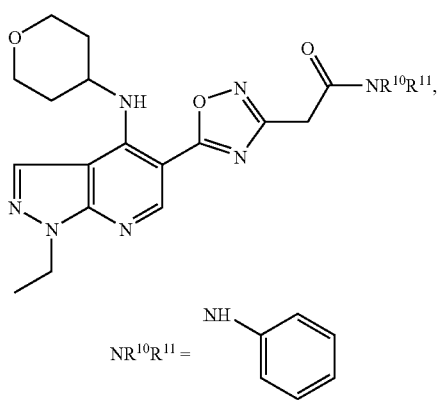

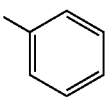

General Procedure for Examples 85 to 90:

N,N-Dimethylformamide (0.1 ml) was added dropwise to a stirred mixture of Intermediate 83 (0.525 g, 1.40 mmol) and oxalyl chloride (0.18 ml, 2.1 mmol) in dichloromethane (15 ml) at 0° C. under an atmosphere of nitrogen. The resultant mixture was stirred at 0° C. for 1 hour.

An aliquot of the above solution (1.1 ml) was added to a solution of the amine $R^{10}R^{11}NH$ (0.6 mmol) in dichloromethane (0.5 ml). The reaction mixture was allowed to stand at room temperature for 2 hours then applied to an SPE cartridge (aminopropyl, 2 g). The cartridge was eluted with chloroform then ethyl acetate/methanol (9:1). Fractions containing the product were concentrated and the residue purified by SPE cartridge (silica, 5 g) eluting with dichloromethane, ether, ethyl acetate then ethyl acetate/methanol (9:1). The desired fractions were concentrated to afford the examples given below.

| Example Number | $NR^{10}R^{11}$ | Source of Starting Amine $R^{10}R^{11}NH$ | MH+ | $T_{RET}$(min) |
|---|---|---|---|---|
| 85 | NH-phenyl | Sigma-Aldrich | 448 | 2.98 |
| 86 | NH-CH(CH₃)-phenyl | Sigma-Aldrich | 476 | 2.97 |
| 87 | piperidinyl | Sigma-Aldrich | 440 | 2.81 |
| 88 | NH-CH₂-phenyl | Sigma-Aldrich | 461 | 2.90 |
| 89 | N(CH₃)₂ dimethylamino | Sigma-Aldrich | 400 | 2.51 |
| 90 | HN-ethyl(methyl) | Sigma-Aldrich | 400 | 2.51 |

Example 92

1-Ethyl-5-{3-[1-(4-morpholinyl)ethyl]-1,2,4-oxadiazol-5-yl}-N-tetrahydro-2H-pyran 4-yl)-1H-pyrazolo[3,4-b]pyridin-4-amine

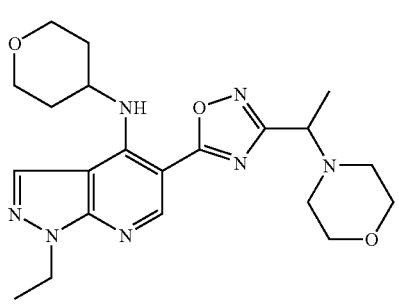

A mixture of Intermediate 16 (0.059 g, 0.2 mmol), Intermediate 121 (0.161 g, 1.54 mmol), a solution of sodium ethoxide in EtOH (0.21 ml, 21% solution) and powdered 4 Å molecular sieves (0.43 g) in EtOH (1.5 ml) were stirred at 82° C. under an atmosphere of nitrogen for 18 hours. The reaction mixture was filtered and the residue purified by mass directed autoprep HPLC to afford Example 92 (0.007 g). LCMS showed MH$^+$=428; T$_{RET}$=2.46 min.

Example 93

5-[3-(Cyclohexylmethyl)-1,2,4-oxadiazol-5-yl]-1-ethyl-N-(tetrahydro-2H-pyran-4-yl)-1H-pyrazolo[3,4-b]pyridin-4-amine

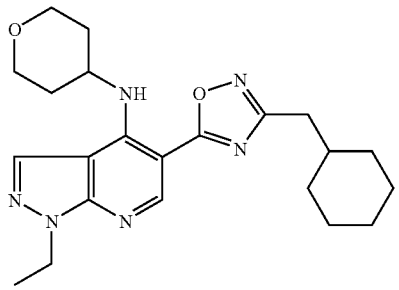

A mixture of Intermediate 16 (0.098 g, 0.31 mmol), Intermediate 122 (0.24 g, 0.93 mmol), a solution of sodium ethoxide in EtOH (0.21 ml, 21% solution) and powdered 4 Å molecular sieves (0.43 g) in EtOH (1.5 ml) were stirred at 82° C. under an atmosphere of nitrogen for 18 hours. The reaction mixture was filtered and the residue purified by mass directed autoprep HPLC to afford Example 93 (0.079 g). LCMS showed MH$^+$+411; T$_{RET}$=3.80 min.

Example 95

1-Ethyl-5-{3-[2-oxo-2-(1-piperidinyl)ethyl]-1,2,4-oxadiazol-5-yl}-N-(tetrahydro-2H-pyran-4-yl)-1H-pyrazolo[3,4-b]pyridin-4-amine Example 95

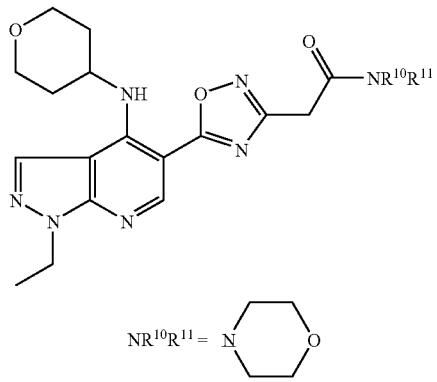

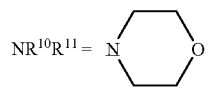

General Procedure for Example 95 to 96:

N,N-Dimethylformamide (0.1 ml) was added dropwise to a stirred mixture of Intermediate 83 (0.525 g, 1.40 mmol) and oxalyl chloride (0.18 ml, 2.11 mmol) in dichloromethane (15 ml) at 0° C. under an atmosphere of nitrogen. The resultant mixture was stirred at 0° C. for 1 hour.

An aliquot of the above solution (1.1 ml) was added to a solution of the R$^{10}$R$^{11}$NH amine (0.6 mmol) in dichloromethane (0.5 ml). The reaction mixture was allowed to stand at room temperature for 2 hours then applied to an SPE cartridge (aminopropyl, 2 g). The cartridge was eluted with chloroform then ethyl acetate/methanol (9:1). Fractions containing the product were concentrated and the residue purified by SPE cartridge (silica, 5 g) eluting with dichloromethane, ether, ethyl acetate then ethyl acetate/methanol (9:1). The desired fractions were concentrated to afford the examples given below.

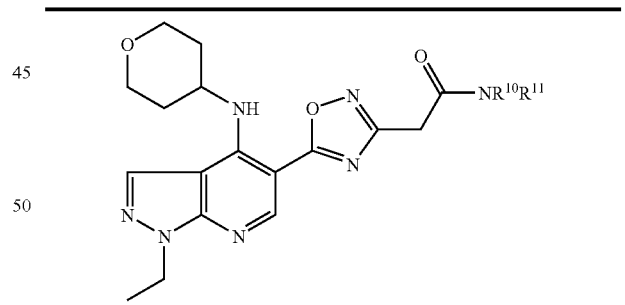

| Example Number | NR$^{10}$R$^{11}$ | Source of Starting Amine R$^{10}$R$^{11}$NH | MH$^+$ | T$_{RET}$(min) |
|---|---|---|---|---|
| 95 | N O | Sigma-Aldrich | 442 | 2.51 |
| 96 | N N— | Sigma-Aldrich | 455 | 2.08 |

Examples 97 to 125

Various 5-{5-[substituted]-1,3,4-oxadiazol-2-yl}-1-ethyl-N-(tetrahydro-2H1-pyran-4-yl)-1H-pyrazolo[3,4-b]pyridin-4-amines Examples 97 to 125 can be made using processes similar to those described for any of Examples 9, 14, 32-40, 44-45, 60-64, 65-66, and 67-81, using a similar or the same number of moles of reagents and/or volumes of solvents.

Example 97

1-Ethyl-N-(tetrahydro-2H-pyran-4-yl)-5-[5-(H-1,2,3-triazol-1-ylmethyl)-1,3,4-oxadiazol-2-yl]-1H-pyrazolo[3,4-b]pyridin-4-amine

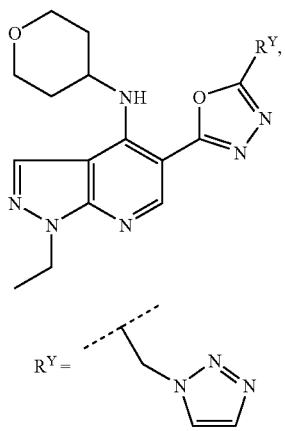

Example 97

General Procedure for Preparation of Examples 97 to 125:

A mixture of diacyl hydrazide Intermediate (one of Intermediates 89-114) and Burgess Reagent (2 equivalents) in N,N-dimethylformamide (1 ml) was heated in a microwave for 10 minutes at 120° C. at 150 Watts. The resultant solution was concentrated in vacuo and partitioned between chloroform and water. The organic phase was separated using a hydrophobic frit (Whatman PTFE Filter Media with Polypropylene Housing 5 μM pore size) then concentrated. The residue was purified by mass directed auto-prep HPLC.

As either formic acid or trifluoroacetic acid are used in the solvents in the mass directed auto-prep HPLC procedure (see "Machine Methods section hereinbefore), some of the Examples were isolated as the formate salt or trifluoroacetate salt as shown below.

The example numbers and corresponding structures of Examples 97 to 125 are as follows:

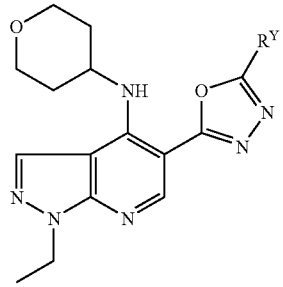

| Example Number | R$^Y$ | Diacyl hydrazide Intermediate number | MH$^+$ | T$_{RET}$ (min) |
|---|---|---|---|---|
| 97 | ![triazole-CH2] | 89 | 396 | 2.47 |
| 98 (as formate salt) | ![dimethylthiazole-CH2] | 90 | 440 | 2.79 |
| 99 (as formate salt) | ![furan-CH2] | 91 | 395 | 2.97 |
| 100 (as formate salt) | ![isoxazole-CH2] | 92 | 396 | 2.69 |
| 103 (as trifluoroacetate salt) | ![methoxyphenyl-CH2] | 93 | 435 | 3.15 |
| 104 (as formate salt) | ![tetrazole-CH2] | 94 | 397 | 2.51 |
| 105 | ![isothiazole-CH2] | 95 | 412 | 2.79 |
| 106 (as formate salt) | ![methylisoxazole-CH2] | 96 | 410 | 2.77 |
| 107 | ![dimethylaminophenyl-CH2] | 97 | 448 | 3.01 |

| Example Number | R^Y | Diacyl hydrazide Intermediate number | MH+ | T_RET (min) |
|---|---|---|---|---|
| 108 (as formate salt) | 2-methylthiazol-4-yl-methyl | 98 | 426 | 2.76 |
| 109 (as trifluoroacetate salt) | 1-(methylaminocarbonylmethyl)cyclopentylmethyl | 99 | 468 | 2.85 |
| 111 | cyclopropylcarbonylaminomethyl-CH2 | 100 | 412 | 2.53 |
| 112 (as formate salt) | (5-methylisoxazol-3-yl)methyl | 101 | 396 | 3.03 |
| 113 | (5-methylisoxazol-3-yl)ethyl | 102 | 410 | 2.81 |
| 114 (as formate salt) | (4-methylthiazol-5-yl)ethyl | 103 | 440 | 2.79 |
| 117 (as trifluoroacetate salt) | (3,5-dimethylisoxazol-4-yl)ethyl | 106 | 424 | 2.80 |
| 118 | 1-(acetylamino)ethyl | 107 | 400 | 2.43 |
| 119 (as trifluoroacetate salt) | (1-acetylpiperidin-4-yl)methyl | 108 | 454 | 2.63 |
| 120 | 4-methylbenzyl | 109 | 419 | 3.20 |
| 121 | 4-methylphenyl | 110 | 405 | 3.41 |
| 122 | 3,4-dimethylphenyl | 111 | 419 | 3.53 |
| 123 | 2,4-dimethylphenyl | 112 | 419 | 3.65 |
| 125 | 4-bromobenzyl | 114 | 483/485 | 3.30 |

Examples 126 to 147

Various 5-{4-[substituted]-oxazol-2-yl}-1-ethyl-N-(tetrahydro-2H-pyran-4-yl)-1H-pyrazolo[3,4-b]pyridin-4-amines Examples 126 to 147 (all amides) can be prepared by reacting Example 57 and the appropriate amine to form the amide bond using a process similar to that described for Example 58, except that HATU is preferably used instead of EDC as coupling agent, and using a similar or the same number of moles of reagents and/or volumes of solvents as in Example 58.

Example 126

2-[1-Ethyl-4-(tetrahydro-2H-pyran-4-ylamino)-1H-pyrazolo[3,4-b]pyridin-5-yl]-N-(phenylmethyl)-1,3-oxazole-4-carboxamide Example 126

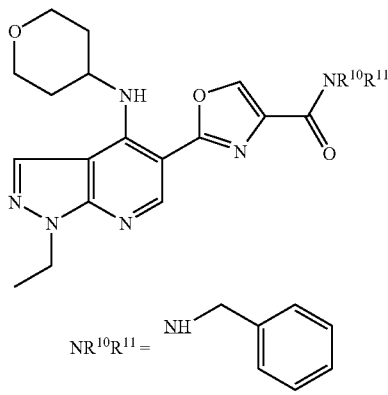

General Procedure for Examples 126 to 147:

A mixture of Example 57 (0.014 g, 0.04 mmol), diisopropylethylamine (0.0017 ml, 0.096 mmol) and HATU (0.016 g, 0.042 mmol) in N,N-dimethylformamide (0.4 ml) was allowed to stand for 10 minutes. The resultant solution was added to the appropriate amine $R^{10}R^{11}NH$ (0.05 mmol) and mixture agitated by sonication. After standing for 18 hours the solvent was removed in vacuo. The residue was applied to an SPE cartridge (aminopropyl, 0.5 g) and the cartridge eluted with chloroform (1.5 ml) followed by ethyl acetate:methanol (9:1, 2 ml). Appropriate fractions were evaporated in vacuo and the residue purified by mass directed auto-prep HPLC The example numbers and corresponding structures of Examples 126 to 147 are as follows:

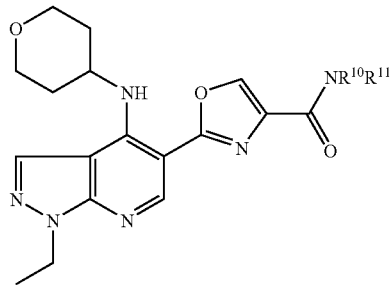

| Example Number | $NR^{10}R^{11}$ | Source of Starting Amine $R^{10}R^{11}NH$ | $MH^+$ | $T_{RET}$ (min) |
|---|---|---|---|---|
| 126 | NH-CH2-Ph | Sigma-Aldrich | 447 | 3.14 |
| 127 | NH-CH2-C6H4-OMe (4-) | Sigma-Aldrich | 477 | 3.16 |
| 128 | NH-CH2-C6H4-Me (2-) | Sigma-Aldrich | 461 | 3.26 |
| 129 | NH-CH2-C6H4-Me (4-) | Sigma-Aldrich | 461 | 3.36 |
| 130 | NH-CH2-C6H4-Me (3-) | Sigma-Aldrich | 461 | 3.23 |
| 131 | NH-CH2-C6H4-Cl (4-) | Sigma-Aldrich | 481 | 3.35 |
| 132 | NH-CH2-C6H3-(2,3-diMe) | Matrix Scientific or Maybridge | 475 | 3.57 |
| 133 | NH-CH2-C6H3-(3,5-diMe) | Matrix Scientific | 475 | 3.55 |
| 134 | NH-CH2-C6H3-(3,4-diMe) | Matrix Scientific or Pfaulz-Bauer | 475 | 3.46 |
| 135 | NH-CH(Me)-Ph | Sigma-Aldrich | 461 | 3.21 |

203

-continued

[Structure: 1-ethyl-4-(tetrahydro-2H-pyran-4-ylamino)-1H-pyrazolo[3,4-b]pyridin-5-yl connected to oxazole-4-carboxamide NR$^{10}$R$^{11}$]

| Example Number | NR$^{10}$R$^{11}$ | Source of Starting Amine R$^{10}$R$^{11}$NH | MH$^+$ | T$_{RET}$ (min) |
|---|---|---|---|---|
| 136 | NH-CH(CH₃)-C₆H₄-OCH₃ | Pfaulz-Bauer | 491 | 3.22 |
| 137 | NH-CH(Et)-Ph | Sigma-Aldrich | 475 | 3.32 |
| 138 | NH-C₆H₄-CH₃ | Sigma-Aldrich | 447 | 3.42 |
| 139 | NH-CH₂-C₆H₄-NH-SO₂-CH₃ | J. Med. Chem. 2003, 46(14), 3116 | 540 | 2.87 |
| 140 | NH-CH₂-C₆H₄-SO₂-CH₃ | WO 02/016318 | 525 | 2.86 |
| 141 | NH-(4-acetylpiperidinyl) | Intermediate 25 | 482 | 2.55 |
| 142 | NH-(tetrahydropyran-4-yl) | Intermediate 21 | 441 | 2.68 |
| 143 | NH-CH₂-(tetrahydrofuran-2-yl) | Sigma-Aldrich | 441 | 2.89 |
| 144 | NH-CH₂CH₂-(4-methylpiperazinyl) | J. Med. Chem. 1999, 42(15), 2870 or Matrix Scientific | 483 | 2.21 |
| 145 | NH-CH₂-(1-methylamino-cyclohexyl) | WO 96/05166 | 482 | 3.32 |

204

-continued

[Same core structure]

| Example Number | NR$^{10}$R$^{11}$ | Source of Starting Amine R$^{10}$R$^{11}$NH | MH$^+$ | T$_{RET}$ (min) |
|---|---|---|---|---|
| 146 | NH-(2,6-dimethylphenyl) | Sigma-Aldrich | 461 | 3.23 |
| 147 | HN-CH₂-C₆H₄-C(O)NH₂ | Intermediate 115 | 490 | 2.58 |

Example 148

2-{5-[1-Ethyl(tetrahydro-2H-pyran-4-ylamino)-1H-pyrazolo[3,4-b]pyridin-5-yl]-1,2,4-oxadiazol-3-yl}-N-(tetrahydro-2H-pyran-4-yl)acetamide Example 148

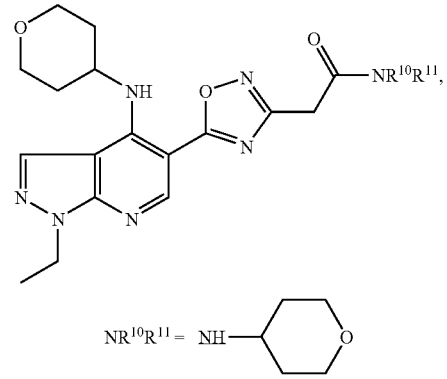

NR$^{10}$R$^{11}$ = NH-(tetrahydro-2H-pyran-4-yl)

General Procedure for Examples 148-155 and for Alternative Preparation of Example 84:

N,N-Dimethylformamide (0.1 ml) was added dropwise to a stirred mixture of Intermediate 83 and oxalyl chloride (0.18 ml, 2.1 mmol) in dichloromethane (15 ml) at 0° C. under an atmosphere of nitrogen. The resultant mixture was stirred at 0° C. for 1 hour.

An aliquot of the above solution (1.1 ml) was added to a solution of the amine R$^{10}$R$^{11}$NH (0.6 mmol) in dichloromethane (0.5 ml). The reaction mixture was allowed to stand at room temperature for 2 hours then applied to an SPE cartridge (aminopropyl, 2 g). The cartridge was eluted with chloroform then ethyl acetate/methanol (9:1). Fractions containing the product were concentrated and the residue purified by SPE cartridge (silica, 5 g) eluting with dichloromethane, ether, ethyl acetate then ethyl acetate/methanol (9:1). The desired fractions were concentrated to afford the examples given below.

| Example Number | NR<sup>10</sup>R<sup>11</sup> | Source of Amine R<sup>10</sup>R<sup>11</sup>NH | MH<sup>+</sup> | T$_{RET}$(min) |
|---|---|---|---|---|
| 148 | | Intermediate 21 | 456 | 2.49 |
| 149 | | Sigma-Aldrich (mixture of isomers) | 470 | 2.66, 2.71 |
| 150 | | Sigma-Aldrich | 454 | 2.96 |
| 152 | | Sigma-Aldrich | 444 | 2.57 |
| 153 | | Sigma-Aldrich | 468 | 3.13 |
| 154 | | Sigma-Aldrich | 454 | 2.96 |
| 155 | | Sigma-Aldrich | 449 | 2.51 |
| 84 (alternative preparation) | | Sigma-Aldrich | 426 | 2.63 |

Example 157

6-{5-[1-Ethyl-4-(tetrahydro-2H-pyran-4-ylamino)-1H-pyrazolo[3,4-b]pyridin-5-yl]-1,3,4-oxadiazol-2-yl}-2-piperidinone

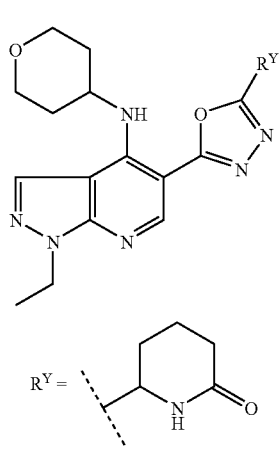

Example 157

General Procedure for Examples 157 to 158:

A mixture of diacyl hydrazide Intermediate 104 or 105 and Burgess Reagent (2 equivalents) in N,N-dimethylformamide (1 ml) was heated in a microwave for 10 minutes at 120° C. at 150 Watts. The resultant solution was concentrated in vacuo and partitioned between chloroform and water. The organic phase was separated using a hydrophobic frit (Whatman PTFE Filter Media with Polypropylene Housing 5 μM pore size) then concentrated. The residue was purified by mass directed auto-prep HPLC

| Example Number | R<sup>Y</sup> | Diacyl hydrazide Intermediate | MH<sup>+</sup> | T$_{RET}$(min) |
|---|---|---|---|---|
| 157 | | Intermediate 104 | 411 | 2.45 |
| 158 | | Intermediate 105 | 409 | 2.38 |

Example 159

N-({5-[1-Ethyl-4-(tetrahydro 2-pyran-4-ylamino)-1H-pyrazolo[3,4-b]pyridin-5-yl]-1,2,4-oxadiazol-3-yl}methyl)acetamide Example 159

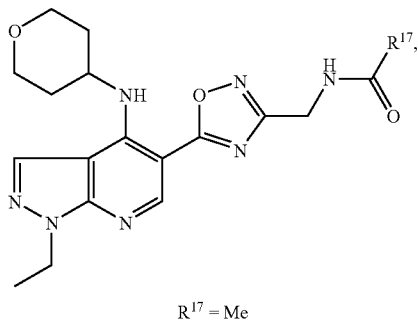

R[17] = Me

General Procedure for Examples 159 to 165:

The appropriate carboxylic acid chloride R[17]C(O)Cl (0.12 mmol) was added to a stirred solution of amine Intermediate 118 (0.1 mmol) and diisopropylethylamine (0.3 mmol) in chloroform (1 ml) at room temperature. After stirring at room temperature for 16 h, the reaction mixture was applied to a SPE cartridge (aminopropyl, 2 g) and the cartridge was eluted sequentially with chlororm, ethyl acetate and methanol. Fractions containing the desired product were combined and blown down under nitrogen. The resulting residue was further purified on a SPE cartidge (silica, 1 g) eluting with a gradient of 30-100% ethyl acetate in petroleum ether. Appropriate fractions were combined and the solvents were evaporated to afford the product.

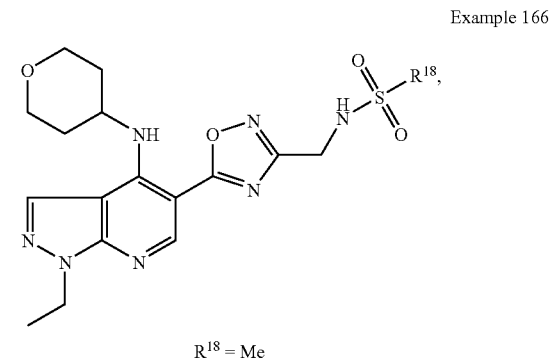

| Example Number | R[17] | Source of Acyl chloride R[17]C(O)Cl | MH+ | T$_{RET}$(min) |
|---|---|---|---|---|
| 159 | CH$_3$ | Sigma-Aldrich | 386 | 2.38 |
| 160 | phenyl | Sigma-Aldrich | 448 | 2.82 |
| 161 | benzyl | Sigma-Aldrich | 462 | 2.85 |
| 162 | isopropyl | Sigma-Aldrich | 414 | 2.66 |
| 163 | isobutyl | Sigma-Aldrich | 428 | 2.79 |
| 164 | cyclohexyl | Sigma-Aldrich | 454 | 2.99 |
| 165 | 2-furyl | Lancaster | 438 | 2.68 |

Example 166

N-({5-[1-Ethyl-4-(tetrahydro-2H-pyran-4-ylamino)-1H-pyrazolo[3,4-b]pyridin-5-yl]-1,2,4-oxadiazol-3-yl}methyl)methanesulfonamide Example 166

R[18] = Me

General Procedure for Examples 166 to 172:

The appropriate sulphonyl chloride R[18]S(O)$_2$Cl (0.12 mmol) was added to a stirred solution of amine Intermediate 118 (0.1 mmol) and pyridine (0.2 mmol) in chloroform (1 ml) at room temperature. After stirring at room temperature for 16 h, the reaction mixture was applied to a SPE cartridge (aminopropyl, 2 g) and the cartridge was eluted sequentially with chlororm, ethyl acetate and methanol. Fractions containing the desired product were combined and blown down under nitrogen. The resulting residue was further purified on a SPE cartidge (silica, 1 g) eluting with a gradient of 30-100% ethyl acetate in petroleum ether. Appropriate fractions were combined and the solvents were evaporated to afford the product.

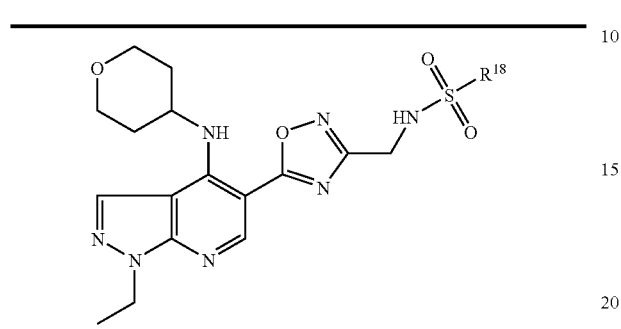

| Example Number | $R^{18}$ | Source of Sulphonyl chloride $R^{18}S(O)_2Cl$ | $MH^+$ | $T_{RET}(min)$ |
|---|---|---|---|---|
| 166 | $CH_3$ | Sigma-Aldrich | 422 | 2.59 |
| 167 | phenyl | Sigma-Aldrich | 484 | 3.00 |
| 168 | benzyl | Sigma-Aldrich | 498 | 3.04 |
| 169 | isopropyl | Sigma-Aldrich | 450 | 2.79 |
| 170 | n-butyl | Sigma-Aldrich | 450 | 2.83 |
| 171 | cyclopropyl | Array Biopharma Inc | 448 | 2.69 |
| 172 | thiophenyl | Avocado | 490 | 2.93 |

Example 173

1-({5-[1-Ethyl(tetrahydro-2H-pyran-4-ylamino)-1H-pyrazolo[3,4-b]pyridin-5-yl]-1,2,4-oxadiazol-3-yl}methyl)-2-pyrrolidinone

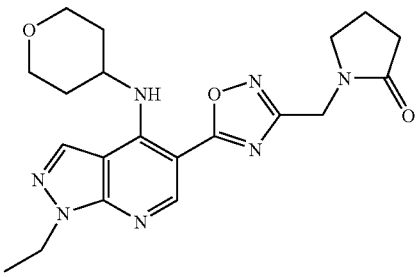

A solution of Intermediate 119 (45 mg, 0.1 mmol) in dry dimethylformamide (2 ml) was added to sodium hydride (60% dispersion in mineral oil, 4.4 mg, 0.11 mmol), and the resulting mixture was stirred at room temperature. After 16 h, the reaction mixture was diluted with water (2 ml) and extracted with chloroform (3×5 ml). The combined organic extracts were dried over anhydrous sodium sulphate and evaporated to give the crude product. Purification of the crude product on a SPE cartridge (silica, 2 g) using a gradient of ethyl acetate in petroleum ether afforded Example 173. LCMS showed $MH^+$=412, $T_{RET}$=2.59 min.

Example 174

1-({5-[1-Ethyl-4-(tetrahydro-2H-pyran-4-ylamino)-1H-pyrazolo[3,4-b]pyridin-5-yl]-1,2,4-oxadiazol-3-yl}methyl)-2-piperidinone

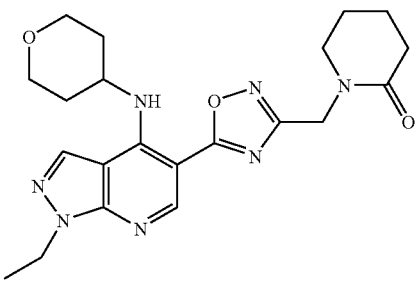

A solution of Intermediate 120 (46 mg, 0.1 mmol) in dry dimethylformamide (2 ml) was added to sodium hydride (60% dispersion in mineral oil, 4.4 mg, 0.11 mmol), and the resulting mixture was stirred at room temperature. After 16 h, the reaction mixture was diluted with water (2 ml) and extracted with chloroform (3×5 ml). The combined organic extracts were dried over anhydrous sodium sulphate and evaporated to give the crude product. Purification of the crude product on a SPE cartridge (silica, 2 g) using a gradient of ethyl acetate in petroleum ether afforded Example 174. LCMS showed $MH^+$=426, $T_{RET}$=2.66 min.

Example 175

5-{3-[(1-Acetyl-4-piperidinyl)methyl]-1,2,4-oxadiazol-5-yl}-1-ethyl-N-(tetrahydro-2H-pyran-4-yl)-1H-pyrazolo[3,4-b]pyridin-4-amine

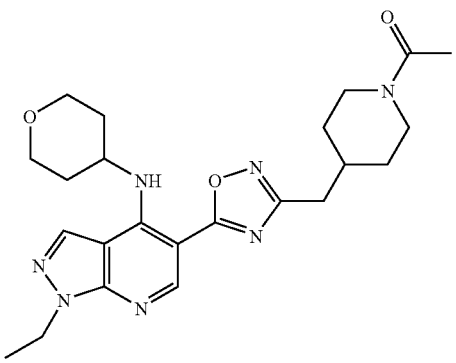

Acetyl chloride (0.04 mmol) was added to a stirred solution of Intermediate 125 (0.033 mmol) and diisopropylethylamine (0.1 mmol) in chloroform (1 ml) at room temperature. After stirring at room temperature for 1.5 h, a further quantity of acetyl chloride (0.04 mmol) and diisopropylethylamine (0.1 mmol) were added to the reaction mixture. After 3.5 h the reaction mixture was applied to a SPE cartridge (aminopropyl, 1 g) and the cartridge was eluted sequentially with chlororm, ethyl acetate and methanol. Fractions containing the desired product were combined and blown down under nitrogen. The resulting residue was further purified on a SPE cartridge (silica, 1 g) eluting with a gradient of 30-100% ethyl acetate in petroleum ether to afford Example 175 LCMS showed MH$^+$=454, T$_{RET}$=2.79 min.

Example 176

1-Ethyl-5-(3-{[1-(3-methylbutanoyl)-4-piperidinyl]methyl}-1,2,4-oxadiazol-5-yl)-N-(tetrahydro-2H-pyran-4-yl)-1H-pyrazolo[3,4-b]pyridin-4-amine

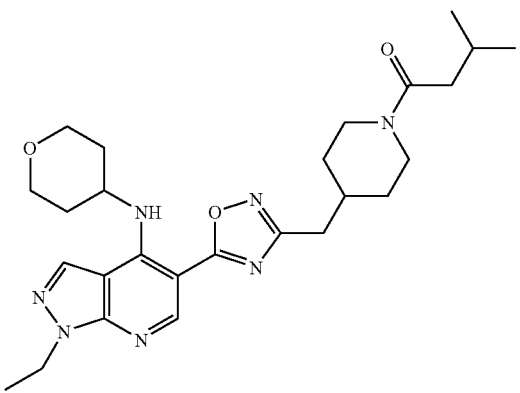

Isovaleryl chloride (0.04 mmol) was added to a stirred solution of Intermediate 125 (0.033 mmol) and diisopropylethylamine (0.1 mmol) in chloroform (1 ml) at room temperature. After stirring at room temperature for 1.5 h, the reaction mixture was applied to a SPE cartridge (aminopropyl, 1 g) and the cartridge was eluted sequentially with chloroform, ethyl acetate and methanol. Fractions containing the desired product were combined and blown down under nitrogen. The resulting residue was further purified on a SPE cartridge (silica, 1 g) eluting with a gradient of 30-100% ethyl acetate in petroleum ether to afford Example 176. LCMS showed MH$^+$=496, T$_{RET}$=3.17 min.

Example 177

1-Ethyl-5-(3-{[1-(methylsulfonyl)-4-piperidinyl]methyl}-1,2,4-oxadiazol-5-yl)-N-(tetrahydro-2H-pyran-4-yl)-1H-pyrazolo[3,4-b]pyridin-4-amine

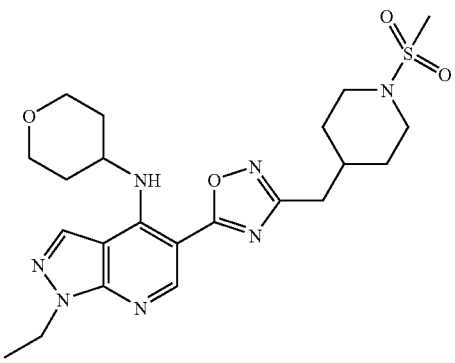

Methanesulphonyl chloride (1.16 mmol) was added to a stirred solution of Intermediate 125 (0.033 mmol) and pyridine (0.5 ml) in chloroform (1 ml) at room temperature. After stirring at room temperature for 31 h, the reaction mixture was applied to a SPE cartridge (aminopropyl, 5 g) and the cartridge was eluted sequentially with chloroform, ethyl acetate and methanol. Fractions containing the desired product were evaporated in vacuo. The resulting residue was further purified on a SPE cartridge (silica, 1 g) eluting with a gradient of 30-100% ethyl acetate in petroleum ether to afford Example 176. LCMS showed MH$^+$=490, T$_{RET}$=2.97 min.

Example 178

Example 178

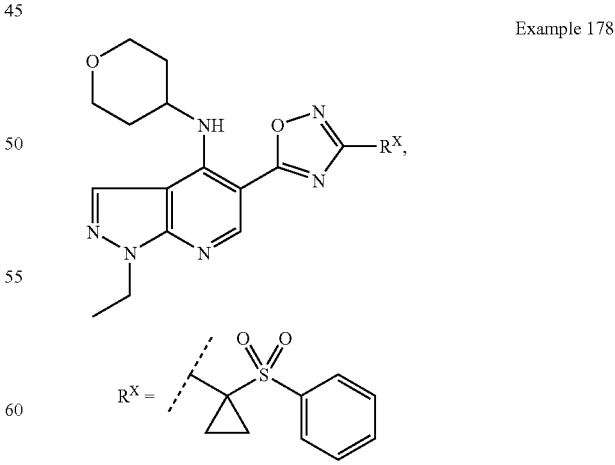

A mixture of Intermediate 16 (0.067 g, 0.26 mmol), amidoxime Intermediate 126 (0.255 g, 1.06 mmol), a solution of sodium ethoxide in EtOH (0.87 ml, 21% solution) and powdered 4 Å molecular sieves (0.68 g) in EtOH (2 ml) were stirred at 82° C. under an atmosphere of nitrogen for 12 hours. The reaction mixture was filtered and the solvent was evaporated in vacuo. The residue was applied to an SPE cartridge (silica, 5 g) and eluted with ethyl acetate: cyclohexane (0 to 70% in 10% increments). Appropriate fractions were combined and evaporated, the residue was purified further by mass directed auto prep HPLC to give Example 178 (0.011 g) LCMS showed MH$^+$=495; T$_{RET}$=3.2 min.

Similarly prepared using the same or similar numbers of moles of reagents and/or volumes of solvents were the following:

| Example Number | R$^X$ | Amidoxime Intermediate number (instead of Intermediate 126) | MH$^+$ | T$_{RET}$ (min) |
|---|---|---|---|---|
| 179 | | 127 | 405 | 3.35 |
| 180 | | 128 | 419 | 3.44 |
| 181 | | 129 | 435 | 3.34 |
| 182 | | 130 | 435 | 3.35 |
| 183 | | 132 | 448 | 3.2 |
| 184 | | 131 | 448 | 3.30 |
| 185 | | 133 | 421 | 3.35 |
| 186 | | 134 | 450 | 2.47 |
| 187 | | 135 | 489 | 3.01 |

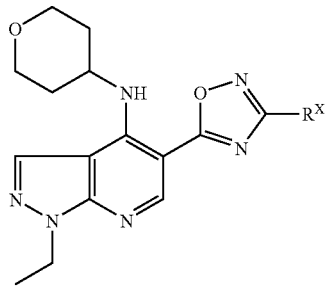

Example 188

1-Ethyl-5-(5-ethyl-1,2,4-oxadiazol-3-yl)-N-(tetrahydro-2H-pyran-4-yl)-1H-pyrazolo[3,4-b]pyridin-4-amine

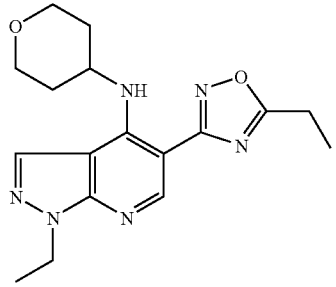

Propionic anhydride (0.015 ml, 0.12 mmol) was added to Intermediate 138 (0.030 g, 0.1 mmol) in glacial acetic acid (1.5 ml). The reaction mixture was stirred at room temperature for 2 hours then heated at 80° C. for 5 hours. The solvent was concentrated in vacuo and the residue applied to an SPE cartridge (silica, 1 g). The cartridge was eluted with cyclo-

Example 189

5-(5-{[4-(Dimethylamino)phenyl]methyl}-1,2,4-oxadiazol-3-yl)-1-ethyl-N-(tetrahydro-2H-pyran-4-yl)-1H-pyrazolo[3,4-b]pyridin-4-amine

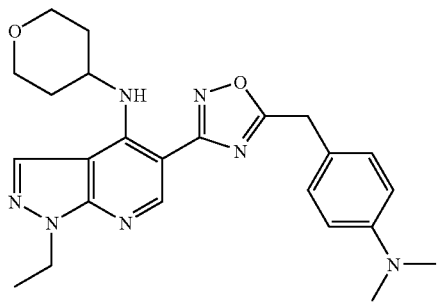

4-(Dimethylamino)phenylacetic acid (0.09 g, 0.504 mmol) and 1-(3-dimethylaminopropyl)-3-ethylcarbodiimide hydrochloride (0.097 g, 0.51 mmol) in dichloromethane (1 ml) were stirred at room temperature for 3 hours. The reaction mixture was concentrated then Intermediate 138 (0.07 g, 0.23 mmol) and diglyme (1 ml) were added. After stirring at 20 C for 18 hour glacial acetic acid (0.07 ml) and additional diglyme (0.5 ml) were added and the mixture heated at 60° C. for 2 hours then at 75° C. for 4 hours. The reaction mixture was applied to an SPE cartridge (SCX, 2 g) and the cartridge eluted with methanol then 10% ammonia in methanol. The methanolic ammonia fractions were evaporated in vacuo and the residue purified by mass directed autoprep HPLC to afford Example 189 as a beige solid (0.004 g). LCMS showed $MH^+$=448; $T_{RET}$=3.24 min.

Example 190

1-Ethyl-5-(5-{[4-(methyloxy)phenyl]methyl}-1,2,4-oxadiazol-3-yl)-N-(tetrahydro-2H-pyran-4-yl)-1H-pyrazolo[3,4-b]pyridin-4-amine

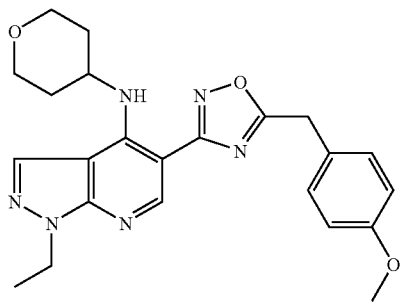

Prepared from Intermediate 138 and 4-methoxyphenylacetic acid using a similar process to that described for Example 189 using similar or the same number of moles of reagents and/or volumes of solvents. LCMS showed $MH^+$=435; $T_{RET}$=3.26 min

Example 191

5-(3,8-Dioxa-1-azaspiro[4.5]dec-1-en-Z-yl)-1-ethyl-N-(tetrahydro-2H-pyran-4-yl)-1H-pyrazolo[3,4-b]pyridin-4-amine

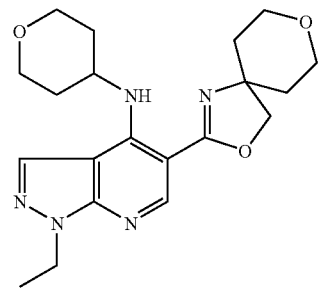

Example 191 was prepared from Intermediate 139 using an analogous method to that for Example 49. LCMS showed $MH^+$=386, $T_{RET}$=2.71 min.

The invention claimed is:
1. A compound of formula (I) or a salt thereof:

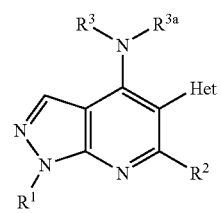

wherein:
$R^1$ is $C_{1-4}$alkyl, $C_{1-3}$fluoroalkyl or —$(CH_2)_2$OH;
$R^2$ is a hydrogen atom (H), methyl or $C_1$fluoroalkyl;
$R^3$ is optionally substituted branched $C_{3-6}$alkyl, optionally substituted $C_{3-8}$cycloalkyl, optionally substituted mono-unsaturated-$C_{5-7}$cycloalkenyl, optionally substituted phenyl, or an optionally substituted heterocyclic group of sub-formula (aa), (bb) or (cc):

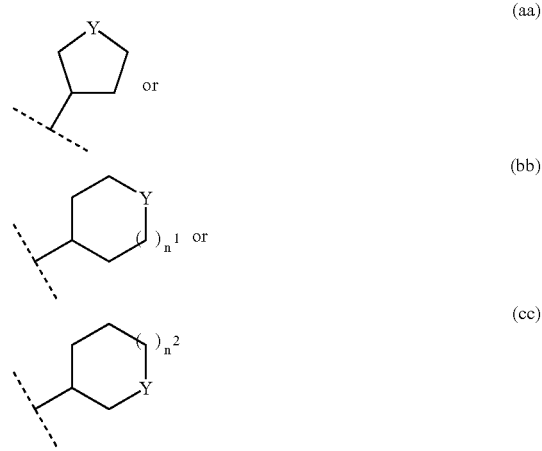

in which $n^1$ and $n^2$ independently are 1 or 2; and Y is O, S, $SO_2$, or $NR^4$; where $R^4$ is a hydrogen atom (H), $C_{1-2}$alkyl, $C_{1-2}$fluoroalkyl, $CH_2C(O)NH_2$, $C(O)NH_2$, $C(O)$—$C_{1-2}$alkyl, or $C(O)$—$C_1$fluoroalkyl;

wherein in $R^3$ the optionally substituted branched $C_{3-6}$alkyl is optionally substituted with one or two substituents being oxo (=O), OH, $C_{1-2}$alkoxy or $C_{1-2}$fluoroalkoxy; and wherein any such substituent is not substituted at the $R^3$ carbon atom attached (bonded) to the —NH— group of formula (I);

wherein in $R^3$ the phenyl is optionally substituted with one substituent being fluoro, chloro, $C_{1-2}$alkyl, $C_{1-2}$fluoroalkyl, $C_{1-2}$alkoxy, $C_{1-2}$fluoroalkoxy or cyano, or with two or three fluoro substituents;

wherein in $R^3$ the $C_{3-8}$cycloalkyl or the heterocyclic group of sub-formula (aa), (bb) or (cc) is optionally substituted with one or two substituents independently being oxo (=O); OH; $C_{1-2}$alkoxy; $C_{1-2}$fluoroalkoxy; $NHR^{21}$ wherein $R^{21}$ is a hydrogen atom (H) or $C_{1-4}$ straight-chain alkyl; $C_{1-2}$alkyl; $C_{1-2}$fluoroalkyl; —$CH_2OH$; —$CH_2CH_2OH$; —$CH_2NHR^{22}$ wherein $R^{22}$ is H or $C_{1-2}$alkyl; —$C(O)OR^{23}$ wherein $R^{23}$ is H or $C_{1-2}$alkyl; —$C(O)NHR^{24}$ wherein $R^{24}$ is H or $C_{1-2}$alkyl; —$C(O)R^{25}$ wherein $R^{25}$ is $C_{1-2}$alkyl; fluoro; hydroxyimino (=N—OH); or ($C_{1-4}$alkoxy)imino (=N—$OR^{26}$ where $R^{26}$ is $C_{1-4}$alkyl); and wherein any OH, alkoxy, fluoroalkoxy or $NHR^{21}$ substituent is not substituted at the $R^3$ ring carbon attached (bonded) to the —NH— group of formula (I) and is not substituted at either $R^3$ ring carbon bonded to the Y group of the heterocyclic group (aa), (bb) or (cc);

and wherein, when $R^3$ is optionally substituted mono-unsaturated-$C_{5-7}$cycloalkenyl, then the cycloalkenyl is optionally substituted with one or two substituents independently being fluoro or $C_{1-2}$alkyl provided that if there are two substituents then they are not both $C_2$alkyl, and the $R^3$ ring carbon bonded to the —NH— group of formula (I) does not partake in the cycloalkenyl double bond;

and $R^{3a}$ is a hydrogen atom (H) or straight-chain $C_{1-3}$alkyl;

provided that when $R^{3a}$ is $C_{1-3}$alkyl then $R^3$ is tetrahydro-2H-pyran-4-yl, cyclohexyl (i.e. unsubstituted), 3-hydroxy-cyclohexyl, 4-oxo-cyclohexyl or 4-(hydroxyimino)cyclohexyl;

and wherein Het is of sub-formula (i), (ii), (iii), (iv) or (v):

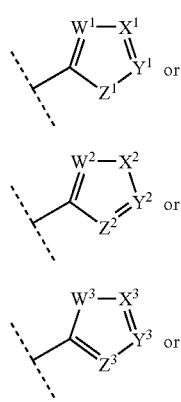

(i)

(ii)

(iii)

-continued

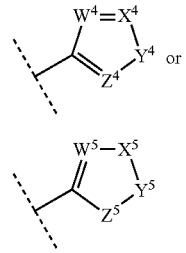

(iv)

(v)

wherein:
$W^1$, $W^2$, $W^4$ and $W^5$ is N; and $W^3$ is $NR^W$;
$X^1$, $X^3$ and $X^4$ is N or $CR^X$; $X^2$ is O, S or $NR^X$; and $X^5$ is $CR^{X1}R^{X2}$ or $CR^{X3}R^{X4}$;
$Y^1$, $Y^2$ and $Y^3$ is $CR^Y$ or N; $Y^4$ is O, S or $NR^Y$; and $Y^5$ is $CR^{Y1}R^{Y2}$;
$Z^1$ and $Z^5$ is O, S or $NR^Z$; and $Z^2$, $Z^3$ and $Z^4$ is N or $CR^Z$;

wherein:
$R^W$ is a hydrogen atom (H) or $C_{1-2}$alkyl;
$R^X$, $R^{X2}$, $R^Y$ and $R^{Y2}$ independently are:
  a hydrogen atom (H);
  $C_{1-8}$alkyl;
  $C_{3-6}$cycloalkyl optionally substituted by one or two $C_{1-2}$alkyl groups and/or by one oxo (=O) group;
  —$(CH_2)_n^{2a}$—$C_{3-6}$cycloalkyl optionally substituted, in the —$(CH_2)_n^{2a}$-moiety or in the $C_{3-6}$cycloalkyl moiety, by a $C_{1-2}$alkyl group, or optionally substituted in the $C_{3-6}$cycloalkyl moiety by a —$CH_2C(O)NHC_{1-2}$alkyl group, wherein $n^{2a}$ is 1, 2 or 3;
  —$(CH_2)_n^3$—$S(O)_2$—$R^5$, —$CH(C_{1-2}alkyl)$-$S(O)_2$—$R^5$, —$CMe_2$-$S(O)_2$—$R^5$, or $C_{3-5}$cycloalkyl substituted at the connecting carbon atom by —$S(O)_2$—$R^5$, wherein $n^3$ is 1 or 2;
  and $R^5$ is $C_{1-4}$alkyl, —$NR^{15}R^{16}$, phenyl, carbon-linked-pyridinyl or benzyl (wherein the phenyl and benzyl are independently optionally substituted on the aromatic ring by one or two substituents independently being fluoro, chloro, $C_{1-2}$alkyl, $C_1$fluoroalkyl, $C_{1-2}$alkoxy, $C_1$fluoroalkoxy or OH, and wherein the pyridinyl is optionally substituted by one methyl, methoxy or OH (including any tautomer thereof));
  wherein $R^{15}$ is H, $C_{1-4}$alkyl, phenyl, benzyl (wherein the phenyl and benzyl are independently optionally substituted on the aromatic ring by one or two substituents independently being fluoro, chloro, $C_{1-2}$alkyl, $C_1$fluoroalkyl, $C_{1-2}$alkoxy or $C_1$fluoroalkoxy), CH(Me)Ph, or carbon-linked-pyridinyl optionally substituted by one methyl, methoxy or OH (including any tautomer thereof);
  and $R^{16}$ is H or $C_{1-2}$alkyl;
  or wherein $R^{15}$ and $R^{16}$ together are —$(CH_2)_n^{3a}$—$X^{3a}$—$(CH_2)_n^{3b}$— in which $n^{3a}$ and $n^{3b}$ independently are 2 or 3 and $X^{3a}$ is a bond, —$CH_2$—, O, or $NR^{8a}$ wherein $R^{8a}$ is H or $C_{1-2}$alkyl, acetyl, —$S(O)_2Me$ or phenyl, and wherein the ring formed by $NR^{15}R^{16}$ is optionally substituted on a ring carbon by one or two substituents independently being methyl or oxo (=O);
  —$(CH_2)_n^4$—$NR^6R^7$, —$CH(C_{1-2}alkyl)$-$NR^6R^7$, —$CMe_2$-$NR^6R^7$, or $C_{3-5}$cycloalkyl substituted at the connecting carbon atom by —$NR^6R^7$, wherein $n^4$ is 0, 1, 2 or 3;

and $R^6$ and $R^7$ independently are H, $C_{1-6}$alkyl, $C_{3-6}$cycloalkyl, —$CH_2$—$C_{3-6}$cycloalkyl, —$C(O)R^{17}$, —$S(O)_2R^{18}$, phenyl, benzyl (wherein the phenyl and benzyl are independently optionally substituted on the aromatic ring by one or two substituents independently being fluoro, chloro, $C_{1-2}$alkyl, $C_1$fluoroalkyl, $C_{1-2}$alkoxy or $C_1$fluoroalkoxy), or carbon-linked-pyridinyl optionally substituted by one methyl, methoxy or OH (including any tautomer thereof);

and wherein $R^{17}$ and $R^{18}$ independently are $C_{1-6}$alkyl, $C_{3-6}$cycloalkyl, optionally substituted 5-membered heteroaryl being furyl (furanyl) or 1,3-oxazolyl or isoxazolyl or oxadiazolyl or thienyl or 1,3-thiazolyl or isothiazolyl or pyrrolyl or imidazolyl or pyrazolyl (all independently optionally substituted by one oxo and/or one or two methyl), or phenyl or benzyl (wherein the phenyl and benzyl are independently optionally substituted on the aromatic ring by one or two substituents independently being fluoro, chloro, $C_{1-2}$alkyl, $C_1$fluoroalkyl, $C_{1-2}$alkoxy, $C_1$fluoroalkoxy or OH), or carbon-linked-pyridinyl optionally substituted by one methyl, methoxy or OH (including any tautomer thereof);

or $R^6$ and $R^7$ together are —$(CH_2)_{n^5}$—$X^5$—$(CH_2)_{n^6}$— in which $n^5$ and $n^6$ independently are 2 or 3 and $X^5$ is a bond, —$CH_2$—, O, or $NR^8$ wherein $R^8$ is H, $C_{1-2}$alkyl, acetyl, —$S(O)_2Me$ or phenyl, and wherein the ring formed by $NR^6R^7$ is optionally substituted on a ring carbon by one or two substituents independently being methyl or oxo (=O);

—$(CH_2)_{n^7}$—O—$R^9$; wherein $n^7$ is 0, 1, 2 or 3 and $R^9$ is H, $C_{1-6}$alkyl, $C_{3-6}$cycloalkyl, —$CH_2$—$C_{3-6}$cycloalkyl, —$C(O)R^{17}$, phenyl, or benzyl (wherein the phenyl and benzyl are independently optionally substituted on the aromatic ring by one or two of fluoro, chloro, $C_{1-2}$alkyl, $C_1$fluoroalkyl, $C_{1-2}$alkoxy or $C_1$fluoroalkoxy); wherein $n^7$ is 0 only when the —$(CH_2)_{n^7}$—O—$R^9$ is bonded to a carbon atom in the Het ring; and wherein $n^7$ is not 0 when Het is of sub-formula (v) (i.e. $n^7$ is not 0 for $R^{X2}$ and for $R^{Y2}$);

—$(CH_2)_{n^{11}}$—$C(O)$—$NR^{10}R^{11}$, —$CH(C_{1-2}$alkyl)-$C(O)$—$NR^{10}R^{11}$, —$CMe_2$-$C(O)$—$NR^{10}R^{11}$, or $C_{3-5}$cycloalkyl substituted at the connecting carbon atom by —$C(O)$—$NR^{10}R^{11}$, wherein $n^{11}$ is 0, 1 or 2; and wherein $R^{10}$ and $R^{11}$ independently are H; $C_{1-6}$alkyl; $C_{1-4}$fluoroalkyl; $C_{2-4}$alkyl substituted by one OH or —$OC_{1-2}$alkyl other than at the connection point; $C_{3-6}$cycloalkyl optionally substituted by one or two methyl groups; —$CH_2$—$C_{3-6}$cycloalkyl optionally substituted by one methyl, $NH_2$ or NHMe group; —$(CH_2)_{n^{17}}$-Het$^2$; carbon-linked-pyridinyl optionally substituted by one methyl, methoxy or OH (including any tautomer thereof); phenyl; benzyl; or —$CH(C_{1-2}$alkyl)Ph [wherein the phenyl, benzyl and —$CH(C_{1-2}$alkyl)Ph are independently optionally substituted on the aromatic ring by one or two substituents independently being: fluoro, chloro, $C_{1-2}$alkyl, $C_1$fluoroalkyl, $C_{1-2}$alkoxy, $C_1$fluoroalkoxy, OH, —$NR^{10a}R^{10b}$ (wherein $R^{10a}$ is H or $C_{1-2}$alkyl and $R^{10b}$ is H, $C_{1-2}$alkyl, —$C(O)$—$C_{1-2}$alkyl or —$S(O)_2$—$C_{1-2}$alkyl), —$C(O)$—$NR^{10c}R^{10d}$ (wherein $R^{10c}$ and $R^{10d}$ independently are H or $C_{1-2}$alkyl), or —$S(O)_2$—$R^{10e}$ (wherein $R^{10e}$ is $C_{1-2}$alkyl, $NH_2$, NHMe or $NMe_2$)];

wherein $n^{17}$ is 0, 1 or 2 and wherein Het$^2$ is a 4-, 5- or 6-membered saturated heterocyclic ring containing one O or S ring atom or one $NR^{27}$ ring group wherein $R^{27}$ is H, $C_{1-2}$alkyl, —$C(O)Me$, or —$S(O)_2$ Me, wherein the Het$^2$ ring is optionally substituted on a ring carbon by one or two substituents independently being methyl or oxo (=O);

and wherein when $n^{17}$ is 2 then the Het$^2$ ring can optionally contain one additional ring N atom at the Het$^2$ ring position bonded to the —$(CH_2)_{n^{17}}$— moiety; provided that, when Het$^2$ contains one O or S or $NR^{27}$ ring atom/group and one additional ring N atom, then the O/S/$NR^{27}$ ring atom/group and the one additional ring N atom are not directly bonded to each other, and are separated by more than one carbon atom;

or $R^{10}$ and $R^{11}$ together are —$(CH_2)_{n^8}$—$X^6$—$(CH_2)_{n^9}$— in which $n^8$ and $n^9$ independently are 2 or 3 and $X^6$ is a bond, —$CH_2$—, O, or $NR^{12}$ wherein $R^{12}$ is H, $C_{1-2}$alkyl, acetyl, —$S(O)_2Me$ or phenyl, and wherein the ring formed by $NR^{10}R^{11}$ is optionally substituted on a ring carbon by one or two substituents independently being methyl or oxo (=O);

—$(CH_2)_{n^{12}}$—$C(O)$—$OR^{13}$ wherein $n^{12}$ is 0, 1 or 2; and wherein $R^{13}$ is H, $C_{1-6}$alkyl, $C_{3-6}$cycloalkyl, —$CH_2$—$C_{3-6}$cycloalkyl, phenyl, or benzyl (wherein the phenyl and benzyl are independently optionally substituted on the aromatic ring by one or two of (independently) fluoro, chloro, $C_{1-2}$alkyl, $C_1$fluoroalkyl, $C_{1-2}$alkoxy or $C_1$fluoroalkoxy);

—$(CH_2)_{n^{13}}$—$C(O)$—$R^{13a}$ wherein $n^{13}$ is 0, 1 or 2; and wherein $R^{13a}$ is a hydrogen atom (H), $C_{1-6}$alkyl, $C_{1-2}$fluoroalkyl, $C_{3-6}$cycloalkyl, —$CH_2$—$C_{3-6}$cycloalkyl, benzyl, or phenyl; wherein the phenyl and benzyl are independently optionally substituted on the aromatic ring by one or two of (independently) fluoro, chloro, $C_{1-2}$alkyl, $C_1$fluoroalkyl, $C_{1-2}$alkoxy or $C_1$fluoroalkoxy;

—$(CH_2)_{n^{14}}$-Het$^1$, —$CH(C_{1-2}$alkyl)-Het$^1$, —$CMe_2$-Het$^1$, or $C_{3-5}$cycloalkyl substituted at the connecting carbon atom by Het$^1$, wherein $n^{14}$ is 0, 1 or 2 and wherein Het$^1$ is a 4-, 5-, 6- or 7-membered saturated heterocyclic ring;

wherein said heterocyclic ring Het$^1$ contains one O or S ring atom and/or one $NR^{14}$ ring group wherein $R^{14}$ is H, $C_{1-4}$alkyl, $C_{3-6}$cycloalkyl, benzyl, phenyl, —$C(O)R^{19}$, or —$S(O)_2R^{19}$;

wherein $R^{19}$, independent of any other $R^{19}$, is $C_{1-6}$alkyl, $C_{3-6}$cycloalkyl, thienyl, furyl (furanyl), or phenyl or benzyl; wherein the phenyl and benzyl are independently optionally substituted by one or two of (independently) fluoro, methyl or methoxy;

and wherein said heterocyclic ring Het$^1$ is optionally substituted (at a position or positions other than any $NR^{14}$ position) by one or two oxo (=O) and/or one $C_{1-4}$alkyl substituents;

provided that, when the heterocyclic ring Het$^1$ contains one O or S ring atom and one $NR^{14}$ ring group then: (a) the O/S ring atom and the $NR^{14}$ ring group are not directly bonded to each other, and (b) the O/S ring atom and the $NR^{14}$ ring group are separated by more than one carbon atom unless Het$^1$ contains an —$NR^{14}$—$C(O)$—O— or —$NR^{14}$—$C(O)$—S— moiety as part of the ring; or —(CH$_2$)$_n^{10}$—Ar, —CH(C$_{1-2}$alkyl)-Ar, —CMe$_2$—Ar, or C$_{3-5}$cycloalkyl substituted at the connecting carbon atom by Ar, wherein n$^{10}$ is 0, 1 or 2 and (i) Ar is phenyl optionally substituted by one or two substituents independently being fluoro, chloro, bromo, C$_{1-2}$alkyl, C$_{1-2}$fluoroalkyl, C$_{1-2}$alkoxy, C$_{1-2}$fluoroalkoxy, OH, —NR$^{11a}$R$^{11b}$ (wherein R$^{11a}$ is H or C$_{1-2}$alkyl and R$^{11b}$ is H, C$_{1-2}$alkyl, —C(O)—C$_{1-2}$alkyl or —S(O)$_2$—C$_{1-2}$alkyl), cyano, —C(O)—NR$^{11c}$R$^{11d}$ (wherein R$^{1c}$ and R$^{11d}$ independently are H or C$_{1-2}$alkyl), —C(O)—OR$^{11e}$ wherein R$^{11e}$ is H or C$_{1-2}$alkyl, or —S(O)$_2$—R$^{11f}$ (wherein R$^{11f}$ is C$_{1-2}$alkyl, NH$_2$, NHMe or NMe$_2$); or the phenyl Ar is optionally substituted at two adjacent Ar ring atoms by the two ends of a chain which is: —(CH$_2$)$_4$—, —(CH$_2$)$_3$—, or —CH=CH—CH=CH—; or (ii) Ar is an optionally substituted 5- or 6-membered heterocyclic aromatic ring containing 1, 2, 3 or 4 heteroatoms selected from O, N or S; and wherein when the heterocyclic aromatic ring Ar contains 2, 3 or 4 heteroatoms, one is selected from O, N and S and the remaining heteroatom(s) are N; and wherein the heterocyclic aromatic ring Ar is optionally substituted by one or two groups independently being C$_{1-4}$alkyl or OH (including any keto tautomer of an OH-substituted aromatic ring), or the heterocyclic aromatic ring Ar is optionally substituted at two adjacent Ar ring atoms by the two ends of a chain which is: —(CH$_2$)$_4$—, —(CH$_2$)$_3$—, or —CH=CH—CH=CH—;

R$^{X1}$ and R$^{Y1}$ independently are a hydrogen atom (H), C$_{1-2}$alkyl or C$_1$fluoroalkyl;

R$^{X3}$ and R$^{X4}$ together are —(CH$_2$)$_n^{15}$—X$^7$—(CH$_2$)$_n^{16}$— wherein n$^{15}$ and n$^{16}$ independently are 1 or 2 and X$^7$ is a bond, —CH$_2$—, O, or NR$^{X5}$ wherein R$^{X5}$ is H, C$_{1-2}$alkyl, acetyl or —S(O)$_2$Me; and R$^Z$ is a hydrogen atom (H) or C$_{1-2}$alkyl, provided that:

when R$^3$ is the heterocyclic group of sub-formula (bb), n$^1$ is 1, and Y is NR$^4$, then R$^4$ is not C$_{1-2}$alkyl, C$_{1-2}$fluoroalkyl or CH$_2$C(O)NH$_2$.

2. A compound of formula (IA) or a salt thereof:

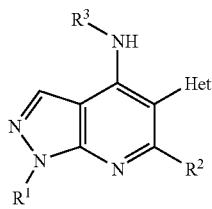

(IA)

wherein:

R$^1$ is C$_{1-4}$alkyl, C$_{1-3}$fluoroalkyl or —(CH$_2$)$_2$OH;

R$^2$ is a hydrogen atom (H), methyl or C$_1$fluoroalkyl;

R$^3$ is optionally substituted branched C$_{3-6}$alkyl, optionally substituted C$_{3-8}$cycloalkyl, optionally substituted phenyl, or an optionally substituted heterocyclic group of sub-formula (aa), (bb) or (cc):

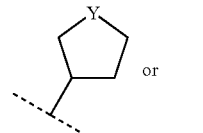
(aa)

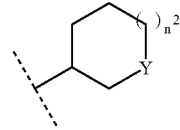
(bb)

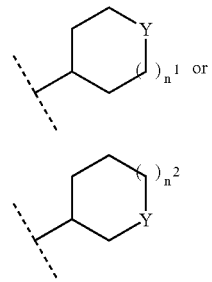
(cc)

in which n$^1$ and n$^2$ independently are 1 or 2; and Y is O, S, SO$_2$, or NR$^4$; where R$^4$ is a hydrogen atom (H), C$_{1-2}$alkyl, C$_{1-2}$fluoroalkyl, CH$_2$C(O)NH$_2$, C(O)NH$_2$, C(O)—C$_{1-2}$alkyl, or C(O)—C$_1$fluoroalkyl;

wherein in R$^3$ the optionally substituted branched C$_{3-6}$alkyl is optionally substituted with one or two substituents being oxo (=O), OH, C$_{1-2}$alkoxy or C$_{1-2}$fluoroalkoxy; and wherein any such substituent is not substituted at the R$^3$ carbon atom attached (bonded) to the —NH— group of formula (IA);

wherein in R$^3$ the phenyl is optionally substituted with one substituent being fluoro, chloro, C$_{1-2}$alkyl, C$_{1-2}$fluoroalkyl, C$_{1-2}$alkoxy, C$_{1-2}$fluoroalkoxy or cyano;

wherein in R$^3$ the C$_{3-8}$cycloalkyl or the heterocyclic group of sub-formula (aa), (bb) or (cc) is optionally substituted with one or two substituents being oxo (=O), OH, C$_{1-2}$alkoxy, C$_{1-2}$fluoroalkoxy, or C$_{1-2}$alkyl; and wherein any OH, alkoxy or fluoroalkoxy substituent is not substituted at the R$^3$ ring carbon attached (bonded) to the —NH— group of formula (IA) and is not substituted at either R$^3$ ring carbon bonded to the Y group of the heterocyclic group (aa), (bb) or (cc);

and wherein Het is of sub-formula (i), (ii), (iii), (iv) or (v):

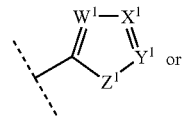
(i)

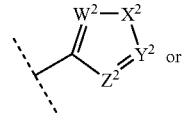
(ii)

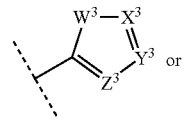
(iii)

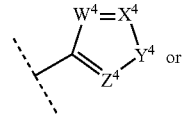
(iv)

-continued

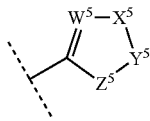

(v)

wherein:
$W^1$, $W^2$, $W^4$ and $W^5$ is N; and $W^3$ is $NR^W$;
$X^1$, $X^3$ and $X^4$ is N or $CR^X$; $X^2$ is O, S or $NR^X$; and $X^5$ is $CR^{X1}R^{X2}$;
$Y^1$, $Y^2$ and $Y^3$ is $CR^Y$ or N; $Y^4$ is O, S or $NR^Y$; and $Y^5$ is $CR^{Y1}R^{Y2}$;
$Z^1$ and $Z^5$ is O, S or $NR^Z$; and $Z^2$, $Z^3$ and $Z^4$ is N or $CR^Z$;
wherein:
$R^W$ is a hydrogen atom (H) or $C_{1-2}$alkyl;
$R^X$, $R^{X2}$, $R^Y$ and $R^{Y2}$ independently are:
  a hydrogen atom (H);
  $C_{1-8}$alkyl;
  $C_{3-6}$cycloalkyl optionally substituted by a $C_{1-2}$alkyl group;
  —$(CH_2)_n{}^{2a}$—$C_{3-6}$cycloalkyl optionally substituted, in the —$(CH_2)_n{}^{2a}$-moiety or in the $C_{3-6}$cycloalkyl moiety, by a $C_{1-2}$alkyl group, wherein $n^{2a}$ is 1, 2 or 3;
  —$(CH_2)_n{}^3$—$SO_2$—$R^5$ wherein $n^3$ is 1 or 2 and $R^5$ is $C_{1-3}$alkyl or —NH—$C_{1-2}$alkyl or phenyl;
  —$(CH_2)_n{}^4$—$NR^6R^7$ wherein $n^4$ is 0, 1, 2 or 3, and $R^6$ and $R^7$ independently are H, $C_{1-6}$alkyl, $C_{3-6}$cycloalkyl, —$CH_2$—$C_{3-6}$cycloalkyl, —$C(O)$—$C_{1-2}$alkyl, —$SO_2$—$C_{1-2}$alkyl, phenyl, or benzyl (wherein the phenyl or benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy); or $R^6$ and $R^7$ together are —$(CH_2)_n{}^5$—$X^5$—$(CH_2)_n{}^6$— in which $n^5$ and $n^6$ independently are 2 and $X^5$ is a bond, —$CH_2$—, O, or $NR^8$ wherein $R^8$ is H or $C_{1-2}$alkyl;
  —$(CH_2)_n{}^7$—O—$R^9$; wherein $n^7$ is 0, 1, 2 or 3 and $R^9$ is H or $C_{1-6}$alkyl; wherein $n^7$ is 0 only when the —$(CH_2)_n{}^7$—O—$R^9$ is bonded to a carbon atom in the Het ring;
  and wherein $n^7$ is not 0 when Het is of sub-formula (v) (i.e. $n^7$ is not 0 for $R^{X2}$ and for $R^{Y2}$);
  —$C(O)$—$NR^{10}R^{11}$ wherein $R^{10}$ and $R^{11}$ independently are H, $C_{1-6}$alkyl, $C_{3-6}$cycloalkyl, —$CH_2$—$C_{3-6}$cycloalkyl, phenyl, or benzyl (wherein the phenyl or benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy); or $R^{10}$ and $R^{11}$ together are —$(CH_2)_n{}^8$—$X^6$—$(CH_2)_n{}^9$— in which $n^8$ and $n^9$ independently are 2 or 3 and $X^6$ is a bond, —$CH_2$—, O, or $NR^{12}$ wherein $R^{12}$ is H or $C_{1-2}$alkyl;
  —$C(O)$—$OR^{13}$ wherein $R^{13}$ is H, $C_{1-6}$alkyl, $C_{3-6}$cycloalkyl, —$CH_2$—$C_{3-6}$cycloalkyl, phenyl, or benzyl (wherein the phenyl or benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy);
  —$C(O)$—$R^{13a}$ wherein $R^{13a}$ is a hydrogen atom (H), $C_{1-6}$alkyl, $C_{1-2}$fluoroalkyl, $C_{3-6}$cycloalkyl, —$CH_2$—$C_{3-6}$cycloalkyl, benzyl, or phenyl; wherein the phenyl or benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy;
  a 4-, 5-, 6- or 7-membered saturated heterocyclic ring containing one O ring atom or one $NR^{14}$ ring group wherein $R^{14}$ is H or $C_{1-4}$alkyl, said heterocyclic ring being optionally substituted (at a position or positions other than any $NR^{14}$ position) by one oxo (=O) and/or one $C_{1-4}$alkyl substituent; or
  —$(CH_2)_n{}^{10}$—Ar wherein $n^{10}$ is 0, 1 or 2 and
    (i) Ar is phenyl optionally substituted by one or two substituents being fluoro, chloro, $C_{1-2}$alkyl, $C_{1-2}$fluoroalkyl, $C_{1-2}$alkoxy, $C_{1-2}$fluoroalkoxy or cyano; or
    (ii) Ar is an optionally substituted 5- or 6-membered heterocyclic aromatic ring containing 1, 2 or 3 heteroatoms selected from O, N or S; and wherein when the heterocyclic aromatic ring Ar contains 2 or 3 heteroatoms, one is selected from O, N and S and the remaining heteroatom(s) are N; and wherein the heterocyclic aromatic ring Ar is optionally substituted by one or two $C_{1-4}$alkyl groups;
$R^{X1}$ and $R^{Y1}$ independently are a hydrogen atom (H), $C_{1-2}$alkyl or $C_1$fluoroalkyl; and
$R^Z$ is a hydrogen atom (H) or $C_{1-2}$alkyl;
provided that, when $R^3$ is the heterocyclic group of subformula (bb), $n^1$ is 1, and Y is $NR^4$, then $R^4$ is not $C_{1-2}$alkyl, $C_{1-2}$fluoroalkyl or $CH_2C(O)NH_2$.

3. A compound or salt as claimed in claim 1, wherein $R^{3a}$ is a hydrogen atom (H).

4. A compound or salt as claimed in claim 1, wherein $R^2$ is a hydrogen atom (H) or methyl.

5. A compound or salt as claimed in claim 1, wherein $R^1$ is $C_{1-3}$alkyl, $C_{1-2}$fluoroalkyl or —$CH_2CH_2OH$.

6. A compound or salt as claimed in claim 1, wherein $R^1$ is ethyl, n-propyl, $C_2$fluoroalkyl or —$CH_2CH_2OH$.

7. A compound or salt as claimed in claim 1, wherein $R^1$ is ethyl.

8. A compound or salt as claimed in claim 1, wherein in $R^3$ there is one substituent or no substituent.

9. A compound or salt as claimed in claim 1, wherein, where $R^3$ is optionally substituted branched $C_{3-6}$cycloalkyl or the optionally substituted heterocyclic group of sub-formula (aa), (bb) or (cc).

10. A compound or salt as claimed in claim 7, wherein, $R^3$ is optionally substituted $C_{3-8}$cycloalkyl or the optionally substituted heterocyclic group of sub-formula (aa), (bb) or (cc).

11. A compound or salt as claimed in claim 9, wherein, where $R^3$ is optionally substituted $C_{3-8}$cycloalkyl, then $R^3$ is optionally substituted $C_{6-8}$cycloalkyl.

12. A compound or salt as claimed in claim 11, wherein, where $R^3$ is optionally substituted $C_{3-8}$cycloalkyl, then $R^3$ is optionally substituted cyclohexyl.

13. A compound or salt as claimed in claim 9, wherein, where $R^3$ is optionally substituted $C_{3-8}$cycloalkyl, then the one or two optional substituents is or independently are: oxo (=O); OH; $NHR^{21}$ wherein $R^{21}$ is a hydrogen atom (H); methyl; —$CH_2F$; —$CHF_2$; —$C(O)OR^{23}$ wherein $R^{23}$ is H; fluoro; hydroxyimino (=N—OH); or ($C_{1-2}$alkoxy)imino (=N—$OR^{26}$ where $R^{26}$ is $C_{1-2}$alkyl).

14. A compound or salt as claimed in claim 9, wherein, where $R^3$ is optionally substituted $C_{3-8}$cycloalkyl, then the one or two optional substituents is or independently are OH, oxo (=O) or hydroxyimino (=N—OH).

15. A compound or salt as claimed in claim 9, wherein, where $R^3$ is optionally substituted $C_{3-8}$cycloalkyl, then the one or two optional substituents if present is or are substituent(s) at the 3-, 4- or 5-position(s) of the $R^3$ cycloalkyl ring, wherein the 1-position of the R³ cycloalkyl ring is deemed to be the connection point to the —NH— in formula (I).

16. A compound or salt as claimed in claim 9, wherein, where R³ is optionally substituted C₆cycloalkyl, then R³ is cyclohexyl (i.e. unsubstituted), 3-hydroxy-cyclohexyl (i.e. 3-hydroxycyclohexan-1-yl), 4-oxo-cyclohexyl (i.e. 4-oxocyclohexan-1-yl), 4-(hydroxyimino)cyclohexyl (i.e. 4-(hydroxyimino)cyclohexan-1-yl), 4-($C_{1-2}$alkoxyimino)cyclohexyl, 1-methylcyclohexyl or 3-methylcyclohexyl.

17. A compound or salt as claimed in claim 1, wherein, where R³ is optionally substituted mono-unsaturated-$C_{5-7}$cycloalkenyl, then R³ is optionally substituted mono-unsaturated-$C_6$cycloalkenyl (i.e. optionally substituted mono-unsaturated-cyclohexenyl), and wherein the R³ cycloalkenyl is optionally substituted with one or two substituents independently being fluoro or methyl.

18. A compound or salt as claimed in claim 9, wherein R⁴ is a hydrogen atom (H) or C(O)-Me.

19. A compound or salt as claimed in claim 9, wherein, where R³ is the heterocyclic group of sub-formula (aa), (bb) or (cc), then Y is O.

20. A compound or salt as claimed in claim 9, wherein where R³ is the heterocyclic group of sub-formula (aa), (bb) or (cc), then R³ is the heterocyclic group of sub-formula (bb) and n¹ is 1.

21. A compound or salt as claimed in claim 9, wherein, in R³, the heterocyclic group of sub-formula (aa), (bb) or (cc) is unsubstituted (wherein, where Y is NR⁴, R⁴ is not classified as a substituent).

22. A compound or salt as claimed in claim 9, wherein, in the R³ heterocyclic group of sub-formula (aa), (bb) or (cc), the one or two optional substituents is or are oxo (=O).

23. A compound or salt as claimed in claim 9, wherein when R³ is the heterocyclic group of sub-formula (aa), then Y is not NR⁴, and when R³ is the heterocyclic group of sub-formula (bb) and Y is NR⁴, then R⁴ is not $C_{1-2}$alkyl, $C_{1-2}$fluoroalkyl or $CH_2C(O)NH_2$.

24. A compound or salt as claimed in claim 1, wherein NR³R³ᵃ is of sub-formula (a), (a1), (b), (c), (c1), (c2), (c3), (c4), (c5), (d), (e), (f), (g), (g1), (g2), (g3), (g4), (h), (h1), (i), (j), (k), (k1), (L), (m), (m1), (m2), (m3), (m5), (n), (o), (o1), (o2), (o3), (o4), (o5), (p), (p2), (p3), (p5), (p6), (p7), (p8), (q), (r), (s), (t), (t1) or (t2):

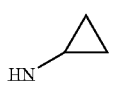 (a)

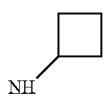 (a1)

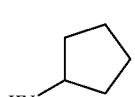 (b)

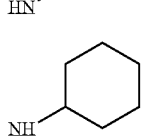 (c)

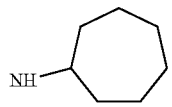 (c1)

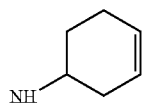 (c2)

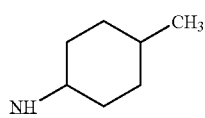 (c3)

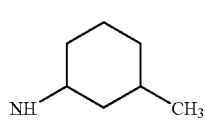 (c4)

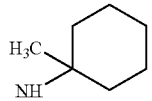 (c5)

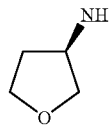 (d)

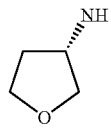 (e)

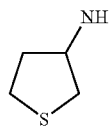 (f)

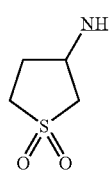 (g)

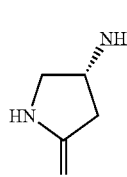 (g1)

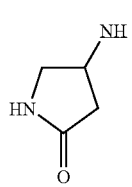 (g2)

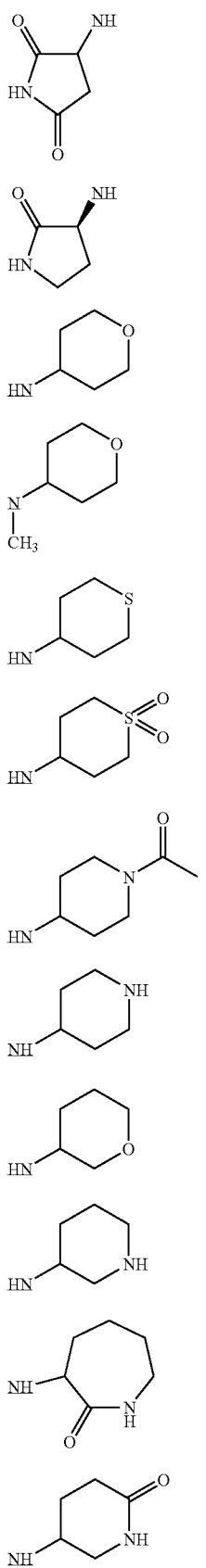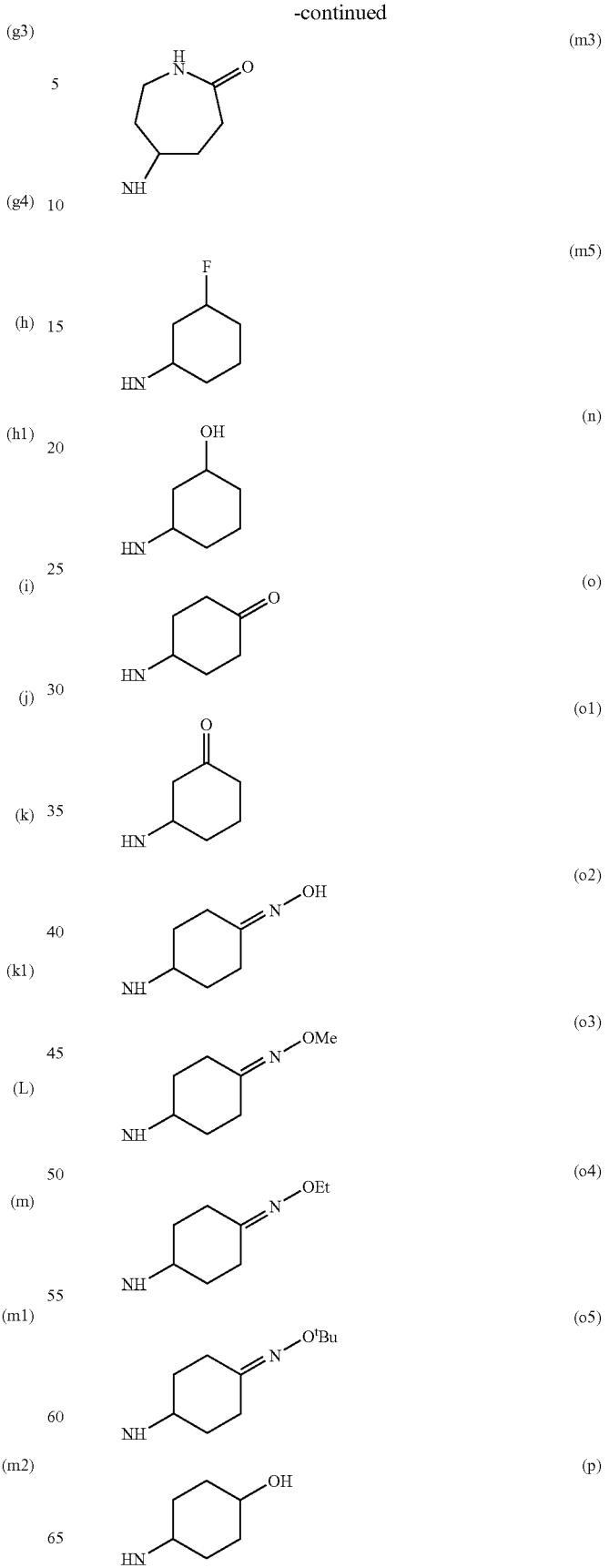

-continued (p2) 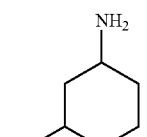

(p3) 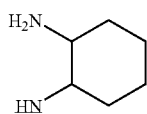

(p5) 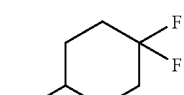

(p6) 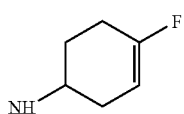

(p7) 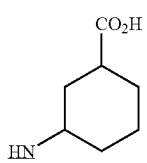

(p8) 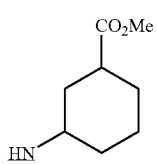

(q) 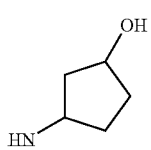

(r) 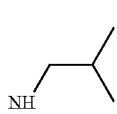

(s) 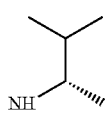

(t) 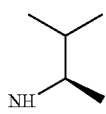

(t1) 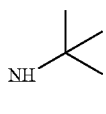

(t2) 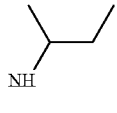

25. A compound or salt as claimed in claim 24, wherein $NR^3R^{3a}$ is of sub-formula (c), (c1), (c4), (c5), (h), (i), (j), (k), (m1), (m2), (n), (o), (o2), (o3), (p2), (p5), (p6), (r), (s) or (t1).

26. A compound or salt as claimed in claim 24, wherein $NR^3R^{3a}$ is of sub-formula (c), (h), (k), (n), (o), (o2) or (s).

27. A compound or salt as claimed in claim 24, wherein $NR^3R^{3a}$ is of sub-formula (a), (b), (c), (d), (e), (f), (g), (h), (i), (j), (k), (L), (m), (n), (o), (p), (q), (r), (s) or (t).

28. A compound or salt as claimed in claim 24, wherein $R^3$ is tetrahydro-2H-pyran-4-yl and $R^{3a}$ is H; that is $NR^3R^{3a}$ is of sub-formula (h).

29. A compound or salt as claimed in claim 1, wherein Het is of sub-formula (i), (ii) or (v).

30. A compound or salt as claimed in claim 29, wherein $Z^1$ and $Z^5$ are O.

31. A compound or salt as claimed in claim 29, wherein Het is of sub-formula (ia), (ib), (ic), (id), (ie), (if), (ig), (va), (vb) or (iia):

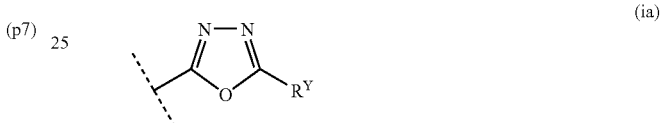 (ia)

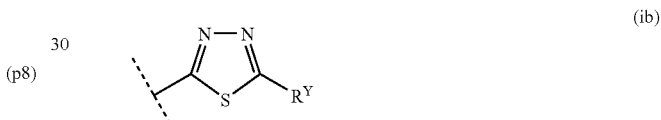 (ib)

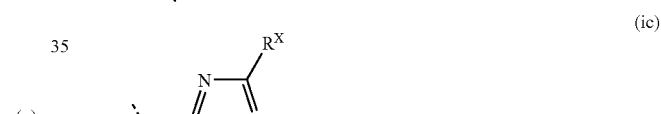 (ic)

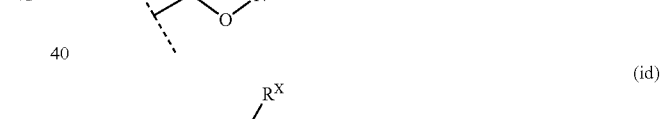 (id)

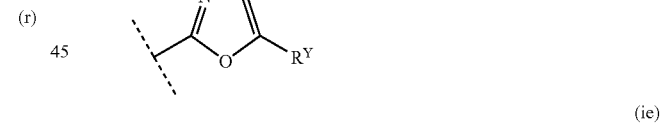 (ie)

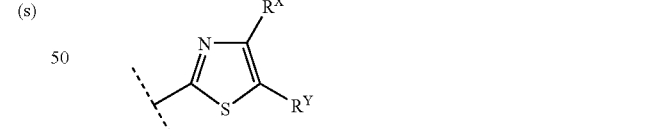 (if)

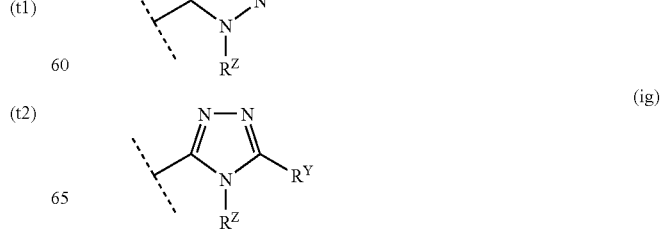 (ig)

-continued

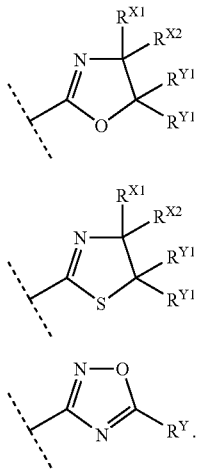

(va)

(vb)

(iia)

32. A compound or salt as claimed in claim 31, wherein Het is of sub-formula (ia), (ib), (ic), or (id).

33. A compound or salt as claimed in claim 31, wherein Het is of sub-formula (ia), (ic), or (id).

34. A compound or salt as claimed in claim 1, wherein $R^W$ and $R^Z$ are a hydrogen atom (H).

35. A compound or salt as claimed in claim 1, wherein for the Het group, one of $R^X$ and $R^Y$ (or $R^{X2}$ and $R^{Y2}$) is as defined herein and the other of $R^X$ and $R^Y$ (or $R^{X2}$ and $R^{Y2}$) is a hydrogen atom (H).

36. A compound or salt as claimed in claim 1, wherein $R^X$, $R^{X2}$, $R^Y$ and $R^{Y2}$ independently are:
a hydrogen atom (H);
$C_{1-8}$alkyl;
optionally substituted $C_{3-6}$cycloalkyl;
optionally substituted —$(CH_2)_n{}^{2a}$—$C_{3-6}$cycloalkyl;
—$(CH_2)_n{}^3$—$S(O)_2$—$R^5$, —CH(Me)-$S(O)_2$—$R^5$, or $C_3$cycloalkyl substituted at the connecting carbon atom by —$S(O)_2$—$R^5$;
—$(CH_2)_n{}^4$—$NR^6R^7$ or —CH(Me)-$NR^6R^7$;
—$(CH_2)_n{}^7$—O—$R^9$;
—$(CH_2)_n{}^{11}$—C(O)—$NR^{10}R^{11}$ or —CH(Me)-C(O)—$NR^{10}R^{11}$;
—$(CH_2)_n{}^{12}$—C(O)—$OR^{13}$;
—$(CH_2)_n{}^{13}$—C(O)—$R^{13a}$;
—$(CH_2)_n{}^{14}$-$Het^1$ or —CH(Me)-$Het^1$; or
—$(CH_2)_n{}^{10}$Ar or —CH(Me)-Ar.

37. A compound or salt as claimed in claim 1, wherein one of $R^X$ and $R^Y$, and for Het of sub-formula (v) one of $R^{X2}$ and $R^{Y2}$, is: —$(CH_2)_n{}^4$—$NR^6R^7$, —CH(Me)-$NR^6R^7$, —$(CH_2)_n{}^{11}$—C(O)—$NR^{10}R^{11}$, —$(CH_2)_n{}^{14}$-$Het^1$, or —$(CH_2)_n{}^{10}$—Ar.

38. A compound or salt as claimed in claim 1, wherein $R^X$, $R^{X2}$, $R^Y$ and $R^{Y2}$ independently are:
$C_{1-6}$alkyl;
optionally substituted $C_{3-6}$cycloalkyl;
—$(CH_2)_n{}^{2a}$—$C_{3-6}$cycloalkyl optionally substituted by a $C_{1-2}$alkyl group; wherein $n^{2a}$ is 1;
—$(CH_2)_n{}^3$—$S(O)_2$—$R^5$ or $C_3$cycloalkyl substituted at the connecting carbon atom by —$S(O)_2$—Ph, wherein $n^3$ is 1 and $R^5$ is $C_{1-4}$alkyl, —$NR^{15}R^{16}$, optionally substituted phenyl or optionally substituted benzyl; wherein $R^{16}$ is H or methyl and $R^{15}$ is H, $C_{1-4}$alkyl or optionally substituted phenyl; or $R^{15}$ and $R^{16}$ together are —$(CH_2)_n{}^{3a}$—$X^{3a}$—$(CH_2)_n{}^{3b}$— wherein $n^{3a}$ and $n^{3b}$ are 2 and $X^{3a}$ is a bond, —$CH_2$—, O, or $NR^{8a}$ wherein $R^{8a}$ is $C_{1-2}$alkyl or acetyl; and the ring formed by $NR^{15}R^{16}$ is not substituted on a ring carbon or is substituted on a ring carbon by one methyl or oxo (=O) substituent;

—$(CH_2)_n{}^4$—$NR^6R^7$, —CH(Me)-$NR^6R^7$ or —$CMe_2$-$NR^6R^7$ wherein $n^4$ is 0 (when the —$(CH_2)_n{}^4$—$NR^6R^7$ is bonded to a carbon atom in the Het ring) or wherein $n^4$ is 1; and wherein $R^6$ is H or $C_{1-4}$alkyl and $R^7$ is H, $C_{1-4}$alkyl, —C(O)$R^{17}$ or —$S(O)_2R^{18}$; or $R^6$ and $R^7$ together are —$(CH_2)_n{}^5$—$X^5$—$(CH_2)_n{}^6$— in which $n^5$ and $n^6$ are 2 and $X^5$ is a bond, —$CH_2$—, O, or $NR^8$, and wherein the ring formed by $NR^6R^7$ is not substituted on a ring carbon or is substituted on a ring carbon by one methyl or oxo (=O) substituent;

—$(CH_2)_n{}^7$—O—$R^9$, wherein $n^7$ is 1 or 2 and $R^9$ is H, $C_{1-4}$alkyl or phenyl;

—$(CH_2)_n{}^{11}$—C(O)—$NR^{10}R^{11}$, —CH(Me)-C(O)—$NR^{10}R^{11}$ or —$CMe_2$-C(O)—$NR^{10}R^{11}$, wherein $n^{11}$ is 0 or 1, and $R^{10}$ is H or $C_{1-6}$alkyl, and $R^{11}$ is: H; $C_{1-6}$alkyl; $C_{3-6}$cycloalkyl optionally substituted by one or two methyl groups; —$CH_2$—$C_{3-6}$cycloalkyl (unsubstituted); —$(CH_2)_n{}^{17}$-$Het^2$; optionally substituted carbon-linked-pyridinyl; optionally substituted phenyl, optionally substituted benzyl; or optionally substituted —CH($C_{1-2}$alkyl)Ph; wherein the phenyl, the benzyl and the —CH($C_{1-2}$alkyl)Ph are independently optionally substituted on the aromatic ring by one or two substituents independently being: fluoro, chloro, $C_{1-2}$alkyl, $C_1$fluoroalkyl, $C_{1-2}$alkoxy, $C_1$fluoroalkoxy, —$NR^{10a}R^{10b}$ (wherein $R^{10a}$ is H or methyl and $R^{10b}$ is H, $C_{1-2}$alkyl, —C(O)Me or —$S(O)_2$Me), —C(O)—$NR^{10c}R^{10d}$ (wherein $R^{10c}$ and $R^{10d}$ independently are H or $C_{1-2}$alkyl), or —$S(O)_2$—$R^{10e}$ (wherein $R^{10e}$ is $C_{1-2}$alkyl, $NH_2$, NHMe or $NMe_2$); and wherein the carbon-linked-pyridinyl is preferably optionally substituted by one OH (including any keto tautomer thereof);

or $R^{10}$ and $R^{11}$ together are —$(CH_2)_n{}^8$—$X^6$—$(CH_2)_n{}^9$— in which $n^8$ and $n^9$ are 2 and $X^6$ is a bond, —$CH_2$—, O, or $NR^{12}$; and wherein the ring formed by $NR^{10}R^{11}$ is not substituted on a ring carbon or is substituted on a ring carbon by one methyl or oxo (=O) substituent;

—$(CH_2)_n{}^{12}$—C(O)—$OR^{13}$, wherein $n^{12}$ is 0 or 1, and $R^{13}$ is H or $C_{1-4}$alkyl;

—$(CH_2)_n{}^{13}$—C(O)—$R^{13a}$, $n^{13}$ is 0 or 1, and $R^{13a}$ is $C_{1-6}$alkyl, $C_{1-2}$fluoroalkyl, $C_{3-6}$cycloalkyl, —$CH_2$—$C_{3-6}$cycloalkyl, benzyl, or phenyl (wherein the phenyl and benzyl are independently optionally substituted on the aromatic ring by one of fluoro, chloro, $C_{1-2}$alkyl, $C_1$fluoroalkyl, $C_{1-2}$alkoxy or $C_1$fluoroalkoxy);

—$(CH_2)_n{}^{14}$-$Het^1$, —CH(Me)-$Het^1$, or —$CMe_2$-$Het^1$, wherein $n^{14}$ is 0 or 1, and $Het^1$ is 4-, 5- or 6-membered heterocyclic ring, and $R^{14}$ is $C_{1-4}$alkyl, C(O)$R^{19}$ or $S(O)_2$ $R^{19}$ wherein $R^{19}$ is $C_{1-4}$alkyl, $C_{3-6}$cycloalkyl, 2-thienyl, furan-2-yl, phenyl (unsubstituted) or benzyl (unsubstituted); or —$(CH_2)_n{}^{10}$—Ar wherein $n^{10}$ is 0 or 1.

39. A compound or salt as claimed in claim 1, which is:
N-cyclopentyl-1-ethyl-5-(5-methyl-1,3,4-oxadiazol-2-yl)-1H-pyrazolo[3,4-b]pyridin-4-amine,
N-cyclopentyl-1-ethyl-5-{5-[(methylsulfonyl)methyl]-1,3,4-oxadiazol-2-yl}-1H-pyrazolo[3,4-b]pyridin-4-amine,
N-cyclopentyl-1-ethyl-5-(5-isopropyl-1,3,4-oxadiazol-2-yl)-1H-pyrazolo[3,4-b]pyridin-4-amine, N-cyclopentyl-1-ethyl-5-(5-methyl-1,3,4-thiadiazol-2-yl)-1H-pyrazolo[3,4-b]pyridin-4-amine,
N-cyclopentyl-1-ethyl-5-{5-[(methylsulfonyl)methyl]-1,3,4-thiadiazol-2-yl}-1H-pyrazolo[3,4-b]pyridin-4-amine,
N-cyclopentyl-1-ethyl-5-(5-isopropyl-1,3,4-thiadiazol-2-yl)-1H-pyrazolo[3,4-b]pyridin-4-amine,
1-ethyl-N-(4-fluorophenyl)-5-(3-methyl-1,2,4-oxadiazol-5-yl)-1H-pyrazolo[3,4-b]pyridin-4-amine,
N-cyclopentyl-5-(1,3-dimethyl-1H-1,2,4-triazol-5-yl)-1-ethyl-1H-pyrazolo[3,4-b]pyridin-4-amine,
1-ethyl-5-(5-isopropyl-1,3,4-oxadiazol-2-yl)-N-tetrahydro-2H-pyran-4-yl-1H-pyrazolo[3,4-b]pyridin-4-amine,
N-cyclopentyl-1-ethyl-5-(5-isopropyl-1,3,4-oxadiazol-2-yl)-1H-pyrazolo[3,4-b]pyridin-4-amine,
1-ethyl-N-isobutyl-5-(5-isopropyl-1,3,4-oxadiazol-2-yl)-1H-pyrazolo[3,4-b]pyridin-4-amine,
1-ethyl-N-isobutyl-5-(5-methyl-1,3,4-oxadiazol-2-yl)-1H-pyrazolo[3,4-b]pyridin-4-amine,
N-cyclohexyl-1-ethyl-5-(5-methyl-1,3,4-oxadiazol-2-yl)-1H-pyrazolo[3,4-b]pyridin-4-amine,
1-ethyl-5-(5-methyl-1,3,4-oxadiazol-2-yl)-N-tetrahydro-2H-pyran-4-yl-1H-pyrazolo[3,4-b]pyridin-4-amine,
N-[(1R)-1,2-dimethylpropyl]-1-ethyl-5-(5-methyl-1,3,4-oxadiazol-2-yl)-1H-pyrazolo[3,4-b]pyridin-4-amine,
N-[(1S)-1,2-dimethylpropyl]-1-ethyl-5-(5-methyl-1,3,4-oxadiazol-2-yl)-1H-pyrazolo[3,4-b]pyridin-4-amine,
5-(5-tert-butyl-1,3,4-oxadiazol-2-yl)-1-ethyl-N-tetrahydro-2H-pyran-4-yl-1H-pyrazolo[3,4-b]pyridin-4-amine,
5-(5-tert-butyl-1,3,4-oxadiazol-2-yl)-N-cyclohexyl-1-ethyl-1H-pyrazolo[3,4-b]pyridin-4-amine,
5-(5-tert-butyl-1,3,4-oxadiazol-2-yl)-N-cyclopentyl-1-ethyl-1H-pyrazolo[3,4-b]pyridin-4-amine,
5-(5-tert-butyl-1,3,4-oxadiazol-2-yl)-1-ethyl-N-isobutyl-1H-pyrazolo[3,4-b]pyridin-4-amine,
5-(5-tert-butyl-1,3,4-oxadiazol-2-yl)-N-[(1S)-1,2-dimethylpropyl]-1-ethyl-1H-pyrazolo[3,4-b]pyridin-4-amine,
5-(5-tert-butyl-1,3,4-oxadiazol-2-yl)-N-[(1R)-1,2-dimethylpropyl]-1-ethyl-1H-pyrazolo[3,4-b]pyridin-4-amine,
1-ethyl-5-{5-[(methylsulfonyl)methyl]-1,3,4-oxadiazol-2-yl}-N-tetrahydro-2H-pyran-4-yl-1H-pyrazolo[3,4-b]pyridin-4-amine,
N-cyclohexyl-1-ethyl-5-{5-[(methylsulfonyl)methyl]-1,3,4-oxadiazol-2-yl}-1H-pyrazolo[3,4-b]pyridin-4-amine,
1-ethyl-N-isobutyl-5-{5-[(methylsulfonyl)methyl]-1,3,4-oxadiazol-2-yl}-1H-pyrazolo[3,4-b]pyridin-4-amine,
N-[(1S)-1,2-dimethylpropyl]-1-ethyl-5-{5-[(methylsulfonyl)methyl]-1,3,4-oxadiazol-2-yl}-1H-pyrazolo[3,4-b]pyridin-4-amine,
N-[(1R)-1,2-dimethylpropyl]-1-ethyl-5-{5-[(methylsulfonyl)methyl]-1,3,4-oxadiazol-2-yl}-1H-pyrazolo[3,4-b]pyridin-4-amine,
1-ethyl-5-(3-methyl-1,2,4-oxadiazol-5-yl)-N-tetrahydro-2H-pyran-4-yl-1H-pyrazolo[3,4-b]pyridin-4-amine,
1-ethyl-5-[3-(methoxymethyl)-1,2,4-oxadiazol-5-yl]-N-tetrahydro-2H-pyran-4-yl-1H-pyrazolo[3,4-b]pyridin-4-amine,
5-{3-[(dimethylamino)methyl]-1,2,4-oxadiazol-5-yl}-1-ethyl-N-tetrahydro-2H-pyran-4-yl-1H-pyrazolo[3,4-b]pyridin-4-amine,
1-ethyl-5-[3-(morpholin-4-ylmethyl)-1,2,4-oxadiazol-5-yl]-N-tetrahydro-2H-pyran-4-yl-1H-pyrazolo[3,4-b]pyridin-4-amine,
5-(5-cyclopropyl-1,3,4-oxadiazol-2-yl)-1-ethyl-N-tetrahydro-2H-pyran-4-yl-1H-pyrazolo[3,4-b]pyridin-4-amine,
N-(1-acetylpiperidin-4-yl)-1-ethyl-5-(5-methyl-1,3,4-oxadiazol-2-yl)-1H-pyrazolo[3,4-b]pyridin-4-amine,
1-ethyl-5-[5-(3-methyloxetan-3-yl)-1,3,4-oxadiazol-2-yl]-N-tetrahydro-2H-pyran-4-yl-1H-pyrazolo[3,4-b]pyridin-4-amine,
1-ethyl-5-{5-[(4-methylpiperazin-1-yl)methyl]-1,3,4-oxadiazol-2-yl}-N-tetrahydro-2H-pyran-4-yl-1H-pyrazolo[3,4-b]pyridin-4-amine,
5-[1-ethyl-4-(tetrahydro-2H-pyran-4-ylamino)-1H-pyrazolo[3,4-b]pyridin-5-yl]-N-isopropyl-1,3,4-oxadiazole-2-carboxamide,
4-{5-[1-ethyl-4-(tetrahydro-2H-pyran-4-ylamino)-1H-pyrazolo[3,4-b]pyridin-5-yl]-1,3,4-oxadiazol-2-yl}-1-methylpyrrolidin-2-one,
1-ethyl-N-tetrahydro-2H-pyran-4-yl-5-(5-tetrahydro-2H-pyran-4-yl-1,3,4-oxadiazol-2-yl)-1H-pyrazolo[3,4-b]pyridin-4-amine,
1-ethyl-5-[5-(morpholin-4-ylmethyl)-1,3,4-oxadiazol-2-yl]-N-tetrahydro-2H-pyran-4-yl-1H-pyrazolo[3,4-b]pyridin-4-amine,
5-[5-(tert-butoxymethyl)-1,3,4-oxadiazol-2-yl]-1-ethyl-N-tetrahydro-2H-pyran-4-yl-1H-pyrazolo[3,4-b]pyridin-4-amine, or
methyl 2-[1-ethyl-4-(tetrahydro-2H-pyran-4-ylamino)-1H-pyrazolo[3,4-b]pyridin-5-yl]-1,3-oxazole-4-carboxylate;
or a salt thereof.

40. A compound or salt as claimed in claim 1, which is:
methyl 2-[1-ethyl-4-(tetrahydro-2H-pyran-4-ylamino)-1H-pyrazolo[3,4-b]pyridin-5-yl]-4,5-dihydro-1,3-oxazole-4-carboxylate,
1-ethyl-5-(4-methyl-4,5-dihydro-1,3-oxazol-2-yl)-N-(tetrahydro-2H-pyran-4-yl)-1H-pyrazolo[3,4-b]pyridin-4-amine,
1-(n-propyl)-5-(5-methyl-1,3,4-oxadiazol-2-yl)-N-(tetrahydro-2H-pyran-4-yl)-1H-pyrazolo[3,4-b]pyridin-4-amine,
1-ethyl-5-[5-(tetrahydrofuran-2-yl)-1,3,4-oxadiazol-2-yl]-N-(tetrahydro-2H-pyran-4-yl)-1H-pyrazolo[3,4-b]pyridin-4-amine,
1-ethyl-5-[5-(dimethylamino)-1,3,4-oxadiazol-2-yl]-N-(tetrahydro-2H-pyran-4-yl)-1H-pyrazolo[3,4-b]pyridin-4-amine,
1-ethyl-5-(5-methyl-1,2,4-triazol-3-yl)-N-(tetrahydro-2H-pyran-4-yl)-1H-pyrazolo[3,4-b]pyridin-4-amine,
N-(1-acetylpiperidin-4-yl)-1-ethyl-5-(3-methyl-1,2,4-oxadiazol-5-yl)-1H-pyrazolo[3,4-b]pyridin-4-amine, or
N-(1-acetylpiperidin-4-yl)-1-ethyl-5-[3-(morpholin-4-ylmethyl)-1,2,4-oxadiazol-5-yl]-1H-pyrazolo[3,4-b]pyridin-4-amine;
or a salt thereof.

41. A compound or salt as claimed in claim 1, which is:
1-ethyl-5-[(4R)-4-phenyl-4,5-dihydro-1,3-oxazol-2-yl]-N-(tetrahydro-2H-pyran-4-yl)-1H-pyrazolo[3,4-b]pyridin-4-amine,
1-ethyl-5-[(4S)-4-phenyl-4,5-dihydro-1,3-oxazol-2-yl]-N-(tetrahydro-2H-pyran-4-yl)-1H-pyrazolo[3,4-b]pyridin-4-amine,
1-ethyl-5-[(4S)-4-(phenylmethyl)-4,5-dihydro-1,3-oxazol-2-yl]-N-(tetrahydro-2H-pyran-4-yl)-1H-pyrazolo[3,4-b]pyridin-4-amine, 1-ethyl-5-[(4R)-4-(phenylmethyl)-4,5-dihydro-1,3-oxazol-2-yl]-N-(tetrahydro-2H-pyran-4-yl)-1H-pyrazolo[3,4-b]pyridin-4-amine,
1-ethyl-5-[(4S,5R)-5-methyl-4-phenyl-4,5-dihydro-1,3-oxazol-2-yl]-N-(tetrahydro-2H-pyran-4-yl)-1H-pyrazolo[3,4-b]pyridin-4-amine,
1-ethyl-5-[(5R)-5-phenyl-4,5-dihydro-1,3-oxazol-2-yl]-N-(tetrahydro-2H-pyran-4-yl)-1H-pyrazolo[3,4-b]pyridin-4-amine,
1-ethyl-5-[(5S)-5-phenyl-4,5-dihydro-1,3-oxazol-2-yl]-N-(tetrahydro-2H-pyran-4-yl)-1H-pyrazolo[3,4-b]pyridin-4-amine,
5-(4,4-dimethyl-4,5-dihydro-1,3-oxazol-2-yl)-1-ethyl-N-(tetrahydro-2H-pyran-4-yl)-1H-pyrazolo[3,4-b]pyridin-4-amine,
2-[1-ethyl-4-(tetrahydro-2H-pyran-4-ylamino)-1H-pyrazolo[3,4-b]pyridin-5-yl]-1,3-oxazole-4-carboxylic acid,
2-[1-ethyl-4-(tetrahydro-2H-pyran-4-ylamino)-1H-pyrazolo[3,4-b]pyridin-5-yl]-N-(1-methylethyl)-1,3-oxazole-4-carboxamide,
1-ethyl-5-[4-(4-morpholinylcarbonyl)-1,3-oxazol-2-yl]-N-(tetrahydro-2H-pyran-4-yl)-1H-pyrazolo[3,4-b]pyridin-4-amine,
1-ethyl-N-methyl-5-(5-methyl-1,3,4-oxadiazol-2-yl)-N-(tetrahydro-2H-pyran-4-yl)-1H-pyrazolo[3,4-b]pyridin-4-amine,
trans-4-{[1-ethyl-5-(5-methyl-1,3,4-oxadiazol-2-yl)-1H-pyrazolo[3,4-b]pyridin-4-yl]amino}cyclohexanol,
1-ethyl-5-(5-methyl-1,3,4-oxadiazol-2-yl)-N-(tetrahydro-2H-pyran-3-yl)-1H-pyrazolo[3,4-b]pyridin-4-amine,
4-{[1-ethyl-5-(5-methyl-1,3,4-oxadiazol-2-yl)-1H-pyrazolo[3,4-b]pyridin-4-yl]amino}cyclohexanone,
1-ethyl-5-(5-methyl-1,3,4-oxadiazol-2-yl)-N-n-propyl-N-(tetrahydro-2H-pyran-4-yl)-1H-pyrazolo[3,4-b]pyridin-4-amine,
5-[5-(1,1-dimethylethyl)-1,3,4-oxadiazol-2-yl]-1-ethyl-6-methyl-N-(tetrahydro-2H-pyran-4-yl)-1H-pyrazolo[3,4-b]pyridin-4-amine,
1-ethyl-6-methyl-N-(tetrahydro-2H-pyran-4-yl)-5-[5-(tetrahydro-2H-pyran-4-yl)-1,3,4-oxadiazol-2-yl]-1H-pyrazolo[3,4-b]pyridin-4-amine,
5-(5-cyclobutyl-1,3,4-oxadiazol-2-yl)-1-ethyl-N-(tetrahydro-2H-pyran-4-yl)-1H-pyrazolo[3,4-b]pyridin-4-amine,
5-{5-[1-ethyl-4-(tetrahydro-2H-pyran-4-ylamino)-1H-pyrazolo[3,4-b]pyridin-5-yl]-1,3,4-oxadiazol-2-yl}-2-pyrrolidinone,
N-({5-[1-ethyl-4-(tetrahydro-2H-pyran-4-ylamino)-1H-pyrazolo[3,4-b]pyridin-5-yl]-1,3,4-oxadiazol-2-yl}methyl)acetamide,
1-ethyl-5-[5-(1-methyl-2-piperidinyl)-1,3,4-oxadiazol-2-yl]-N-(tetrahydro-2H-pyran-4-yl)-1H-pyrazolo[3,4-b]pyridin-4-amine,
1-ethyl-5-{5-[(4-methyl-1,2,5-oxadiazol-3-yl)methyl]-1,3,4-oxadiazol-2-yl}-N-(tetrahydro-2H-pyran-4-yl)-1H-pyrazolo[3,4-b]pyridin-4-amine,
3-{5-[1-ethyl-4-(tetrahydro-2H-pyran-4-ylamino)-1H-pyrazolo[3,4-b]pyridin-5-yl]-1,3,4-oxadiazol-2-yl}cyclopentanone,
1-ethyl-5-[5-(tetrahydro-3-furanyl)-1,3,4-oxadiazol-2-yl]-N-(tetrahydro-2H-pyran-4-yl)-1H-pyrazolo[3,4-b]pyridin-4-amine,
(4S)-4-{5-[1-ethyl-4-(tetrahydro-2H-pyran-4-ylamino)-1H-pyrazolo[3,4-b]pyridin-5-yl]-1,3,4-oxadiazol-2-yl}-1,3-thiazolidin-2-one,
5-[5-(2,2-dimethylcyclopropyl-1,3,4-oxadiazol-2-yl]-1-ethyl-N-(tetrahydro-2H-pyran-4-yl)-1H-pyrazolo[3,4-b]pyridin-4-amine,
N-({5-[1-ethyl-4-(tetrahydro-2H-pyran-4-ylamino)-1H-pyrazolo[3,4-b]pyridin-5-yl]-1,3,4-oxadiazol-2-yl}methyl)-N-methylacetamide,
1-ethyl-N-(tetrahydro-2H-pyran-4-yl)-5-[5-(tetrahydro-2H-pyran-4-ylmethyl)-1,3,4-oxadiazol-2-yl]-1H-pyrazolo[3,4-b]pyridin-4-amine,
1-ethyl-5-[5-(1-methylcyclobutyl)-1,3,4-oxadiazol-2-yl]-N-(tetrahydro-2H-pyran-4-yl)-1H-pyrazolo[3,4-b]pyridin-4-amine,
1-ethyl-5-[5-(3-methyl-5-isoxazolyl)-1,3,4-oxadiazol-2-yl]-N-(tetrahydro-2H-pyran-4-yl)-1H-pyrazolo[3,4-b]pyridin-4-amine,
1-ethyl-5-[5-(1-methyl-1H-pyrazol-5-yl)-1,3,4-oxadiazol-2-yl]-N-(tetrahydro-2H-pyran-4-yl)-1H-pyrazolo[3,4-b]pyridin-4-amine,
5-[5-(1-acetyl-4-piperidinyl)-1,3,4-oxadiazol-2-yl]-1-ethyl-N-(tetrahydro-2H-pyran-4-yl)-1H-pyrazolo[3,4-b]pyridin-4-amine,
1-ethyl-5-{3-[(4-methyl-1-piperazinyl)methyl]-1,2,4-oxadiazol-5-yl}-N-(tetrahydro-2H-pyran-4-yl)-1H-pyrazolo[3,4-b]pyridin-4-amine,
1-ethyl-5-[3-(4-fluorophenyl)-1,2,4-oxadiazol-5-yl]-N-(tetrahydro-2H-pyran-4-yl)-1H-pyrazolo[3,4-b]pyridin-4-amine, or
1-ethyl-5-{3-[2-oxo-2-(1-pyrrolidinyl)ethyl]-1,2,4-oxadiazol-5-yl}-N-(tetrahydro-2H-pyran-4-yl)-1H-pyrazolo[3,4-b]pyridin-4-amine;
or a salt thereof.

42. A compound or salt as claimed in claim 1, which is:
2-{5-[1-ethyl-4-(tetrahydro-2H-pyran-4-ylamino)-1H-pyrazolo[3,4-b]pyridin-5-yl]-1,2,4-oxadiazol-3-yl}-N-phenylacetamide,
2-{5-[1-ethyl-4-(tetrahydro-2H-pyran-4-ylamino)-1H-pyrazolo[3,4-b]pyridin-5-yl]-1,2,4-oxadiazol-3-yl}-N-(1-phenylethyl)acetamide,
1-ethyl-5-{3-[2-oxo-2-(1-piperidinyl)ethyl]-1,2,4-oxadiazol-5-yl}-N-(tetrahydro-2H-pyran-4-yl)-1H-pyrazolo[3,4-b]pyridin-4-amine,
2-{5-[1-ethyl-4-(tetrahydro-2H-pyran-4-ylamino)-1H-pyrazolo[3,4-b]pyridin-5-yl]-1,2,4-oxadiazol-3-yl}-N-(phenylmethyl)acetamide,
2-{5-[1-ethyl-4-(tetrahydro-2H-pyran-4-ylamino)-1H-pyrazolo[3,4-b]pyridin-5-yl]-1,2,4-oxadiazol-3-yl}-N,N-dimethylacetamide,
N-ethyl-2-{5-[1-ethyl-4-(tetrahydro-2H-pyran-4-ylamino)-1H-pyrazolo[3,4-b]pyridin-5-yl]-1,2,4-oxadiazol-3-yl}acetamide,
1-ethyl-5-{3-[1-(4-morpholinyl)ethyl]-1,2,4-oxadiazol-5-yl}-N-(tetrahydro-2H-pyran-4-yl)-1H-pyrazolo[3,4-b]pyridin-4-amine,
5-[3-(cyclohexylmethyl)-1,2,4-oxadiazol-5-yl]-1-ethyl-N-(tetrahydro-2H-pyran-4-yl)-1H-pyrazolo[3,4-b]pyridin-4-amine,
1-ethyl-5-{3-[2-oxo-2-(1-piperidinyl)ethyl]-1,2,4-oxadiazol-5-yl}-N-(tetrahydro-2H-pyran-4-yl)-1H-pyrazolo[3,4-b]pyridin-4-amine,
1-ethyl-5-{3-[2-(4-methyl-1-piperazinyl)-2-oxoethyl]-1,2,4-oxadiazol-5-yl}-N-(tetrahydro-2H-pyran-4-yl)-1H-pyrazolo[3,4-b]pyridin-4-amine,
1-ethyl-N-(tetrahydro-2H-pyran-4-yl)-5-[5-(1H-1,2,3-triazol-1-ylmethyl)-1,3,4-oxadiazol-2-yl]-1H-pyrazolo[3,4-b]pyridin-4-amine, 1-ethyl-5-[5-(2-furanylmethyl)-1,3,4-oxadiazol-2-yl]-N-(tetrahydro-2H-pyran-4-yl)-1H-pyrazolo[3,4-b]pyridin-4-amine, 1-ethyl-5-[5-(3-isoxazolylmethyl)-1,3,4-oxadiazol-2-yl]-N-(tetrahydro-2H-pyran-4-yl)-1H-pyrazolo[3,4-b]pyridin-4-amine, 1-ethyl-5-(5-{[4-(methyloxy)phenyl]methyl}-1,3,4-oxadiazol-2-yl)-N-(tetrahydro-2H-pyran-4-yl)-1H-pyrazolo[3,4-b]pyridin-4-amine, 1-ethyl-N-(tetrahydro-2H-pyran-4-yl)-5-[5-(1H-tetrazol-1-ylmethyl)-1,3,4-oxadiazol-2-yl]-1H-pyrazolo[3,4-b]pyridin-4-amine, 1-ethyl-5-[5-(5-isothiazolylmethyl)-1,3,4-oxadiazol-2-yl]-N-(tetrahydro-2H-pyran-4-yl)-1H-pyrazolo[3,4-b]pyridin-4-amine, 1-ethyl-5-{5-[(3-methyl-5-isoxazolyl)methyl]-1,3,4-oxadiazol-2-yl}-N-(tetrahydro-2H-pyran-4-yl)-1H-pyrazolo[3,4-b]pyridin-4-amine, 5-(5-{[4-(dimethylamino)phenyl]methyl}-1,3,4-oxadiazol-2-yl)-1-ethyl-N-(tetrahydro-2H-pyran-4-yl)-1H-pyrazolo[3,4-b]pyridin-4-amine (1:1), 1-ethyl-5-{5-[(2-methyl-1,3-thiazol-4-yl)methyl]-1,3,4-oxadiazol-2-yl}-N-(tetrahydro-2H-pyran-4-yl)-1H-pyrazolo[3,4-b]pyridin-4-amine, 2-[1-({5-[1-ethyl-4-(tetrahydro-2H-pyran-4-ylamino)-1H-pyrazolo[3,4-b]pyridin-5-yl]-1,3,4-oxadiazol-2-yl}methyl)cyclopentyl]-N-methylacetamide, N-({5-[1-ethyl-4-(tetrahydro-2H-pyran-4-ylamino)-1H-pyrazolo[3,4-b]pyridin-5-yl]-1,3,4-oxadiazol-2-yl}methyl)cyclopropanecarboxamide, 1-ethyl-5-{5-[(5-methyl-3-isoxazolyl)methyl]-1,3,4-oxadiazol-2-yl}-N-(tetrahydro-2H-pyran-4-yl)-1H-pyrazolo[3,4-b]pyridin-4-amine, 1-ethyl-5-{5-[(5-methyl-3-isoxazolyl)methyl]-1,3,4-oxadiazol-2-yl}-N-(tetrahydro-2H-pyran-4-yl)-1H-pyrazolo[3,4-b]pyridin-4-amine, 1-ethyl-5-{5-[2-(4-methyl-1,3-thiazol-5-yl)ethyl]-1,3,4-oxadiazol-2-yl}-N-(tetrahydro-2H-pyran-4-yl)-1H-pyrazolo[3,4-b]pyridin-4-amine, 5-{5-[(3,5-dimethyl-4-isoxazolyl)methyl]-1,3,4-oxadiazol-2-yl}-1-ethyl-N-(tetrahydro-2H-pyran-4-yl)-1H-pyrazolo[3,4-b]pyridin-4-amine, N-(1-{5-[1-ethyl-4-(tetrahydro-2H-pyran-4-ylamino)-1H-pyrazolo[3,4-b]pyridin-5-yl]-1,3,4-oxadiazol-2-yl}ethyl)acetamide, 5-{5-[(1-acetyl-4-piperidinyl)methyl]-1,3,4-oxadiazol-2-yl}-1-ethyl-N-(tetrahydro-2H-pyran-4-yl)-1H-pyrazolo[3,4-b]pyridin-4-amine, 1-ethyl-5-{5-[(4-methylphenyl)methyl]-1,3,4-oxadiazol-2-yl}-N-(tetrahydro-2H-pyran-4-yl)-1H-pyrazolo[3,4-b]pyridin-4-amine, 1-ethyl-5-[5-(4-methylphenyl)-1,3,4-oxadiazol-2-yl]-N-(tetrahydro-2H-pyran-4-yl)-1H-pyrazolo[3,4-b]pyridin-4-amine, 5-[5-(3,4-dimethylphenyl)-1,3,4-oxadiazol-2-yl]-1-ethyl-N-(tetrahydro-2H-pyran-4-yl)-1H-pyrazolo[3,4-b]pyridin-4-amine, 5-[5-(2,4-dimethylphenyl)-1,3,4-oxadiazol-2-yl]-1-ethyl-N-(tetrahydro-2H-pyran-4-yl)-1H-pyrazolo[3,4-b]pyridin-4-amine, 5-{5-[(4-bromophenyl)methyl]-1,3,4-oxadiazol-2-yl}-1-ethyl-N-(tetrahydro-2H-pyran-4-yl)-1H-pyrazolo[3,4-b]pyridin-4-amine, 2-[1-ethyl-4-(tetrahydro-2H-pyran-4-ylamino)-1H-pyrazolo[3,4-b]pyridin-5-yl]-N-(phenylmethyl)-1,3-oxazole-4-carboxamide, 2-[1-ethyl-4-(tetrahydro-2H-pyran-4-ylamino)-1H-pyrazolo[3,4-b]pyridin-5-yl]-N-{[4-(methyloxy)phenyl]methyl}-1,3-oxazole-4-carboxamide, 2-[1-ethyl-4-(tetrahydro-2H-pyran-4-ylamino)-1H-pyrazolo[3,4-b]pyridin-5-yl]-N-[(2-methylphenyl)methyl]-1,3-oxazole-4-carboxamide, 2-[1-ethyl-4-(tetrahydro-2H-pyran-4-ylamino)-1H-pyrazolo[3,4-b]pyridin-5-yl]-N-[(4-methylphenyl)methyl]-1,3-oxazole-4-carboxamide, 2-[1-ethyl-4-(tetrahydro-2H-pyran-4-ylamino)-1H-pyrazolo[3,4-b]pyridin-5-yl]-N-[(3-methylphenyl)methyl]-1,3-oxazole-4-carboxamide, N-[(4-chlorophenyl)methyl]-2-[1-ethyl-4-(tetrahydro-2H-pyran-4-ylamino)-1H-pyrazolo[3,4-b]pyridin-5-yl]-1,3-oxazole-4-carboxamide, N-[(2,3-dimethylphenyl)methyl]-2-[1-ethyl-4-(tetrahydro-2H-pyran-4-ylamino)-1H-pyrazolo[3,4-b]pyridin-5-yl]-1,3-oxazole-4-carboxamide, N-[(3,5-dimethylphenyl)methyl]-2-[1-ethyl-4-(tetrahydro-2H-pyran-4-ylamino)-1H-pyrazolo[3,4-b]pyridin-5-yl]-1,3-oxazole-4-carboxamide, N-[(3,4-dimethylphenyl]-2-[1-ethyl-4-(tetrahydro-2H-pyran-4-ylamino)-1H-pyrazolo[3,4-b]pyridin-5-yl]-1,3-oxazole-4-carboxamide, 2-[1-ethyl-4-(tetrahydro-2H-pyran-4-ylamino)-1H-pyrazolo[3,4-b]pyridin-5-yl]-N-(1-phenylethyl)-1,3-oxazole-4-carboxamide, 2-[1-ethyl-4-(tetrahydro-2H-pyran-4-ylamino)-1H-pyrazolo[3,4-b]pyridin-5-yl]-N-{(1R)-1-[4-(methyloxy)phenyl]ethyl}-1,3-oxazole-4-carboxamide, 2-[1-ethyl-4-(tetrahydro-2H-pyran-4-ylamino)-1H-pyrazolo[3,4-b]pyridin-5-yl]-N-[(1R)-1-phenylpropyl]-1,3-oxazole-4-carboxamide, 2-[1-ethyl-4-(tetrahydro-2H-pyran-4-ylamino)-1H-pyrazolo[3,4-b]pyridin-5-yl]-N-(4-methylphenyl)-1,3-oxazole-4-carboxamide, 2-[1-ethyl-4-(tetrahydro-2H-pyran-4-ylamino)-1H-pyrazolo[3,4-b]pyridin-5-yl]-N-({4-[(methylsulfonyl)amino]phenyl}methyl)-1,3-oxazole-4-carboxamide, 2-[1-ethyl-4-(tetrahydro-2H-pyran-4-ylamino)-1H-pyrazolo[3,4-b]pyridin-5-yl]-N-{[4-(methylsulfonyl)phenyl]methyl}-1,3-oxazole-4-carboxamide, N-(1-Acetyl-4-piperidinyl)-2-[1-ethyl-4-(tetrahydro-2H-pyran-4-ylamino)-1H-pyrazolo[3,4-b]pyridin-5-yl]-1,3-oxazole-4-carboxamide, 2-[1-ethyl-4-(tetrahydro-2H-pyran-4-ylamino)-1H-pyrazolo[3,4-b]pyridin-5-yl]-N-(tetrahydro-2H-pyran-4-yl)-1,3-oxazole-4-carboxamide, 2-[1-ethyl-4-(tetrahydro-2H-pyran-4-ylamino)-1H-pyrazolo[3,4-b]pyridin-5-yl]-N-(tetrahydro-2-furanylmethyl)-1,3-oxazole-4-carboxamide, 2-[1-ethyl-4-(tetrahydro-2H-pyran-4-ylamino)-1H-pyrazolo[3,4-b]pyridin-5-yl]-N-[2-(4-methyl-1-piperazinyl)ethyl]-1,3-oxazole-4-carboxamide, N-[1-(aminomethyl)cyclohexyl]-2-[1-ethyl-4-(tetrahydro-2H-pyran-4-ylamino)-1H-pyrazolo[3,4-b]pyridin-5-yl]-N-methyl-1,3-oxazole-4-carboxamide, N-(2,6-dimethylphenyl)-2-[1-ethyl-4-(tetrahydro-2H-pyran-4-ylamino)-1H-pyrazolo[3,4-b]pyridin-5-yl]-1,3-oxazole-4-carboxamide, N-{[4-(aminocarbonyl)phenyl]methyl}-2-[1-ethyl-4-(tetrahydro-2H-pyran-4-ylamino)-1H-pyrazolo[3,4-b]pyridin-5-yl]-1,3-oxazole-4-carboxamide, 2-{5-[1-ethyl-4-(tetrahydro-2H-pyran-4-ylamino)-1H-pyrazolo[3,4-b]pyridin-5-yl]-1,2,4-oxadiazol-3-yl}-N-(tetrahydro-2H-pyran-4-yl)acetamide, 5-{3-[2-(2,6-dimethyl-4-morpholinyl)-2-oxoethyl]-1,2,4-oxadiazol-5-yl}-1-ethyl-N-(tetrahydro-2H-pyran-4-yl)-1H-pyrazolo[3,4-b]pyridin-4-amine,
1-ethyl-5-{3-[2-(4-methyl-1-piperidinyl)-2-oxoethyl]-1,2,4-oxadiazol-5-yl}-N-(tetrahydro-2H-pyran-4-yl)-1H-pyrazolo[3,4-b]pyridin-4-amine,
2-{5-[1-ethyl-4-(tetrahydro-2H-pyran-4-ylamino)-1H-pyrazolo[3,4-b]pyridin-5-yl]-1,2,4-oxadiazol-3-yl}-N-[1-methyl-2-(methyloxy)ethyl]acetamide,
5-{3-[2-(3,5-dimethyl-1-piperidinyl)-2-oxoethyl]-1,2,4-oxadiazol-5-yl}-1-ethyl-N-(tetrahydro-2H-pyran-4-yl)-1H-pyrazolo[3,4-b]pyridin-4-amine,
1-ethyl-5-{3-[2-(3-methyl-1-piperidinyl)-2-oxoethyl]-1,2,4-oxadiazol-5-yl}-N-(tetrahydro-2H-pyran-4-yl)-1H-pyrazolo[3,4-b]pyridin-4-amine,
2-{5-[1-ethyl-4-(tetrahydro-2H-pyran-4-ylamino)-1H-pyrazolo[3,4-b]pyridin-5-yl]-1,2,4-oxadiazol-3-yl}-N-3-pyridinylacetamide,
6-{5-[1-ethyl-4-(tetrahydro-2H-pyran-4-ylamino)-1H-pyrazolo[3,4-b]pyridin-5-yl]-1,3,4-oxadiazol-2-yl}-2-piperidinone,
1-ethyl-5-{5-[(3-methyl-1H-1,2,4-triazol-5-yl)methyl]-1,3,4-oxadiazol-2-yl}-N-(tetrahydro-2H-pyran-4-yl)-1H-pyrazolo[3,4-b]pyridin-4-amine,
N-({5-[1-ethyl-4-(tetrahydro-2H-pyran-4-ylamino)-1H-pyrazolo[3,4-b]pyridin-5-yl]-1,2,4-oxadiazol-3-yl}methyl)acetamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)benzamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)-2-phenylacetamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)-2-methylpropanamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)-3-methylbutanamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)cyclohexanecarboxamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)-2-furancarboxamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)methanesulfonamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)benzenesulfonamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)-1-phenylmethanesulfonamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)-2-propanesulfonamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)-1-propanesulfonamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)cyclopropanesulfonamide,
N-({5-[1-ethyl-4-(tetrahydro-2H-pyran-4-ylamino)-1H-pyrazolo[3,4-b]pyridin-5-yl]-1,2,4-oxadiazol-3-yl}methyl)-2-thiophenesulfonamide,
1-({5-[1-ethyl-4-(tetrahydro-2H-pyran-4-ylamino)-1H-pyrazolo[3,4-b]pyridin-5-yl]-1,2,4-oxadiazol-3-yl}methyl)-2-pyrrolidinone,
1-({5-[1-ethyl-4-(tetrahydro-2H-pyran-4-ylamino)-1H-pyrazolo[3,4-b]pyridin-5-yl]-1,2,4-oxadiazol-3-yl}methyl)-2-piperidinone,
5-{3-[(1-acetyl-4-piperidinyl)methyl]-1,2,4-oxadiazol-5-yl}-1-ethyl-N-(tetrahydro-2H-pyran-4-yl)-1H-pyrazolo[3,4-b]pyridin-4-amine,
1-ethyl-5-(3-{[1-(3-methylbutanoyl)-4-piperidinyl]methyl}-1,2,4-oxadiazol-5-yl)-N-(tetrahydro-2H-pyran-4-yl)-1H-pyrazolo[3,4-b]pyridin-4-amine,
1-ethyl-5-(3-{[1-(methylsulfonyl)-4-piperidinyl]methyl}-1,2,4-oxadiazol-5-yl)-N-(tetrahydro-2H-pyran-4-yl)-1H-pyrazolo[3,4-b]pyridin-4-amine,
1-ethyl-5-{3-[1-(phenylsulfonyl)cyclopropyl]-1,2,4-oxadiazol-5-yl}-N-(tetrahydro-2H-pyran-4-yl)-1H-pyrazolo[3,4-b]pyridin-4-amine,
1-ethyl-5-[3-(phenylmethyl)-1,2,4-oxadiazol-5-yl]-N-(tetrahydro-2H-pyran-4-yl)-1H-pyrazolo[3,4-b]pyridin-4-amine,
1-ethyl-5-[3-(1-phenylethyl)-1,2,4-oxadiazol-5-yl]-N-(tetrahydro-2H-pyran-4-yl)-1H-pyrazolo[3,4-b]pyridin-4-amine,
1-ethyl-5-(3-{[4-(methyloxy)phenyl]methyl}-1,2,4-oxadiazol-5-yl)-N-(tetrahydro-2H-pyran-4-yl)-1H-pyrazolo[3,4-b]pyridin-4-amine,
5-(3-{[4-(dimethylamino)phenyl]methyl}-1,2,4-oxadiazol-5-yl)-1-ethyl-N-(tetrahydro-2H-pyran-4-yl)-1H-pyrazolo[3,4-b]pyridin-4-amine,
5-(3-{[3-(methylamino)phenyl]methyl}-1,2,4-oxadiazol-5-yl)-1-ethyl-N-(tetrahydro-2H-pyran-4-yl)-1H-pyrazolo[3,4-b]pyridin-4-amine,
5-(3-{[4-(dimethylamino)phenyl]methyl}-1,2,4-oxadiazol-5-yl)-1-ethyl-N-(tetrahydro-2H-pyran-4-yl)-1H-pyrazolo[3,4-b]pyridin-4-amine,
1-ethyl-5-{3-[(phenyloxy)methyl]-1,2,4-oxadiazol-5-yl}-N-(tetrahydro-2H-pyran-4-yl)-1H-pyrazolo[3,4-b]pyridin-4-amine,
1-ethyl-N-(tetrahydro-2H-pyran-4-yl)-5-[3-(5,6,7,8-tetrahydro[1,2,4]triazolo[4,3-a]pyridin-3-ylmethyl)-1,2,4-oxadiazol-5-yl]-1H-pyrazolo[3,4-b]pyridin-4-amine,
1-ethyl-5-{3-[(4-phenyl-1-piperazinyl)methyl]-1,2,4-oxadiazol-5-yl}-N-(tetrahydro-2H-pyran-4-yl)-1H-pyrazolo[3,4-b]pyridin-4-amine,
1-ethyl-5-(5-ethyl-1,2,4-oxadiazol-3-yl)-N-(tetrahydro-2H-pyran-4-yl)-1H-pyrazolo[3,4-b]pyridin-4-amine,
5-(5-{[4-(dimethylamino)phenyl]methyl}-1,2,4-oxadiazol-3-yl)-1-ethyl-N-(tetrahydro-2H-pyran-4-yl)-1H-pyrazolo[3,4-b]pyridin-4-amine,
1-ethyl-5-(5-{[4-(methyloxy)phenyl]methyl}-1,2,4-oxadiazol-3-yl)-N-(tetrahydro-2H-pyran-4-yl)-1H-pyrazolo[3,4-b]pyridin-4-amine, or
5-(3,8-dioxa-1-azaspiro[4.5]dec-1-en-2-yl)-1-ethyl-N-(tetrahydro-2H-pyran-4-yl)-1H-pyrazolo[3,4-b]pyridin-4-amine;
or a salt thereof.

43. A compound or salt as claimed in claim 1, which is:
1-ethyl-5-(5-methyl-1,3,4-oxadiazol-2-yl)-N-(tetrahydro-2H-pyran-4-yl)-1H-pyrazolo[3,4-b]pyridin-4-amine (the compound of Example 14),
5-(5-tert-butyl-1,3,4-oxadiazol-2-yl)-1-ethyl-N-(tetrahydro-2H-pyran-4-yl)-1H-pyrazolo[3,4-b]pyridin-4-amine (the compound of Example 17),
1-ethyl-5-{5-[(methylsulfonyl)methyl]-1,3,4-oxadiazol-2-yl}-N-(tetrahydro-2H-pyran-4-yl)-1H-pyrazolo[3,4-b]pyridin-4-amine (the compound of Example 23), 1-ethyl-5-[5-(3-methyloxetan-3-yl)-1,3,4-oxadiazol-2-yl]-N-(tetrahydro-2H-pyran-4-yl)-1H-pyrazolo[3,4-b]pyridin-4-amine (the compound of Example 34), 1-ethyl-5-{5-[(4-methylpiperazin-1-yl)methyl]-1,3,4-oxadiazol-2-yl}-N-(tetrahydro-2H-pyran-4-yl)-1H-pyrazolo[3,4-b]pyridin-4-amine, 1-ethyl-N-(tetrahydro-2H-pyran-4-yl)-5-[5-(tetrahydro-2H-pyran-4-yl)-1,3,4-oxadiazol-2-yl]-1H-pyrazolo[3,4-b]pyridin-4-amine, also named: 1-ethyl-5-[5-(morpholin-4-ylmethyl)-1,3,4-oxadiazol-2-yl]-N-(tetrahydro-2H-pyran-4-yl)-1H-pyrazolo[3,4-b]pyridin-4-amine (the compound of Example 39), 1-ethyl-5-[5-(tetrahydrofuran-2-yl)-1,3,4-oxadiazol-2-yl]-N-(tetrahydro-2H-pyran-4-yl)-1H-pyrazolo[3,4-b]pyridin-4-amine (the compound of Example 44), 1-ethyl-N-(tetrahydro-2H-pyran-4-yl)-5-[5-(tetrahydro-2H-pyran-4-ylmethyl)-1,3,4-oxadiazol-2-yl]-1H-pyrazolo[3,4-b]pyridin-4-amine (the compound of Example 77), or 1-ethyl-5-{3-[2-oxo-2-(1-pyrrolidinyl)ethyl]-1,2,4-oxadiazol-5-yl}-N-(tetrahydro-2H-pyran-4-yl)-1H-pyrazolo[3,4-b]pyridin-4-amine (the compound of Example 84);

or a salt thereof.

44. A pharmaceutical composition comprising a compound of formula (I), as defined in claim 1, or a pharmaceutically acceptable salt thereof, and one or more pharmaceutically acceptable carriers and/or excipients.

45. A pharmaceutical composition as claimed in claim 44 which is suitable for and/or adapted for oral administration.

46. A compound or salt as claimed in claim 24, wherein $R^1$ is ethyl.

47. A compound or salt as claimed in claim 28, wherein $R^1$ is ethyl.

48. A compound or salt as claimed in claim 24, wherein Het is of sub-formula (ia), (ib), (ic), or (id):

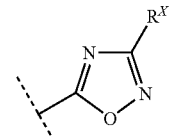
(ia)

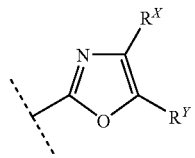
(ib)

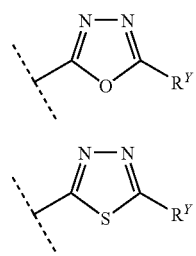

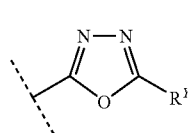
(ic)

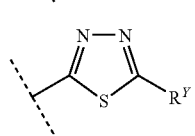
(id)

49. A compound or salt as claimed in claim 48 wherein wherein $R^1$ is ethyl.

50. A compound or salt as claimed in claim 28, wherein Het is of sub-formula (ia), (ib), (ic), or (id):

(ia)

(ib)

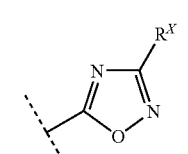
(ic)

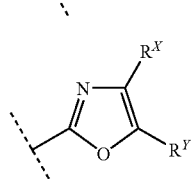
(id)

51. A compound or salt as claimed in claim 50, wherein wherein $R^1$ is ethyl.

52. A compound according to claim 1 which is 5-{5-[(2,4-dimethyl-1,3-thiazol-5-yl)methyl]-1,3,4-oxadiazol-2-yl}-1-ethyl-N-(tetrahydro-2H-pyran-4-yl)-1H-pyrazolo[3,4-b]pyridin-4-amine or a pharmaceutically acceptable salt thereof.

* * * * *

UNITED STATES PATENT AND TRADEMARK OFFICE
CERTIFICATE OF CORRECTION

PATENT NO. : 7,528,148 B2
APPLICATION NO. : 10/540371
DATED : May 5, 2009
INVENTOR(S) : David George Allen et al.

It is certified that error appears in the above-identified patent and that said Letters Patent is hereby corrected as shown below:

| | |
|---|---|
| In Column 198, line 25 | Delete "(as" |
| In Column 198, line 25 | Delete "2.79" and Insert -- 2.74 -- |
| In Column 198, line 26 | Delete "formate" |
| In Column 198, line 27 | Delete "salt)" |

Signed and Sealed this
Fifth Day of April, 2011

David J. Kappos
*Director of the United States Patent and Trademark Office*